(12) United States Patent
Nagase et al.

(10) Patent No.: US 8,952,030 B2
(45) Date of Patent: Feb. 10, 2015

(54) MORPHINAN DERIVATIVE

(75) Inventors: Hiroshi Nagase, Ibaraki (JP); Hideaki Fujii, Kanagawa (JP); Eriko Nakata, Saitama (JP); Yoshikazu Watanabe, Chiba (JP); Toshihiro Takahashi, Saitama (JP)

(73) Assignees: The Kitasato Institute, Tokyo (JP); Nippon Chemiphar Co., Ltd., Tokyo (JP)

( * ) Notice: Subject to any disclaimer, the term of this patent is extended or adjusted under 35 U.S.C. 154(b) by 0 days.

(21) Appl. No.: 14/343,218

(22) PCT Filed: Sep. 7, 2012

(86) PCT No.: PCT/JP2012/072868
§ 371 (c)(1),
(2), (4) Date: Jul. 3, 2014

(87) PCT Pub. No.: WO2013/035833
PCT Pub. Date: Mar. 14, 2013

(65) Prior Publication Data
US 2014/0343015 A1 Nov. 20, 2014

(30) Foreign Application Priority Data

Sep. 9, 2011 (JP) ................................ 2011-196641
Jul. 30, 2012 (JP) ................................ 2012-168401

(51) Int. Cl.
*A61K 31/485* (2006.01)
*C07D 491/18* (2006.01)
*C07D 487/08* (2006.01)
*C07F 7/18* (2006.01)

(52) U.S. Cl.
CPC ............ *C07D 491/18* (2013.01); *C07D 487/08* (2013.01); *C07F 7/1856* (2013.01)
USPC .......................................... 514/279; 546/40

(58) Field of Classification Search
USPC ............................................ 514/279; 546/40
See application file for complete search history.

(56) References Cited

FOREIGN PATENT DOCUMENTS

| JP | 2009-196933 A | 9/2009 |
| WO | 98/43978 A1 | 10/1998 |
| WO | 2008/001859 A1 | 1/2008 |
| WO | 2012/102360 A1 | 8/2012 |

OTHER PUBLICATIONS

Nemoto et al., "Synthesis of 6,14-epoxymorphinan derivatives and their pharmacologies", Bioorganic & Medicinal Chemistry 19, 2011, pp. 1205-1221.

Hayashida et al., "Rearrangement of a 4.5-epoxymorphinan derivatives with carbamoylepoxy rings provide novel oxazatricyclodecane structures", Tetrahedron 67, 2011, pp. 6682-6688.
Nagase et al., "Synthesis of 6,14-epoxymorphinan derivatives and their pharmacologies", Bioorganic & Medicinal Chemistry 19, 2011, pp. 1205-1221.
Nagase et al., "Drug design ans synthesis of a novel & opioid receptor agonist with an oxabicyclo[2.2.2]octane skeleton and its pharmacology", Bioorganic & Medicinal Letters 20, 2010, pp. 121-124.
Nagase et al., "Rearrangement of a 4.5-epoxyrnorphinan derivatives with carbamoylepoxy rings provide novel oxazatricyclodecane structures", Tetrahedron 67, 2011, pp. 6682-6688.
International Preliminary Report on patentability issued with respect to International application PCT/JP2012/072868, mail date is Oct. 2, 2012.
8th AFMC International Medicinal Chemistry Symposium, "Frontier of Medicinal Science", Nov. 29, 2011.
Italian-Japanese International Seminar of Neurosciences, Tohoku Pharmaceutical University, Sep. 1, 2011.

*Primary Examiner* — Charanjit Aulakh
(74) *Attorney, Agent, or Firm* — Greenblum & Bernstein, P.L.C.

(57) ABSTRACT

A morphinan derivative represented by the following general formula (I):

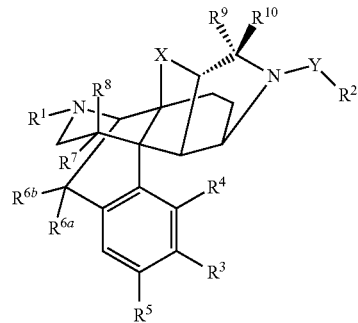

(in the formula, $R^1$ represents hydrogen, $C_{1-6}$ alkyl, cycloalkylalkyl (the cycloalkyl moiety has 3 to 6 carbon atoms, and the alkylene moiety has 1 to 5 carbon atoms), aralkyl (the aryl moiety has 6 to 10 carbon atoms, and the alkylene moiety has 1 to 5 carbon atoms) and the like,
$R^2$ represents hydrogen, $C_{1-6}$ alkyl, $C_{3-6}$ cycloalkyl, $C_{6-10}$ aryl, aralkyl (the aryl moiety has 6 to 10 carbon atoms, and the alkylene moiety has 1 to 5 carbon atoms) and the like,
$R^3$, $R^4$ and $R^5$ represent hydrogen, hydroxy, carbamoyl, $C_{1-6}$ alkoxy, $C_{6-10}$ aryloxy and the like,
$R^{6a}$, $R^{6b}$, $R^7$, $R^8$, $R^9$, and $R^{10}$ represent hydrogen and the like,
X represents O or $CH_2$, and
Y represents C=O, $SO_2$, an atomic bond and the like), or an acid addition salt thereof is used as an analgesic.

30 Claims, No Drawings

MORPHINAN DERIVATIVE

TECHNICAL FIELD

The present invention relates to a morphinan derivative having an opioid δ receptor agonist activity.

BACKGROUND ART

Three types of opioid receptors, i.e., μ, δ, and κ receptors, are known, and morphine having potent affinity to μ receptor has been used as an analgesic for a long time. Although morphine has potent analgesic effect, it is known that morphine causes adverse events such as formation of dependence, respiratory depression, and constipation via μ receptor. It is also known that δ receptor agonists are not involved in the adverse events observed for morphine, although δ receptor also participates in the analgesic effect. Therefore, it is considered that a δ receptor-selective agonist may have a potential as an analgesic superior to morphine, and for this reason, researches focusing on the discovery of such analgesic have been actively conducted. However, any δ receptor agonist has not yet been approved as a therapeutic or prophylactic agent.

Patent document 1 describes that a compound represented by the following formula (A):

[Formula 1]

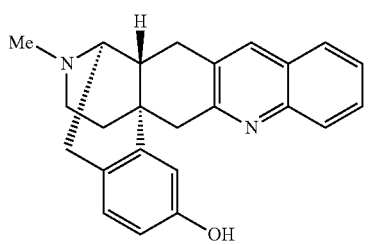

(A)

has an opioid δ receptor agonistic activity. Further, in Non-patent document 1, the inventors of the present invention made reports concerning a compound represented by the following formula (B):

[Formula 2]

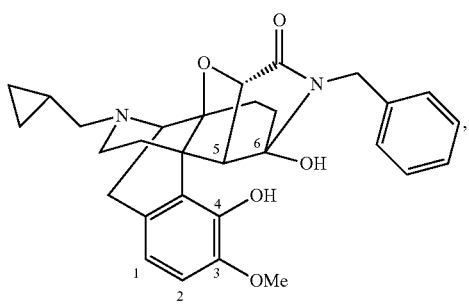

(B)

however, this compound has higher affinity to μ receptor than δ receptors.

Further, by comparison of the compound represented by the aforementioned formula (B) and the morphinan derivatives represented by the general formula (I) mentioned below, it is noted that there is difference in chemical structure, i.e., the components of the rings of the two compounds are significantly different. More specifically, in the compound represented by the aforementioned formula (B), the five membered ring moiety containing nitrogen has an amide structure, and one of the carbon atoms binding to the nitrogen atom is further substituted with hydroxy group (hemiaminal structure is formed). Whilst, in the morphinan derivatives of the present invention represented by the general formula (I) mentioned below, the corresponding five membered ring moiety has an amine structure (i.e., not having carbonyl group), and moreover, this five membered ring moiety does not have hydroxy group.

The inventors of the present invention recently filed a patent application for compounds corresponding to the compound represented by the aforementioned formula (B) in which two of the hydroxy groups at the 4- and 6-positions are bound via a methylene chain (Patent document 2, Non-patent document 2). However, the morphinan derivatives represented by the general formula (I) mentioned below do not have any bond between the 4- and 6-positions.

PRIOR ART REFERENCES

Patent Documents

Patent document 1: WO2008/001859
Patent document 2: WO2012/102360

Non-Patent Documents

Non-patent document 1: Tetrahedron, 2011, 67, 6682
Non-patent document 2: 8th AFMC International Medicinal Chemistry Symposium, 2011

DISCLOSURE OF THE INVENTION

Object to be Achieved by the Invention

An object of the present invention is to provide a morphinan derivative represented by the following general formula (I) or a pharmacologically acceptable acid addition salt thereof, and an analgesic comprising the aforementioned substance as an active ingredient.

Means for Achieving the Object

The present invention thus provides a morphinan derivative represented by the following general formula (I)

[Formula 3]

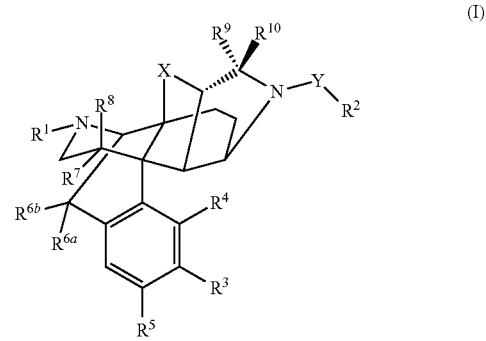

(I)

(wherein, $R^1$ represents hydrogen, $C_{1-10}$ alkyl, $C_{6-10}$ aryl, $C_{2-6}$ alkenyl, cycloalkylalkyl (the cycloalkyl moiety has 3 to 6 carbon atoms, and the alkylene moiety has 1 to 5 carbon atoms), aralkyl (the aryl moiety has 6 to 10 carbon atoms, and the alkylene moiety has 1 to 5 carbon atoms), $C_{3-6}$ cycloalkyl, or heteroarylalkyl (the heteroaryl contains 1 to 4 heteroatoms selected from N, O and S as ring-constituting atoms, and the alkylene moiety has 1 to 5 carbon atoms), $R^2$ represents hydrogen, $C_{1-10}$ alkyl, $C_{3-6}$ cycloalkyl, $C_{6-10}$ aryl, heteroaryl (containing 1 to 4 heteroatoms selected from N, O and S as ring-constituting atoms), aralkyl (the aryl moiety has 6 to 10 carbon atoms, and the alkylene moiety has 1 to 5 carbon atoms), heteroarylalkyl (the heteroaryl contains 1 to 4 heteroatoms selected from N, O and S as ring-constituting atoms, and the alkylene moiety has 1 to 5 carbon atoms), cycloalkylalkyl (the cycloalkyl moiety has 3 to 6 carbon atoms, and the alkylene moiety has 1 to 5 carbon atoms), $C_{2-6}$ alkenyl, arylalkenyl (the aryl moiety has 6 to 10 carbon atoms, and the alkenyl moiety has 2 to 6 carbon atoms), heteroarylalkenyl (the heteroaryl contains 1 to 4 heteroatoms selected from N, O and S as ring-constituting atoms, and the alkenyl moiety has 2 to 6 carbon atoms), cycloalkylalkenyl (the cycloalkyl moiety has 3 to 6 carbon atoms, and the alkenyl moiety has 2 to 6 carbon atoms), $C_{4-6}$ cycloalkenyl, cycloalkenylalkyl (the cycloalkenyl moiety has 4 to 6 carbon atoms, and the alkylene moiety has 1 to 5 carbon atoms), or cycloalkenylalkenyl (the cycloalkenyl moiety has 4 to 6 carbon atoms, and the alkenyl moiety has 2 to 6 carbon atoms), $R^3$, $R^4$ and $R^5$, which are the same or different, represent hydrogen, hydroxy, halogen, cyano, carbamoyl, $C_{1-6}$ alkoxy, $C_{6-10}$ aryloxy, $C_{1-6}$ alkanoyloxy, nitro, amino, $C_{1-8}$ alkylamino, $C_{6-10}$ arylamino, or acylamino (the acyl moiety has 2 to 6 carbon atoms), $R^{6a}$ and $R^{6b}$, which are the same or different, represent hydrogen, fluorine or hydroxy, or $R^{6a}$ and $R^{6b}$ combine together to represent =O, $R^7$ and $R^8$, which are the same or different, represent hydrogen, fluorine or hydroxy, $R^9$ and $R^{10}$ which are the same or different, represent hydrogen, $C_{1-6}$ alkyl, $C_{6-10}$ aryl, heteroaryl (containing 1 to 4 heteroatoms selected from N, O and S as ring-constituting atoms), aralkyl (the aryl moiety has 6 to 10 carbon atoms, and the alkylene moiety has 1 to 5 carbon atoms), heteroarylalkyl (the heteroaryl contains 1 to 4 heteroatoms selected from N, O and S as ring-constituting atoms, and the alkylene moiety has 1 to 5 carbon atoms), cycloalkylalkyl (the cycloalkyl moiety has 3 to 6 carbon atoms, and the alkylene moiety has 1 to 5 carbon atoms), or $C_{2-6}$ alkenyl, X represents O or $CH_2$, and Y represents C=O, C=S, $SO_2$, C(=O)O, C(=O)$NR^{11}$, C(=S)$NR^{11}$, or an atomic bond, where $R^{11}$ represents hydrogen, $C_{1-6}$ alkyl, aralkyl (the aryl moiety has 6 to 10 carbon atoms, and the alkylene moiety has 1 to 5 carbon atoms), heteroarylalkyl (the heteroaryl contains 1 to 4 heteroatoms selected from N, O and S as ring-constituting atoms, and the alkylene moiety has 1 to 5 carbon atoms), or cycloalkylalkyl (the cycloalkyl moiety has 3 to 6 carbon atoms, and the alkylene moiety has 1 to 5 carbon atoms), or may form a 4- to 7-membered ring together with the N atom to which $R^{11}$ bonds and $R^2$, wherein the 4- to 7-membered ring may contain heteroatom(s) selected from N, O, and S atoms as a ring-constituting atom other than the N atom to which $R^{11}$ binds, and may have 1 to 3 substituents selected from halogen, hydroxy, $C_{1-6}$ alkyl, aralkyl (the aryl moiety has 6 to 10 carbon atoms, and the alkylene moiety has 1 to 5 carbon atoms), $C_{2-6}$ acyl, and oxo group, provided that the $C_{1-10}$ alkyl as $R^1$ or $R^2$ the alkylene moiety and the cycloalkyl moiety of the cycloalkylalkyl (the cycloalkyl moiety has 3 to 6 carbon atoms, and the alkylene moiety has 1 to 5 carbon atoms) as $R^1$ or $R^2$ the alkylene moiety of the aralkyl (the aryl moiety has 6 to 10 carbon atoms, and the alkylene moiety has 1 to 5 carbon atoms) as $R^1$ or $R^2$, as well as the alkylene moiety of the heteroarylalkyl (the heteroaryl contains 1 to 4 heteroatoms selected from N, O and S as ring-constituting atoms, and the alkylene moiety has 1 to 5 carbon atoms) as $R^1$ or $R^2$ may be substituted with at least one substituent selected from 1 to 6 halogens, hydroxy, $C_{1-6}$ alkoxy, $C_{6-10}$ aryloxy, $C_{1-6}$ alkanoyl, $C_{1-6}$ alkanoyloxy, carboxyl, alkoxycarbonyl (the alkoxy moiety has 1 to 6 carbon atoms), carbamoyl, alkylcarbamoyl (the alkyl moiety has 1 to 6 carbon atoms), dialkylcarbamoyl (each alkyl moiety has 1 to 6 carbon atoms), alkylsulfonyl (the alkyl moiety has 1 to 6 carbon atoms), alkylthio (the alkyl moiety has 1 to 6 carbon atoms), $C_{1-6}$ alkoxy substituted with 1 to 6 halogens, arylcarbonyl, and oxetanyl, the aryl as $R^1$, aryl moiety of the aralkyl (the aryl moiety has 6 to 10 carbon atoms, and the alkylene moiety has 1 to 5 carbon atoms) as $R^1$, the aryl as $R^2$, the heteroaryl (containing 1 to 4 heteroatoms selected from N, O and S as ring-constituting atoms) as $R^2$, or the aryl moiety of the aralkyl (the aryl moiety has 6 to 10 carbon atoms, and the alkylene moiety has 1 to 5 carbon atoms) as $R^2$, the heteroaryl moiety of the heteroarylalkyl (the heteroaryl contains 1 to 4 heteroatoms selected from N, O and S as ring-constituting atoms, and the alkylene moiety has 1 to 5 carbon atoms) as $R^2$, the aryl moiety of the arylalkenyl (the aryl moiety has 6 to 10 carbon atoms, and the alkenyl moiety has 2 to 6 carbon atoms) as $R^2$ the heteroaryl moiety of the heteroarylalkenyl (the heteroaryl contains 1 to 4 heteroatoms selected from N, O and S as ring-constituting atoms, and the alkenyl moiety has 2 to 6 carbon atoms) as $R^2$, the aryl moiety of the $C_{6-10}$ aryloxy as $R^3$, $R^4$ or $R^5$, the aryl moiety of the $C_{6-10}$ arylamino as $R^3$, $R^4$ or $R^5$, the $C_{6-10}$ aryl as $R^9$ or $R^{10}$, the heteroaryl (containing 1 to 4 heteroatoms selected from N, O and S as ring-constituting atoms) as $R^9$ or $R^{10}$, or the aryl moiety of the aralkyl (the aryl moiety has 6 to 10 carbon atoms, and the alkylene moiety has 1 to 5 carbon atoms) as $R^9$ or $R^{10}$, and the heteroaryl moiety of the heteroarylalkyl (the heteroaryl contains 1 to 4 heteroatoms selected from N, O and S as ring-constituting atoms, and the alkylene moiety has 1 to 5 carbon atoms) as $R^9$ or $R^{10}$ may be substituted with at least one substituent selected from $C_{1-6}$ alkyl, $C_{1-6}$ alkoxy, $C_{1-6}$ alkanoyloxy, hydroxy, alkoxycarbonyl (the alkoxy moiety has 1 to 6 carbon atoms), carbamoyl, alkylcarbamoyl (the alkyl moiety has 1 to 6 carbon atoms), dialkylcarbamoyl (each alkyl moiety has 1 to 6 carbon atoms), halogen, nitro, cyano, $C_{1-6}$ alkyl substituted with 1 to 3 halogens, $C_{1-6}$ alkoxy substituted with 1 to 3 halogens, phenyl, heteroaryl (containing 1 to 4 heteroatoms selected from N, O and S as ring-constituting atoms), phenoxy, phenylalkyl (the alkyl has 1 to 3 carbon atoms), methylenedioxy, and $NR^{12}R^{13}$, where $R^{12}$ and $R^{13}$ independently represent hydrogen, $C_{1-6}$ alkyl, $C_{2-6}$ alkenyl, $C_{3-6}$ cycloalkyl, $C_{1-6}$ alkanoyl, or alkoxycarbonyl (the alkoxy moiety has 1 to 6 carbon atoms), or $R^{12}$ and $R^{13}$ may form a 4- to 7-membered ring together with the N atom to which they bond, where the 4- to 7-membered ring may further contain heteroatom(s) selected from N, O and S, and furthermore, the alkylene moiety of the aralkyl (the aryl moiety has 6 to 10 carbon atoms, and the alkylene moiety has 1 to 5 carbon atoms) as $R^1$ or $R^2$ may be substituted with at least one substituent selected from phenyl and $C_{1-6}$ alkyl substituted with 1 to 3 halogens), or a pharmacologically acceptable acid addition salt thereof.

The present invention also relates to a medicament comprising a morphinan derivative represented by the aforementioned general formula (I) or a pharmacologically acceptable acid addition salt thereof.

The present invention also relates to a pharmaceutical composition comprising a morphinan derivative represented by the aforementioned general formula (I) or a pharmacologically acceptable acid addition salt thereof as an active ingredient.

The present invention also relates to an analgesic comprising a morphinan derivative represented by the aforementioned general formula (I) or a pharmacologically acceptable acid addition salt thereof as an active ingredient.

The present invention further relates to a method for treating a pain, which comprises administration of an effective amount of a morphinan derivative represented by the aforementioned general formula (I) or a pharmacologically acceptable acid addition salt thereof.

MODES FOR CARRYING OUT THE INVENTION

Hereafter, the present invention will be explained in more detail.

Preferred embodiments of the morphinan derivative represented by the aforementioned general formula (I) or a pharmacologically acceptable acid addition salt thereof include the followings.

(1) The morphinan derivative represented by the aforementioned general formula (I) or a pharmacologically acceptable acid addition salt thereof, wherein:

$R^1$ represents hydrogen, $C_{1-6}$ alkyl, $C_{6-10}$ aryl, $C_{2-6}$ alkenyl, cycloalkylalkyl (the cycloalkyl moiety has 3 to 6 carbon atoms, and the alkylene moiety has 1 to 5 carbon atoms), aralkyl (the aryl moiety has 6 to 10 carbon atoms, and the alkylene moiety has 1 to 5 carbon atoms), $C_{3-6}$ cycloalkyl, or heteroarylalkyl (the heteroaryl contains 1 to 4 heteroatoms selected from N, O and S as ring-constituting atoms, and the alkylene moiety has 1 to 5 carbon atoms), $R^2$ represents hydrogen, $C_{1-6}$ alkyl, $C_{3-6}$ cycloalkyl, $C_{6-10}$ aryl, heteroaryl (containing 1 to 4 heteroatoms selected from N, O and S as ring-constituting atoms), aralkyl (the aryl moiety has 6 to 10 carbon atoms, and the alkylene moiety has 1 to 5 carbon atoms), heteroarylalkyl (the heteroaryl contains 1 to 4 heteroatoms selected from N, O and S as ring-constituting atoms, and the alkylene moiety has 1 to 5 carbon atoms), cycloalkylalkyl (the cycloalkyl moiety has 3 to 6 carbon atoms, and the alkylene moiety has 1 to 5 carbon atoms), $C_{2-6}$ alkenyl, arylalkenyl (the aryl moiety has 6 to 10 carbon atoms, and the alkenyl moiety has 2 to 6 carbon atoms), heteroarylalkenyl (the heteroaryl contains 1 to 4 heteroatoms selected from N, O and S as ring-constituting atoms, and the alkenyl moiety has 2 to 6 carbon atoms), cycloalkylalkenyl (the cycloalkyl moiety has 3 to 6 carbon atoms, and the alkenyl moiety has 2 to 6 carbon atoms), $C_{4-6}$ cycloalkenyl, cycloalkenylalkyl (the cycloalkenyl moiety has 4 to 6 carbon atoms, and the alkylene moiety has 1 to 5 carbon atoms), or cycloalkenylalkyl (the cycloalkenyl moiety has 4 to 6 carbon atoms, and the alkenyl moiety has 2 to 6 carbon atoms), $R^3$, $R^4$ and $R^5$, which are the same or different, represent hydrogen, hydroxy, halogen, cyano, carbamoyl, $C_{1-6}$ alkoxy, $C_{6-10}$ aryloxy, $C_{1-6}$ alkanoyloxy, nitro, amino, $C_{1-8}$ alkylamino, aralkylamino (the aryl moiety has 6 to 10 carbon atoms, and the alkylene moiety has 1 to 5 carbon atoms), or acylamino (the acyl moiety has 2 to 6 carbon atoms), $R^{6a}$ and $R^{6b}$, which are the same or different, represent hydrogen, fluorine or hydroxy, or $R^{6a}$ and $R^{6b}$ combine together to represent =O, $R^7$ and $R^8$, which are the same or different, represent hydrogen, fluorine or hydroxy, $R^9$ and $R^{10}$, which are the same or different, represent hydrogen, $C_{1-6}$ alkyl, $C_{6-10}$ aryl, heteroaryl (containing 1 to 4 heteroatoms selected from N, O and S as ring-constituting atoms), aralkyl (the aryl moiety has 6 to 10 carbon atoms, and the alkylene moiety has 1 to 5 carbon atoms), heteroarylalkyl (the heteroaryl contains 1 to 4 heteroatoms selected from N, O and S as ring-constituting atoms, and the alkylene moiety has 1 to 5 carbon atoms), cycloalkylalkyl (the cycloalkyl moiety has 3 to 6 carbon atoms, and the alkylene moiety has 1 to 5 carbon atoms), or $C_{2-6}$ alkenyl, X represents O or $CH_2$, and Y represents C=O, C=S, $SO_2$, C(=O)O, C(=O)$NR^{11}$, C(=S)$NR^{11}$, or an atomic bond, where $R^{11}$ represents hydrogen, $C_{1-6}$ alkyl, aralkyl (the aryl moiety has 6 to 10 carbon atoms, and the alkylene moiety has 1 to 5 carbon atoms), heteroarylalkyl (the heteroaryl contains 1 to 4 heteroatoms selected from N, O and S as ring-constituting atoms, and the alkylene moiety has 1 to 5 carbon atoms), or cycloalkylalkyl (the cycloalkyl moiety has 3 to 6 carbon atoms, and the alkylene moiety has 1 to 5 carbon atoms), or may form a 4- to 7-membered ring together with the N atom to which $R^{11}$ bonds and $R^2$, where the 4- to 7-membered ring may contain heteroatom(s) selected from N, O, and S atoms as a ring-constituting atom other than the N atom to which $R^{11}$ bonds, and may have 1 to 3 substituents selected from halogen, hydroxy, $C_{1-6}$ alkyl, aralkyl (the aryl moiety has 6 to 10 carbon atoms, and the alkylene moiety has 1 to 5 carbon atoms), $O_{2-6}$ acyl, and oxo group, provided that the $C_{1-10}$ alkyl as $R^1$ or $R^2$, the alkylene moiety and the cycloalkyl moiety of the cycloalkylalkyl (the cycloalkyl moiety has 3 to 6 carbon atoms, and the alkylene moiety has 1 to 5 carbon atoms) as $R^1$ or $R^2$, as well as the alkylene moiety of the aralkyl (the aryl moiety has 6 to 10 carbon atoms, and the alkylene moiety has 1 to 5 carbon atoms) as $R^1$ or $R^2$ may be substituted with at least one substituent selected from 1 to 6 halogens, hydroxy, $C_{1-6}$ alkoxy, $C_{6-10}$ aryloxy, $C_{1-6}$ alkanoyl, $C_{1-6}$ alkanoyloxy, carboxyl, and alkoxycarbonyl (the alkoxy moiety has 1 to 6 carbon atoms), the aryl as $R^1$, aryl moiety of the aralkyl (the aryl moiety has 6 to 10 carbon atoms, and the alkylene moiety has 1 to 5 carbon atoms) as $R^1$, the aryl as $R^2$, the heteroaryl (containing 1 to 4 heteroatoms selected from N, O and S as ring-constituting atoms) as $R^2$, or the aryl moiety of the aralkyl (the aryl moiety has 6 to 10 carbon atoms, and the alkylene moiety has 1 to 5 carbon atoms) as $R^2$, the heteroaryl moiety of the heteroarylalkyl (the heteroaryl contains 1 to 4 heteroatoms selected from N, O and S as ring-constituting atoms, and the alkylene moiety has 1 to 5 carbon atoms) as $R^2$ the aryl moiety of the arylalkenyl (the aryl moiety has 6 to 10 carbon atoms, and the alkenyl moiety has 2 to 6 carbon atoms) as $R^2$, the heteroaryl moiety of the heteroarylalkenyl (the heteroaryl contains 1 to 4 heteroatoms selected from N, O and S as ring-constituting atoms, and the alkenyl moiety has 2 to 6 carbon atoms) as $R^2$ the aryl moiety of the $C_{6-10}$ aryloxy as $R^3$, $R^4$ or $R^5$, the aryl moiety of the aralkylamino as $R^3$, $R^4$ or $R^5$, the $C_{6-10}$ aryl as $R^9$ or $R^{10}$, the heteroaryl (containing 1 to 4 heteroatoms selected from N, O and S as ring-constituting atoms) as $R^9$ or $R^{10}$, or the aryl moiety of the aralkyl (the aryl moiety has 6 to 10 carbon atoms, and the alkylene moiety has 1 to 5 carbon atoms) as $R^9$ or $R^{10}$, and the heteroaryl moiety of the heteroarylalkyl (the heteroaryl contains 1 to 4 heteroatoms selected from N, O and S as ring-constituting atoms, and the alkylene moiety has 1 to 5 carbon atoms) as $R^9$ or $R^{10}$ may be substituted with at least one substituent selected from $C_{1-6}$ alkyl, $C_{1-6}$ alkoxy, $C_{1-6}$ alkanoyloxy, hydroxy, alkoxycarbonyl (the alkoxy moiety has 1 to 6 carbon atoms), carbamoyl, alkylcarbamoyl (the alkyl moiety has 1 to 6 carbon atoms), dialkylcarbamoyl (each alkyl moiety has 1 to 6 carbon atoms), halogen, nitro, cyano, $C_{1-6}$ alkyl substituted with 1 to 3 halogens, $C_{1-6}$ alkoxy substituted with 1 to 3 halogens, phenyl, heteroaryl (containing 1 to 4 heteroatoms selected from N, O and S as ring-constituting atoms), phenoxy, phenylalkyl (the alkyl has 1 to 3 carbon atoms), methylenedioxy, and $NR^{12}R^{13}$, where $R^{12}$ and $R^{13}$ independently represent hydrogen, $C_{1-6}$ alkyl, $C_{2-6}$ alkenyl, $C_{3-6}$ cycloalkyl, $C_{1-6}$ alkanoyl, or alkoxycarbonyl (the alkoxy moiety has 1 to 6 carbon atoms), or $R^{12}$ and $R^{13}$ may form a 4- to 7-membered ring together with the N atom to which they bond, where the 4- to 7-membered ring may further contain heteroatom(s) selected from N, O and S, and furthermore, the alkylene moiety of the aralkyl (the aryl moiety has 6 to 10 carbon atoms, and the alkylene moiety has 1 to 5 carbon atoms) as $R^1$ or $R^2$ may be substituted with at least one substituent selected from phenyl and $C_{1-6}$ alkyl substituted with 1 to 3 halogens.

(2) The morphinan derivative represented by the aforementioned general formula (I) or the morphinan derivative according to (1) mentioned above, or a pharmacologically acceptable acid addition salt thereof, wherein $R^1$ is $C_{1-6}$ alkyl, cycloalkylalkyl (the cycloalkyl moiety has 3 to 6 carbon atoms, and the alkylene moiety has 1 to 5 carbon atoms), or aralkyl (the aryl moiety has 6 to 10 carbon atoms, and the alkylene moiety has 1 to 5 carbon atoms).

(3) The morphinan derivative represented by the aforementioned general formula (I) or the morphinan derivative according to (1) mentioned above, or a pharmacologically acceptable acid addition salt thereof, wherein $R^{11}$ is $C_{2-6}$ alkyl substituted with hydroxy, $C_{1-6}$ alkyl substituted with 1 to 6 halogens, or $C_{2-6}$ alkyl substituted with $C_{1-6}$ alkoxy.

(4) The morphinan derivative represented by the aforementioned general formula (I) or the morphinan derivative according to any one of (1) to (3) mentioned above, or a pharmacologically acceptable acid addition salt thereof, wherein Y is C=O, C(=O)O, C(=O)$NR^{11}$, or an atomic bond.

(5) The morphinan derivative represented by the aforementioned general formula (I) or the morphinan derivative according to any one of (1) to (3) mentioned above, or a pharmacologically acceptable acid addition salt thereof, wherein Y is C(=O)O, or C(=O)$NR^{11}$ (6) The morphinan derivative represented by the aforementioned general formula (I) or the morphinan derivative according to any one of (1) to (3) mentioned above, or a pharmacologically acceptable acid addition salt thereof, wherein Y is an atomic bond, and $R^2$ is $C_{6-10}$ aryl or heteroaryl (containing 1 to 4 heteroatoms selected from N, O and S as ring-constituting atoms).

(7) The morphinan derivative represented by the aforementioned general formula (I) or the morphinan derivative according to any one of (1) to (3) mentioned above, or a pharmacologically acceptable acid addition salt thereof, wherein Y is an atomic bond, and $R^2$ is heteroaryl (it contains at least one N atom as a ring-constituting atom, and may further contain 1 to 3 heteroatoms selected from N, O and S).

(8) The morphinan derivative represented by the aforementioned general formula (I) or the morphinan derivative according to any one of (1) to (3) mentioned above, or a pharmacologically acceptable acid addition salt thereof, wherein Y is C(=O), $R^2$ is $C_{1-6}$ alkyl, $C_{6-10}$ aryl, heteroaryl (containing 1 to 4 heteroatoms selected from N, O and S as ring-constituting atoms), aralkyl (the aryl moiety has 6 to 10 carbon atoms, and the alkylene moiety has 1 to 5 carbon atoms), or heteroarylalkyl (the heteroaryl contains 1 to 4 heteroatoms selected from N, O and S as ring-constituting atoms, and the alkylene moiety has 1 to 5 carbon atoms).

(9) The morphinan derivative represented by the aforementioned general formula (I) or the morphinan derivative according to any one of (1) to (3) mentioned above, or a pharmacologically acceptable acid addition salt thereof, wherein Y is C(=O), and $R^2$ is $C_{6-10}$ aryl or heteroaryl (containing 1 to 4 heteroatoms selected from N, O and S as ring-constituting atoms).

(10) The morphinan derivative represented by the aforementioned general formula (I) or the morphinan derivative according to any one of (1) to (9) mentioned above, or a pharmacologically acceptable acid addition salt thereof, wherein X is $CH_2$.

(11) The morphinan derivative represented by the aforementioned general formula (I) or the morphinan derivative according to any one of (1) to (10) mentioned above, or a pharmacologically acceptable acid addition salt thereof, wherein one of $R^3$ and $R^4$ is hydroxy, and the other is hydrogen.

(12) The morphinan derivative represented by the aforementioned general formula (I) or the morphinan derivative according to any one of (1) to (10) mentioned above, or a pharmacologically acceptable acid addition salt thereof, wherein $R^3$ is halogen, cyano, carbamoyl, $C_{1-6}$ alkoxy, $C_{1-6}$ alkanoyloxy, amino, or acylamino (the acyl moiety has 2 to 6 carbon atoms), $R^4$ is hydrogen or hydroxy, and $R^5$ is hydrogen.

(13) The morphinan derivative represented by the aforementioned general formula (I) or the morphinan derivative according to any one of (1) to (10) mentioned above, or a pharmacologically acceptable acid addition salt thereof, wherein $R^3$ is hydroxy or carbamoyl, $R^4$ is hydrogen, and $R^5$ is hydrogen.

(14) The morphinan derivative represented by the aforementioned general formula (I) or the morphinan derivative according to any one of (1) to (10) mentioned above, or a pharmacologically acceptable acid addition salt thereof, wherein all of $R^3$, $R^4$ and $R^5$ are hydrogens.

(15) The morphinan derivative represented by the aforementioned general formula (I) or the morphinan derivative according to any one of (1) to (14) mentioned above, or a pharmacologically acceptable acid addition salt thereof, wherein all of $R^{6a}$, $R^{6b}$, $R^7$, $R^8$, $R^9$ and $R^{10}$ are hydrogens.

(16) The morphinan derivative represented by the aforementioned general formula (I) or a pharmacologically acceptable acid addition salt thereof, wherein:

$R^5$, $R^{6a}$, $R^{6b}$, $R^7$, $R^8$, $R^9$ and $R^{10}$ are hydrogens, $R^1$ is hydrogen, $C_{1-6}$ alkyl, $C_{2-6}$ alkenyl, cycloalkylalkyl (the cycloalkyl moiety has 3 to 6 carbon atoms, and the alkylene moiety has 1 to 5 carbon atoms), or aralkyl (the aryl moiety has 6 to 10 carbon atoms, and the alkylene moiety has 1 to 5 carbon atoms), $R^2$ is hydrogen, $C_{1-6}$ alkyl, $C_{3-6}$ cycloalkyl, $C_{6-10}$ aryl, heteroaryl (containing 1 to 4 heteroatoms selected from N, O and S as ring-constituting atoms), aralkyl (the aryl moiety has 6 to 10 carbon atoms, and the alkylene moiety has 1 to 5 carbon atoms), heteroarylalkyl (the heteroaryl contains 1 to 4 heteroatoms selected from N, O and S as ring-constituting atoms, and the alkylene moiety has 1 to 5 carbon atoms), cycloalkylalkyl (the cycloalkyl moiety has 3 to 6 carbon atoms, and the alkylene moiety has 1 to 5 carbon atoms), $C_{2-6}$ alkenyl, arylalkenyl (the aryl moiety has 6 to 10 carbon atoms, and the alkenyl moiety has 2 to 6 carbon atoms), heteroarylalkenyl (the heteroaryl contains 1 to 4 heteroatoms selected from N, O and S as ring-constituting atoms, and the alkenyl moiety has 2 to 6 carbon atoms), cycloalkylalkenyl (the cycloalkyl moiety has 3 to 6 carbon atoms, and the alkenyl moiety has 2 to 6 carbon atoms), $C_{4-6}$ cycloalkenyl, cycloalkenylalkyl (the cycloalkenyl moiety has 4 to 6 carbon atoms, and the alkylene moiety has 1 to 5 carbon atoms), or cycloalkenylalkyl (the cycloalkenyl moiety has 4 to 6 carbon atoms, and the alkenyl moiety has 2 to 6 carbon atoms), $R^3$ and $R^4$, which are the same or different, are each hydrogen, hydroxy, halogen, cyano, carbamoyl, $C_{1-6}$ alkoxy, $C_{6-10}$ aryloxy, $C_{1-6}$ alkanoyloxy, amino, or acylamino (the acyl moiety has 2 to 6 carbon atoms), X is O or $CH_2$, and Y is C=O, $SO_2$, or an atomic bond, provided that the $C_{1-6}$ alkyl as $R^1$ or $R^2$, the alkylene moiety and the cycloalkyl moiety of the cycloalkylalkyl (the cycloalkyl moiety has 3 to 6 carbon atoms, and the alkylene moiety has 1 to 5 carbon atoms) as $R^1$ or $R^2$, as well as the alkylene moiety of the aralkyl (the aryl moiety has 6 to 10 carbon atoms, and the alkylene moiety has 1 to 5 carbon atoms) as $R^1$ or $R^2$ may be substituted with at least one substituent selected from 1 to 3 halogens, hydroxy, $C_{1-6}$ alkoxy, $C_{6-10}$ aryloxy, $C_{1-6}$ alkanoyl, $C_{1-6}$ alkanoyloxy, and alkoxycarbonyl (the alkoxy moiety has 1 to 6 carbon atoms), the aryl moiety of the aralkyl as $R^1$, the aryl as $R^2$, the heteroaryl as $R^2$ or the aryl moiety of the aralkyl as $R^2$ the heteroaryl moiety of the heteroarylalkyl as $R^2$ the aryl moiety of the arylalkenyl as $R^2$, the heteroaryl moiety of the heteroarylalkenyl as $R^2$ and the aryl moiety of the $C_{6-10}$ aryloxy as $R^3$ or $R^4$ may be substituted with at least one substituent selected from $C_{1-6}$ alkyl, $C_{1-6}$ alkoxy, $C_{1-6}$ alkanoyloxy, hydroxy, alkoxycarbonyl (the alkoxy moiety has 1 to 6 carbon atoms), carbamoyl, alkylcarbamoyl (the alkyl moiety has 1 to 6 carbon atoms), dialkylcarbamoyl (each alkyl moiety has 1 to 6 carbon atoms), halogen, nitro, cyano, $C_{1-6}$ alkyl substituted with 1 to 3 halogens, $C_{1-6}$ alkoxy substituted with 1 to 3 halogens, phenyl, heteroaryl (containing 1 to 4 heteroatoms selected from N, O and S as ring-constituting atoms), phenoxy, phenylalkyl (the alkyl has 1 to 3 carbon atoms), methylenedioxy, and $NR^{12}R^{13}$, where $R^{12}$ and $R^{13}$ independently represent hydrogen, $C_{1-6}$ alkyl, $C_{2-6}$ alkenyl, $C_{3-6}$ cycloalkyl, $C_{1-6}$ alkanoyl, or alkoxycarbonyl (the alkoxy moiety has 1 to 6 carbon atoms), or $R^{12}$ and $R^{13}$ may form a 4- to 7-membered ring together with the N atom to which they bond, which 4- to 7-membered ring may further contain heteroatom(s) selected from N, O and S, and furthermore, the alkylene moiety of the aralkyl (the aryl moiety has 6 to 10 carbon atoms, and the alkylene moiety has 1 to 5 carbon atoms) as $R^1$ or $R^2$ may be substituted with at least one substituent selected from phenyl and $C_{1-6}$ alkyl substituted with 1 to 3 halogens.

(17) The morphinan derivative or a pharmacologically acceptable acid addition salt thereof according to (16) mentioned above, wherein $R^1$ is $C_{1-6}$ alkyl, cycloalkylalkyl (the cycloalkyl moiety has 3 to 6 carbon atoms, and the alkylene moiety has 1 to 5 carbon atoms), or aralkyl (the aryl moiety has 6 to 10 carbon atoms, and the alkylene moiety has 1 to 5 carbon atoms).

(18) The morphinan derivative or a pharmacologically acceptable acid addition salt thereof according to (16) mentioned above, wherein $R^1$ is $C_{2-6}$ alkyl substituted with hydroxy, $C_{1-6}$ alkyl substituted with 1 to 3 halogens, or $C_{2-6}$ alkyl substituted with $C_{1-6}$ alkoxy.

(19) The morphinan derivative or a pharmacologically acceptable acid addition salt thereof according to any one of (16) to (18) mentioned above, wherein $R^2$ is $C_{6-10}$ aryl.

(20) The morphinan derivative or a pharmacologically acceptable acid addition salt thereof according to any one of (16) to (19) mentioned above, wherein X is O.

(21) The morphinan derivative or a pharmacologically acceptable acid addition salt thereof according to any one of (16) to (19) mentioned above, wherein X is $CH_2$.

(22) The morphinan derivative or a pharmacologically acceptable acid addition salt thereof according to any one of (16) to (21) mentioned above, wherein Y is C=O or an atomic bond.

(23) The morphinan derivative or a pharmacologically acceptable acid addition salt thereof according to any one of (16) to (21) mentioned above, wherein Y is C=O.

(24) The morphinan derivative or a pharmacologically acceptable acid addition salt thereof according to any one of (16) to (23) mentioned above, wherein one of $R^3$ and $R^4$ is hydroxy, and the other is hydrogen.

(25) The morphinan derivative or a pharmacologically acceptable acid addition salt thereof according to any one of (16) to (23) mentioned above, wherein $R^3$ is carbamoyl, halogen, $C_{1-6}$ alkoxy, $C_{1-6}$ alkanoyloxy, cyano, amino, or acylamino (the acyl moiety has 2 to 6 carbon atoms), and $R^4$ is hydrogen or hydroxy.

(26) The morphinan derivative or a pharmacologically acceptable acid addition salt thereof according to any one of (16) to (23) mentioned above, wherein $R^3$ is hydroxy or carbamoyl, and $R^4$ is hydrogen.

(27) The morphinan derivative or a pharmacologically acceptable acid addition salt thereof according to any one of (16) to (23) mentioned above, wherein $R^3$ is carbamoyl, and $R^4$ is hydroxy.

In the present invention:

Examples of the $C_{1-10}$ alkyl include methyl, ethyl, propyl, i-propyl, butyl, t-butyl, pentyl, neopentyl, hexyl, heptyl, octyl, and the like.

Examples of the $C_{1-6}$ alkyl include methyl, ethyl, propyl, i-propyl, butyl, t-butyl, pentyl, neopentyl, hexyl, and the like.

Examples of the $C_{1-6}$ alkyl substituted with 1 to 3 halogens include 2-chloroethyl, 2-fluoroethyl, 3-fluoropropyl, 2,2-difluoroethyl, trifluoromethyl, 3,3,3-trifluoropropyl, and the like.

Examples of the $C_{2-6}$ alkenyl include 2-propenyl, 3-methyl-2-butenyl, and the like.

Examples of the cycloalkylalkyl (the cycloalkyl moiety has 3 to 6 carbon atoms, and the alkylene moiety has 1 to 5 carbon atoms) include methyl, ethyl, and the like substituted with $C_{3-6}$ cycloalkyl such as cyclopropyl, cyclobutyl, cyclopentyl, and cyclohexyl.

Examples of the aralkyl (the aryl moiety has 6 to 10 carbon atoms, and the alkylene moiety has 1 to 5 carbon atoms) include benzyl group, and phenethyl group.

Examples of the $C_{3-6}$ cycloalkyl include cyclopropyl, cyclobutyl, cyclopentyl, cyclohexyl, and the like.

Examples of the $C_{6-10}$ aryl include phenyl, naphthyl, and the like.

Examples of the heteroaryl (containing 1 to 4 heteroatoms selected from N, O and S as ring-constituting atoms) include pyridyl, furyl, imidazolyl, pyrimidinyl, pyrazinyl, thiazolyl, and the like.

Examples of the heteroarylalkyl (the heteroaryl contains 1 to 4 heteroatoms selected from N, O and S as ring-constituting atoms, and the alkylene moiety has 1 to 5 carbon atoms) include (pyridin-2-yl)methyl, (pyridin-3-yl)methyl, (pyridin-4-yl)methyl, (furan-2-yl)methyl, (furan-3-yl)methyl, (imidazol-2-yl)methyl, (imidazol-4-yl-methyl, (imidazol-5-yl)methyl, (thiazol-2-yl)methyl, (thiazol-4-yl)methyl, (thiazol-5-yl)methyl, and the like.

Examples of the arylalkenyl (the aryl moiety has 6 to 10 carbon atoms, and the alkenyl moiety has 2 to 6 carbon atoms) include 2-propenyl, 3-methyl-2-butenyl, and the like substituted with phenyl, naphthyl, or the like.

Examples of the heteroarylalkenyl (the heteroaryl contains 1 to 4 heteroatoms selected from N, O and S as ring-constituting atoms, and the alkenyl moiety has 2 to 6 carbon atoms) include 2-propenyl, 3-methyl-2-butenyl, and the like substituted with pyridyl, furyl, imidazolyl, thiazolyl, or the like.

Examples of the cycloalkylalkenyl (the cycloalkyl moiety has 3 to 6 carbon atoms, and the alkenyl moiety has 2 to 6 carbon atoms) include 2-propenyl, 3-methyl-2-butenyl, and the like substituted with $C_{3-6}$ cycloalkyl such as cyclopropyl, cyclobutyl, cyclopentyl, and cyclohexyl.

Examples of the $C_{4-6}$ cycloalkenyl include cyclobutenyl, cyclopentenyl, and the like.

Examples of the cycloalkenylalkyl (the cycloalkenyl moiety has 4 to 6 carbon atoms, and the alkylene moiety has 1 to 5 carbon atoms) include methyl, ethyl, and the like substituted with cyclobutenyl, cyclopentenyl, or the like.

Examples of the cycloalkenylalkenyl (the cycloalkenyl moiety has 4 to 6 carbon atoms, and the alkenyl moiety has 2 to 6 carbon atoms) include 2-propenyl, 3-methyl-2-butenyl substituted with cyclobutenyl, cyclopentenyl, or the like.

Examples of the $C_{1-3}$ alkyl include methyl, ethyl, and the like.

Examples of the $C_{2-6}$ alkyl substituted with hydroxy include 2-hydroxyethyl, 2-hydroxy-2-methylpropyl, and the like.

Examples of the $C_{2-6}$ alkyl substituted with $C_{1-6}$ alkoxy include 2-methoxyethyl, and the like.

Examples of the $C_{1-6}$ alkanoyl include acetyl, propionyl, and the like.

Examples of the $C_{1-6}$ alkoxy include methoxy, ethoxy, propoxy, and the like.

Examples of the $C_{1-6}$ alkanoyloxy include acetoxy, and the like.

Examples of the alkoxycarbonyl (the alkoxy moiety has 1 to 6 carbon atoms) include methoxycarbonyl, ethoxycarbonyl, and the like.

Examples of the halogen include fluorine, chlorine, bromine, and the like.

Examples of the $C_{1-6}$ alkoxy substituted with 1 to 3 halogens include fluoromethoxy, trifluoromethoxy, and the like.

Examples of the phenylalkyl (the alkyl has 1 to 3 carbon atoms) include benzyl, and the like.

Examples of the $C_{6-10}$ aryloxy include phenoxy, and the like.

Examples of the $C_{6-10}$ arylamino include phenylamino, and the like.

Examples of the $C_{1-8}$ alkylamino include methylamino, ethylamino, and the like.

Examples of the aralkylamino (the aryl moiety has 6 to 10 carbon atoms, and the alkylene moiety has 1 to 5 carbon atoms) include benzylamino, and the like.

Examples of the acylamino (the acyl moiety has 2 to 6 carbon atoms) include acetylamino, and the like.

Examples of the alkylcarbamoyl (the alkyl moiety has 1 to 6 carbon atoms) include ethylcarbamoyl, and the like.

Examples of the dialkylcarbamoyl (the alkyl moiety has 1 to 6 carbon atoms) include diethylcarbamoyl, and the like.

Examples of the alkylsulfonyl (the alkyl moiety has 1 to 6 carbon atoms) include methylsulfonyl, and the like.

Examples of the arylcarbonyl include benzoyl, and the like.

Examples of the 4- to 7-membered ring formed by $R^2$ and $R^{11}$ bound together with the N atom, or $R^{12}$ and $R^{13}$ bound together with the N atom, which may further contain heteroatom(s) selected from N, O and S, include piperidine ring, piperazine ring, and morpholine ring.

Examples of the pharmacologically acceptable acid addition salt of the morphinan derivative represented by the aforementioned general formula (I) include a salt with an organic acid or inorganic acid such as hydrochloride, sulfate, fumarate, oxalate, methanesulfonate, and camphorsulfonate.

The morphinan derivative represented by the aforementioned general formula (I) and a pharmacologically acceptable acid addition salt thereof include cis- and trans-isomers, racemates, optical isomers thereof, and the like.

The morphinan derivative represented by the aforementioned general formula (I) and a pharmacologically acceptable acid addition salt thereof include hydrates and solvates thereof.

Hereafter, methods for preparing the morphinan derivative represented by the aforementioned general formula (I) or a pharmacologically acceptable acid addition salt thereof will be explained.

(I) Morphinan derivatives represented by the aforementioned general formula (I) wherein $R^1$=CPM, $R^4$=hydroxy, $R^5$, $R^{6a}$, $R^{6b}$, $R^7$, $R^8$, $R^9$ and $R^{10}$=hydrogen, Y=atomic bond, and $R^3$=hydrogen or $C_{1-6}$ alkoxy (CPM means cyclopropylmethyl):

[Formula 4]

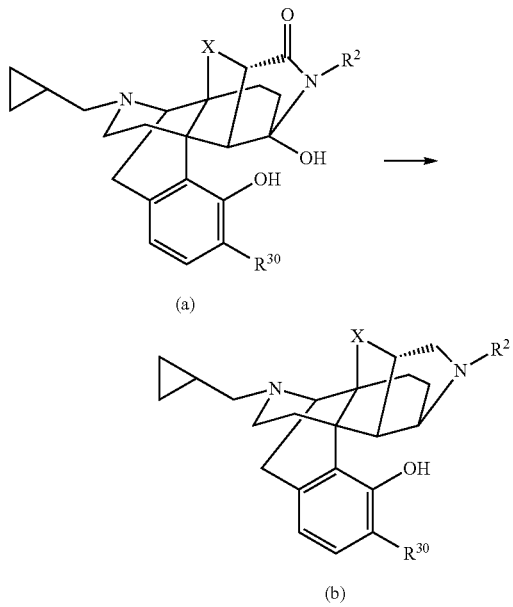

(In the formulas, $R^{30}$ represents hydrogen or $C_{1-6}$ alkoxy, and X and $R^2$ have the same meanings as those defined above.)

The compound (b) of the present invention can be synthesized by reducing the compound (a) with a borane-tetrahydrofuran (THF) complex or the like in a solvent such as THF. The compound (a) as the starting material is prepared by any of the following methods A, B and methods similar to those methods.

(Method A) Method for preparing compound (a) wherein X is O atom

[Formula 5]

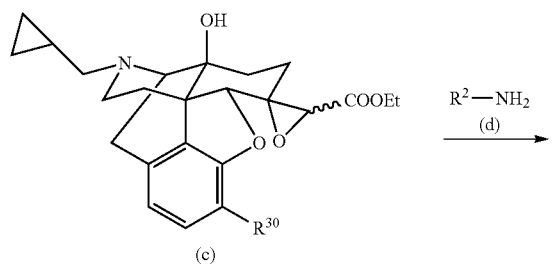

(c)

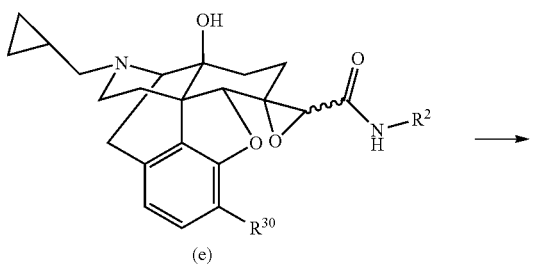

(e)

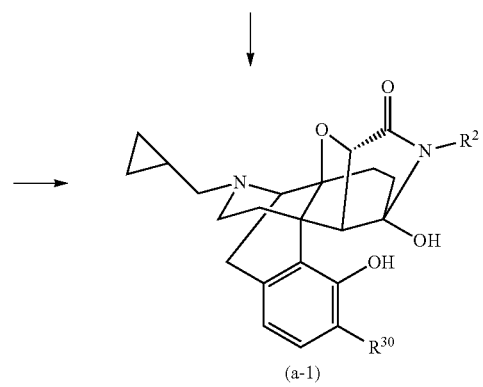

(f) → (a-1)

(In the formulas, $R^{30}$ represents hydrogen or $C_{1-6}$ alkoxy, and $R^2$ has the same meaning as that defined above.)

(1) Synthesis of Compound (e)

The compound (e) can be obtained by reacting the compound (c) with an amine referred to as compound (d) in a solvent such as THF and N,N-dimethylformamide (DMF) in the presence or absence of a base such as n-butyllithium and sodium hydride. The amine (d) can be used as both reagent and solvent. The compound (c) can be synthesized by any of known methods (Bioorg. Med. Chem. Lett., 2010, 20, 121 and the like) and methods similar thereto.

(2) Synthesis of Compound (a-1)

The compound (a-1), which corresponds to the compound (a) wherein X is O atom, can be synthesized from the compound (e) by either of the following two kinds of methods.

Method A-1:

The compound (a-1) can be obtained by treating the compound (e) with a base such as potassium t-butoxide or sodium hydride in a solvent such as t-butanol, cyclopentyl methyl ether, DMF, or dimethyl sulfoxide. The reaction is performed at the temperature ranging from room temperature to the reflux temperature of the solvent used, preferably at 80° C. or higher. As the solvent, cyclopentyl methyl ether and t-butanol are preferred.

Method A-2:

The compound (a-1) can be obtained by treating the compound (e) with a base such as sodium hydride in THF at the reflux temperature to make the compound (f), and then by treating the resulting compound (f) with a base such as potassium t-butoxide or sodium hydride at a temperature of 80° C. or higher in a solvent such as t-butanol or cyclopentyl methyl ether.

(Method B) Method for preparing compound (a) wherein X is $CH_2$

[Formula 6]

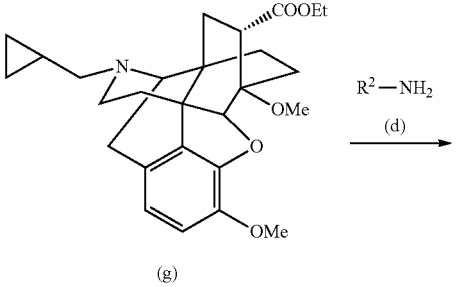

(g)

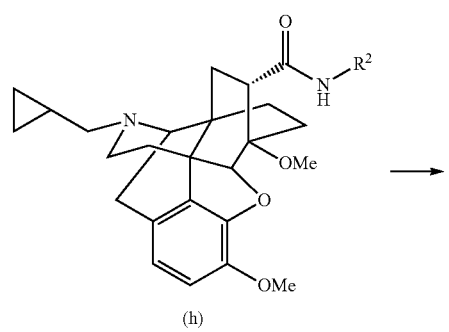

(h)

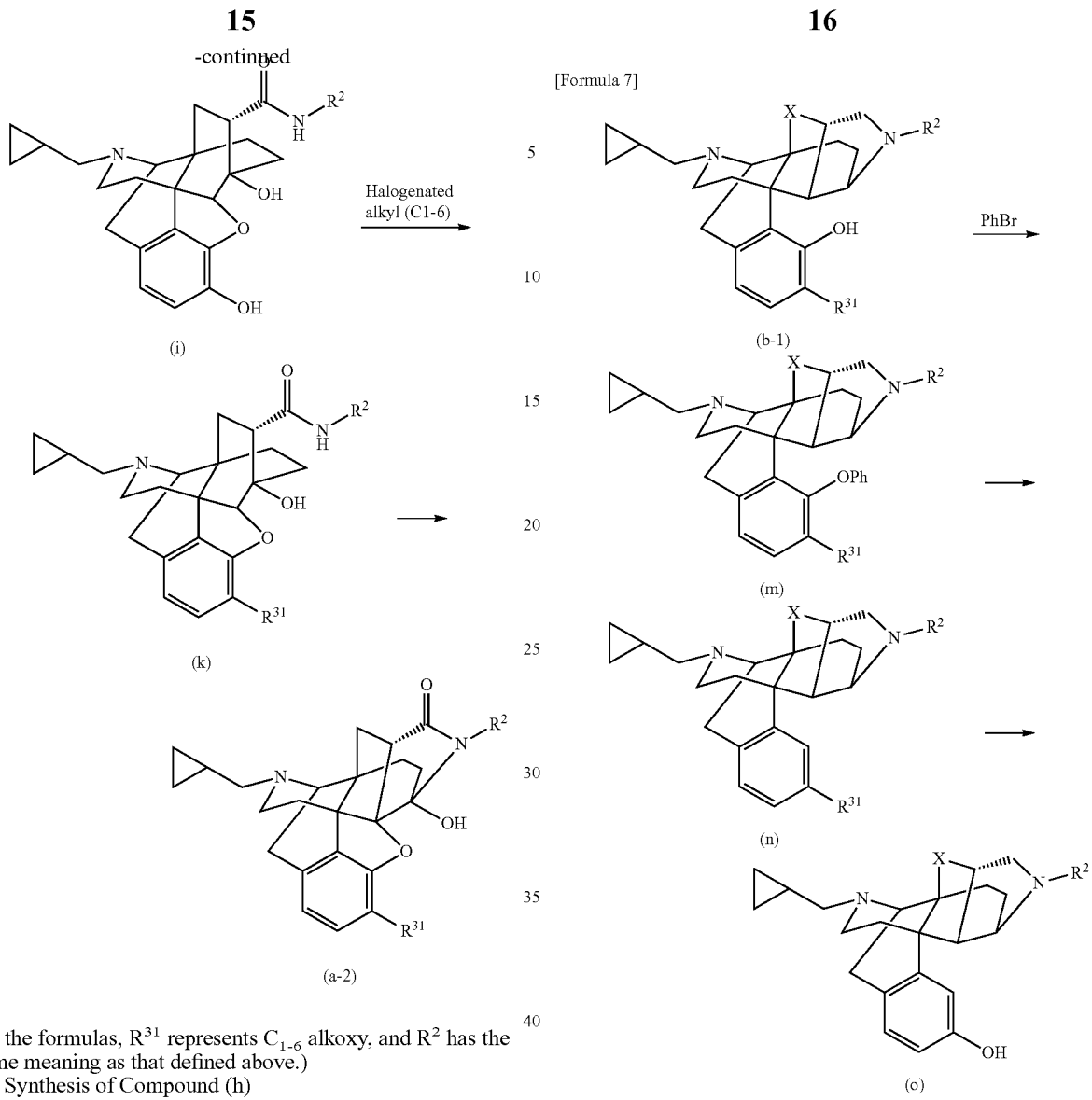

(In the formulas, $R^{31}$ represents $C_{1-6}$ alkoxy, and $R^2$ has the same meaning as that defined above.)

(1) Synthesis of Compound (h)

The compound (h) can be obtained by reacting the compound (g) with an amine referred to as compound (d) in a solvent such as THF in the presence of a base such as n-butyllithium. The compound (g) as the starting material is synthesized by any of known methods (Tetrahedron, 2009, 65, 4808 and the like) and methods similar thereto.

(2) Synthesis of Compound (i)

The compound (i) can be synthesized by treating the compound (h) with boron tribromide or the like in a solvent such as dichloromethane. The compound (i) can also be synthesized by a known method using 17-(cyclopropylmethyl)northebaine as a starting material (Bioorg. Med. Chem., 2004, 12, 4133).

(3) Synthesis of Compound (k)

The compound (k) can be synthesized by treating the compound (i) with an alkyl halide in a solvent such as DMF in the presence of a base such as potassium carbonate.

(4) Synthesis of Compound (a-2)

The compound (k) is converted into the compound (a-2), which is the compound (a) wherein X is $CH_2$, by using the reaction described in the method A-1. (II) Morphinan derivatives represented by the aforementioned general formula (I) wherein $R^1$=CPM, $R^4$, $R^5$, $R^{6a}$, $R^{6b}$, $R^7$, $R^8$, $R^9$ and $R^{10}$=hydrogen, Y=atomic bond, and $R^3$=hydroxy or $C_{1-6}$ alkoxy:

(In the formulas, $R^{31}$ represents $C_{1-6}$ alkoxy, and X and $R^2$ have the same meanings as those defined above.)

First Step

The compound (m) is synthesized by reacting the compound (b-1) with bromobenzene in a solvent such as pyridine in the presence of a catalyst such as copper powder and a base such as potassium carbonate.

Second Step

The compound (n), which is the compound of the present invention, is synthesized by the Birch reduction of the compound (m). This reaction is performed by, for example, using Sodium silica gel Stage I and ethylenediamine as reagents in a solvent such as THF.

Third Step

The compound (o) of the present invention, where the compound of the general formula (I) wherein $R^3$ is hydroxy group, is synthesized by a method of treating the compound (n) with boron tribromide or the like in dichloromethane, or a method of treating the compound (n) with an alkanethiol such as 1-dodecanethiol in DMF in the presence of a base such as potassium t-butoxide.

(III) Morphinan derivatives represented by the aforementioned general formula (I) wherein $R^1$ is not CPM:

These compounds can be synthesized by either of the following methods C and D.

(Method C) Method for preparing the compounds wherein X=O, $R^4$=hydroxy, $R^5$, $R^{6a}$, $R^{6b}$, $R^7$, $R^8$, $R^9$, and $R^{10}$=hydrogen, Y=atomic bond, and $R^3$=hydrogen or $C_{1-6}$ alkoxy

[Formula 8]

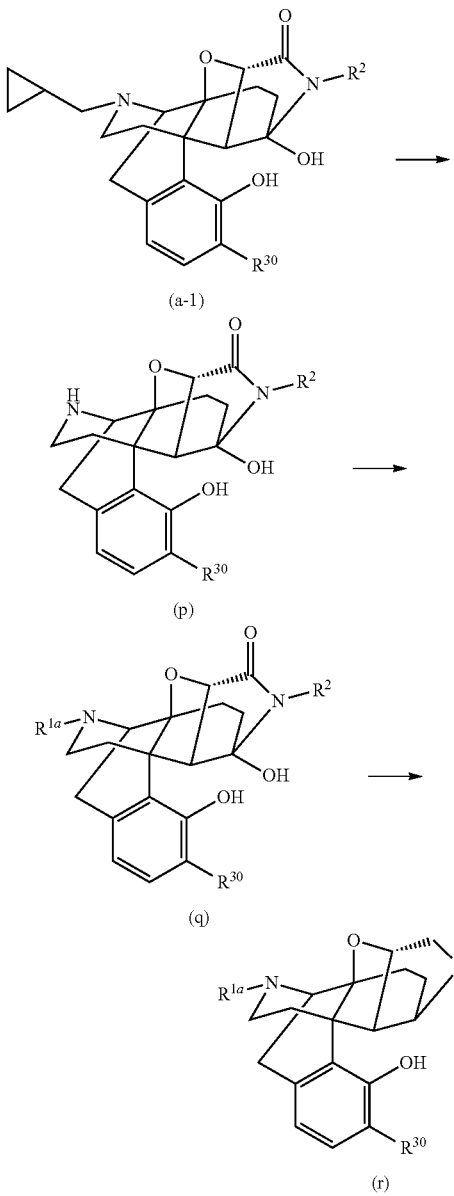

(In the formulas, $R^{1a}$ represents a group defined as $R^1$ other than CPM, $R^{30}$ represents hydrogen or $C_{1-6}$ alkoxy, and $R^2$ has the same meaning as that defined above.)

First Step

The compound (a-1) can be converted into the compound (p) by using a known de-N-alkylation method comprising a reaction with a chloroformic acid ester and subsequent decarbamation reaction (Bioorg. Med. Chem. Lett., 2010, 20, 6302 and the like).

Second Step

The compound (p) can be converted into the compound (q) by a usual N-alkylation reaction or reductive amination reaction.

Third Step

The compound (r) of the present invention is synthesized from the compound (q) by the converting method described in the above-mentioned method (I), wherein the compound (a) is converted into the compound (b).

(Method D) Method for preparing the compounds wherein $R^5$, $R^{6a}$, $R^{6b}$, $R^7$, $R^8$, $R^9$, and $R^{10}$=hydrogen, and $R^3$ and $R^4$=hydrogen or $C_{1-6}$ alkoxy

[Formula 9]

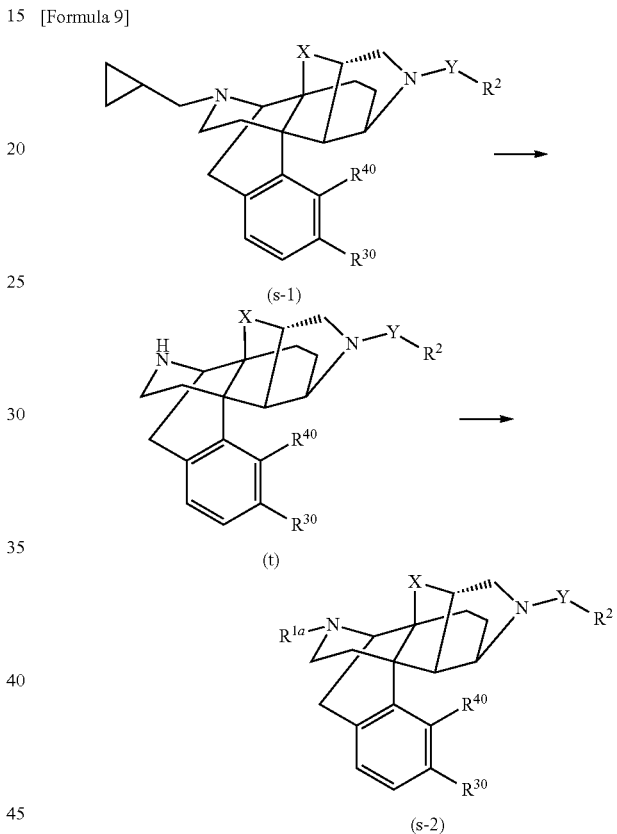

(In the formulas, $R^{30}$ and $R^{40}$, which are different from each other, represent hydrogen or $C_{1-6}$ alkoxy, $R^{1a}$ represents a group defined as $R^1$ other than CPM, and X, Y and $R^2$ have the same meanings as those defined above.)

First Step

Dealkylation of the compound (s-1) is performed by the method described in the first step of the above-mentioned synthesis method (III) C (the reaction with a chloroformic acid ester and the subsequent decarbamation), or a method of using diethyl azodicarboxylate (Synthetic Communications, 1995, 25, 829 and the like). The compound (s-1) as the starting material is prepared by any of the methods E to I described later and methods similar thereto.

Second Step

The compound (t) can be converted into the compound (s-2) by a usual N-alkylation reaction, a reductive amination reaction, the Michel reaction with an α,β-unsaturated carbonyl compound or the like, or a two-step method (amidation based on condensation with a carboxylic acid(s) and subsequent reduction of the amide).

(IV) Morphinan derivatives represented by the aforementioned general formula (I) wherein $R^5$, $R^{6a}$, $R^{6b}$, $R^7$, $R^8$, $R^9$ and $R^{10}$=hydrogen, and Y=atomic bond:

These compounds can be synthesized by either of the following methods E or F.
(Method E)

[Formula 10]

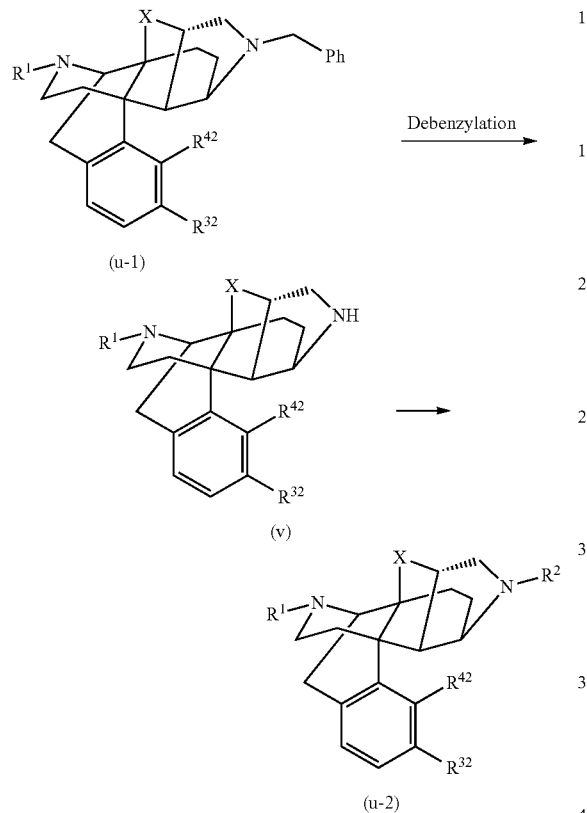

(In the formulas, $R^{32}$ and $R^{42}$, which are different from each other, represent hydrogen, hydroxy, or $C_{1-6}$ alkoxy, and X, $R^1$ and $R^2$ have the same meanings as those defined above.)

First Step

The compound (v) can be obtained by catalytic reduction of the compound (u-1) using palladium-carbon as a catalyst, or the like. The compound (u-1) as the starting material is synthesized by any of the above-mentioned preparation method I, II and III (method C) or methods similar thereto.

Second Step

The compound (u-2) of the present invention is obtained by an N-alkylation, N-arylation or N-heteroarylation reaction of the compound (v). When $R^2$ is aryl or heteroaryl, a cross-coupling reaction with a corresponding halogenated compound in the presence of a palladium catalyst, or the like, or an addition-elimination reaction with a corresponding heteroaryl halide in the presence of a base such as potassium carbonate, or the like is used. When $R^2$ is alkyl, alkenyl or aralkyl, any of the reactions of the following three kinds of methods is used.

Alkylation reaction of the compound (v) with alkyl halide in the presence of a base Reductive amination reaction of the compound (v) with an aldehyde or ketone Amidation of the compound (v) through a reaction with a carboxylic acid or carboxylic acid chloride and subsequent reduction of amide (V) Morphinan derivatives represented by the aforementioned general formula (I) wherein $R^5$, $R^{6a}$, $R^{6b}$, $R^7$, $R^8$, $R^9$, and $R^{10}$=hydrogen, and Y=CO or $SO_2$:

These compounds can be synthesized by the following method F.
(Method F)

Formula 11

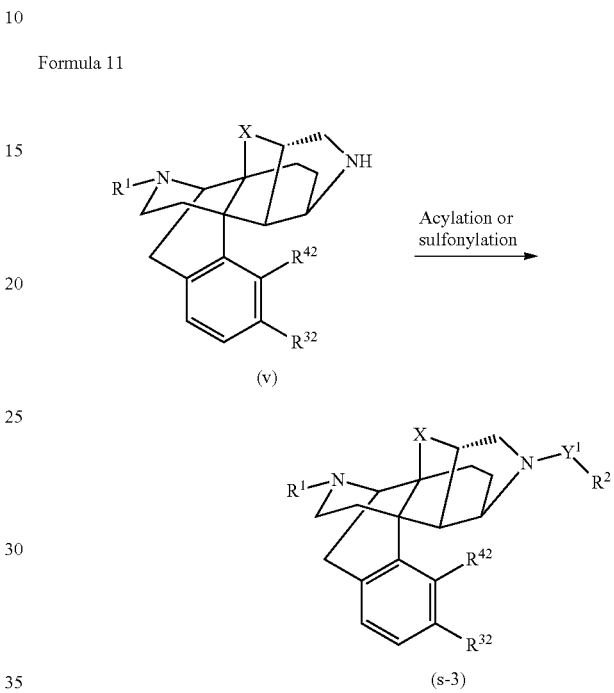

(In the formula, $R^{32}$ and $R^{42}$, which are different from each other, represent hydrogen, hydroxy, or $C_{1-6}$ alkoxy, $Y^1$ represents CO or $SO_2$, and X, $R^1$ and $R^2$ have the same meanings as those defined above.)

The compound (s-3) of the present invention is synthesized by an acylation reaction or sulfonylation reaction of the compound (v). As the acylating agent, a carboxylic acid chloride, acid anhydride, or the like is used. A method of reacting a carboxylic acid in the presence of a condensing agent may be employed as one type of the acylation reaction.

When $R^{32}$ or $R^{42}$ is hydroxy group, the acylation of the hydroxy group may simultaneously proceed in the above acylation reaction. In many cases, the resulting reaction product can be converted into the compound where $R^{32}$ or $R^{42}$ is hydroxy group by a treatment with aqueous sodium hydroxide, or the like.

As the sulfonylating agent, an alkylsulfonyl chloride, an arylsulfonyl chloride, or the like is used.

(VI) Morphinan derivatives represented by the aforementioned general formula (I) wherein $R^5$, $R^{6a}$, $R^{6b}$, $R^7$, $R^8$, $R^9$, and $R^{10}$=hydrogen, and Y=C(=O)O or C(=O)$NR^{11}$:

These compounds can be synthesized by any one of the following methods G to J.

(Method G)

[Formula 12]

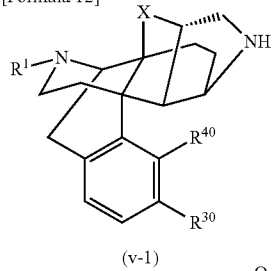

(v-1)

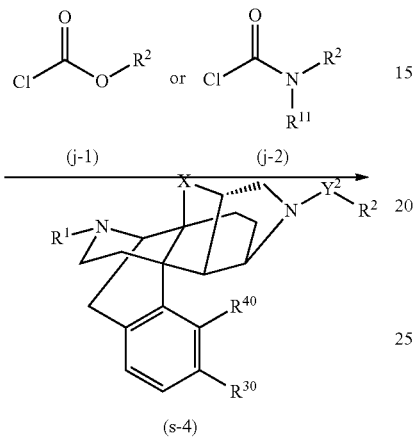

(s-4)

(In the formulas, $R^{30}$ and $R^{40}$, which are different from each other, represent hydrogen or $C_{1-6}$ alkoxy, $Y^2$ represents $C(=O)O$ or $C(=O)NR^{11}$, and $R^1$, $R^2$, $R^{11}$ and X have the same meanings as those defined above.)

According to the aforementioned method G, the compound (s-4) of the present invention wherein $Y^2$ is $C(=O)O$ or $Y^2$ is $C(=O)NR^{11}$ can be synthesized by reacting the compound (v-1) with the compound (j-1) or the compound (j-2), respectively, in the presence of a base such as triethylamine.

(Method H) (Method for preparing the compounds where Y is $C(=O)NR^{11}$)

[Formula 13]

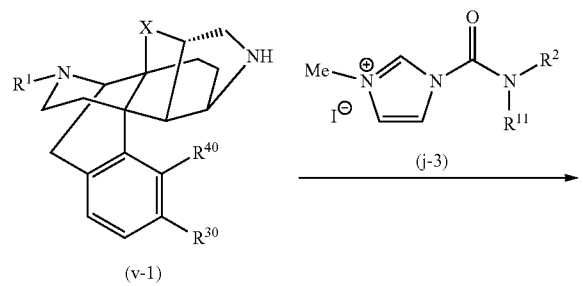

(In the formulas, $R^{30}$ and $R^{40}$, which are different from each other, represent hydrogen or $C_{1-6}$ alkoxy, and $R^1$, $R^2$, $R^{11}$ and X have the same meanings as those defined above.)

According to the aforementioned method H, the urea compound (s-5) of the present invention can be synthesized by reacting the compound (v-1) with the compound (j-3) in the presence of a base such as triethylamine. The compound (j-3) as a reaction reagent can be synthesized by a method described in the literature (Tetrahedron, 2005, 61, 7153), or the like.

(Method I) (Method for preparing the compounds where Y is $C(=O)NH$)

[Formula 14]

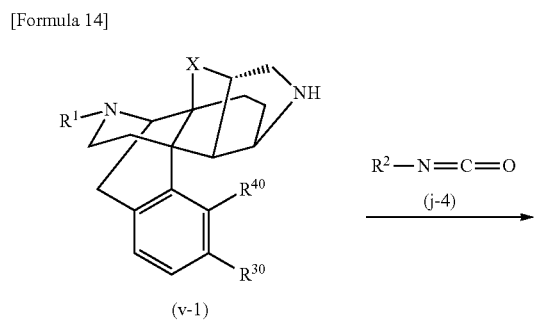

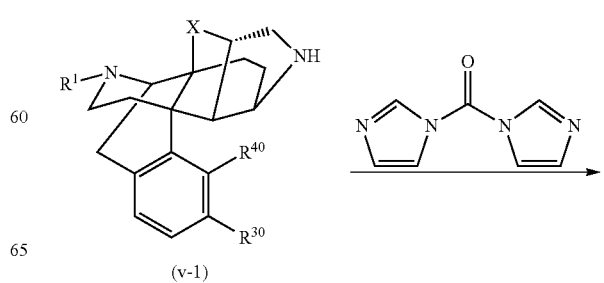

(s-6)

(In the formulas, $R^{30}$ and $R^{40}$, which are different from each other, represent hydrogen or $C_{1-6}$ alkoxy, and $R^1$, $R^2$ and X have the same meanings as those defined above.)

According to the aforementioned method I, the urea compound (s-6) of the present invention can be synthesized by reacting the compound (v-1) with the isocyanate (j-4).

(Method J) (Method for preparing the compounds where Y is $C(=O)NH$)

[Formula 15]

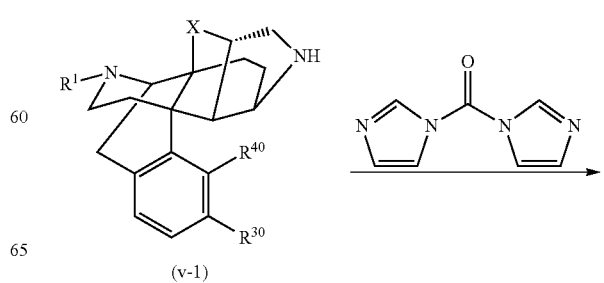

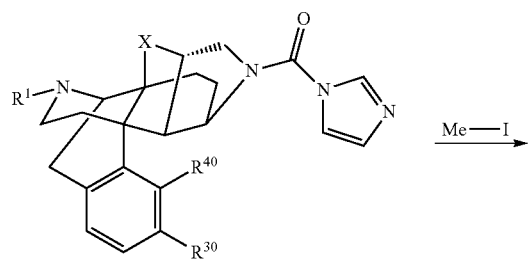

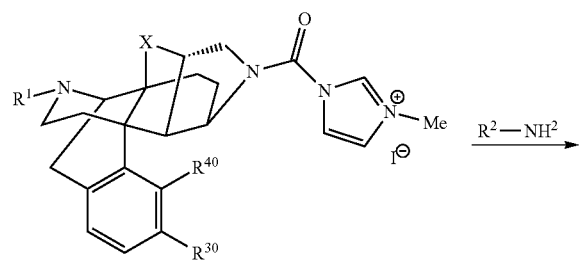

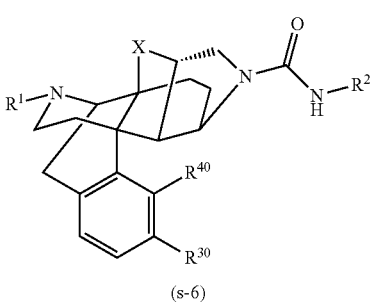

(s-6)

(In the formulas, $R^{30}$ and $R^{40}$, which are different from each other, represent hydrogen or $C_{1-6}$ alkoxy, and $R^1$, $R^2$ and X have the same meanings as those defined above.)

The urea compound (s-6) of the present invention can be synthesized from the compound (v-1) in three steps (condensation with carbodiimidazole, N-methylation with methyl iodide, and subsequent reaction with amine) according to the aforementioned method J.

(VII) Morphinan derivatives represented by the aforementioned general formula (I) wherein Y=CO, SO$_2$, C(=O)O or C(=O)NR$^{11}$, R$^3$=hydroxy, and R$^4$, R$^5$, R$^{6a}$, R$^{6b}$, R$^7$, R$^8$, R$^9$, and R$^{10}$=hydrogen:

[Formula 16]

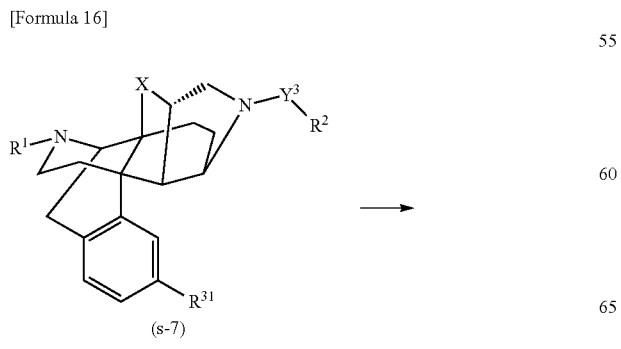

(s-7)

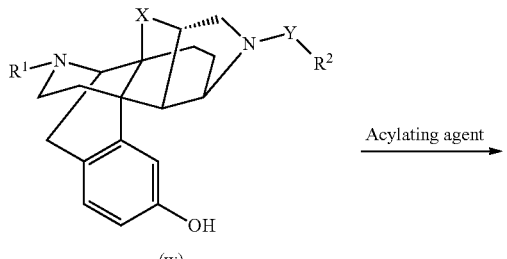

(s-8)

(In the formulas, $R^{31}$ represents $C_{1-6}$ alkoxy, $Y^3$ represents CO, SO$_2$, C(=O)O or C(=O)NR$^{11}$, and R$^1$, X and R$^2$ have the same meanings as those defined above.)

As for the compound (s-7) wherein R$^{31}$ is methoxy group, for example, the compound (s-8) of the present invention can be synthesized by a method of treating the compound (s-7) with boron tribromide in dichloromethane.

(VIII) Morphinan derivatives represented by the aforementioned general formula (I) wherein R$^3$ is alkanoyloxy, cyano, CONH$_2$, amino, acylamino, alkylamino or aralkylamino, and R$^4$, R$^5$, R$^{6a}$, R$^{6b}$, R$^7$, R$^8$, R$^9$, and R$^{10}$=hydrogen:

(1) Method for preparing the compounds where R$^3$=C$_{1-6}$ alkanoyloxy

[Formula 17]

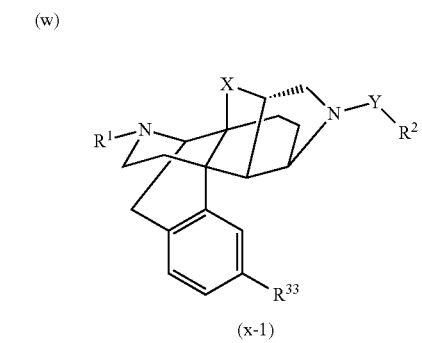

(w)

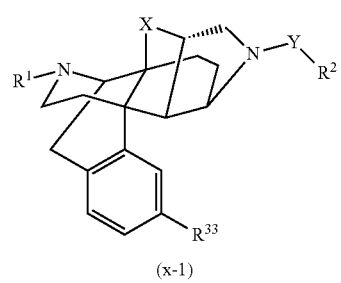

(x-1)

(In the formulas, R$^{33}$ represents C$_{1-6}$ alkanoyloxy, and R$^1$, R$^2$, X and Y have the same meanings as those defined above.)

The above reaction is performed by using an acid chloride or an acid anhydride as an acylating agent in a solvent such as pyridine.

(2) Method for preparing the compounds where $R^3$=cyano or $CONH_2$

[Formula 18]

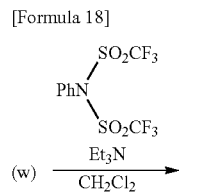

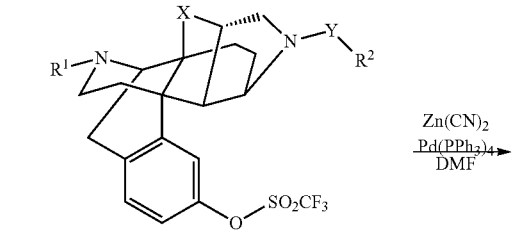

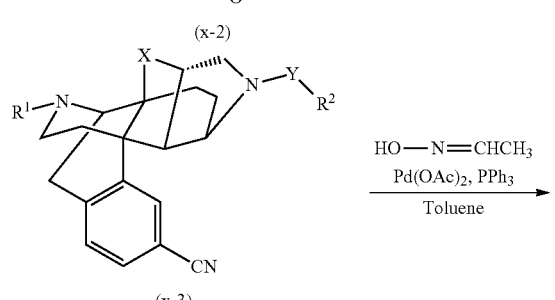

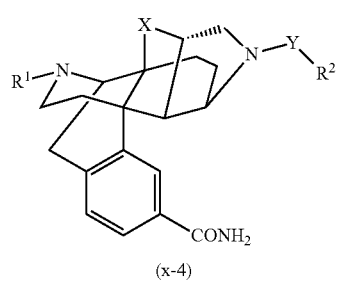

(In the formulas, $R^1$, $R^2$, X and Y have the same meanings as those defined above.)

As shown in the aforementioned scheme, the compound (x-4) of the present invention is synthesized from the compound (w) in three steps (first step: trifluoromethanesulfonylation of hydroxy group; second step: introduction of cyano group in the presence of a palladium catalyst; third step: conversion of cyano group into a primary amide). For the third step, a conventional hydrolysis reaction may be used instead of the method described in the aforementioned scheme.

(3) Method for preparing the compounds where $R^3$=amino or $C_{1-6}$ acylamino

[Formula 19]

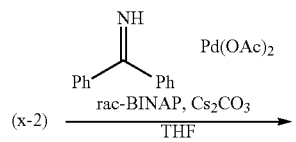

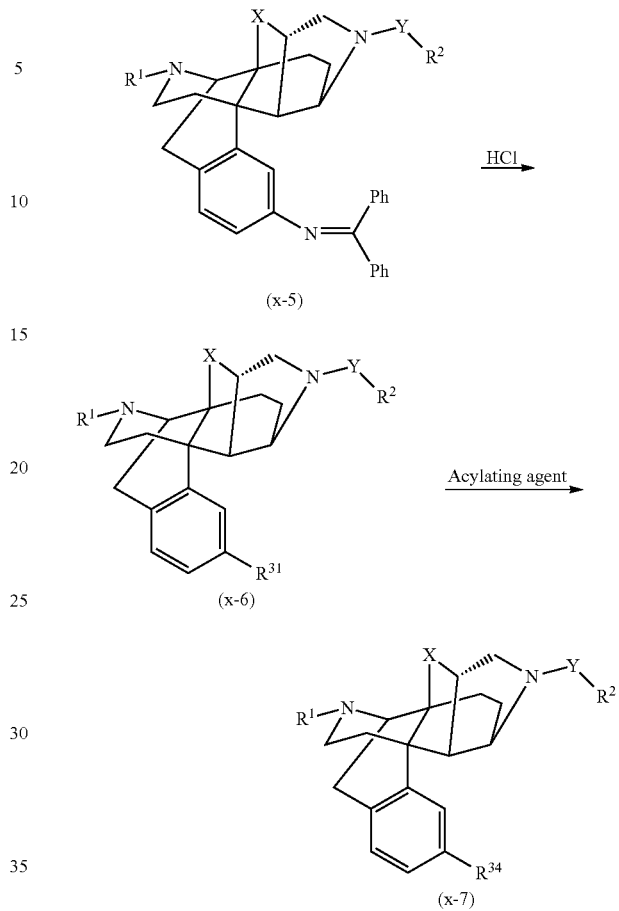

(In the formulas, $R^{34}$ represents $C_{1-6}$ acylamino, and $R^1$, $R^2$, X and Y have the same meanings as those defined above.)

As shown in the aforementioned scheme, the compound (x-7) of the present invention is synthesized from the compound (x-2) via three steps (first step: cross-coupling reaction of the triflate (x-2) with benzophenonimine in the presence of a palladium catalyst; second step: hydrolysis of the imine (x-5); third step: acylation of amino group with an acid chloride or the like).

(4) Method for preparing the compounds where $R^3$=$C_{1-6}$ alkylamino or aralkylamino

[Formula 20]

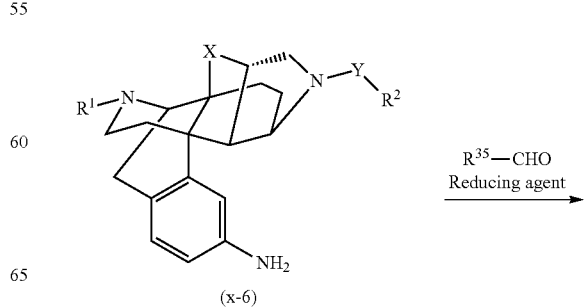

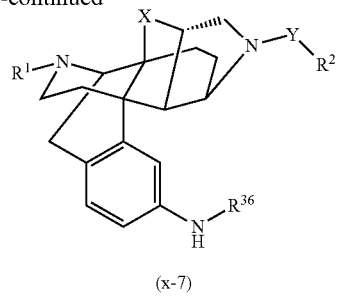

(x-7)

(In the formulas, $R^{35}$ represents hydrogen, $C_{1-5}$ alkyl, $C_{6-10}$ aryl or aralkyl (the aryl moiety has 6 to 10 carbon atoms, and the alkylene moiety has 1 to 4 carbon atoms), $R^{36}$ represents $C_{1-6}$ alkyl or aralkyl (the aryl moiety has 6 to 10 carbon atoms, and the alkylene moiety has 1 to 5 carbon atoms), and $R^1$, $R^2$, X and Y have the same meanings as those defined above.)

The compound (x-7) of the present invention can be obtained by a reductive amination reaction of the compound (x-6) with an aldehyde using sodium borohydride or the like as a reducing agent.

(IX) Morphinan derivatives represented by the aforementioned general formula (I) wherein $R^3$, $R^4$, $R^5$, $R^{6a}$, $R^{6b}$, $R^7$, $R^8$, $R^9$, and $R^{10}$=hydrogen:

[Formula 21]

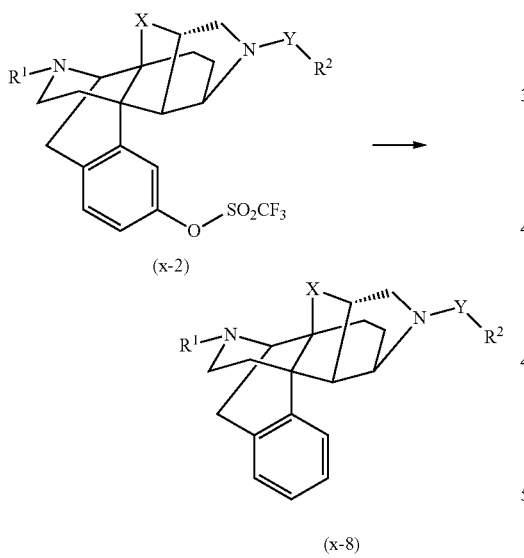

(In the formulas, $R^1$, $R^2$, X and Y have the same meanings as those defined above.)

The compound (x-8) of the present invention can be obtained by a reduction reaction of the compound (x-2) in the presence of a palladium catalyst (the method described in Tetrahedron Letters, 2010, 51, 2359 and the like).

(X) Morphinan derivatives represented by the aforementioned general formula (I) wherein $R^5$, $R^{6a}$, $R^{6b}$, $R^7$, and $R^8$ are hydrogen, and wherein $R^9$ and $R^{10}$ is a group other than hydrogen:

These compounds can be synthesized by the following method K or L.

(Method K)

[Formula 23]

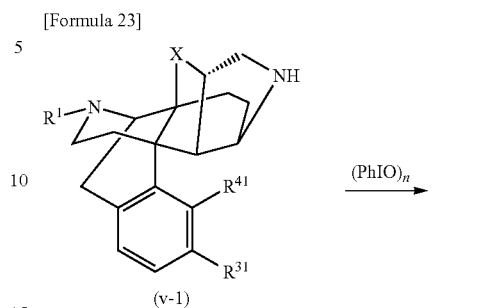

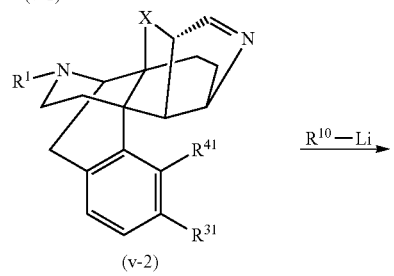

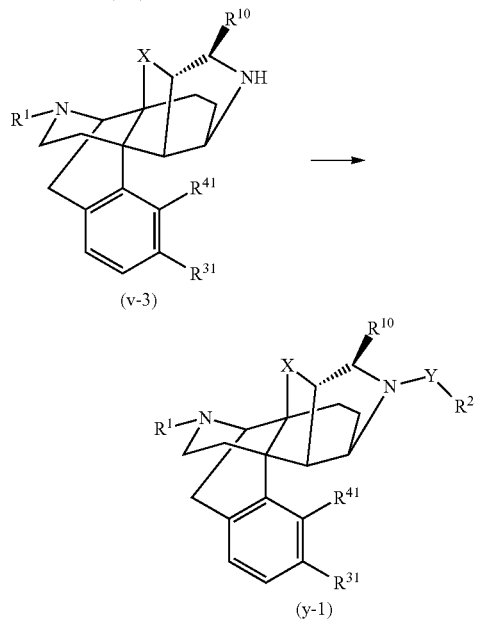

(In the formulas, $R^{31}$ and $R^{41}$, which are different from each other, represent hydrogen or $C_{1-6}$ alkoxy, and X, Y, $R^1$ and $R^2$ have the same meanings as those defined above.)

First Step

The imine (v-2) is synthesized by oxidizing the compound (v-1) with an oxidizing agent such as iodosobenzene in a solvent such as dichloromethane.

Second Step

The compound (v-3) is synthesized by treating the compound (v-2) with an alkyllithium or aryllithium at −50 to −80° C. in a solvent such as THF.

Third Step

The compound (y-1) of the present invention is synthesized from the compound (v-3) by using synthesis methods already described above.

(Method L)

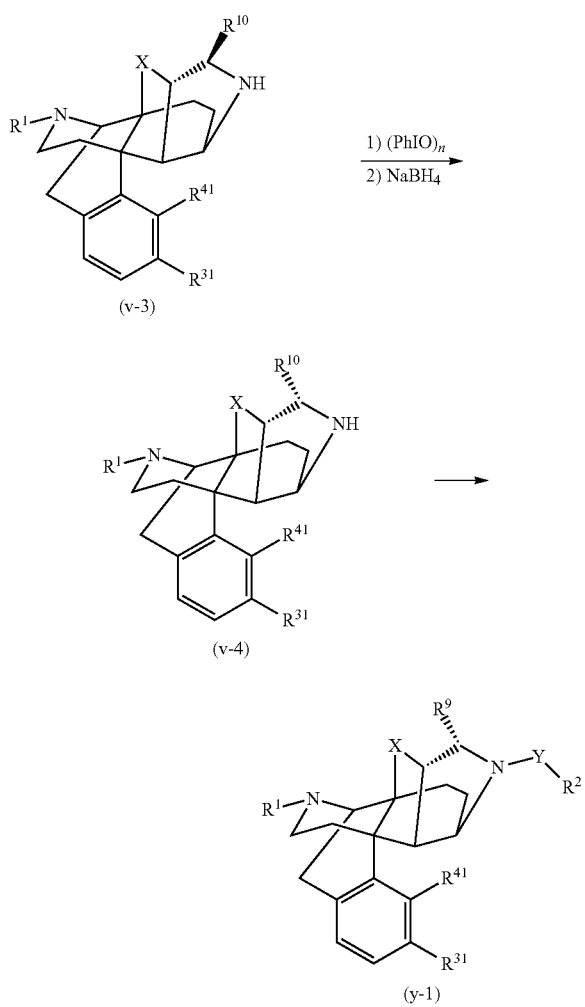

[Formula 24]

(In the formulas, $R^{31}$ and $R^{41}$, which are different from each other, represent hydrogen or $C_{1-6}$ alkoxy, and X, Y, $R^1$ and $R^2$ have the same meanings as those defined above.)

First Step

The compound (v-4) is synthesized by oxidative imination of the compound (v-3) with iodosobenzene or the like, and subsequent reduction with sodium borohydride.

Second Step

The compound (y-1) of the present invention is synthesized from the compound (v-4) by using synthesis methods already described above.

Other compounds of the general formula (I) can also be prepared by a combination of the aforementioned synthesis methods and the methods described in the examples mentioned later, and the like.

Hereafter, the results of the pharmacological tests will be explained.

As shown in Example 250, Tables 24 to 26 mentioned later, it was revealed that the morphinan derivatives represented by the aforementioned general formula (I) and pharmacologically acceptable acid addition salts thereof have excellent δ receptor agonistic activities in the opioid receptor functional test.

Further, as shown in Example 251, Table 27 mentioned later, it was revealed that the morphinan derivatives represented by the aforementioned general formula (I) and pharmacologically acceptable acid addition salts thereof have excellent analgesic effects.

Therefore, the morphinan derivatives represented by the aforementioned general formula (I) and pharmacologically acceptable acid addition salts thereof can be used for therapies of pains in diseases accompanied by an acute pain or chronic pain, or as prophylactic and therapeutic agents for pains of rheumatoid arthritis, osteoarthritis deformans, cancer pain accompanied by severe pain such as osteoncus, diabetic neuropathic pain, postherpetic neuralgia, visceral pains, and the like.

Further, the morphinan derivatives represented by the aforementioned general formula (I) and pharmacologically acceptable acid addition salts thereof can be used as therapeutic agents for neurological disease accompanied by anxiety such as depression, panic disorders, anxiety disorders, and stress disorders (PTSD, acute stress disorder), and as prophylactic and therapeutic agents for urinary incontinence, myocardial ischemia, hypertension, Parkinson's disease, and other motor dysfunctions.

The morphinan derivatives represented by the aforementioned general formula (I) and pharmacologically acceptable acid addition salts thereof can be administered to a human by an appropriate administration method such as oral administration or parenteral administration. Further, they can be used together with other analgesics.

As for pharmaceutical preparations thereof, they can be prepared in a dosage form of tablet, granule, powder, capsule, suspension, injection, suppository or the like by methods common in the field of pharmaceuticals.

For preparation of pharmaceutical formulations, for example, ordinary excipients, disintegrating agents, binders, lubricants, dyes, and the like are used in the case of tablet. Examples of the excipients include lactose, D-mannitol, crystalline cellulose, glucose, and the like. Examples of the disintegrating agents include starch, carboxymethylcellulose calcium (CMC-Ca), and the like. Examples of the lubricants include magnesium stearate, talc, and the like. Examples of the binders include hydroxypropylcellulose (HPC), gelatin, polyvinylpyrrolidone (PVP), and the like. For the preparation of injection, solvents, stabilizers, dissolving aids, suspending agents, emulsifiers, soothing agents, buffering agents, preservatives, and the like are used.

As for the dose of the morphinan derivatives represented by the aforementioned general formula (I) and pharmacologically acceptable acid addition salts thereof as active ingredient, the morphinan derivatives are usually administered to adults at a dose of 0.1 μg to 1 g/day, preferably 0.001 to 200 mg/day, in the case of injection, or a dose of 1 μg to 10 g/day, preferably 0.01 to 2000 mg/day, in the case of oral administration, but the dose may be reduced or increased depending on age, symptoms, and the like.

Hereafter, the present invention will be further explained in more detail with reference to reference examples and examples of the present invention. However, the present invention is not limited to these examples.

Reference Example 1

Synthesis of (5R,6S,6'R,9R,13S,14S)—N-benzyl-17-(cyclopropylmethyl)-4,5-epoxy-6,6'-epoxy-14-hydroxy-3-methoxy-6-methylmorphinan-6'-carboxamide (2a)

[Formula 25]

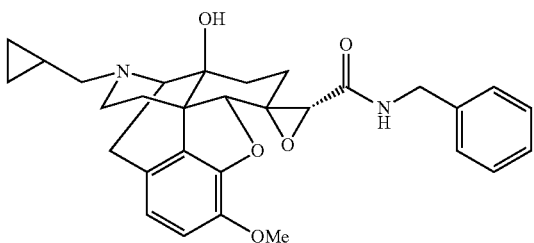

2a

Under an argon atmosphere, benzylamine (4.4 mL, 40 mmol) was dissolved in THF (100 mL), the solution was cooled to −78° C. and then slowly added with a solution of n-butyllithium in hexane (1.65 mol/L, 24.2 mL, 40 mmol), and the mixture was stirred for 15 minutes. Then, the reaction mixture was added dropwise with a solution of ethyl (5R,6S,6'R,9R,13S,14S)-17-(cyclopropylmethyl)-4,5-epoxy-6,6'-epoxy-14-hydroxy-3-methoxy-6-methylmorphinan-6'-carboxylate [Compound 1a: the compound described in Bioorg. Med. Chem. Lett., 2010, 20, 121](4.42 g, 10 mmol) in THF (50 mL) over 15 minutes, and the mixture was stirred for 1 hour. Under ice cooling, the reaction mixture was poured into saturated aqueous sodium hydrogencarbonate, and the mixture was extracted three times with ethyl acetate. The organic layers were combined, washed with saturated brine, dried over anhydrous sodium sulfate, and then concentrated. The obtained crude product was purified by silica gel column chromatography to give the title compound 2a as white amorphous (4.97 g, 99%).

$^1$H NMR (CDCl$_3$, 300 MHz): δ 0.05-0.22 (m, 2H), 0.43-0.62 (m, 2H), 0.83-0.95 (m, 1H), 1.26-1.36 (m, 1H), 1.41-1.66 (m, 3H), 2.12 (dt, J=3.6, 12.0 Hz, 1H), 2.20-2.43 (m, 4H), 2.53-2.71 (m, 2H), 3.04 (d, J=18.6 Hz, 1H), 3.10 (d, J=5.4 Hz, 1H), 3.68 (s, 1H), 3.85 (s, 3H), 4.31-4.46 (m, 2H), 4.75 (s, 1H), 5.15 (br s, 1H), 6.37-6.53 (m, 1H), 6.61 (d, J=8.4 Hz, 1H), 6.72 (d, J=8.4 Hz, 1H), 7.12-7.34 (m, 5H)

Reference Example 2

Synthesis of (5R,6S,6'S,9R,13S,14S)—N-benzyl-17-(cyclopropylmethyl)-4,5-epoxy-6,6'-epoxy-14-hydroxy-3-methoxy-6-methylmorphinan-6'-carboxamide (2b)

[Formula 26]

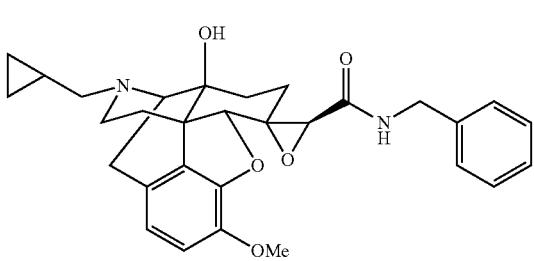

2b

Under an argon atmosphere, benzylamine (4.4 mL, 40 mmol) was dissolved in THF (100 mL), the solution was cooled to −78° C., and then slowly added with a solution of n-butyllithium in hexane (1.65 mol/L, 24.2 mL, 40 mmol), and the mixture was stirred for 15 minutes. Then, the reaction mixture was added dropwise with a solution of ethyl (5R,6S,6'S,9R,13S,14S)-17-(cyclopropylmethyl)-4,5-epoxy-6,6'-epoxy-14-hydroxy-3-methoxy-6-methylmorphinan-6'-carboxylate [Compound 1b: the compound described in Bioorg. Med. Chem. Lett., 2010, 20, 121](4.42 g, 10 mmol) in HF (50 mL) over 15 minutes, and the mixture was stirred for 1 hour. The reaction mixture was poured into saturated aqueous sodium hydrogencarbonate under ice cooling, and the mixture was extracted three times with ethyl acetate. The organic layers were combined, washed with saturated brine, dried over anhydrous sodium sulfate, and then concentrated. The obtained crude product was purified by silica gel column chromatography, and recrystallized from ethyl acetate to give the title compound 2b as white crystals (4.01 g, 80%).

$^1$H NMR (CDCl$_3$, 300 MHz): δ 0.06-0.22 (m, 2H), 0.44-0.60 (m, 2H), 0.74-0.94 (m, 1H), 1.14 (dt, J=3.6, 14.4 Hz, 1H), 1.44-1.62 (m, 3H), 2.08-2.30 (m, 2H), 2.30-2.42 (m, 2H), 2.44-2.70 (m, 3H), 3.04 (d, J=18.6 Hz, 1H), 3.09 (d, J=6.0 Hz, 1H), 3.28 (s, 1H), 3.49 (s, 3H), 4.24 (dd, J=4.2, 15.0 Hz, 1H), 4.75 (s, 1H), 4.87 (dd, J=5.1, 15.0 Hz, 1H), 6.63 (d, J=8.1 Hz, 1H), 6.66 (d, J=8.1 Hz, 1H), 7.17 (s, 1H), 7.22-7.41 (m, 5H)

Reference Example 3

Synthesis of (5R,6S,7S,9R,13S,14S)—N-benzyl-17-(cyclopropylmethyl)-4,5-epoxy-6-hydroxy-3-methoxy-8-oxa-6,14-ethanomorphinan-7-carboxamide (3)

[Formula 27]

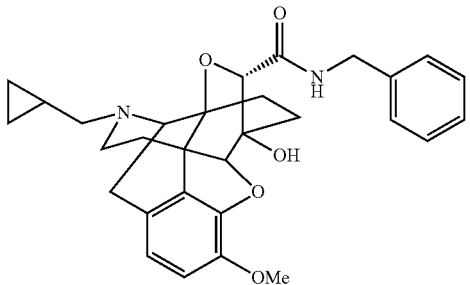

3

Under an argon atmosphere, 60% sodium hydride (2.54 g, 64 mmol) was washed with anhydrous hexane, and suspended in THF (50 mL), the suspension was added with a solution of the compound 2a (2.54 g, 5.1 mmol) which was prepared in Reference Example 1 in THF (50 mL), and the mixture was stirred for 30 minutes under reflux. The reaction mixture was poured into saturated aqueous sodium hydrogencarbonate under ice cooling, and the mixture was extracted three times with ethyl acetate. The organic layers were combined, washed with saturated brine, dried over anhydrous sodium sulfate, and then concentrated. The obtained crude product was purified by silica gel column chromatography to give the title compound 3 as white amorphous (2.11 g, 83%).

$^1$H NMR (CDCl$_3$, 300 MHz): δ 0.05-0.18 (m, 2H), 0.42-0.64 (m, 2H), 0.79-1.06 (m, 2H), 1.31-1.53 (m, 2H), 1.66-1.91 (m, 2H), 2.12 (dd, J=8.1, 12.6 Hz, 1H), 2.18-2.35 (m, 2H), 2.41 (dt, J=3.6, 12.6 Hz, 1H), 2.66-2.82 (m, 2H), 3.20 (d, J=18.3 Hz, 1H), 3.54 (d, J=6.6 Hz, 1H), 3.89 (s, 3H), 4.28 (d, J=2.4 Hz, 1H), 4.46 (dd, J=5.7, 14.7 Hz, 1H), 4.54 (d, J=1.5 Hz, 1H), 4.59 (dd, J=6.6, 14.7 Hz, 1H), 5.49 (br s, 1H), 6.53 (d, J=8.1 Hz, 1H), 6.72 (d, J=8.1 Hz, 1H), 7.23-7.38 (m, 5H), 7.51-7.73 (m, 1H)

Reference Example 4

Synthesis of (1S,3aS,5aS,6R,11bR,11cR)-3-benzyl-14-(cyclopropylmethyl)-3a,11-dihydroxy-10-methoxy-1,3,3a,4,5,6,7,11c-octahydro-2H-6,11b-(iminoethano)-1,5a-epoxynaphtho[1,2-e]indol-2-one (4)

[Formula 28]

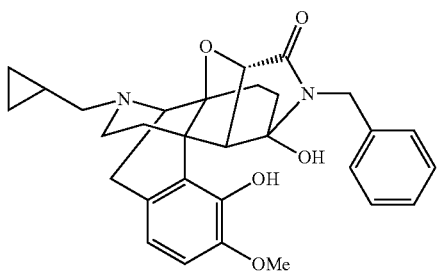

4

Under an argon atmosphere, 60% sodium hydride (4.31 g, 110 mmol) was washed with anhydrous hexane, and suspended in cyclopentyl methyl ether (30 mL), the suspension was added with a solution of the compound 2a (4.32 g, 8.6 mmol) which was prepared in Reference Example 1 in cyclopentyl methyl ether (20 mL), and the mixture was stirred for 3 hours under reflux. The reaction mixture was poured into saturated aqueous sodium hydrogencarbonate under ice cooling, and the mixture was extracted three times with ethyl acetate. The organic layers were combined, washed with saturated brine, dried over anhydrous sodium sulfate, and then concentrated. The obtained crude product was recrystallized from methanol to give the title compound 4 as white crystals (3.51 g, 81%).

$^1$H NMR (CDCl$_3$, 300 MHz): δ 0.02-0.14 (m, 2H), 0.40-0.58 (m, 2H), 0.87-1.00 (m, 2H), 1.32-1.42 (m, 3H), 1.63 (dd, J=7.8, 4.4 Hz, 1H), 1.91 (dt, J=4.8, 12.6 Hz, 1H), 2.10 (dt, J=3.0, 12.3 Hz, 1H), 2.25 (dd, J=7.5, 2.6 Hz, 1H), 2.63 (dt, J=3.6, 11.4 Hz, 2H), 2.86 (dd, J=6.3, 18.6 Hz, 1H), 3.09 (d, J=18.6 Hz, 1H), 3.30 (d, J=5.7 Hz, 1H), 3.68 (d, J=6.0 Hz, 1H), 3.84 (s, 3H), 4.40 (d, J=14.7 Hz, 1H), 4.51 (d, J=14.7 Hz, 1H), 4.72 (d, J=6.0 Hz, 1H), 6.68 (d, J=8.7 Hz, 1H), 6.70 (d, J=8.4 Hz, 1H), 7.13-7.30 (m, 3H), 7.41 (d, J=6.9 Hz, 2H)

Reference Example 5

Synthesis of (1S,3aS,5aS,6R,11bR,11cR)-3-benzyl-14-(cyclopropylmethyl)-3a,11-dihydroxy-10-methoxy-1,3,3a,4,5,6,7,11c-octahydro-2H-6,11b-(iminoethano)-1,5a-epoxynaphtho[1,2-e]indol-2-one (4)

Under an argon atmosphere, the compound 2b (101 mg, 0.20 mmol) which was prepared in Reference Example 2 was dissolved in t-butyl alcohol (2 mL), the solution was added with potassium t-butoxide (224 mg, 2.0 mmol), and the mixture was refluxed for 1 hour. The reaction mixture was made acidic by adding 2 M aqueous hydrochloric acid under ice cooling, and then added with chloroform and potassium carbonate to adjust the aqueous layer to pH 11. The reaction mixture was added with distilled water, and then the mixture was extracted three times with chloroform. The organic layers were combined, dried over anhydrous sodium sulfate, and then concentrated. The obtained crude product was purified by silica gel column chromatography to give the title compound 4 as colorless oil (89.4 mg, 89%).

Example 1

Synthesis of (1S,3aR,5aS,6R,11bR,11cS)-3-benzyl-14-(cyclopropylmethyl)-10-methoxy-2,3,3a,4,5,6,7,11c-octahydro-1H-6,11b-(iminoethano)-1,5a-epoxynaphtho[1,2-e]indol-11-ol (5)

[Formula 29]

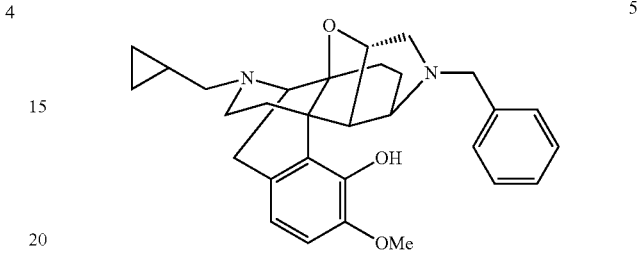

5

Under an argon atmosphere, the compound 4 (10.1 g, 20 mmol) was dissolved in THF (100 mL), the solution was added with a solution of borane-tetrahydrofuran complex in THF (1.0 mol/L, 100 mL, 100 mmol), and the mixture was refluxed for 2 hours. The reaction mixture was concentrated under reduced pressure, and added with 6 M hydrochloric acid (200 mL), and the mixture was refluxed for 1 hour. The reaction mixture was adjusted to pH 11 with potassium carbonate, and extracted three times with chloroform. The organic layers were combined, dried over anhydrous sodium sulfate, and then concentrated. The obtained crude product was purified by silica gel column chromatography to give the title compound 5 as white amorphous (8.84 g, 94%).

$^1$H NMR (CDCl$_3$, 400 MHz): δ 0.02-0.16 (m, 2H), 0.42-0.70 (m, 3H), 0.90-1.02 (m, 1H), 1.37-1.47 (m, 1H), 1.51 (dd, J=7.6, 14.8 Hz, 1H), 1.66-1.89 (m, 2H), 1.97-2.12 (m, 2H), 2.22 (dd, J=7.2, 12.8 Hz, 1H), 2.55 (dd, J=5.6, 12.8 Hz, 1H), 2.56-2.68 (m, 1H), 2.81-2.93 (m, 2H), 3.05 (d, J=18.4 Hz, 1H), 3.31 (dd, J=6.8, 10.8 Hz, 1H), 3.46-3.59 (m, 2H), 3.60 (d, J=6.4 Hz, 1H), 3.74 (d, J=13.6 Hz, 1H), 3.75 (d, J=13.6 Hz, 1H), 3.79 (s, 3H), 4.91-4.98 (m, 1H), 6.25 (br s, 1H), 6.60 (d, J=8.4 Hz, 1H), 6.64 (d, J=8.4 Hz, 1H), 7.11-7.31 (m, 5H)

Example 2

Synthesis of (1S,3aR,5aS,6R,11bR,11cS)-3-benzyl-14-(cyclopropylmethyl)-10-methoxy-11-phenoxy-2,3,3a,4,5,6,7,11c-octahydro-1H-6,11b-(iminoethano)-1,5a-epoxynaphtho[1,2-e]indole (6)

[Formula 30]

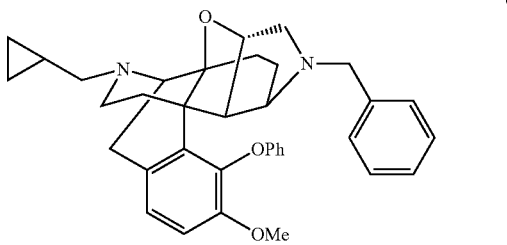

6

Under an argon atmosphere, the compound 5 (8.84 g, 19 mmol) was dissolved in pyridine (100 mL), the solution was added with bromobenzene (98.5 mL, 94 mmol), potassium carbonate (7.76 g, 56 mmol), and copper powder (1.19 g, 19 mmol), and the mixture was refluxed for 16 hours. The reaction mixture was further added with bromobenzene (4.92 g, 47 mmol), potassium carbonate (7.76 g, 56 mmol), and copper powder (1.19 g, 19 mmol), and the mixture was refluxed for further 24 hours. The reaction mixture was filtered through Celite, and then poured into distilled water, and the mixture was extracted three times with chloroform. The organic layers were combined, dried over anhydrous sodium sulfate, and then concentrated. The obtained crude product was purified by silica gel column chromatography to give the title compound 6 as black oil (10.1 g, 98%).

$^1$H NMR (CDCl$_3$, 300 MHz): δ 0.00-0.16 (m, 2H), 0.40-0.78 (m, 3H), 0.86-1.02 (m, 1H), 1.04-1.14 (m, 1H), 1.41-1.53 (m, 1H), 1.68-1.93 (m, 3H), 2.06 (dt, J=3.0, 12.3 Hz, 1H), 2.23 (dd, J=7.2, 12.3 Hz, 1H), 2.49-2.61 (m, 2H), 2.86 (dd, J=2.4, 10.8 Hz, 1H), 2.83-2.99 (m, 1H), 3.11 (d, J=18.6 Hz, 1H), 3.15 (dd, J=6.3, 11.1 Hz, 1H), 3.22 (dd, J=6.0, 7.5 Hz, 1H), 3.53-3.63 (m, 2H), 3.66 (d, J=13.5 Hz, 1H), 3.67 (s, 3H), 3.75 (d, J=13.5 Hz, 1H), 4.77-4.86 (m, 1H), 6.76 (d, J=7.8 Hz, 2H), 6.80 (d, J=8.4 Hz, 1H), 6.96 (t, J=7.2 Hz, 1H), 6.99 (d, J=8.1 Hz, 1H), 7.16-7.32 (m, 7H)

Example 3

Synthesis of (1S,3aR,5aS,6R,11bR,11cS)-3-benzyl-14-(cyclopropylmethyl)-10-methoxy-2,3,3a,4,5,6,7,11c-octahydro-1H-6,11b-(iminoethano)-1,5a-epoxynaphtho[1,2-e]indole (7)

[Formula 31]

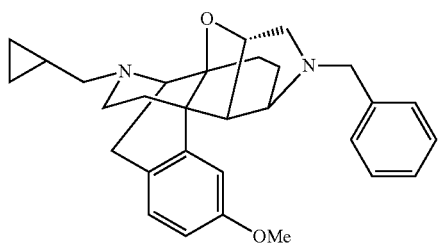

Under an argon atmosphere, the compound 6 (90.7 mg, 0.17 mmol) was dissolved in THF (2 mL), the solution was added with ethylenediamine (333 μL, 6.2 mmol), and the mixture was stirred at room temperature for 5 hours with adding each of 5 divided portions of sodium silica gel (Stage I, 900 mg) every 1 hour. The reaction mixture was poured into distilled water under ice cooling, and the mixture was extracted three times with ethyl acetate. The organic layers were combined, washed with saturated brine, dried over anhydrous sodium sulfate, and then concentrated. The obtained crude product was purified by silica gel column chromatography to give the title compound 7 as colorless oil (68.2 mg, 90%).

$^1$H NMR (CDCl$_3$, 300 MHz): δ 0.00-0.16 (m, 2H), 0.41-0.59 (m, 3H), 0.87-1.03 (m, 1H), 1.13-1.30 (m, 1H), 1.51 (dd, J=6.9, 15.0 Hz, 1H), 1.62-1.84 (m, 2H), 2.00-2.16 (m, 2H), 2.23 (dd, J=7.2, 12.3 Hz, 1H), 2.54-2.67 (m, 1H), 2.55 (dd, J=5.4, 12.6 Hz, 1H), 2.73-2.87 (m, 2H), 2.97-3.07 (m, 1H), 3.07 (d, J=18.6 Hz, 1H), 3.30 (dd, J=6.9, 10.8 Hz, 1H), 3.47 (t, J=6.6 Hz, 1H), 3.62 (d, J=6.9 Hz, 1H), 3.66 (d, J=13.5 Hz, 1H), 3.75 (s, 3H), 3.78 (d, J=13.5 Hz, 1H), 4.93-5.02 (m, 1H), 6.66-6.74 (m, 2H), 6.88-7.07 (m, 1H), 7.17-7.34 (m, 5H)

Example 4

Synthesis of (1S,3aR,5aS,6R,11bR,11cS)-14-(cyclopropylmethyl)-10-methoxy-2,3,3a,4,5,6,7,11c-octahydro-1H-6,11b-(iminoethano)-1,5a-epoxynaphtho[1,2-e]indole (8)

[Formula 32]

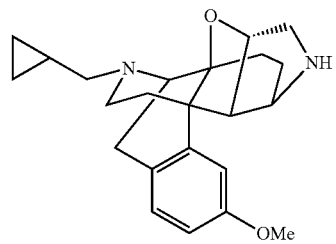

The compound 7 (1.83 g, 4.0 mmol) was dissolved in ethanol (20 mL), the solution was added with 10% palladium-carbon (1.12 g), and the mixture was stirred at 40° C. for 15 hours under a hydrogen atmosphere. The reaction mixture was filtered through Celite, and then concentrated. The obtained crude product was purified by silica gel column chromatography to give the title compound 8 as yellow oil (1.27 g, 86%).

$^1$H NMR (CDCl$_3$, 300 MHz): δ 0.02-0.16 (m, 2H), 0.42-0.60 (m, 2H), 0.80-1.11 (m, 3H), 1.20-1.35 (m, 1H), 1.76 (dd, J=4.8, 10.8 Hz, 2H), 1.96 (br s, 1H), 2.00-2.20 (m, 2H), 2.25 (dd, J=7.2, 12.3 Hz, 1H), 2.55-2.70 (m, 1H), 2.56 (dd, J=5.4, 12.3 Hz, 1H), 2.74-2.93 (m, 2H), 3.08 (d, J=18.3 Hz, 1H), 3.22 (dd, J=2.4, 12.6 Hz, 1H), 3.38 (dd, J=6.3, 12.6 Hz, 1H), 3.56-3.68 (m, 2H), 3.79 (s, 3H), 4.97 (dt, J=2.1, 6.3 Hz, 1H), 6.66-6.77 (m, 2H), 6.99-7.08 (m, 1H)

Example 5

[(1S,3aR,5aS,6R,11bR,11cS)-14-(Cyclopropylmethyl)-10-methoxy-1,2,3a,4,5,6,7,11c-octahydro-3H-6,11b-(iminoethano)-1,5a-epoxynaphtho[1,2-e]indol-3-yl](phenyl)methanone

[Formula 33]

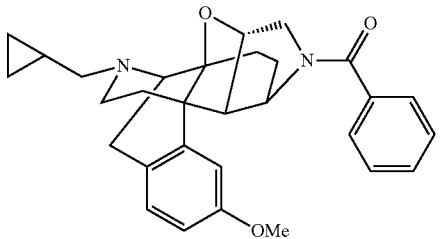

Under an argon atmosphere, the compound 8 (1.27 g, 3.5 mmol) was dissolved in dichloromethane (20 mL), the solution was added with benzoic anhydride (1.17 g, 5.2 mmol), and triethylamine (723 μL, 5.2 mmol), and the mixture was stirred at room temperature for 30 minutes. The reaction mixture was poured into distilled water, and the mixture was extracted three times with chloroform. The organic layers were combined, dried over anhydrous sodium sulfate, and then concentrated. The obtained crude product was purified by silica gel column chromatography to give the title compound 9 as white amorphous (1.34 g, 82%).

$^1$H NMR (CDCl$_3$, 300 MHz): δ 0.01-0.18 (m, 2H), 0.43-0.79 (m, 2.3H), 0.83-1.04 (m, 1.7H), 1.14 (dd, J=6.9, 14.7 Hz, 0.3H), 1.20-1.39 (m, 1H), 1.46-1.59 (m, 0.7H), 1.69-1.92 (m, 2H), 1.97-2.18 (m, 2H), 2.20-2.40 (m, 1H), 2.45-2.72 (m, 2H), 2.74-2.86 (m, 0.3H), 2.80 (dd, J=6.3, 18.0 Hz, 0.7H), 3.00-3.19 (m, 2H), 3.58-3.75 (m, 1.7H), 3.71 (s, 0.9H), 3.80 (s, 2.1H), 3.82-3.93 (m, 1H), 4.19-4.31 (m, 0.6H), 4.91-5.05 (m, 1.4H), 5.10 (t, J=5.7 Hz, 0.3H), 6.52 (d, J=2.7 Hz, 0.3H), 6.63-6.72 (m, 0.3H), 6.69 (d, J=2.7 Hz, 6.73 (dd, J=2.7, 8.4 Hz, 0.7H), 7.01 (d, J=8.4 Hz, 0.3H), 7.06 (d, J=8.4 Hz, 0.7H), 7.31-7.50 (m, 5H)

Example 6

Synthesis of [(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl](phenyl)methanone (10)

[Formula 34]

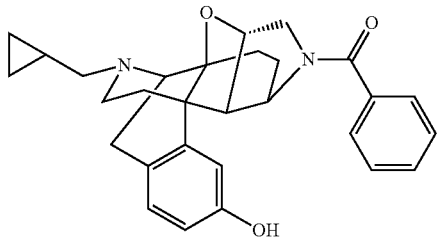

Under an argon atmosphere, the compound 9 (47.1 mg, 0.10 mmol) was dissolved in dichloromethane (3 mL), the solution was added with a solution of boron tribromide in dichloromethane (1.0 mol/L, 0.5 mL, 0.50 mmol) under ice cooling, and the mixture was stirred at room temperature for 30 minutes. The reaction mixture was added with 6 M aqueous ammonia (3 mL) under ice cooling, and the mixture was stirred at room temperature for 30 minutes. The reaction mixture was added with distilled water, and the mixture was extracted three times with chloroform. The organic layers were combined, dried over anhydrous sodium sulfate, and then concentrated. The obtained crude product was purified by preparative TLC to give the title compound 10 as colorless oil (18.0 mg, 39%).

The obtained compound 10 was treated with a 20% solution of hydrogen chloride in methanol to give the hydrochloride of the compound 10.

Compound 10 (free base) $^1$H NMR (CDCl$_3$, 300 MHz): δ 0.02-0.18 (m, 2H), 0.41-0.62 (m, 2H), 0.65-1.37 (m, 3.2H), 1.47-1.60 (m, 0.8H), 1.68-1.91 (m, 2H), 1.96-2.37 (m, 3H), 2.49-2.73 (m, 2H), 2.83 (dd, J=6.3, 18.3 Hz, 1H), 2.97-3.15 (m, 2H), 3.62 (dd, J=6.0, 12.9 Hz, 0.8H), 3.68 (d, J=6.3 Hz, 1.0H), 3.86 (d, J=12.9 Hz, 1H), 4.15-4.28 (m, 0.4H), 4.89-5.01 (m, 1.6H), 5.04 (t, J=5.7 Hz, 0.2H), 6.52 (d, J=2.4 Hz, 0.2H), 6.58 (dd, J=2.4, 8.4 Hz, 0.2H), 6.66 (dd, J=2.4, 8.4 Hz, 0.8H), 6.73 (d, J=2.1 Hz, 0.8H), 6.86-6.94 (m, 0.2H), 6.91 (d, J=8.1 Hz, 0.8H), 7.30-7.54 (m, 5H)

Example 7

Synthesis of [(1S,3aR,5aS,6R,11bR,11cS)-10-methoxy-1,2,3a,4,5,6,7,11c-octahydro-3H-6,11b-(iminoethano)-1,5a-epoxynaphtho[1,2-e]indol-3-yl](phenyl)methanone (11)

[Formula 35]

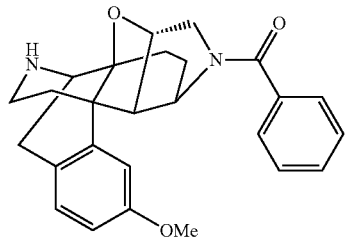

Under an argon atmosphere, the compound 9 (905 mg, 1.9 mmol) was dissolved in 1,1,2,2-tetrachloroethane (20 mL), the solution was added with potassium carbonate (531 mg, 3.8 mmol), and 2,2,2-trichloroethyl chloroformate (517 μL, 3.8 mmol), and the mixture was stirred at 150° C. for 1 hour. The reaction mixture was poured into distilled water, the mixture was extracted three times with chloroform, and the organic layers were combined, dried over anhydrous sodium sulfate, and then concentrated. From the obtained crude product, excessive regents were removed by silica gel column chromatography. The obtained crude product was dissolved in acetic acid (20 mL), the solution was added with zinc (1.00 g), and the mixture was stirred at room temperature for 3 hours. The reaction mixture was filtered through Celite, concentrated, and azeotroped with toluene. Then, the residue was added with distilled water, and the mixture was adjusted to pH 11 with potassium carbonate, and extracted three times with chloroform. The organic layers were combined, dried over anhydrous sodium sulfate, and then concentrated. The obtained crude product was purified by silica gel column chromatography to give the title compound 11 as white amorphous (564 mg, 70%).

$^1$H NMR (CDCl$_3$, 300 MHz): δ 0.65-1.29 (m, 2.3H), 1.47-1.59 (m, 0.7H), 1.63-1.86 (m, 3H), 2.10 (br s, 1H), 2.54-2.73 (m, 2H), 2.96-3.13 (m, 2H), 3.28-3.48 (m, 2H), 3.66 (dd, J=6.3, 12.9 Hz, 0.7H), 3.72 (s, 0.9H), 3.81 (s, 2.1H), 3.84 (d, J=13.2 Hz, 1H), 4.22-4.34 (m, 0.6H), 4.88-5.01 (m, 1.4H), 5.05 (t, J=5.7 Hz, 0.3H), 6.50 (d, J=2.7 Hz, 0.3H), 6.68 (d, J=2.4 Hz, 0.7H), 6.66-6.72 (m, 0.3H), 6.76 (dd, J=2.7, 8.4 Hz, 0.7H), 7.06 (d, J=8.4 Hz, 0.3H), 7.10 (d, J=8.7 Hz, 0.7H), 7.30-7.54 (m, 5H)

Example 8

Synthesis of [(1S,3aR,5aS,6R,11bR,11cS)-10-hydroxy-14-methyl-1,2,3a,4,5,6,7,11c-octahydro-3H-6,11b-(iminoethano)-1,5a-epoxynaphtho[1,2-e]indol-3-yl](phenyl)methanone (12)

[Formula 36]

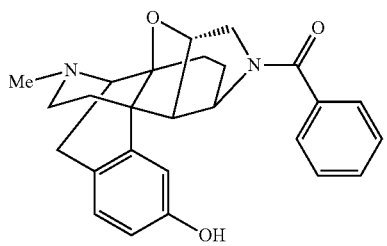

Under an argon atmosphere, the compound 11 (41.7 mg, 0.10 mmol) was dissolved in DMF (2 mL), the solution was added with methyl iodide (9.30 μL, 0.15 mmol), and potassium carbonate (20.7 mg, 0.15 mmol), and the mixture was stirred at room temperature for 1 hour. The reaction mixture was poured into distilled water, and the mixture was extracted three times with chloroform. The organic layers were combined, dried over anhydrous sodium sulfate, and then concentrated. Under an argon atmosphere, the obtained crude product was dissolved in dichloromethane (2 mL), the solution was added with a solution of boron tribromide in dichloromethane (1.0 mol/L, 0.5 mL, 0.50 mmol) under ice cooling, and the mixture was stirred at room temperature for 30 minutes. The reaction mixture was added with 6 M aqueous ammonia (10 mL) under ice cooling, and the mixture was stirred at room temperature for 30 minutes, and extracted three times with chloroform. The organic layers were combined, dried over anhydrous sodium sulfate, and then concentrated. The obtained crude product was purified by preparative TLC to give the title compound 12 as white amorphous (23.2 mg, 56%).

The obtained compound 12 was treated with a 20% solution of hydrogen chloride in methanol to give the hydrochloride of the compound 12.

Compound 12 (free base) $^1$H NMR (CDCl$_3$, 300 MHz): δ 0.64-1.36 (m, 2.2H), 1.45-1.58 (m, 0.8H), 1.68-1.89 (m, 2H), 1.94-2.25 (m, 2H), 2.32-2.50 (m, 1H), 2.38 (s, 3H), 2.84 (dd, J=6.3, 18.6 Hz, 1H), 3.00-3.15 (m, 1H), 3.15 (d, J=18.3 Hz, 1H), 3.22 (d, J=6.0 Hz, 1H), 3.63 (dd, J=6.0, 12.9 Hz, 0.8H), 3.85 (d, J=12.9 Hz, 1H), 4.15-4.28 (m, 0.4H), 4.89-5.01 (m, 1.6H), 5.03 (t, J=5.7 Hz, 0.2H), 6.50 (d, J=2.7 Hz, 0.2H), 6.57 (dd, J=2.7, 8.4 Hz, 0.2H), 6.65 (dd, J=2.7, 8.4 Hz, 0.8H), 6.71 (d, J=2.4 Hz, 0.8H), 6.91 (d, J=8.4 Hz, 0.2H), 6.93 (d, J=8.4 Hz, 0.8H), 7.30-7.54 (m, 5H)

Example 9

Synthesis of [(1S,3aR,5aS,6R,11bR,11cS)-14-ethyl-10-hydroxy-1,2,3a,4,5,6,7,11c-octahydro-3H-6,11b-(iminoethano)-1,5a-epoxynaphtho[1,2-e]indol-3-yl](phenyl)methanone (13)

[Formula 37]

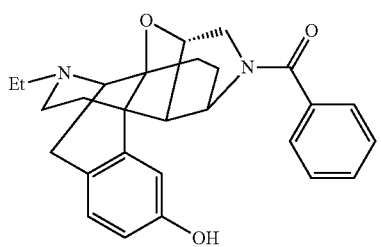

13

According to the method described in Example 8, the title compound 13 was obtained as colorless oil by using the compound 11 and ethyl iodide.

The obtained compound 13 was treated with a 20% solution of hydrogen chloride in methanol to give the hydrochloride of the compound 13.

Compound 13 (free base) $^1$H NMR (CDCl$_3$, 300 MHz): δ 0.62-1.36 (m, 2.2H), 1.11 (t, J=7.2 Hz, 3H), 1.45-1.59 (m, 0.8H), 1.70-1.89 (m, 2H), 1.93-2.22 (m, 2H), 2.45-2.69 (m, 3H), 2.72-2.90 (m, 1H), 2.99-3.18 (m, 2H), 3.40 (d, J=6.0 Hz, 1H), 3.61 (dd, J=6.0, 12.9 Hz, 0.8H), 3.84 (d, J=13.2 Hz, 1H), 4.15-4.28 (m, 0.4H), 4.89-5.01 (m, 1.6H), 5.03 (t, J=5.7 Hz, 0.2H), 6.52 (d, J=2.1 Hz, 0.2H), 6.57 (dd, J=2.4, 8.4 Hz, 0.2H), 6.67 (dd, J=2.4, 8.4 Hz, 0.8H), 6.72 (d, J=2.4 Hz, 0.8H), 6.86-6.94 (m, 0.2H), 6.92 (d, J=8.4 Hz, 0.8H), 7.30-7.54 (m, 5H)

Example 10

Synthesis of [(1S,3aR,5aS,6R,11bR,11cS)-10-hydroxy-14-isopropyl-1,2,3a,4,5,6,7,11c-octahydro-3H-6,11b-(iminoethano)-1,5a-epoxynaphtho[1,2-e]indol-3-yl](phenyl)methanone (14)

[Formula 38]

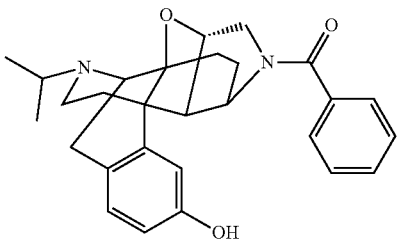

14

Under an argon atmosphere, the compound 11 (41.7 mg, 0.10 mmol) was dissolved in DMF (2 mL), the solution was added with 2-chloropropane (91.4 μL, 1.0 mmol), potassium carbonate (207 mg, 1.5 mmol), and sodium iodide (249 mg, 1.5 mmol), and the mixture was stirred at 80° C. for 22 hours. The reaction mixture was further added with DMF (1 mL), 2-chloropropane (366 μL, 4.0 mmol), potassium carbonate (828 mg, 6.0 mmol), and sodium iodide (996 mg, 6.0 mmol), and the mixture was further stirred at 80° C. for 22 hours. The reaction mixture was poured into distilled water, and the mixture was extracted three times with chloroform. The organic layers were combined, dried over anhydrous sodium sulfate, and then concentrated. Under an argon atmosphere, the obtained crude product was dissolved in dichloromethane (2 mL), the solution was added with a solution of boron tribromide in dichloromethane (1.0 mol/L, 0.5 mL, 0.50 mmol) under ice cooling, and the mixture was stirred at room temperature for 30 minutes. The reaction mixture was added with 6 M aqueous ammonia (10 mL) under ice cooling, and the mixture was stirred at room temperature for 30 minutes, and extracted three times with chloroform. The organic layers were combined, dried over anhydrous sodium sulfate, and then concentrated. The obtained crude product was purified by preparative TLC to give the title compound 14 as white amorphous (22.3 mg, 50%).

The obtained compound 14 was treated with a 20% solution of hydrogen chloride in methanol to give the hydrochloride of the compound 14.

Compound 14 (free base) $^1$H NMR (CDCl$_3$, 300 MHz): δ 0.64-1.36 (m, 2.2H), 1.14 (d, J=5.4 Hz, 6H), 1.40-1.58 (m, 0.8H), 1.66-1.87 (m, 2H), 1.90-2.22 (m, 2H), 2.62-3.18 (m, 5H), 3.52-3.70 (m, 1.8H), 3.84 (d, J=12.9 Hz, 1H), 4.15-4.28 (m, 0.4H), 4.85-4.98 (m, 1.6H), 5.00 (t, J=5.4 Hz, 0.2H), 6.49-6.75 (m, 2H), 6.86-6.94 (m, 0.2H), 6.91 (d, J=8.1 Hz, 0.8H), 7.30-7.54 (m, 5H)

Example 11

Synthesis of [(1S,3aR,5aS,6R,11bR,11cS)-10-hydroxy-14-isobutyl-1,2,3a,4,5,6,7,11c-octahydro-3H-6,11b-(iminoethano)-1,5a-epoxynaphtho[1,2-e]indol-3-yl](phenyl)methanone (15)

[Formula 39]

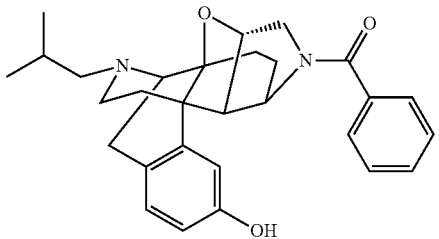

Under an argon atmosphere, the compound 11 (41.7 mg, 0.10 mmol) was dissolved in DMF (2 mL), the solution was added with 1-bromo-2-methylpropane (32.6 μL, 0.30 mmol), and potassium carbonate (41.4 mg, 0.3 mmol), and the mixture was stirred at 80° C. for 18 hours. The reaction mixture was poured into distilled water, and the mixture was extracted three times with chloroform. The organic layers were combined, dried over anhydrous sodium sulfate, and then concentrated. Under an argon atmosphere, the obtained crude product was dissolved in dichloromethane (2 mL), the solution was added with a solution of boron tribromide in dichloromethane (1.0 mol/L, 0.5 mL, 0.50 mmol) under ice cooling, and the mixture was stirred at room temperature for 30 minutes. The reaction mixture was added with 6 M aqueous ammonia (10 mL) under ice cooling, and the mixture was stirred at room temperature for 30 minutes, and extracted three times with chloroform. The organic layers were combined, dried over anhydrous sodium sulfate, and then concentrated. The obtained crude product was purified by preparative TLC to give the title compound 15 as white amorphous (18.6 mg, 41%).

The obtained compound 15 was treated with a 20% solution of hydrogen chloride in methanol to give the hydrochloride of the compound 15.

Compound 15 (free base) $^1$H NMR (CDCl$_3$, 300 MHz): δ 0.64-1.32 (m, 2.2H), 0.90 (d, J=6.3 Hz, 6H), 1.45-1.58 (m, 0.8H), 1.68-1.88 (m, 3H), 1.92-2.52 (m, 5H), 2.87 (dd, J=6.3, 10.6 Hz, 1H), 2.98-3.16 (m, 2H), 3.22-3.34 (m, 1H), 3.60 (dd, J=6.0, 12.9 Hz, 0.8H), 3.80-3.96 (m, 1H), 4.17-4.30 (m, 0.4H), 4.89-5.07 (m, 1.8H), 6.53 (d, J=2.7 Hz, 0.2H), 6.57 (dd, J=2.7, 8.4 Hz, 0.2H), 6.66 (dd, J=2.4, 8.4 Hz, 0.8H), 6.72 (d, J=2.4 Hz, 0.8H), 6.87-6.94 (m, 0.2H), 6.91 (d, J=8.1 Hz, 0.8H), 7.30-7.54 (m, 5H)

Example 12

Synthesis of [(1S,3aR,5aS,6R,11bR,11cS)-14-(cyclobutylmethyl)-10-hydroxy-1,2,3a,4,5,6,7,11c-octahydro-3H-6,11b-(iminoethano)-1,5a-epoxynaphtho[1,2-e]indol-3-yl](phenyl)methanone (16)

[Formula 40]

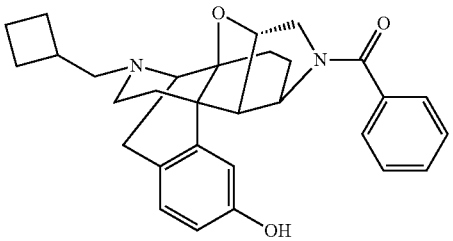

According to the method described in Example 11, the title compound 16 was obtained as colorless oil by using the compound 11 and (bromomethyl)cyclobutane.

The obtained compound 16 was treated with a 20% solution of hydrogen chloride in methanol to give the hydrochloride of the compound 16.

Compound 16 (free base) $^1$H NMR (CDCl$_3$, 300 MHz): δ 0.62-1.32 (m, 2.2H), 1.42-1.57 (m, 0.8H), 1.59-2.22 (m, 10H), 2.33-2.67 (m, 4H), 2.78 (dd, J=6.6, 18.3 Hz, 1H), 3.01 (dd, J=5.1, 8.4 Hz, 1H), 3.15 (d, J=18.6 Hz, 1H), 3.25 (d, J=5.7 Hz, 1H), 3.60 (dd, J=6.0, 12.9 Hz, 0.8H), 3.85 (d, J=12.9 Hz, 1H), 4.15-4.27 (m, 0.4H), 4.87-5.00 (m, 1.6H), 5.01 (t, J=6.0 Hz, 0.2H), 6.49 (d, J=2.4 Hz, 0.2H), 6.57 (dd, J=2.7, 8.4 Hz, 0.2H), 6.65 (dd, J=2.7, 8.4 Hz, 0.8H), 6.70 (d, J=2.4 Hz, 0.8H), 6.88-6.94 (m, 0.8H), 6.92 (d, J=8.4 Hz, 0.2H), 7.30-7.54 (m, 5H)

Example 13

Synthesis of [(1S,3aR,5aS,6R,11bR,11cS)-14-(cyclopentylmethyl)-10-methoxy-1,2,3a,4,5,6,7,11c-octahydro-3H-6,11b-(iminoethano)-1,5a-epoxynaphtho[1,2-e]indol-3-yl](phenyl)methanone (17)

[Formula 41]

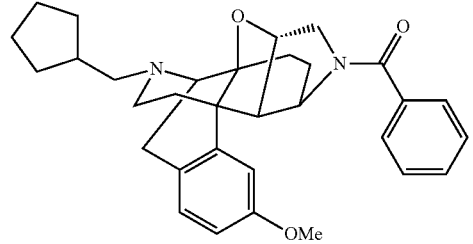

Under an argon atmosphere, the compound 11 (41.7 mg, 0.10 mmol) was dissolved in dichloromethane (5 mL), the solution was added with cyclopentanecarboaldehyde (43.0 μL, 0.40 mmol), acetic acid (48.0 μL, 0.8 mmol), and sodium triacetoxyborohydride (212 mg, 1.0 mmol), and the mixture was stirred at room temperature for 1 hour. The reaction mixture was added with 12 M aqueous ammonia (5 mL), the mixture was stirred at room temperature for 30 minutes, and poured into water, and the mixture was extracted three times with chloroform. The organic layers were combined, dried over anhydrous sodium sulfate, and then concentrated. The obtained crude product was purified by preparative TLC to give the title compound 17 as white amorphous (43.7 mg, 88%).

$^1$H NMR (CDCl$_3$, 300 MHz): δ 0.59-1.02 (m, 1H), 1.07-1.23 (m, 3.3H), 1.42-1.90 (m, 8.7H), 1.96-2.27 (m, 3H), 2.40-2.60 (m, 3H), 2.79-2.98 (m, 1H), 3.02-3.22 (m, 2H), 3.32-3.45 (m, 1H), 3.61 (dd, J=6.0, 12.6 Hz, 0.7H), 3.71 (s, 0.9H), 3.80 (s, 2.1H), 3.81-3.93 (m, 1H), 4.19-4.31 (m, 0.6H), 4.91-5.02 (m, 1.4H), 5.08 (t, J=5.7 Hz, 0.3H), 6.51 (d, J=2.7 Hz, 0.3H), 6.62-6.70 (m, 0.3H), 6.68 (d, J=2.4 Hz, 0.7H), 6.74 (dd, J=2.7, 8.7 Hz, 0.7H), 7.02 (d, J=8.4 Hz, 0.3H), 7.07 (d, J=8.7 Hz, 0.7H), 7.32-7.50 (m, 5H)

Example 14

Synthesis of [(1S,3aR,5aS,6R,11bR,11cS)-14-(cyclopentylmethyl)-10-hydroxy-1,2,3a,4,5,6,7,11c-octahydro-3H-6,11b-(iminoethano)-1,5a-epoxynaphtho[1,2-e]indol-3-yl](phenyl)methanone (18)

[Formula 42]

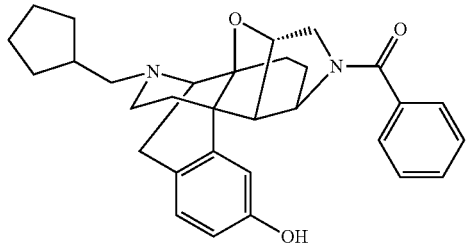

18

According to the method described in Example 6, the title compound 18 and the hydrochloride thereof were obtained as white amorphous from the compound 17. Compound 18 (free base) $^1$H NMR (CDCl$_3$, 300 MHz): δ 0.62-1.33 (m, 4.2H), 1.38-1.90 (m, 8.8H), 1.92-2.29 (m, 3H), 2.36-2.60 (m, 3H), 2.85 (dd, J=6.9, 12.3 Hz, 1H), 2.97-3.18 (m, 2H), 3.32-3.44 (m, 1H), 3.60 (dd, J=6.0, 12.6 Hz, 0.8H), 3.80-3.93 (m, 1H), 4.16-4.27 (m, 0.4H), 4.88-5.01 (m, 1.6H), 5.02 (t, J=5.7 Hz, 0.2H), 6.52 (d, J=2.7 Hz, 0.2H), 6.58 (dd, J=2.4, 8.4 Hz, 0.2H), 6.66 (dd, J=2.4, 8.4 Hz, 0.8H), 6.72 (d, J=2.4 Hz, 0.8H), 6.86-6.93 (m, 0.2H), 6.91 (d, J=8.1 Hz, 0.8H), 7.28-7.53 (m, 5H)

Example 15

Synthesis of [(1S,3aR,5aS,6R,11bR,11cS)-14-(cyclohexylmethyl)-10-hydroxy-1,2,3a,4,5,6,7,11c-octahydro-3H-6,11b-(iminoethano)-1,5a-epoxynaphtho[1,2-e]indol-3-yl](phenyl)methanone (19)

[Formula 43]

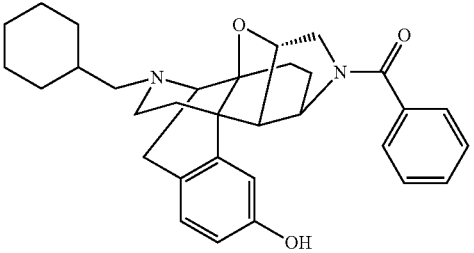

19

According to the method described in Example 11, the title compound 19 was obtained as white amorphous by using the compound 11 and (bromomethyl)cyclohexane.

The obtained compound 19 was treated with a 20% solution of hydrogen chloride in methanol to give the hydrochloride of the compound 19.

Compound 19 (free base) $^1$H NMR (CDCl$_3$, 300 MHz): δ 0.60-1.88 (m, 16H), 1.91-2.48 (m, 5H), 2.73-2.92 (m, 1H), 2.96-3.07 (m, 1H), 3.09 (d, J=18.6 Hz, 1H), 3.26 (d, J=5.7 Hz, 1H), 3.60 (dd, J=5.7, 12.9 Hz, 0.8H), 3.81-3.95 (m, 1H), 4.17-4.28 (m, 0.4H), 4.87-5.00 (m, 1.6H), 5.02 (t, J=6.0 Hz, 0.2H), 6.50 (d, J=2.4 Hz, 0.2H), 6.56 (dd, J=2.7, 8.4 Hz, 0.2H), 6.65 (dd, J=2.7, 8.4 Hz, 0.8H), 6.71 (d, J=2.4 Hz, 0.8H), 6.84-6.92 (d, J=8.4 Hz, 0.2H), 6.90 (d, J=8.1 Hz, 0.8H), 7.30-7.54 (m, 5H)

Example 16

Synthesis of [(1S,3aR,5aS,6R,11bR,11cS)-14-allyl-10-hydroxy-1,2,3a,4,5,6,7,11c-octahydro-3H-6,11b-(iminoethano)-1,5a-epoxynaphtho[1,2-e]indol-3-yl](phenyl)methanone (20)

[Formula 44]

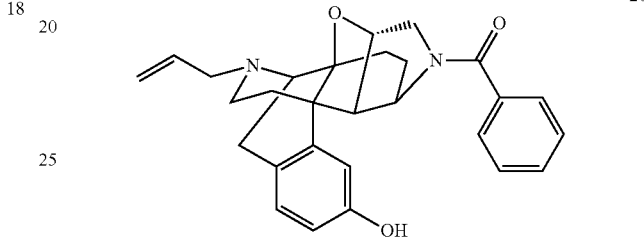

20

According to the method described in Example 8, the title compound 20 was obtained as white amorphous by using the compound 11 and allyl bromide.

The obtained compound 20 was treated with a 20% solution of hydrogen chloride in methanol to give the hydrochloride of the compound 20.

Compound 20 (free base) $^1$H NMR (CDCl$_3$, 300 MHz): δ 0.63-1.36 (m, 2.2H), 1.44-1.58 (m, 0.8H), 1.66-1.89 (m, 2H), 1.92-2.23 (m, 2H), 2.44-2.58 (m, 1H), 2.79 (dd, J=6.3, 18.3 Hz, 1H), 2.98-3.27 (m, 4H), 3.37 (d, J=6.0 Hz, 1H), 3.62 (dd, J=6.0, 12.9 Hz, 0.8H), 3.85 (d, J=13.2 Hz, 1H), 4.16-4.28 (m, 0.4H), 4.89-5.01 (m, 1.6H), 5.04 (t, J=6.0 Hz, 0.2H), 5.13 (d, J=10.2 Hz, 1H), 5.19 (d, J=17.4 Hz, 1H), 5.84-6.02 (m, 1H), 6.50 (d, J=2.4 Hz, 0.2H), 6.57 (dd, J=2.7, 8.4 Hz, 0.2H), 6.65 (dd, J=2.4, 8.4 Hz, 0.8H), 6.72 (d, J=2.4 Hz, 0.8H), 6.86-6.94 (m, 0.2H), 6.92 (d, J=8.4 Hz, 0.8H), 7.28-7.52 (m, 5H)

Example 17

Synthesis of [(1S,3aR,5aS,6R,11bR,11cS)-14-benzyl-10-hydroxy-1,2,3a,4,5,6,7,11c-octahydro-3H-6,11b-(iminoethano)-1,5a-epoxynaphtho[1,2-e]indol-3-yl](phenyl)methanone (21)

[Formula 45]

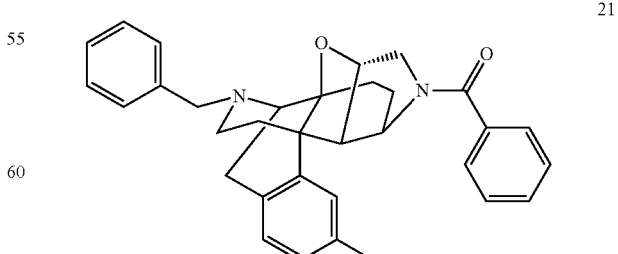

21

According to the method described in Example 8, the title compound 21 was obtained as white amorphous by using the compound 11 and benzyl bromide.

The obtained compound 21 was treated with a 20% solution of hydrogen chloride in methanol to give the hydrochloride of the compound 21.

Compound 21 (free base) $^1$H NMR (CDCl$_3$, 300 MHz): δ 0.60-1.37 (m, 2.2H), 1.40-1.58 (m, 0.8H), 1.60-1.85 (m, 2H), 1.90-2.37 (m, 2H), 2.38-2.57 (m, 1H), 2.84 (dd, J=6.3, 18.6 Hz, 1H), 3.03 (dd, J=5.4, 8.7 Hz, 1H), 3.16 (d, J=18.0 Hz, 0.2H), 3.19 (d, J=18.3 Hz, 0.8H), 3.31 (d, J=6.0 Hz, 1H), 3.55-3.86 (m, 2.8H), 3.90 (d, J=12.6 Hz, 1H), 4.14-4.31 (m, 0.4H), 4.89-5.00 (m, 1.6H), 5.06 (t, J=5.7 Hz, 0.2H), 6.48 (d, J=2.4 Hz, 0.2H), 6.58 (dd, J=2.4, 8.4 Hz, 0.2H), 6.67 (dd, J=2.7, 8.7 Hz, 0.8H), 6.72 (d, J=2.4 Hz, 0.8H), 6.92 (d, J=8.4 Hz, 0.2H), 6.93 (d, J=8.4 Hz, 0.8H), 7.18-7.52 (m, 10H)

Example 18

Synthesis of [(1S,3aR,5aS,6R,11bR,11cS)-10-hydroxy-14-phenethyl-1,2,3a,4,5,6,7,11e-octahydro-3H-6,11b-(iminoethano)-1,5a-epoxynaphtho[1,2-e]indol-3-yl](phenyl)methanone (22)

[Formula 46]

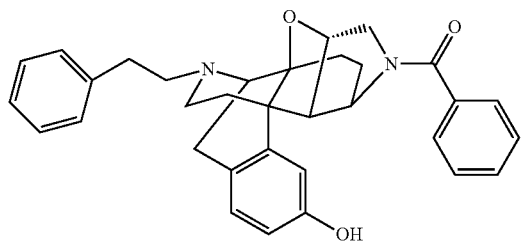

22

According to the method described in Example 11, the title compound 22 was obtained as colorless oil by using the compound 11 and (2-bromoethyl)benzene.

The obtained compound 22 was treated with a 20% solution of hydrogen chloride in methanol to give the hydrochloride of the compound 22. Compound 22 (free base) $^1$H NMR (CDCl$_3$, 300 MHz): δ 0.63-1.39 (m, 2.2H), 1.42-1.62 (m, 0.8H), 1.67-1.93 (m, 2H), 1.95-2.36 (m, 2H), 2.51-2.97 (m, 6H), 3.04 (d, J=5.4, 8.7 Hz, 1H), 3.16 (d, J=18.3 Hz, 1H), 3.46 (d, J=5.7 Hz, 1H), 3.64 (dd, J=6.0, 12.9 Hz, 0.8H), 3.87 (d, J=12.9 Hz, 1H), 4.14-4.33 (m, 0.4H), 4.87-5.05 (m, 1.6H), 5.06 (t, J=5.7 Hz, 0.2H), 6.54 (d, J=2.1 Hz, 0.2H), 6.60 (dd, J=2.4, 8.1 Hz, 0.2H), 6.67 (dd, J=2.4, 8.1 Hz, 0.8H), 6.74 (d, J=2.4 Hz, 0.8H), 6.85-6.94 (m, 0.2H), 6.92 (d, J=8.4 Hz, 0.8H), 7.08-7.54 (m, 10H)

Example 19

Synthesis of [(1S,3aR,5aS,6R,11bR,11cS)-10-hydroxy-14-(3-phenylpropyl)-1,2,3a,4,5,6,7,11c-octahydro-3H-6,11b-(iminoethano)-1,5a-epoxynaphtho[1,2-e]indol-3-yl](phenyl)methanone (23)

[Formula 47]

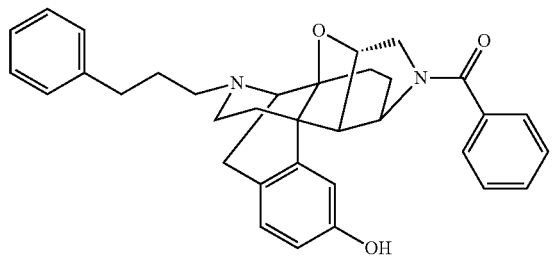

23

According to the method described in Example 11, the title compound 23 was obtained as white amorphous by using the compound 11 and (3-bromopropyl)benzene.

The obtained compound 23 was treated with a 20% solution of hydrogen chloride in methanol to give the hydrochloride of the compound 23.

Compound 23 (free base) $^1$H NMR (CDCl$_3$, 300 MHz): δ 0.59-1.33 (m, 2.2H), 1.41-1.56 (m, 0.8H), 1.63-2.25 (m, 6H), 2.42-2.68 (m, 5H), 2.81 (dd, J=6.3, 18.3 Hz, 1H), 3.00 (dd, J=5.1, 9.0 Hz, 1H), 3.09 (d, J=18.3 Hz, 1H), 3.35 (d, J=6.0 Hz, 1H), 3.60 (dd, J=6.0, 12.9 Hz, 0.8H), 3.84 (d, J=12.6 Hz, 1H), 4.14-4.26 (m, 0.4H), 4.87-4.99 (m, 1.6H), 5.01 (t, J=5.7 Hz, 0.2H), 6.51 (d, J=2.1 Hz, 0.2H), 6.57 (dd, J=2.4, 8.4 Hz, 0.2H), 6.65 (dd, J=2.4, 8.1 Hz, 0.8H), 6.71 (d, J=2.4 Hz, 0.8H), 6.88 (d, J=8.4 Hz, 0.2H), 6.89 (d, J=8.4 Hz, 0.8H), 7.11-7.51 (m, 10H)

Example 20

Synthesis of [(1S,3aR,5aS,6R,11bR,11cS)-10-hydroxy-14-(4-phenylbutyl)-1,2,3a,4,5,6,7,11c-octahydro-3H-6,11b-(iminoethano)-1,5a-epoxynaphtho[1,2-e]indol-3-yl](phenyl)methanone (24)

[Formula 48]

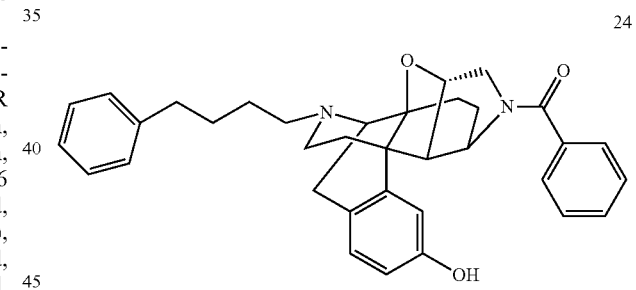

24

According to the method described in Example 11, the title compound 24 was obtained as white amorphous by using the compound 11 and (4-bromobutyl)benzene.

The obtained compound 24 was treated with a 20% solution of hydrogen chloride in methanol to give the hydrochloride of the compound 24.

Compound 24 (free base) $^1$H NMR (CDCl$_3$, 300 MHz): δ 0.59-1.34 (m, 2.2H), 1.41-1.86 (m, 6.8H), 1.92-2.24 (m, 2H), 2.39-2.67 (m, 5H), 2.81 (dd, J=6.6, 18.6 Hz, 1H), 3.03 (dd, J=6.6, 8.7 Hz, 1H), 3.11 (d, J=18.6 Hz, 1H), 3.34 (d, J=5.7 Hz, 1H), 3.61 (dd, J=6.0, 12.9 Hz, 0.8H), 3.85 (d, J=12.9 Hz, 1H), 4.14-4.27 (m, 0.4H), 4.88-5.00 (m, 1.6H), 5.02 (t, J=6.0 Hz, 0.2H), 6.51 (d, J=2.4 Hz, 0.2H), 6.57 (dd, J=2.4, 8.1 Hz, 0.2H), 6.66 (dd, J=2.4, 8.1 Hz, 0.8H), 6.72 (d, J=2.4 Hz, 0.8H), 6.90 (d, J=8.4 Hz, 0.2H), 6.91 (d, J=8.4 Hz, 0.8H), 7.11-7.52 (m, 10H)

Example 21

Synthesis of [(1S,3aR,5aS,6R,11bR,11cS)-10-methoxy-14-(2-methoxyethyl)-1,2,3a,4,5,6,7,11c-octahydro-3H-6,11b-(iminoethano)-1,5a-epoxynaphtho[1,2-e]indol-3-yl](phenyl)methanone (25)

[Formula 49]

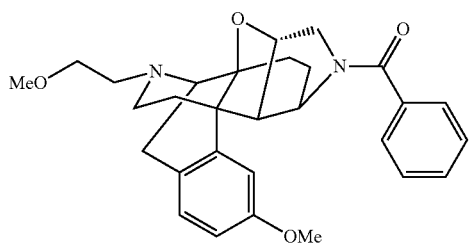

Under an argon atmosphere, the compound 11 (83.3 mg, 0.20 mmol) was dissolved in DMF (5 mL), the solution was added with 1-bromo-2-methoxyethane (188 μL, 2.0 mmol), potassium carbonate (415 mg, 3.0 mmol), and sodium iodide (498 mg, 3.0 mmol), and the mixture was stirred at 100° C. for 3 hours. The reaction mixture was poured into distilled water, and the mixture was extracted three times with chloroform. The organic layers were combined, dried over anhydrous sodium sulfate, and then concentrated. The obtained crude product was purified by preparative TLC to give the title compound 25 as white amorphous (79.9 mg, 88%).

$^1$H NMR (CDCl$_3$, 300 MHz): δ 0.61-0.80 (m, 0.3H), 0.82-1.02 (m, 0.7H), 1.07-1.33 (m, 1.3H), 1.44-1.58 (m, 0.7H), 1.67-1.90 (m, 2H), 1.95-2.33 (m, 2H), 2.46-2.58 (m, 1H), 2.63-3.00 (m, 3H), 3.02-3.13 (m, 1H), 3.19 (d, J=18.6 Hz, 1H), 3.34 (s, 3H), 3.39 (d, J=6.0 Hz, 1H), 3.48-3.68 (m, 2.7H), 3.71 (s, 0.9H), 3.80 (s, 2.1H), 3.85 (d, J=12.6 Hz, 1H), 4.18-4.30 (m, 0.6H), 4.89-5.01 (m, 1.4H), 5.07 (t, J=5.7 Hz, 0.3H), 6.52 (d, J=2.4 Hz, 0.3H), 6.61-6.71 (m, 0.3H), 6.68 (d, J=2.7 Hz, 0.7H), 6.74 (dd, J=2.7, 8.7 Hz, 0.7H), 7.03 (d, J=8.7 Hz, 0.3H), 7.08 (d, J=8.4 Hz, 0.7H), 7.30-7.50 (m, 5H)

Example 22

Synthesis of [(1S,3aR,5aS,6R,11bR,11cS)-10-hydroxy-14-(2-methoxyethyl)-1,2,3a,4,5,6,7,11c-octahydro-3H-6,11b-(iminoethano)-1,5a-epoxynaphtho[1,2-e]indol-3-yl](phenyl)methanone (26)

[Formula 50]

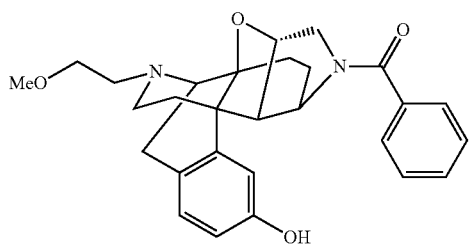

Under an argon atmosphere, the compound 25 (44.1 mg, 0.093 mmol) was dissolved in DMF (2 mL), the solution was added with 1-dodecanethiol (334 μL, 1.4 mmol), and potassium t-butoxide (103 mg, 0.93 mmol), and the mixture was stirred at 150° C. for 5 hours. The reaction mixture was made acidic by adding 2 M hydrochloric acid under ice cooling, and added with diethyl ether, and the mixture was extracted three times with 2 M hydrochloric acid. The aqueous layers were combined, adjusted to pH 10 with potassium carbonate, and extracted three times with chloroform. The organic layers were combined, dried over anhydrous sodium sulfate, and then concentrated. The obtained crude product was purified by preparative TLC to give the title compound 26 (24.5 mg, 57%) as colorless oil.

The obtained compound 26 was treated with a 20% solution of hydrogen chloride in methanol to give the hydrochloride of the compound 26. Compound 26 (free base) $^1$H NMR (CDCl$_3$, 300 MHz): δ 0.63-1.33 (m, 2.2H), 1.43-1.57 (m, 0.8H), 1.65-1.88 (m, 2H), 1.93-2.36 (m, 2H), 2.47-2.60 (m, 1H), 2.66-2.96 (m, 3H), 3.03 (dd, J=5.1, 8.7 Hz, 1H), 3.14 (d, J=18.3 Hz, 1H), 3.30 (s, 3H), 3.38 (d, J=5.7 Hz, 1H), 3.48-3.67 (m, 2.8H), 3.85 (d, J=12.9 Hz, 1H), 4.15-4.27 (m, 0.4H), 4.88-5.01 (m, 5.02 (t, J=5.7 Hz, 0.2H), 6.49 (d, J=2.4 Hz, 0.2H), 6.57 (dd, J=2.7, 8.4 Hz, 0.2H), 6.65 (dd, J=2.4, 8.1 Hz, 0.8H), 6.71 (d, J=2.4 Hz, 0.8H), 6.86-6.95 (m, 0.2H), 6.92 (d, J=8.4 Hz, 0.8H), 7.31-7.53 (m, 5H)

Example 23

Synthesis of [(1S,3aR,5aS,6R,11bR,11cS)-10-hydroxy-14-(2-hydroxyethyl)-1,2,3a,4,5,6,7,11c-octahydro-3H-6,11b-(iminoethano)-1,5a-epoxynaphtho[1,2-e]indol-3-yl](phenyl)methanone (27)

[Formula 51]

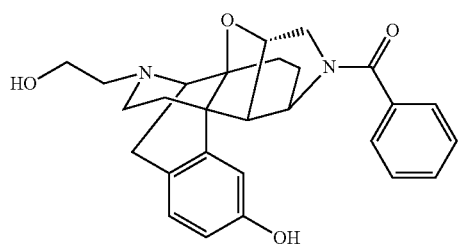

According to the method described in Example 6, the title compound 27 was obtained as white amorphous from the compound 25.

The obtained compound 27 was treated with a 20% solution of hydrogen chloride in methanol to give the hydrochloride of the compound 27.

Compound 27 (free base) $^1$H NMR (CDCl$_3$, 300 MHz): δ 0.65-1.34 (m, 2.2H), 1.44-1.58 (m, 0.8H), 1.66-1.85 (m, 2H), 1.89-2.09 (m, 1H), 2.17-2.83 (m, 4H), 2.92-3.13 (m, 3H), 3.24-3.34 (m, 1H), 3.53-3.69 (m, 2.8H), 3.79-3.92 (m, 1H), 4.17-4.29 (m, 0.4H), 4.84-5.00 (m, 1.6H), 5.03 (t, J=5.7 Hz, 0.2H), 6.51 (d, J=2.1 Hz, 0.2H), 6.59 (dd, J=2.4, 8.1 Hz, 0.2H), 6.67 (dd, J=2.4, 8.4 Hz, 0.8H), 6.72 (d, J=2.4 Hz, 0.8H), 6.87-6.96 (m, 0.2H), 6.92 (d, J=8.4 Hz, 0.8H), 7.31-7.54 (m, 5H)

Example 24

Synthesis of [(1S,3aR,5aS,6R,11bR,11cS)-10-hydroxy-14-(3-methoxypropyl)-1,2,3a,4,5,6,7,11c-octahydro-3H-6,11b-(iminoethano)-1,5a-epoxynaphtho[1,2-e]indol-3-yl](phenyl)methanone (28)

[Formula 52]

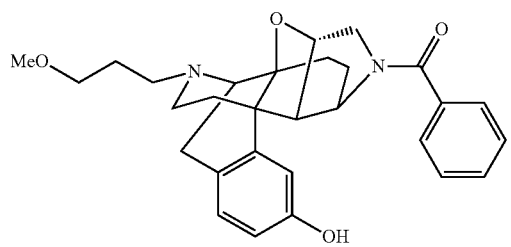

Under an argon atmosphere, the compound 11 (41.7 mg, 0.10 mmol) was dissolved in DMF (2 mL), the solution was added with 1-bromo-3-methoxypropane (34.0 μL, 0.30 mmol), and potassium carbonate (41.4 mg, 0.3 mmol), and the mixture was stirred at 80° C. for 1 hour. The reaction mixture was poured into distilled water, and the mixture was extracted three times with chloroform. The organic layers were combined, dried over anhydrous sodium sulfate, and then concentrated. Under an argon atmosphere, the obtained crude product was dissolved in DMF (2 mL), the solution was added with 1-dodecanethiol (334 μL, 1.4 mmol), and potassium t-butoxide (103 mg, 0.93 mmol), and the mixture was stirred at 150° C. for 3 hours. The reaction mixture was made acidic by adding 2 M hydrochloric acid under ice cooling, and added with diethyl ether, and the mixture was extracted three times with 2 M hydrochloric acid. The aqueous layers were combined, adjusted to pH 10 with potassium carbonate, and extracted three times with chloroform. The organic layers were combined, dried over anhydrous sodium sulfate, and then concentrated. The obtained crude product was purified by preparative TLC to give the title compound 28 as colorless oil (43.9 mg, 93%).

The obtained compound 28 was treated with a 20% solution of hydrogen chloride in methanol to give the hydrochloride of the compound 28.

Compound 28 (free base) $^1$H NMR (CDCl$_3$, 300 MHz): δ 0.63-1.35 (m, 2.2H), 1.42-1.58 (m, 0.8H), 1.65-2.27 (m, 6H), 2.44-2.68 (m, 3H), 2.73-2.92 (m, 1H), 3.02 (dd, J=5.1, 8.4 Hz, 1H), 3.13 (d, J=18.6 Hz, 1H), 3.24-3.48 (m, 6H), 3.60 (dd, J=6.0, 12.9 Hz, 0.8H), 3.84 (d, J=12.9 Hz, 1H), 4.14-4.28 (m, 0.4H), 4.85-5.00 (m, 1.6H), 5.01 (t, J=5.4 Hz, 0.2H), 6.49 (d, J=2.4 Hz, 0.2H), 6.56 (dd, J=2.4, 8.4 Hz, 0.2H), 6.65 (dd, J=2.7, 8.4 Hz, 0.8H), 6.70 (d, J=2.4 Hz, 0.8H), 6.84-6.93 (m, 0.2H), 6.91 (d, J=8.4 Hz, 0.8H), 7.23-7.54 (m, 5H)

Example 25

Synthesis of [(1S,3aR,5aS,6R,11bR,11cS)-10-hydroxy-14-(2-hydroxy-2-methylpropyl)-1,2,3a,4,5,6,7,11c-octahydro-3H-6,11b-(iminoethano)-1,5a-epoxynaphtho[1,2-e]indol-3-yl](phenyl)methanone (29)

[Formula 53]

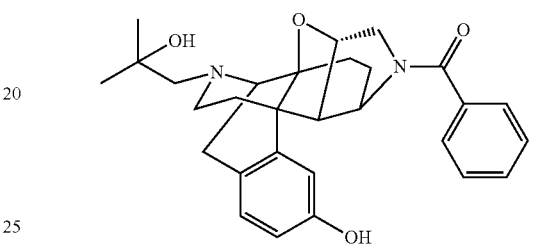

Under an argon atmosphere, the compound 11 (41.7 mg, 0.10 mmol) was dissolved in DMF (2 mL), the solution was added with 1-chloro-2-methyl-2-propanol (103 μL, 1.0 mmol), potassium carbonate (207 mg, 1.5 mmol), and sodium iodide (249 mg, 1.5 mmol), and the mixture was stirred at 100° C. for 12 hours. The reaction mixture was poured into distilled water, and the mixture was extracted three times with chloroform. The organic layers were combined, dried over anhydrous sodium sulfate, and then concentrated. Under an argon atmosphere, the obtained crude product was dissolved in dichloromethane (2 mL), the solution was added with a solution of boron tribromide in dichloromethane (1.0 mol/L, 0.5 mL, 0.50 mmol) under ice cooling, and the mixture was stirred at room temperature for 30 minutes. The reaction mixture was added with 6 M aqueous ammonia (10 mL) under ice cooling, and the mixture was stirred at room temperature for 30 minutes, and extracted three times with chloroform. The organic layers were combined, dried over anhydrous sodium sulfate, and then concentrated. The obtained crude product was purified by preparative TLC to give the title compound 29 as white amorphous (29.7 mg, 63%).

The obtained compound 29 was treated with a 20% solution of hydrogen chloride in methanol to give the hydrochloride of the compound 29.

Compound 29 (free base) $^1$H NMR (CDCl$_3$, 300 MHz): δ 0.63-1.29 (m, 2.2H), 1.15 (s, 6H), 1.43-1.57 (m, 0.8H), 1.60-1.84 (m, 2H), 1.91-2.12 (m, 1H), 2.33-2.73 (m, 4H), 2.92-3.17 (m, 3H), 3.24-3.37 (m, 1H), 3.61 (dd, J=5.7, 12.6 Hz, 0.8H), 3.78-3.92 (m, 1H), 4.18-4.29 (m, 0.4H), 4.86-5.00 (m, 1.6H), 5.03 (t, J=6.0 Hz, 0.2H), 6.50 (d, J=2.4 Hz, 0.2H), 6.60 (dd, J=2.7, 8.4 Hz, 0.2H), 6.67 (dd, J=2.4, 8.1 Hz, 0.8H), 6.72 (d, J=2.4 Hz, 0.8H), 6.90 (d, J=8.1 Hz, 0.2H), 6.91 (d, J=8.1 Hz, 0.8H), 7.30-7.53 (m, 5H)

Example 26

Synthesis of (1S,3aR,5aS,6R,11bR,11cS)-14-(cyclopropylmethyl)-10-methoxy-3-phenyl-2,3,3a,4,5,6,7,11c-octahydro-1H-6,11b-(iminoethano)-1,5a-epoxynaphtho[1,2-e]indole (30)

[Formula 54]

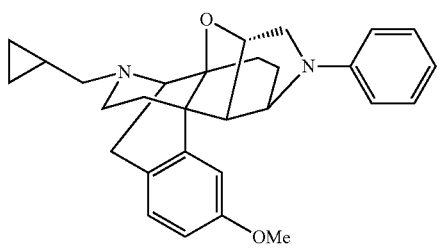

Under an argon atmosphere, the compound 8 (55.0 mg, 0.15 mmol) was dissolved in toluene (2 mL), the solution was added with tris(dibenzylideneacetone)dipalladium (5.80 mg, 0.010 mmol), 2,2'-bis(diphenylphosphino)-1,1'-binaphthyl (12.5 mg, 0.020 mmol), bromobenzene (21.1 μL, 0.20 mmol), and sodium t-butoxide (24.0 mg, 0.25 mmol), and the mixture was stirred at 80° C. for 12 hours. The reaction mixture was added with ethyl acetate (5 mL), and the mixture was filtered through Celite, and then concentrated. The obtained crude product was purified by preparative TLC to give the title compound 30 as colorless oil (30.3 mg, 46%).

$^1$H NMR (CDCl$_3$, 300 MHz): δ 0.03-0.18 (m, 2H), 0.43-0.76 (m, 3H), 0.90-1.05 (m, 1H), 1.23-1.51 (m, 2H), 1.65-1.77 (m, 2H), 2.02-2.35 (m, 3H), 2.58 (dd, J=5.7, 12.6 Hz, 1H), 2.64-2.74 (m, 1H), 2.84 (dd, J=6.3, 18.6 Hz, 1H), 3.04-3.20 (m, 2H), 3.56-3.72 (m, 3H), 3.83 (s, 3H), 4.31 (dd, J=4.8, 8.1 Hz, 1H), 5.13 (t, J=5.4 Hz, 1H), 6.51 (d, J=8.4 Hz, 2H), 6.65 (t, J=7.2 Hz, 1H), 6.71-6.78 (m, 2H), 7.04-7.12 (m, 1H), 7.20 (t, J=7.5 Hz, 2H)

Example 27

Synthesis of (1S,3aR,5aS,6R,11bR,11cS)-14-(cyclopropylmethyl)-3-phenyl-2,3,3a,4,5,6,7,11c-octahydro-1H-6,11b-(iminoethano)-1,5a-epoxynaphtho[1,2-e]indol-10-ol (31)

[Formula 55]

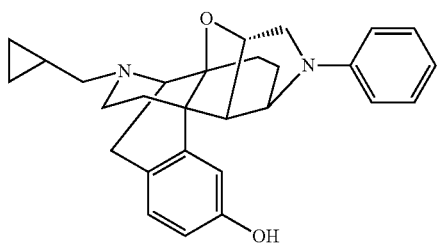

According to the method described in Example 6, the title compound 31 was obtained as white amorphous from the compound 30.

The obtained compound 31 was treated with a 20% solution of hydrogen chloride in methanol to give the hydrochloride of the compound 31.

Compound 31 (free base) $^1$H NMR (CDCl$_3$, 300 MHz): δ 0.06-0.23 (m, 2H), 0.43-1.08 (m, 4H), 1.20-1.53 (m, 2H), 1.60-1.82 (m, 2H), 2.02-2.30 (m, 2H), 2.36 (dd, J=7.2, 12.3 Hz, 1H), 2.63 (dd, J=5.4, 12.3 Hz, 1H), 2.75 (d, J=6.0 Hz, 1H), 2.87 (dd, J=6.0, 18.3 Hz, 1H), 3.01-3.18 (m, 2H), 3.48-3.72 (m, 2H), 3.68 (d, J=5.7 Hz, 1H), 4.22-4.37 (m, 1H), 5.00-5.13 (m, 1H), 6.48 (d, J=8.1 Hz, 2H), 6.58-6.81 (m, 3H), 6.99 (d, J=8.4 Hz, 1H), 7.12-7.30 (m, 2H)

Example 28

Synthesis of (1S,3aR,5aS,6R,11bR,11cS)-3-benzyl-10-methoxy-14-methyl-2,3,3a,4,5,6,7,11c-octahydro-1H-6,11b-(iminoethano)-1,5a-epoxynaphtho[1,2-e]indole (32)

[Formula 56]

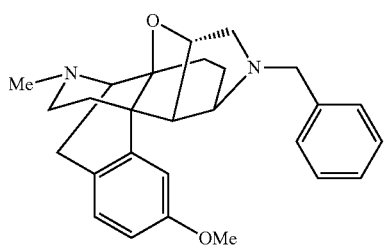

Under an argon atmosphere, the compound 9 (1.28 g, 2.7 mmol) was dissolved in 1,1,2,2-tetrachloroethane (20 mL), the solution was added with potassium carbonate (732 mg, 5.4 mmol), and 2,2,2-trichloroethyl chloroformate (732 μL, 5.4 mmol), and the mixture was stirred at 150° C. for 1 hour. The reaction mixture was poured into distilled water, the mixture was extracted three times with chloroform, the organic layers were combined, dried over anhydrous sodium sulfate, and then concentrated. From the obtained crude product, excessive regents were removed by silica gel column chromatography. A solution of the obtained crude product in THF (10 mL) was added to a suspension of THF (30 mL) and lithium aluminum hydride (448 mg, 12 mmol) under ice cooling, and the mixture was stirred at room temperature for 1 hour. The reaction mixture was added with ethyl acetate (50 mL), and saturated aqueous sodium sulfate (10 mL) under ice cooling, and the mixture was stirred at room temperature for 2 hours. The reaction mixture was filtered through Celite, and then concentrated. The obtained crude product was purified by silica gel column chromatography to give the title compound 32 as colorless oil (575 mg, 51%).

$^1$H NMR (CDCl$_3$, 300 MHz): δ 0.43-0.60 (m, 1H), 1.18-1.31 (m, 1H), 1.44-1.56 (m, 1H), 1.62-1.83 (m, 2H), 2.00-2.20 (m, 2H), 2.34-2.49 (m, 1H), 2.39 (s, 3H), 2.77 (dd, J=2.7, 10.8 Hz, 1H), 2.84 (dd, J=6.6, 18.6 Hz, 1H), 3.03 (t, J=6.6 Hz, 1H), 3.18 (dd, J=18.0 Hz, 1H), 3.20 (d, J=6.3 Hz, 1H), 3.29 (dd, J=6.9, 10.8 Hz, 1H), 3.48 (t, J=6.6 Hz, 1H), 3.67 (d, J=13.2 Hz, 1H), 3.76 (s, 3H), 3.78 (d, J=13.5 Hz, 1H), 4.91-4.99 (m, 1H), 6.66-6.73 (m, 2H), 7.06 (d, J=8.7 Hz, 1H), 7.17-7.36 (m, 5H)

Example 29

Synthesis of (1S,3aR,5aS,6R,11bR,11cS)-10-methoxy-14-methyl-2,3,3a,4,5,6,7,11c-octahydro-1H-6,11b-(iminoethano)-1,5a-epoxynaphtho[1,2-e]indole (33)

[Formula 57]

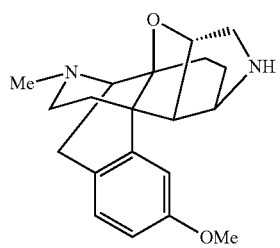

The compound 32 (572 mg, 1.4 mmol) was dissolved in acetic acid (10 mL), the solution was added with 10% palladium-carbon (585 mg), and the mixture was stirred at 50° C. for 12 hours under a hydrogen atmosphere. The reaction mixture was filtered through Celite, and then concentrated. The obtained crude product was purified by silica gel column chromatography to give the title compound 33 as white amorphous (195 mg, 44%).

$^1$H NMR (CD$_3$OD, 300 MHz): δ 0.77-0.98 (m, 1H), 1.09 (dd, J=7.5, 10.5 Hz, 1H), 1.22-1.35 (m, 1H), 1.58-1.86 (m, 2H), 1.96-2.20 (m, 2H), 2.27-2.42 (m, 1H), 2.32 (s, 3H), 2.83-3.01 (m, 2H), 3.07 (dd, J=2.4, 12.6 Hz, 1H), 3.14 (d, J=6.9 Hz, 1H), 3.19 (d, J=18.9 Hz, 1H), 3.27-3.40 (m, 1H), 3.55 (t, J=7.2 Hz, 1H), 3.77 (s, 3H), 4.84-4.91 (m, 1H), 6.72-6.79 (m, 2H), 7.09 (d, J=8.4 Hz, 1H)

Example 30

Synthesis of (1S,3aR,5aS,6R,11bR,11cS)-10-methoxy-14-methyl-3-phenyl-2,3,3a,4,5,6,7,11c-octahydro-1H-6,11b-(iminoethano)-1,5a-epoxynaphtho[1,2-e]indole (34)

[Formula 58]

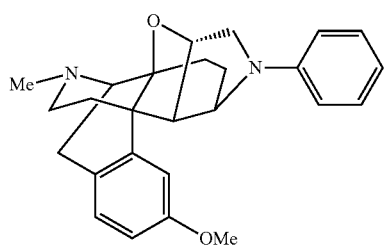

According to the method described in Example 26, the title compound 34 was obtained as white amorphous from the compound 33.

The obtained compound 34 was treated with a 20% solution of hydrogen chloride in methanol to give the hydrochloride of the compound 34. Compound 34 (free base) $^1$H NMR (CDCl$_3$, 300 MHz): δ 0.59-0.77 (m, 1H), 1.27-1.50 (m, 2H), 1.64-1.74 (m, 2H), 2.11-2.27 (m, 1H), 2.37-2.57 (m, 2H), 2.44 (s, 3H), 2.88 (dd, J=6.3, 18.3 Hz, 1H), 3.10-3.28 (m, 3H), 3.55-3.69 (m, 2H), 3.83 (s, 3H), 4.31 (dd, J=4.5, 8.1 Hz, 1H), 5.07-5.14 (m, 1H), 6.50 (d, J=7.8 Hz, 2H), 6.64 (t, J=7.2 Hz, 1H), 6.72-6.78 (m, 2H), 7.10 (d, J=9.0 Hz, 1H), 7.14-7.23 (m, 2H)

Example 31

Synthesis of (1S,3aR,5aS,6R,11bR,11cS)-14-methyl-3-phenyl-2,3,3a,4,5,6,7,11c-octahydro-1H-6,11b-(iminoethano)-1,5a-epoxynaphtho[1,2-e]indol-10-ol (35)

[Formula 59]

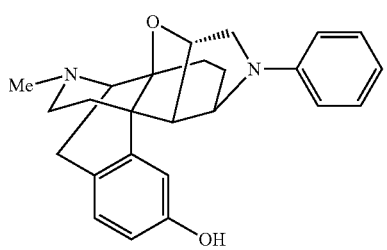

According to the method described in Example 6, the title compound 35 was obtained as white amorphous from the compound 34.

The obtained compound 35 was treated with a 20% solution of hydrogen chloride in methanol to give the hydrochloride of the compound 35.

Compound 35 (free base) $^1$H NMR (CDCl$_3$, 300 MHz): δ 0.65-0.84 (m, 1H), 1.21-1.50 (m, 2H), 1.60-1.78 (m, 2H), 2.10-2.30 (m, 2H), 2.42 (s, 3H), 2.43-2.58 (m, 1H), 2.88 (dd, J=6.3, 18.6 Hz, 1H), 3.09 (dd, J=5.1, 8.4 Hz, 1H), 3.17 (d, J=18.6 Hz, 1H), 3.25 (d, J=6.0 Hz, 1H), 3.51-3.65 (m, 2H), 4.30 (dd, J=4.5, 8.4 Hz, 1H), 5.01-5.10 (m, 1H), 6.48 (d, J=7.8 Hz, 2H), 6.64 (t, J=7.5 Hz, 1H), 6.67-6.75 (m, 2H), 7.01 (d, J=8.7 Hz, 1H), 7.14-7.24 (m, 2H)

Example 32

Synthesis of (3-chlorophenyl)[(1S,3aR,5aS,6R,11bR,11cS)-10-hydroxy-14-methyl-1,2,3a,4,5,6,7,11c-octahydro-3H-6,11b-(iminoethano)-1,5a-epoxynaphtho[1,2-e]indol-3-yl]methanone (36)

[Formula 60]

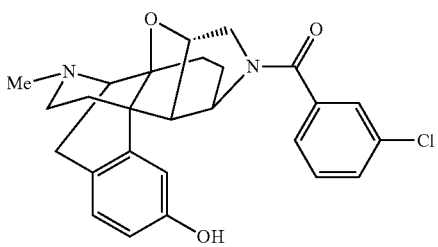

Under an argon atmosphere, the compound 33 (32.6 mg, 0.10 mmol) was dissolved in dichloromethane (2 mL), the solution was added with 3-chlorobenzoyl chloride (15.3 μL, 0.12 mmol), and triethylamine (16.7 μL, 0.12 mmol), and the mixture was stirred at room temperature for 30 minutes. The reaction mixture was poured into 2 M aqueous sodium hydroxide, and the mixture was extracted three times with chloroform. The organic layers were combined, dried over anhydrous sodium sulfate, and then concentrated. Under an argon atmosphere, the obtained crude product was dissolved in dichloromethane (2 mL), the solution was added with a solution of boron tribromide in dichloromethane (1.0 mol/L, 0.5 mL, 0.50 mmol) under ice cooling, and the mixture was stirred at room temperature for 30 minutes. The reaction mixture was added with 6 M aqueous ammonia (10 mL) under ice cooling, and the mixture was stirred at room temperature for 30 minutes, and extracted three times with chloroform. The organic layers were combined, dried over anhydrous sodium sulfate, and then concentrated. The obtained crude product was purified by preparative TLC to give the title compound 36 as white amorphous (26.9 mg, 60%).

The obtained compound 36 was treated with a 20% solution of hydrogen chloride in methanol to give the hydrochloride of the compound 36.

Compound 36 (free base) $^1$H NMR (CDCl$_3$, 300 MHz): δ 0.67-1.39 (m, 2.2H), 1.42-1.57 (m, 0.8H), 1.69-1.90 (m, 2H), 1.94-2.28 (m, 2H), 2.32-2.54 (m, 1H), 2.40 (s, 3H), 2.86 (dd, J=6.3, 18.6 Hz, 1H), 2.99-3.23 (m, 2H), 3.25 (d, J=6.0 Hz, 1H), 3.62 (dd, J=6.0, 12.9 Hz, 0.8H), 3.75-3.88 (m, 1H), 4.11-4.26 (m, 0.4H), 4.85-5.01 (m, 1.6H), 5.03 (t, J=6.0 Hz, 0.2H), 6.51 (d, J=2.4 Hz, 0.2H), 6.59 (dd, J=2.1, 8.4 Hz, 0.2H), 6.65 (dd, J=2.4, 8.4 Hz, 0.8H), 6.69 (d, J=2.4 Hz, 0.8H), 6.93 (d, J=8.1 Hz, 0.2H), 6.95 (d, J=8.4 Hz, 0.8H), 7.18-7.85 (m, 4H)

Example 33

Synthesis of [(1S,3aR,5aS,6R,11bR,11cS)-14-cyclopropylmethyl-10-methoxy-1,2,3a,4,5,6,7,11c-octahydro-3H-6,11b-(iminoethano)-1,5a-epoxynaphtho[1,2-e]-indol-3-yl][(3-trifluoromethyl)phenyl]methanone (37)

[Formula 61]

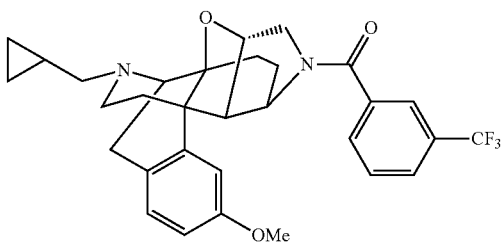

Under an argon atmosphere, the compound 8 (30.0 mg, 0.0819 mmol) was dissolved in dichloromethane (1 mL), the solution was added with 3-(trifluoromethyl)benzoyl chloride (24 μL, 0.16 mmol), and triethylamine (23 μL, 0.16 mmol), and the mixture was stirred at 5° C. for 30 minutes. The reaction mixture was poured into saturated aqueous sodium hydrogencarbonate, and the mixture was extracted three times with chloroform. The organic layers were combined, dried over anhydrous sodium sulfate, and then concentrated. The obtained crude product was purified by preparative TLC to give the title compound 37 as colorless oil (37.7 mg, 86%).

The obtained compound 37 was treated with a 20% solution of hydrogen chloride in methanol to give the hydrochloride of the compound 37.

Compound 37 (hydrochloride) $^1$H NMR (CD$_3$ OD, 400 MHz): δ 0.40-0.56 (m, 2H), 0.60-1.02 (m, 3.6H), 1.06-1.20 (m, 1.4H), 1.54-1.72 (m, 2H), 1.80-2.04 (m, 2H), 2.16-2.34 (m, 1H), 2.78-2.96 (m, 1H), 2.96-3.10 (m, 1H), 3.10-3.23 (m, 1H), 3.23-3.61 (m, 3.3H), 3.71 (s, 0.9H), 3.79 (dd, J=5.9, 12.7 Hz, 0.7H), 3.82-3.92 (m, 1H), 3.84 (s, 2.1H), 4.24 (dd, J=6.7, 14.8 Hz, 0.3H), 4.30-4.40 (m, 1.4H), 4.88-4.98 (m, 0.3H), 5.07 (t, J=5.2 Hz, 0.7H), 5.18 (t, J=5.8 Hz, 0.3H), 6.76 (d, J=2.5 Hz, 0.3H), 6.83 (dd, J=2.5, 8.6 Hz, 0.3H), 6.88-6.98 (m, 1.4H), 7.18 (d, J=8.6 Hz, 0.3H), 7.25 (d, J=8.4 Hz, 0.7H), 7.62-7.92 (m, 4H)

Example 34

Synthesis of [(1S,3aR,5aS,6R,11bR,11cS)-14-cyclopropylmethyl-10-hydroxy-1,2,3a,4,5,6,7,11c-octahydro-3H-6,11b-(iminoethano)-1,5a-epoxynaphtho[1,2-e]indol-3-yl][(3-trifluoromethyl)phenyl]methanone (38)

[Formula 62]

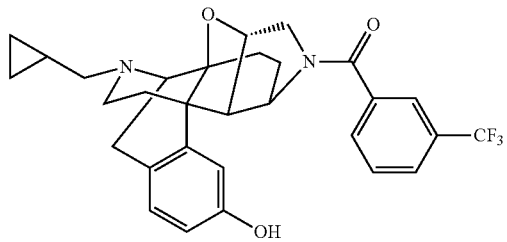

According to the method described in Example 6, the title compound 38 and the hydrochloride thereof were obtained from the compound 37.

Compound 38 (hydrochloride) $^1$H NMR (CD$_3$ OD, 400 MHz): δ 0.43-0.56 (m, 2H), 0.68-0.92 (m, 2.3H), 0.92-1.28 (m, 2.7H), 1.54-1.70 (m, 2H), 1.82-2.02 (m, 2H), 2.16-2.32 (m, 1H), 2.80-2.96 (m, 1H), 2.96-3.08 (m, 1H), 3.12-3.22 (m, 1H), 3.22-3.54 (m, 3.3H), 3.78 (dd, J=5.7, 12.7 Hz, 0.7H), 3.85 (d, J=12.3 Hz, 1H), 4.22-4.36 (m, 1.7H), 4.90-4.96 (m, 0.3H), 5.06 (t, J=5.1 Hz, 0.7H), 5.17 (t, J=5.6 Hz, 0.3H), 6.60 (d, J=2.5 Hz, 0.3H), 6.69 (dd, J=2.5, 8.4 Hz, 0.3H), 6.74-6.82 (m, 1.4H), 7.08 (d, J=8.4 Hz, 0.3H), 7.15 (d, J=8.2 Hz, 0.7H), 7.62-7.88 (m, 4H)

Example 35

Synthesis of (3-chlorophenyl) [(1S,3aR,5aS,6R,11bR,11cS)-14-(cyclopropylmethyl)-10-methoxy-1,2,3a,4,5,6,7,11c-octahydro-3H-6,11b-(iminoethano)-1,5a-epoxynaphtho[1,2-e]indol-3-yl]methanone (39)

[Formula 63]

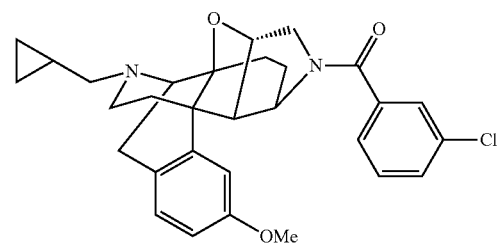

According to the method described in Example 33, the title compound 39 and the hydrochloride thereof were obtained by using the compound 8 and 3-chlorobenzoyl chloride.

Compound 39 (hydrochloride) $^1$H NMR (CD$_3$ OD, 400 MHz): δ 0.42-0.57 (m, 2H), 0.60-1.02 (m, 3H), 1.06-1.21 (m, 1H), 1.52-1.72 (m, 2H), 1.80-2.03 (m, 2H), 2.17-2.34 (m, 1H), 2.77-2.95 (m, 1H), 3.01 (dd, J=7.4, 13.5 Hz, 1H), 3.16 (dd, J=5.0, 12.9 Hz, 1H), 3.24-3.52 (m, 3.4H), 3.53-3.60 (m, 0.3H), 3.72 (s, 0.9H), 3.75-3.89 (m, 2H), 3.82 (s, 2.1H), 4.20 (dd, J=6.7, 14.5 Hz, 0.3H), 4.30-4.43 (m, 1.3H), 4.88-4.93 (m, 0.7H), 5.05 (t, J=5.2 Hz, 0.7H), 5.16 (t, J=5.8 Hz, 0.3H), 6.77 (d, J=2.7 Hz, 0.3H), 6.83 (dd, J=2.7, 8.6 Hz, 0.3H), 6.87-6.95 (m, 1.4H), 7.17 (d, J=8.6 Hz, 0.3H), 7.23 (d, J=8.6 Hz, 0.7H), 7.35-7.54 (m, 4H)

Example 36

Synthesis of (3-chlorophenyl)[(1S,3aR,5aS,6R,11bR,11cS)-14-(cyclopropylmethyl)-10-hydroxy-1,2,3a,4,5,6,7,11c-octahydro-3H-6,11b-(iminoethano) 1,5a-epoxynaphtho[1,2-e]indol-3-yl]methanone (40)

[Formula 64]

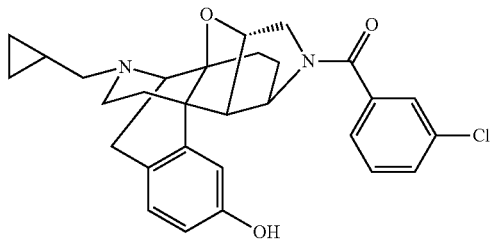

40

According to the method described in Example 6, the title compound 40 and the hydrochloride thereof were obtained from the compound 39.

Compound 40 (hydrochloride) $^1$H NMR (CD$_3$OD, 400 MHz): δ 0.39-0.55 (m, 2H), 0.68-0.90 (m, 2H), 0.92-1.07 (m, 1H), 1.08-1.25 (m, 1H), 1.52-1.68 (m, 2H), 1.81-1.99 (m, 2H), 2.15-2.30 (m, 1H), 2.75-2.94 (m, 1H), 2.95-3.07 (m, 1H), 3.08-3.19 (m, 1H), 3.20-3.55 (m, 4.4H), 3.73-3.88 (m, 2H), 4.20 (dd, J=6.7, 14.5 Hz, 0.3H), 4.25-4.37 (m, 1.3H), 5.04 (t, J=5.5 Hz, 0.7H), 5.15 (t, J=5.5 Hz, 0.3H), 6.60 (d, J=2.5 Hz, 0.3H), 6.68 (dd, J=2.4, 8.4 Hz, 0.3H), 6.73-6.85 (m, 1.4H), 7.07 (d, J=8.4 Hz, 0.3H), 7.13 (d, J=8.0 Hz, 0.7H), 7.35-7.55 (m, 4H)

Example 37

Synthesis of (3-cyanophenyl)[(1S,3aR,5aS,6R,11bR,11cS)-14-(cyclopropylmethyl)-10-methoxy-1,2,3a,4,5,6,7,11c-octahydro-3H-6,11b-(iminoethano)-1,5a-epoxynaphtho[1,2-e]indol-3-yl]methanone (41)

[Formula 65]

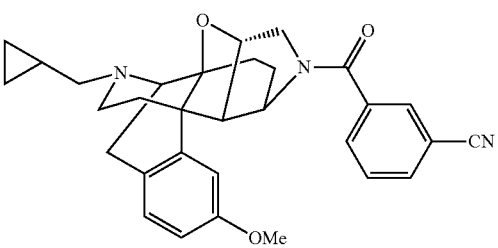

41

According to the method described in Example 33, the title compound 41 and the hydrochloride thereof were obtained by using the compound 8 and 3-cyanobenzoyl chloride.

Compound 41 (free base) $^1$H NMR (CDCl$_3$, 400 MHz): δ 0.04-0.20 (m, 2H), 0.46-0.62 (m, 2H), 0.84-1.02 (m, 2H), 1.02-1.15 (m, 0.2H), 1.20-1.40 (m, 1H), 1.51 (dd, J=6.8, 15.1 Hz, 0.8H), 1.57-1.95 (m, 3H), 2.00-2.23 (m, 2H), 2.23-2.40 (m, 1H), 2.47-2.76 (m, 2H), 2.78-2.97 (m, 1H), 3.03-3.20 (m, 2H), 3.60 (dd, J=5.9, 12.7 Hz, 1H), 3.73 (s, 0.6H), 3.80 (s, 2.4H), 3.67-3.92 (m, 0.8H), 4.10-4.32 (m, 0.4H), 4.93 (dd, J=5.4, 8.3 Hz, 0.8H), 5.02 (t, J=5.4 Hz, 0.8H), 5.07-5.15 (m, 0.2H), 6.52 (d, J=2.9 Hz, 0.2H), 6.68 (d, J=2.9 Hz, 1H), 6.74 (dd, J=2.4, 8.3 Hz, 0.8H), 7.03 (d, J=8.8 Hz, 0.2H), 7.07 (d, J=8.8 Hz, 0.8H), 7.50-7.80 (m, 4H)

Example 38

Synthesis of (3-cyanophenyl)[(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl]methanone (42)

[Formula 66]

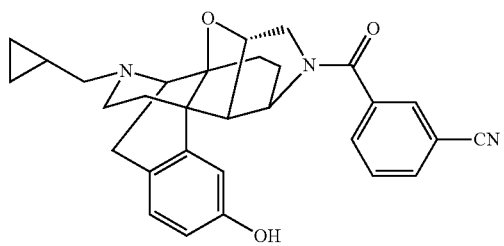

42

According to the method described in Example 6, the title compound 42 and the hydrochloride thereof were obtained from the compound 41.

Compound 42 (free base) $^1$H NMR (CDCl$_3$, 400 MHz): δ 0.03-0.18 (m, 2H), 0.45-0.61 (m, 2H), 0.87-1.03 (m, 2H), 1.04-1.15 (m, 0.2H), 1.20-1.38 (m, 1H), 1.50 (dd, J=5.9, 14.6 Hz, 0.8H), 1.75-1.92 (m, 2H), 1.99-2.20 (m, 2H), 2.22-2.37 (m, 1H), 2.44-2.73 (m, 2H), 2.74-2.90 (m, 1H), 3.01-3.27 (m, 2H), 3.57-3.75 (m, 1.8H), 3.81 (d, J=12.7 Hz, 0.8H), 3.87 (d, J=14.6 Hz, 0.2H), 4.10-4.33 (m, 0.4H), 4.92 (dd, J=5.9, 7.8 Hz, 0.8H), 5.01 (t, J=5.4 Hz, 0.8H), 5.06-5.13 (m, 0.2H), 6.49 (d, J=2.4 Hz, 0.2H), 6.59 (dd, J=2.4, 8.3 Hz, 0.2H), 6.62-6.70 (m, 1.6H), 6.92-7.20 (m, 1H), 7.47-7.80 (m, 4H)

Example 39

Synthesis of [(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl](4-methylphenyl)methanone (43)

[Formula 67]

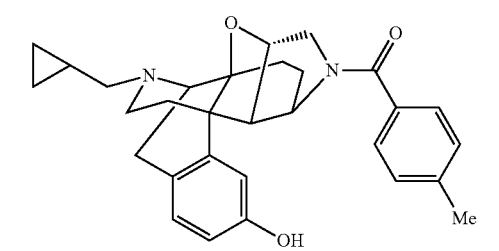

43

According to the method described in Example 32, the title compound 43 and the hydrochloride thereof were obtained by using the compound 8 and 4-methylbenzoyl chloride.

Compound 43 (hydrochloride)

$^1$H NMR (CD$_3$ OD, 400 MHz): δ 0.41-0.56 (m, 2H), 0.68-0.90 (m, 2H), 0.92-1.07 (m, 1H), 1.08-1.25 (m, 1H), 1.52-1.70 (m, 2H), 1.80-2.00 (m, 2H), 2.16-2.31 (m, 1H), 2.36 (s, 1.2H), 2.38 (s, 1.8H), 2.79-2.96 (m, 1H), 3.01 (dd, J=7.2, 13.5 Hz, 1H), 3.16 (dd, J=5.9, 13.5 Hz, 1H), 3.24-3.45 (m, 3.2H), 3.45-3.51 (m, 0.4H), 3.75-3.85 (m, 1.2H), 3.89 (d, J=12.7 Hz, 0.8H), 4.23 (dd, J=6.9, 14.5 Hz, 0.4H), 4.28-4.36 (m, 1H), 4.41 (dd, J=5.3, 7.8 Hz, 0.4H), 4.88-4.96 (m, 0.6H), 5.05 (t, J=5.3 Hz, 0.6H), 5.16 (t, J=5.7 Hz, 0.4H), 6.60 (d, J=2.6 Hz, 0.4H), 6.69 (dd, J=2.5, 8.4 Hz, 0.4H), 6.73-6.81 (m, 1.2H), 7.08 (d, J=8.4 Hz, 0.4H), 7.15 (d, J=8.4 Hz, 0.6H), 7.22-7.43 (m, 4H)

Example 40

Synthesis of [(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl](3-methylphenyl)methanone (44)

[Formula 68]

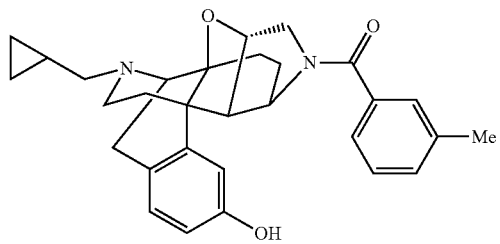

44

According to the method described in Example 32, the title compound 44 and the hydrochloride thereof were obtained by using the compound 8 and 3-methylbenzoyl chloride.

Compound 44 (hydrochloride) $^1$H NMR (CD$_3$ OD, 400 MHz): δ 0.42-0.54 (m, 2H), 0.64-0.88 (m, 2H), 0.95-1.05 (m, 1H), 1.09-1.25 (m, 2H), 1.53-1.68 (m, 2H), 1.82-1.97 (m, 2H), 2.16-2.29 (m, 1H), 2.36 (s, 1.2H), 2.39 (s, 1.8H), 2.80-2.95 (m, 1H), 3.01 (dd, J=7.0, 13.1 Hz, 1H), 3.16 (dd, J=5.3, 13.1 Hz, 1H), 3.25-3.52 (m, 3.6H), 3.73-3.90 (m, 1.6H), 4.22 (dd, J=6.7, 14.5 Hz, 0.4H), 4.28-4.40 (m, 1.4H), 5.04 (t, J=5.5 Hz, 0.6H), 5.16 (t, J=5.5 Hz, 0.4H), 6.60 (d, J=2.5 Hz, 0.4H), 6.69 (dd, J=2.5, 8.4 Hz, 0.4H), 6.76 (dd, J=2.5, 8.4 Hz, 0.6H), 6.78 (d, J=2.5 Hz, 0.6H), 7.08 (d, J=8.4 Hz, 0.4H), 7.14 (d, J=8.4 Hz, 0.6H), 7.19-7.47 (m, 4H)

Example 41

Synthesis of [(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl][4-(trifluoromethyl)phenyl]methanone (45)

[Formula 69]

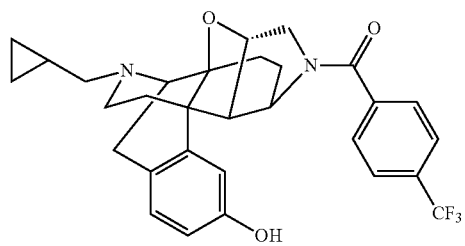

45

According to the method described in Example 32, the title compound 45 and the hydrochloride thereof were obtained by using the compound 8 and 4-(trifluoromethyl)benzoyl chloride.

Compound 45 (hydrochloride) $^1$H NMR (CD$_3$ OD, 400 MHz): δ 0.28-0.56 (m, 2H), 0.67-0.93 (m, 2H), 0.94-1.07 (m, 1H), 1.08-1.26 (m, 2H), 1.52-1.72 (m, 2H), 1.82-2.00 (m, 2H), 2.14-2.31 (m, 1H), 2.74-2.95 (m, 1H), 2.96-3.08 (m, 1H), 3.08-3.21 (m, 1H), 3.22-3.45 (m, 2.6H), 3.46-3.54 (m, 0.3H), 3.76 (dd, J=6.1, 12.7 Hz, 0.7H), 3.85 (d, J=12.3 Hz, 1H), 4.20-4.40 (m, 1.7H), 4.88-4.97 (m, 0.7H), 5.05 (t, J=5.7 Hz, 0.7H), 5.17 (t, J=6.3 Hz, 0.3H), 6.60 (s, 0.3H), 6.68 (dd, J=2.5, 8.4 Hz, 0.3H), 6.73-6.83 (m, 1.4H), 7.08 (d, J=8.4 Hz, 0.3H), 7.15 (d, J=8.4 Hz, 0.7H), 7.61-7.73 (m, 2H), 7.73-7.85 (m, 2H)

Example 42

Synthesis of [(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl](3,5-dichlorophenyl)methanone (46)

[Formula 70]

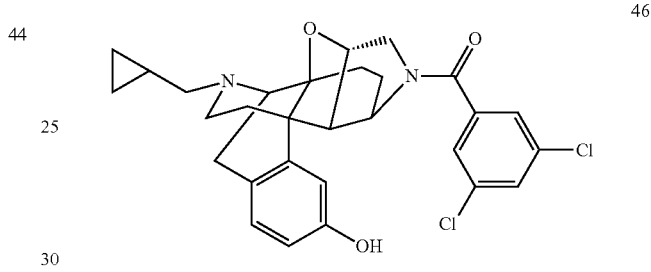

46

According to the method described in Example 32, the title compound 46 and the hydrochloride thereof were obtained by using the compound 8 and 3,5-dichlorobenzoyl chloride.

Compound 46 (free base) $^1$H NMR (CDCl$_3$, 400 MHz): δ 0.04-0.17 (m, 2H), 0.45-0.60 (m, 2H), 0.85-1.01 (m, 2H), 1.05-1.18 (m, 0.2H), 1.20-1.37 (m, 1H), 1.49 (dd, J=6.3, 15.6 Hz, 0.8H), 1.75-1.90 (m, 2H), 1.98-2.21 (m, 2H), 2.22-2.35 (m, 1H), 2.50-2.72 (m, 1H), 2.76-2.92 (m, 1H), 3.01-3.14 (m, 2H), 3.45-3.75 (m, 1.8H), 3.80 (d, J=12.7 Hz, 1H), 4.08-4.32 (m, 0.4H), 4.88 (dd, J=5.4, 8.3 Hz, 0.8H), 4.99 (t, J=5.4 Hz, 0.8H), 5.04-5.10 (m, 0.2H), 6.52 (d, J=2.4 Hz, 0.2H), 6.60 (dd, J=2.9, 8.3 Hz, 0.2H), 6.63-6.68 (m, 1.6H), 6.96 (d, J=9.3 Hz, 1H), 7.23 (d, J=2.0 Hz, 0.4H), 7.32 (d, J=1.5 Hz, 1.6H), 7.37 (t, J=2.0 Hz, 0.2H), 7.41 (t, J=2.0 Hz, 0.8H)

Example 43

Synthesis of (3-carbamoylphenyl)[(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl]methanone (47)

[Formula 71]

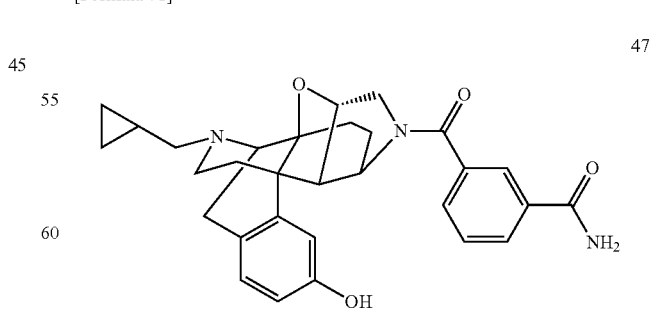

47

According to the method described in Example 32, the title compound 47 and the hydrochloride thereof were obtained by using the compound 8 and 3-carbamoylbenzoyl chloride.

Compound 47 (free base) ¹H NMR (CD₃ OD, 400 MHz): δ 0.10-0.26 (m, 2H), 0.45-0.80 (m, 2.3H), 0.80-1.04 (m, 1.7H), 1.05-1.21 (m, 0.3H), 1.22-1.38 (m, 1H), 1.52 (dd, J=6.3, 14.1 Hz, 0.7H), 1.69-1.96 (m, 2H), 1.97-2.27 (m, 2H), 2.28-2.40 (m, 1H), 2.47-2.61 (m, 2H), 2.78-3.00 (m, 1H), 3.02-3.15 (m, 1H), 3.21 (dd, J=4.4, 8.3 Hz, 0.7H), 3.27-3.40 (m, 1H), 3.62-3.76 (m, 1.7H), 3.81 (d, J=12.7 Hz, 1H), 4.16 (dd, J=6.3, 14.6 Hz, 0.3H), 4.23-4.31 (m, 0.3H), 4.94 (t, J=4.9 Hz, 0.7H), 5.06 (t, J=5.9 Hz, 0.3H), 6.50 (d, J=2.4 Hz, 0.3H), 6.55 (dd, J=2.4, 8.3 Hz, 0.3H), 6.65 (dd, J=2.9, 8.3 Hz, 0.7H), 6.70 (d, J=2.4 Hz, 0.7H), 6.94 (d, J=8.8 Hz, 0.3H), 7.02 (d, J=8.3 Hz, 0.7H), 7.50-7.68 (m, 2H), 7.90-8.01 (m, 2H)

Example 44

Synthesis of [(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl][3-(N,N-diethylcarbamoylphenyl)]methanone (48)

[Formula 72]

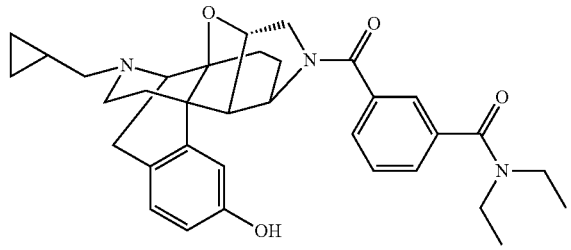

48

According to the method described in Example 32, the title compound 48 and the hydrochloride thereof were obtained by using the compound 8 and 3-(diethylcarbamoyl)benzoyl chloride.

Compound 48 (free base) ¹H NMR (CD₃ OD, 400 MHz): δ 0.09-0.23 (m, 2H), 0.44-0.76 (m, 2H), 0.83-1.40 (m, 9H), 1.51 (dd, J=7.2, 15.2 Hz, 0.6H), 1.68-1.95 (m, 2H), 1.95-2.26 (m, 2H), 2.27-2.40 (m, 1H), 2.44-2.63 (m, 2H), 2.79-2.97 (m, 1H), 3.02-3.16 (m, 1H), 3.17-3.43 (m, 4H), 3.45-3.87 (m, 4.6H), 4.14 (dd, J=7.3, 14.6 Hz, 0.4H), 4.25-4.35 (m, 0.4H), 4.90-4.98 (m, 0.6H), 5.01-5.09 (m, 0.4H), 6.46-6.51 (m, 0.4H), 6.52-6.60 (m, 0.4H), 6.65 (dd, J=2.4, 8.3 Hz, 0.6H), 6.67-6.72 (m, 0.6H), 6.94 (d, J=8.3 Hz, 0.4H), 7.02 (d, J=8.3 Hz, 0.6H), 7.40-7.60 (m, 4H)

Example 45

Synthesis of [(1S,3aR,5aS,6R,11bR,11cS)-14-cyclopropylmethyl-10-hydroxy-1,2,3a,4,5,6,7,11c-octahydro-3H-6,11b-(iminoethano)-1,5a-epoxynaphtho[1,2-e]indol-3-yl](2-fluorophenyl)methanone (49)

[Formula 73]

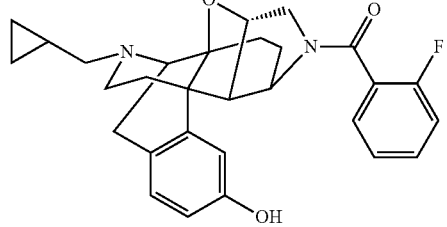

49

According to the method described in Example 32, the title compound 49 and the hydrochloride thereof were obtained by using the compound 8 and 2-fluorobenzoyl chloride.

Compound 49 (hydrochloride)
¹H NMR (CD₃ OD, 400 MHz): δ 0.40-0.55 (m, 2H), 0.66-1.04 (m, 3.4H), 1.06-1.23 (m, 1.6H), 1.54-1.72 (m, 2H), 1.78-2.04 (m, 2H), 2.14-2.32 (m, 1H), 2.76-2.96 (m, 1H), 2.96-3.08 (m, 1H), 3.08-3.22 (m, 1H), 3.22-3.56 (m, 2.6H), 3.62-3.76 (m, 1.6H), 3.85 (d, J=14.7 Hz, 0.4H), 4.16-4.38 (m, 2H), 4.98-5.11 (m, 1H), 5.19 (t, J=5.6 Hz, 0.4H), 6.59 (d, J=2.5 Hz, 0.4H), 6.68 (dd, J=2.5, 8.4 Hz, 0.4H), 6.72-6.83 (m, 1.2H), 7.08 (d, J=8.4 Hz, 0.4H), 7.15 (d, J=8.2 Hz, 0.6H), 7.17-7.58 (m, 4H)

Example 46

Synthesis of [(1S,3aR,5aS,6R,11bR,11cS)-14-cyclopropylmethyl-10-hydroxy-1,2,3a,4,5,6,7,11c-octahydro-3H-6,11b-(iminoethano)-1,5a-epoxynaphtho[1,2-e]indol-3-yl](2-furyl)methanone (50)

[Formula 74]

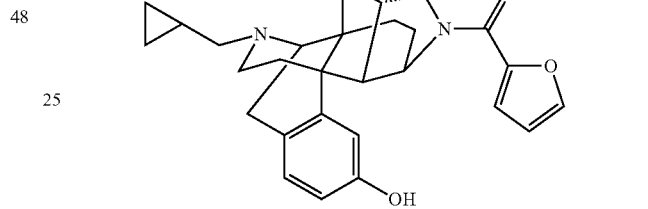

50

According to the method described in Example 32, the title compound 50 and the hydrochloride thereof were obtained by using the compound 8 and 2-furoyl chloride. Compound 50 (hydrochloride) ¹H NMR (CD₃ OD, 400 MHz): δ 0.44-0.56 (m, 2H), 0.70-0.88 (m, 2H), 0.88-1.02 (m, 1H), 1.08-1.34 (m, 2H), 1.39 (dd, J=7.1, 15.2 Hz, 0.4H), 1.53 (dd, J=6.8, 15.2 Hz, 0.6H), 1.60-1.70 (m, 1H), 1.76-1.97 (m, 2H), 2.29 (dt, J=5.1, 13.7 Hz, 1H), 2.82-2.96 (m, 1H), 3.03 (dd, J=7.0, 13.3 Hz, 1H), 3.19 (dd, J=4.4, 12.4 Hz, 1H), 3.24-3.50 (m, 3H), 3.54 (dd, J=5.4, 8.3 Hz, 0.6H), 3.86 (d, J=14.9 Hz, 0.4H), 4.18 (dd, J=6.4, 14.9 Hz, 0.4H), 4.22-4.38 (m, 2.2H), 5.11 (t, J=5.6 Hz, 0.4H), 5.16 (dd, J=5.2, 8.1 Hz, 0.4H), 5.21 (t, J=5.2 Hz, 0.6H), 6.57 (dd, J=1.8, 3.5 Hz, 0.4H), 6.62 (dd, J=1.8, 3.5 Hz, 0.6H), 6.73-6.81 (m, 2H), 7.11-7.20 (m, 2H), 7.68 (d, J=1.0 Hz, 0.4H), 7.75 (d, J=1.2 Hz, 0.6H)

Example 47

Synthesis of [(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl](2-naphthyl)methanone (51)

[Formula 75]

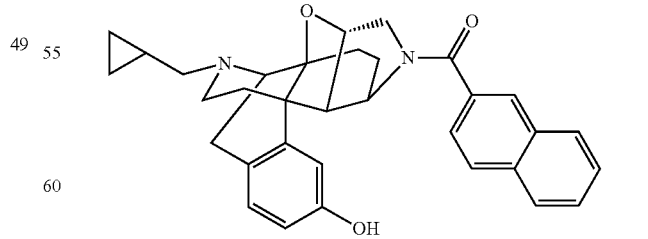

51

According to the method described in Example 32, the title compound 51 and the hydrochloride thereof were obtained by using the compound 8 and 2-naphthoyl chloride.

Compound 51 (hydrochloride) ¹H NMR (CD₃ OD, 400 MHz): δ 0.42-0.55 (m, 2H), 0.67-0.90 (m, 2.4H), 0.98-1.20

(m, 2H), 1.24-1.35 (m, 0.6H), 1.56-1.71 (m, 2H), 1.81-2.05 (m, 2H), 2.18-2.31 (m, 1H), 2.78-2.96 (m, 1H), 3.01 (dd, J=7.2, 13.5 Hz, 1H), 3.16 (dd, J=5.1, 12.9 Hz, 1H), 3.24-3.37 (m, 1.6H), 3.38-3.46 (m, 1H), 3.46-3.54 (m, 0.4H), 3.80-4.00 (m, 1.6H), 4.26-4.37 (m, 1.4H), 4.42-4.48 (m, 0.4H), 4.97 (dd, J=4.9, 8.6 Hz, 0.6H), 5.05 (t, J=5.3 Hz, 0.6H), 5.16-5.22 (m, 0.4H), 6.56 (d, J=2.4 Hz, 0.4H), 6.63 (dd, J=2.5, 8.4 Hz, 0.4H), 6.77 (dd, J=2.5, 8.4 Hz, 0.6H), 6.80 (d, J=2.5 Hz, 0.6H), 7.04 (d, J=8.4 Hz, 0.4H), 7.15 (d, J=8.4 Hz, 0.6H), 7.48-7.61 (m, 3H), 7.87-8.05 (m, 4H)

Example 48

Synthesis of 1-[(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl]-2-phenylethanone (52)

[Formula 76]

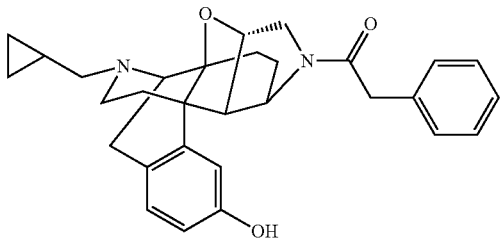

52

According to the method described in Example 32, the title compound 52 and the hydrochloride thereof were obtained by using the compound 8 and phenylacetyl chloride.

Compound 52 (hydrochloride) $^1$H NMR (CD$_3$ OD, 400 MHz): δ 0.40-0.55 (m, 2H), 0.68-0.98 (m, 3H), 1.00-1.20 (m, 1.4H), 1.20-1.36 (m, 1H), 1.48 (dd, J=7.2, 14.9 Hz, 1H), 1.57-1.72 (m, 2H), 1.74-1.94 (m, 1.6H), 2.15-2.31 (m, 1H), 2.88 (dt, J=4.1, 13.1 Hz, 1H), 2.95-3.06 (m, 1H), 3.09-3.21 (m, 1H), 3.24-3.50 (m, 2H), 3.61-3.83 (m, 3H), 3.94-4.06 (m, 1H), 4.26 (d, J=5.5 Hz, 0.6H), 4.31 (d, J=5.5 Hz, 0.4H), 4.58-4.70 (m, 1H), 5.08 (t, J=5.3 Hz, 1H), 6.70-6.78 (m, 2H), 7.12 (d, J=8.8 Hz, 0.6H), 7.13 (d, J=8.2 Hz, 0.4H), 7.19-7.37 (m, 5H)

Example 49

Synthesis of (cyclopropyl)[(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl]methanone (53)

[Formula 77]

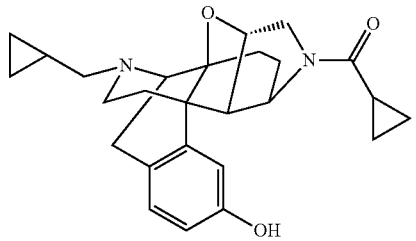

53

According to the method described in Example 32, the title compound 53 and the hydrochloride thereof were obtained by using the compound 8 and cyclopropanecarbonyl chloride.

Compound 53 (hydrochloride) $^1$H NMR (CD$_3$ OD, 400 MHz): δ 0.39-0.54 (m, 2H), 0.69-0.98 (m, 7H), 1.04-1.18 (m, 1.6H), 1.33-1.53 (m, 1H), 1.53-1.68 (m, 1H), 1.68-2.00 (m, 3H), 2.18-2.33 (m, 1H), 2.75-3.20 (m, 3H), 3.20-3.55 (m, 1.6H), 3.69 (d, J=14.6 Hz, 1H), 3.89 (dd, J=6.3, 14.6 Hz, 0.6H), 4.02 (d, J=12.2 Hz, 0.6H), 4.14 (dd, J=5.9, 12.7 Hz, 0.6H), 4.18-4.35 (m, 1H), 4.50-4.65 (m, 2H), 5.03-5.18 (m, 1H), 6.67-6.80 (m, 2H), 7.05-7.16 (m, 1H)

Example 50

Synthesis of (biphenyl-2-yl)[(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl]methanone (54)

[Formula 78]

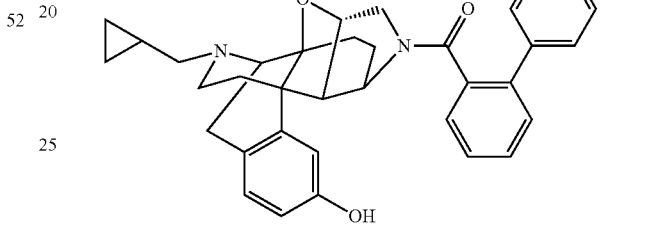

54

According to the method described in Example 32, the title compound 54 and the hydrochloride thereof were obtained by using the compound 8 and biphenyl-2-carbonyl chloride.

Compound 54 (free base) $^1$H NMR (CDCl$_3$, 400 MHz): δ 0.01-0.15 (m, 2H), 0.35-0.57 (m, 2H), 0.57-0.75 (m, 1H), 0.80-1.11 (m, 1.4H), 1.11-1.30 (m, 1.8H), 1.30-1.75 (m, 2H), 1.75-1.98 (m, 2H), 1.98-2.12 (m, 1H), 2.20-2.50 (m, 2H), 2.50-2.77 (m, 2H), 2.92-3.02 (m, 1H), 3.02-3.46 (m, 2.4H), 3.46-3.90 (m, 0.6H), 4.60-4.82 (m, 1.8H), 6.23 (s, 0.2H), 6.53 (dd, J=2.9, 8.3 Hz, 0.2H), 6.57-6.64 (m, 1.6H), 6.87 (d, J=8.3 Hz, 0.2H), 6.88 (d, J=8.3 Hz, 0.8H), 7.30-7.55 (m, 9H)

Example 51

Synthesis of (biphenyl-3-yl)[(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]-indol-3-yl]methanone (55)

[Formula 79]

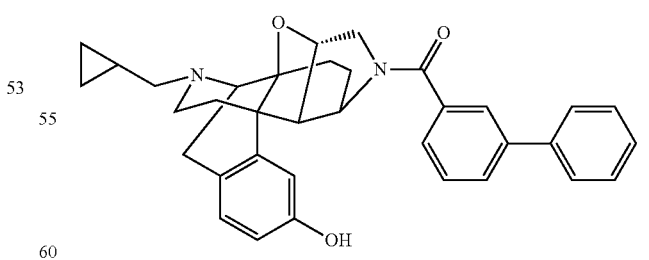

55

According to the method described in Example 32, the title compound 55 and the hydrochloride thereof were obtained by using the compound 8 and biphenyl-3-carbonyl chloride.

Compound 55 (free base) $^1$H NMR (CDCl$_3$, 400 MHz): δ 0.01-0.17 (m, 2H), 0.42-0.60 (m, 2H), 0.68-0.83 (m, 0.2H), 0.85-1.05 (m, 1.8H), 1.12-1.33 (m, 1H), 1.33-1.95 (m, 4H), 1.95-2.20 (m, 2H), 2.20-2.35 (m, 1H), 2.43-2.70 (m, 2H), 2.72-2.90 (m, 1H), 2.97-3.15 (m, 2H), 3.60-3.75 (m, 1.8H), 3.84-3.94 (m, 1H), 4.22-4.31 (m, 0.4H), 4.40-5.20 (m, 1.6H), 5.08 (t, J=5.4 Hz, 0.2H), 6.49 (d, J=2.4 Hz, 0.2H), 6.56 (dd, J=2.4, 8.3 Hz, 0.2H), 6.66 (dd, J=2.4, 8.3 Hz, 0.8H), 6.71 (d, J=2.4 Hz, 0.8H), 6.90-6.99 (m, 1H), 7.30-7.70 (m, 9H)

Example 52

Synthesis of [(1S,3aR,5aS,6R,11bR,11cS)-14-(cyclopropylmethyl)-11-hydroxy-10-methoxy-1,2,3a,4,5,6,7,11c-octahydro-3H-6,11b-(iminoethano)-1,5a-epoxynaphtho[1,2-e]indol-3-yl](phenyl)methanone (56)

[Formula 80]

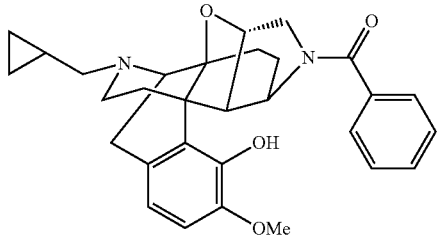

56

By using the compound 5 as a starting material, the title compound 56 and the hydrochloride thereof were obtained according to the methods described in Examples 4 and 33.

Compound 56 (free base) ¹H NMR (CDCl₃, 400 MHz): δ 0.00-0.20 (m, 2H), 0.42-0.65 (m, 2H), 0.70-1.35 (m, 2.75H), 1.39-1.52 (m, 1.5H), 1.75-1.78 (m, 2H), 1.79-2.23 (m, 2H), 2.24-2.27 (m, 1H), 2.45-2.75 (m, 2H), 2.80-2.95 (m, 1H), 3.02-3.14 (m, 1H), 3.50-3.70 (m, 2.5H), 3.82 (s, 0.75H), 3.82-3.92 (m, 1H), 3.88 (s, 2.25H), 4.20 (dd, J=7.0, 15.0 Hz, 0.25H), 4.33-4.40 (m, 0.25H), 4.88-5.12 (m, 1.75H), 5.55 (br s, 0.25H), 5.70 (br s, 0.75H), 6.58 (d, J=8.3 Hz, 0.25H), 6.63 (d, J=8.3 Hz, 0.25H), 6.64 (d, J=8.3 Hz, 0.75H), 6.71 (d, J=8.3 Hz, 0.75H), 6.58-6.72 (m, 5H)

Example 53

Synthesis of (2E)-1-[(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl]-3-phenylpropenone (57)

[Formula 81]

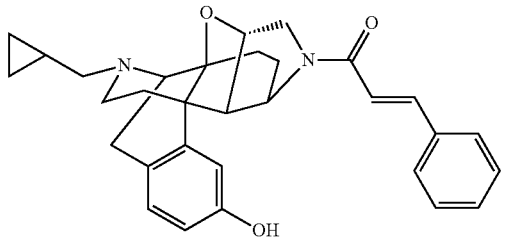

57

According to the method described in Example 32, the title compound 57 and the hydrochloride thereof were obtained by using the compound 8 and cinnamoyl chloride.

Compound 57 (hydrochloride) ¹H NMR (CD₃ OD, 400 MHz): δ 0.43-0.54 (m, 2H), 0.71-0.98 (m, 3H), 1.18-1.24 (m, 2H), 1.36 (dd, J=6.9, 15.3 Hz, 0.5H), 1.53 (dd, J=6.9, 15.3 Hz, 0.5H), 1.66 (dd, J=3.9, 15.1 Hz, 1H), 1.76-1.98 (m, 2H), 2.22-2.36 (m, 1H), 2.84-2.98 (m, 1H), 3.02 (dd, J=6.9, 13.3 Hz, 1H), 3.14-3.22 (m, 1H), 3.24-3.44 (m, 3H), 3.55 (dd, J=4.9, 8.4 Hz, 0.5H), 3.84 (d, J=14.7 Hz, 0.5H), 4.02 (dd, J=6.1, 14.7 Hz, 0.5H), 4.10 (d, J=12.5 Hz, 0.5H), 4.18 (dd, J=6.1, 12.5 Hz, 0.5H), 4.28-4.36 (m, 1H), 4.74-4.78 (m, 0.5H), 5.11 (t, J=6.1 Hz, 0.5H), 5.18 (t, J=5.3 Hz, 0.5H), 6.73-6.80 (m, 1.5H), 6.82 (d, J=2.6 Hz, 0.5H), 6.88 (d, J=15.3 Hz, 0.5H), 6.94 (d, J=15.3 Hz, 0.5H), 7.14 (d, J=8.4 Hz, 1H), 7.34-7.46 (m, 3H), 7.56-7.68 (m, 3H)

Example 54

Synthesis of (1S,3aR,5aS,6R,11bR,11cS)-3-benzenesulfonyl-14-(cyclopropylmethyl)-2,3,3a,4,5,6,7,11c-octahydro-1H-6,11b-(iminoethano)-1,5a-epoxynaphtho[1,2-e]indol-10-ol (58)

[Formula 82]

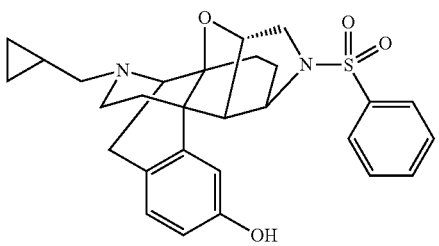

58

According to the method described in Example 32, the title compound 58 and the hydrochloride thereof were obtained by using the compound 8 and benzenesulfonyl chloride.

Compound 58 (hydrochloride) ¹H NMR (CD₃ OD, 400 MHz): δ 0.38-0.47 (m, 2H), 0.67-0.86 (m, 2H), 0.88-1.01 (m, 1H), 1.04-1.14 (m, 1H), 1.42-1.54 (m, 2H), 1.79-1.87 (m, 2H), 2.01-2.14 (m, 1H), 2.63-3.48 (m, 8H), 3.64 (dd, J=5.9, 12.3 Hz, 1H), 3.71 (d, J=12.3 Hz, 1H), 4.14-4.32 (m, 2H), 6.61 (d, J=2.3 Hz, 1H), 6.72 (dd, J=2.3, 8.0 Hz, 1H), 7.10 (d, J=8.0 Hz, 1H), 7.60-7.73 (m, 3H), 7.87-7.91 (m, 2H)

Example 55

Synthesis of (1S,3aR,5aS,6R,11bR,11cS)-3-benzyl-14-(cyclopropylmethyl)-2,3,3a,4,5,6,7,11c-octahydro-1H-6,11b-(iminoethano)-1,5a-epoxynaphtho[1,2-e]indol-10-ol (59)

[Formula 83]

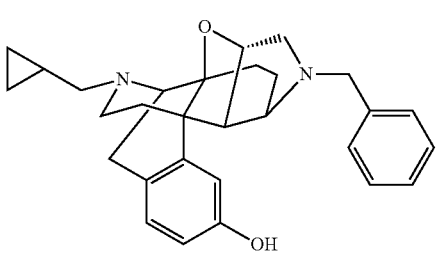

59

By using the compound 7, the title compound 59 and the hydrochloride thereof were obtained according to the method described in Example 6.

Compound 59 (hydrochloride) ¹H NMR (CD₃ OD, 400 MHz): δ 0.44-0.56 (m, 2H), 0.68-0.92 (m, 2H), 1.00-1.20 (m, 2H), 1.52-1.60 (m, 1H), 1.63-1.80 (m, 1H), 1.90-2.30 (m, 3H), 2.82-2.94 (m, 1H), 3.04 (dd, J=7.2, 13.5 Hz, 1H), 3.15-3.36 (m, 2H), 3.37-3.48 (m, 2H), 3.51-3.61 (m, 1H), 3.75-

4.00 (m, 2H), 4.20-4.32 (m, 1H), 4.34-4.56 (m, 3H), 5.10-5.38 (m, 1H), 6.71-6.82 (m, 2H), 7.10-7.20 (m, 1H), 7.43-7.70 (m, 5H)

Example 56

Synthesis of (1S,3aR,5aS,6R,11bR,11cS)-3,14-bis(cyclopropylmethyl)-2,3,3a,4,5,6,7,11c-octahydro-1H-6,11b-(iminoethano)-1,5a-epoxynaphtho[1,2-e]indol-10-ol (60)

[Formula 84]

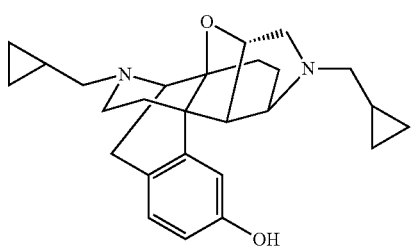

Under a nitrogen atmosphere, lithium aluminum hydride (3.5 mg, 0.092 mmol) was suspended in THF (1 mL), and the suspension was added dropwise with a solution of the compound 53 (20.0 mg, 0.046 mmol) in THF (2 mL). The mixture was stirred at room temperature for 4 hours, and then added with saturated aqueous sodium sulfate (0.5 mL), the insoluble solid was removed by filtration through Celite, and the filtrate was concentrated. The obtained crude product was reacted and treated according to the method described in Example 6 to give the title compound 60 as pale yellow oil (12.7 mg, 69%).

Compound 60 (hydrochloride) $^1$H NMR (CD$_3$ OD, 400 MHz): δ 0.37-0.60 (m, 4H), 0.67-0.90 (m, 4H), 1.00-1.33 (m, 2H), 1.60-1.82 (m, 2H), 1.85-2.08 (m, 2H), 2.12-2.32 (m, 1H), 2.80-2.95 (m, 1H), 3.04 (dd, J=7.8, 13.7 Hz, 1H), 3.21 (dd, J=4.9, 14.1 Hz, 1H), 3.28-3.38 (m, 5H), 3.39-3.45 (m, 2H), 3.50-4.00 (m, 3H), 4.28-4.45 (m, 2H), 5.14-5.31 (m, 1H), 6.75-6.80 (m, 2H), 7.16 (d, J=8.3 Hz, 1H)

Example 57

Synthesis of (1S,3aR,5aS,6R,11bR,11cS)-14-(cyclopropylmethyl)-3-phenethyl-2,3,3a,4,5,6,7,11c-octahydro-1H-6,11b-(iminoethano)-1,5a-epoxynaphtho[1,2-e]indol-10-ol (61)

[Formula 85]

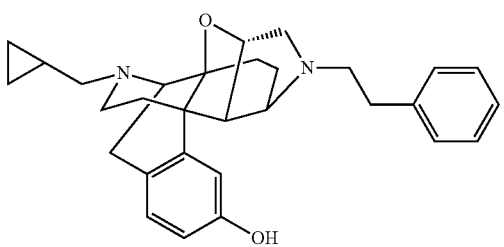

According to the method described in Example 13, the title compound 61 and the hydrochloride thereof were obtained by using the compound 8 and phenylacetaldehyde.

Compound 61 (hydrochloride) $^1$H NMR (CD$_3$ OD, 400 MHz): δ 0.44-0.55 (m, 2H), 0.72-0.90 (m, 2H), 1.00-1.35 (m, 2H), 1.58-1.82 (m, 2H), 1.88-2.07 (m, 2H), 2.12-2.31 (m, 1H), 2.89 (dt, J=3.5, 12.9 Hz, 1H), 2.96-3.15 (m, 2H), 3.20 (dd, J=4.9, 13.1 Hz, 1H), 3.25-3.37 (m, 4H), 3.37-3.44 (m, 2H), 3.45-3.65 (m, 2H), 3.65-4.02 (m, 1H), 4.25-4.42 (m, 2H), 5.12-5.30 (m, 1H), 6.75-6.80 (m, 2H), 7.15 (d, J=8.8 Hz, 1H), 7.20-7.40 (m, 5H)

Example 58

Synthesis of (1S,3aR,5aS,6R,11bR,11cS)-14-(cyclopropylmethyl)-3-(diphenylmethyl)-2,3,3a,4,5,6,7,11c-octahydro-1H-6,11b-(iminoethano)-1,5a-epoxynaphtho[1,2-e]indol-10-ol (62)

[Formula 86]

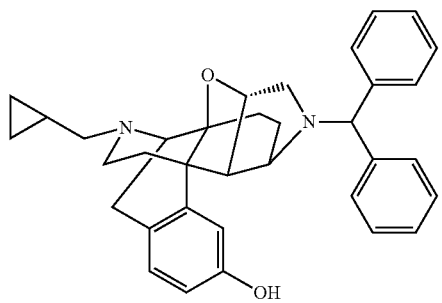

Under a nitrogen atmosphere, the compound 8 (20 mg, 0.054 mmol) was dissolved in acetonitrile (1 mL), the solution was added with chlorodiphenylmethane (19.0 μL, 0.16 mmol), potassium carbonate (35.6 mg, 0.27 mmol), and potassium iodide (0.90 mg, 0.005 mmol), and the mixture was stirred at 60° C. for 19 hours. The reaction mixture was poured into distilled water, and the mixture was extracted three times with chloroform. The organic layers were combined, washed with saturated brine, dried over anhydrous sodium sulfate, and then concentrated. The obtained crude product was reacted and treated according to the method described in Example 6 to give the title compound 62 as colorless oil (7.2 mg, 25%).

Compound 62 (free base) $^1$H NMR (CDCl$_3$, 400 MHz): δ 0.02-0.15 (m, 2H), 0.29-0.59 (m, 3H), 0.80-1.00 (m, 1H), 1.10-1.22 (m, 1H), 1.53 (dd, J=6.3, 14.6 Hz, 1H), 1.65-1.82 (m, 2H), 1.95-2.15 (m, 2H), 2.18-2.33 (m, 1H), 2.45-2.72 (m, 3H), 2.73-2.88 (m, 1H), 2.94-3.11 (m, 2H), 3.19 (dd, J=7.3, 11.2 Hz, 1H), 3.49 (t, J=6.8 Hz, 1H), 3.55-3.65 (m, 1H), 4.67 (s, 1H), 4.85-4.95 (m, 1H), 6.54-6.61 (m, 2H), 6.92 (d, J=7.8 Hz, 1H), 7.10-7.18 (m, 2H), 7.20-7.28 (m, 4H), 7.42 (t, J=7.3 Hz, 4H).

Reference Example 6

Syntheses of ethyl (5R,6S,6'R,9R,13S,14S)-17-(cyclopropylmethyl)-4,5-epoxy-6,6'-epoxy-14-hydroxy-6-methylmorphinan-6'-carboxylate (63a) and ethyl (5R,6S,6'S,9R,13S,14S)-17-(cyclopropylmethyl)-4,5-epoxy-6,6'-epoxy-14-hydroxy-6-methylmorphinan-6'-carboxylate (63b)

[Formula 87]

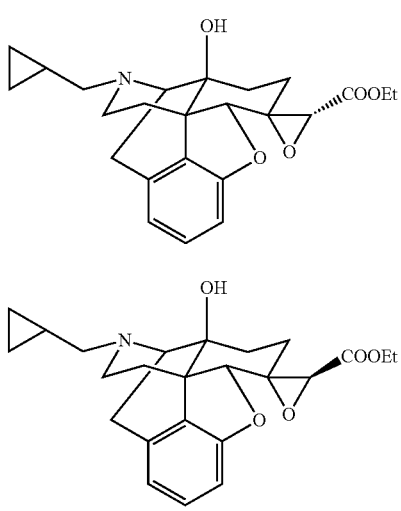

Under an argon atmosphere, 60% sodium hydride (40 mg, 1.0 mmol) was suspended in THF (1 mL), the suspension was cooled to −78° C. and then added with ethyl chloroacetate (1.07 mL, 1.0 mmol), and a solution of (5R,9R,13S,14S)-17-(cyclopropylmethyl)-4,5-epoxy-14-hydroxymorphinan-6-one [the compound described in Heterocycles 1994, 38, 877] (65.1 mg, 0.2 mmol) in THF (1 mL), and the mixture was stirred at room temperature for 12 hours. The reaction mixture was poured into distilled water under ice cooling, and the mixture was extracted three times with chloroform. The organic layers were combined, dried over anhydrous sodium sulfate, and then concentrated. The obtained crude product was purified by preparative TLC to give the title compounds 63a (47.9 mg, 58%) and 63b (20.8 mg, 25%) as colorless oil.

Compound 63a:

$^1$H NMR (CDCl$_3$, 300 MHz): δ 0.06-0.21 (m, 2H), 0.48-0.61 (m, 2H), 0.78-0.96 (m, 1H), 1.27 (t, J=7.2 Hz, 3H), 1.41-1.73 (m, 4H), 2.07-2.39 (m, 3H), 2.39 (d, J=6.6 Hz, 2H), 2.61-2.74 (m, 2H), 3.09 (d, J=18.6 Hz, 1H), 3.14 (d, J=5.7 Hz, 1H), 3.60 (s, 1H), 4.22 (q, J=7.2 Hz, 2H), 4.70 (s, 1H), 6.60 (d, J=7.8 Hz, 1H), 6.66 (d, J=7.5 Hz, 1H), 7.06 (t, J=7.8 Hz, 1H)

Compound 63b:

$^1$H NMR (CDCl$_3$, 300 MHz): δ 0.10-0.19 (m, 2H), 0.48-0.61 (m, 2H), 0.78-0.92 (m, 1H), 1.23-1.77 (m, 4H), 1.38 (t, J=7.2 Hz, 3H), 1.91 (ddd, J=6.3, 7.8, 14.1 Hz, 1H), 2.12-2.26 (m, 2H), 2.37 (d, J=6.6 Hz, 2H), 2.60-2.72 (m, 2H), 3.11 (d, J=18.3 Hz, 1H), 3.15 (d, J=6.0 Hz, 1H), 3.34 (s, 1H), 4.37-4.49 (m, 2H), 4.71 (s, 1H), 6.62 (d, J=7.8 Hz, 1H), 6.67 (d, J=7.8 Hz, 1H), 7.09 (t, J=7.8 Hz, 1H)

Reference Example 7

Synthesis of (5R,6S,6'R,9R,13S,14S)—N-benzyl-17-(cyclopropylmethyl)-4,5-epoxy-6,6'-epoxy-14-hydroxy-6-methylmorphinan-6'-carboxamide (64)

[Formula 88]

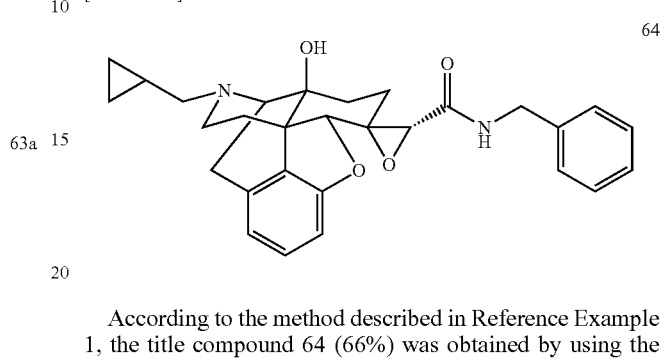

According to the method described in Reference Example 1, the title compound 64 (66%) was obtained by using the compound 63a which was prepared in Reference Example 6 instead of the compound 1a.

$^1$H NMR (CDCl$_3$, 300 MHz): δ 0.08-0.18 (m, 2H), 0.48-0.60 (m, 2H), 0.77-0.92 (m, 1H), 1.26 (td, J=3.6, 14.4 Hz, 1H), 1.41-1.66 (m, 3H), 2.11 (dt, J=3.9, 12.0 Hz, 1H), 2.22-2.42 (m, 4H), 2.57-2.72 (m, 2H), 3.02-3.16 (m, 2H), 3.64 (s, 1H), 4.38 (dd, J=5.7, 14.4 Hz, 1H), 4.41 (dd, J=6.0, 14.4 Hz, 1H), 4.70 (s, 1H), 5.16 (br s, 1H), 6.39 (t, J=6.0 Hz, 1H), 6.60 (d, J=7.8 Hz, 1H), 6.67 (d, J=7.5 Hz, 1H), 7.08 (t, J=7.8 Hz, 1H), 7.14-7.32 (m, 5H)

Reference Example 8

Synthesis of (1S,3aS,5aS,6R,11bR,11cR)-3-benzyl-14-(cyclopropylmethyl)-3a,11-dihydroxy-1,3,3a,4,5,6,7,11c-octahydro-2H-6,11b-(iminoethano)-1,5a-epoxynaphtho[1,2-e]indol-2-one (65)

[Formula 89]

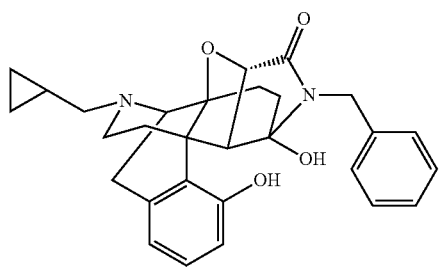

According to the method described in Reference Example 5, the title compound 65 (46%) was obtained by using the compound 64 which was prepared in Reference Example 7 instead of the compound 2b.

$^1$H NMR (CDCl$_3$, 300 MHz): δ 0.00-0.10 (m, 2H), 0.34-0.47 (m, 2H), 0.66-0.81 (m, 2H), 0.98-1.16 (m, 2H), 1.19-1.29 (m, 1H), 1.47-1.60 (m, 1H), 1.63-1.77 (m, 1H), 1.83-1.96 (m, 1H), 2.27 (d, J=6.3 Hz, 2H), 2.86-2.96 (m, 2H), 3.22-3.42 (m, 3H), 4.21 (d, J=15.3 Hz, 1H), 4.38 (d, J=15.3

Hz, 1H), 4.43 (d, J=5.4 Hz, 1H), 6.54 (d, J=7.8 Hz, 1H), 6.57 (d, J=8.1 Hz, 1H), 6.88 (t, J=7.8 Hz, 1H), 7.12-7.37 (m, 5H)

Example 59

Synthesis of (1S,3aR,5aS,6R,11bR,11cS)-3-benzyl-14-(cyclopropylmethyl)-2,3,3a,4,5,6,7,11c-octahydro-1H-6,11b-(iminoethano)-1,5a-epoxynaphtho[1,2-e]indol-11-ol (66)

[Formula 90]

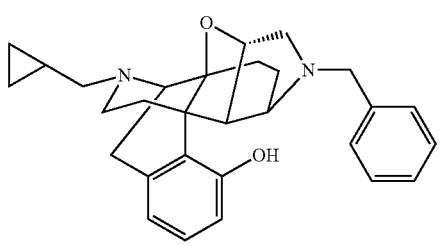

66

According to the method described in Example 1, the title compound 66 was obtained from the compound 65.

Compound 66 (free base) $^1$H NMR (CDCl$_3$, 400 MHz): δ 0.02-0.18 (m, 2H), 0.41-0.70 (m, 3H), 0.90-1.00 (m, 1H), 1.35-1.45 (m, 1H), 1.56 (dd, J=7.3, 15.1 Hz, 1H), 1.60-1.87 (m, 2H), 1.95-2.10 (m, 2H), 2.20-2.30 (m, 1H), 2.50-2.58 (m, 1H), 2.60-2.70 (m, 1H), 2.86 (dd, J=2.9, 11.2 Hz, 1H), 2.91 (dd, J=5.9, 18.5 Hz, 1H), 3.09 (d, J=18.5 Hz, 1H), 3.34 (dd, J=6.8, 10.7 Hz, 1H), 3.46 (t, J=7.3 Hz, 1H), 3.53 (t, J=7.3 Hz, 1H), 3.61 (d, J=5.9 Hz, 1H), 3.73 (s, 2H), 4.90-4.94 (m, 1H), 6.36 (d, J=7.8 Hz, 1H), 6.67 (d, J=7.8 Hz, 1H), 6.91 (t, J=7.8 Hz, 1H), 7.18-7.38 (m, 5H)

Example 60

Synthesis of (1S,3aR,5aS,6R,11bR,11cS)-14-(cyclopropylmethyl)-2,3,3a,4,5,6,7,11c-octahydro-1H-6,11b-(iminoethano)-1,5a-epoxynaphtho[1,2-e]indol-11-ol (67)

[Formula 91]

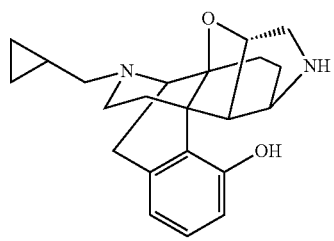

67

According to the method described in Example 4, the title compound 67 was obtained from the compound 66 (the reaction was performed at room temperature by using acetic acid instead of ethanol).

$^1$H NMR (CDCl$_3$, 400 MHz): δ 0.06-0.23 (m, 2H), 0.44-0.63 (m, 2H), 0.80-1.12 (m, 2H), 1.40-1.51 (m, 1H), 1.52-1.70 (m, 1H), 1.71-1.87 (m, 2H), 1.88-2.08 (m, 4H), 2.09-2.20 (m, 1H), 2.30-2.42 (m, 1H), 2.50-2.65 (m, 1H), 2.65-2.78 (m, 1H), 2.80-2.98 (m, 1H), 3.10 (d, J=19.0 Hz, 1H), 3.58-3.76 (m, 3H), 4.19 (br s, 11-0, 5.05 (br s, 1H), 6.59 (d, J=7.3 Hz, 1H), 6.73 (d, J=7.3 Hz, 1H), 6.93 (t, J=7.3 Hz, 1H)

Example 61

Synthesis of [(1S,3aR,5aS,6R,11bR,11cS)-14-(cyclopropylmethyl)-11-hydroxy-1,2,3a,4,5,6,7,11c-octahydro-3H-6,11b-(iminoethano)-1,5a-epoxynaphtho[1,2-e]indol-3-yl](phenyl)methanone (68)

[Formula 92]

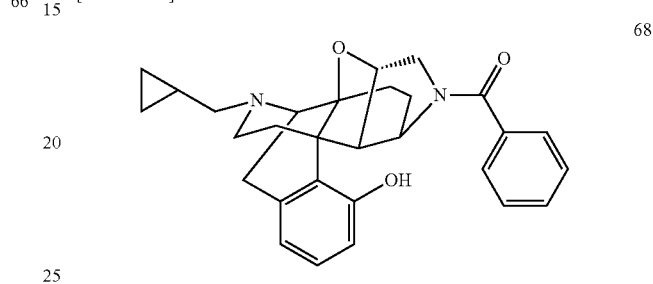

68

According to the method described in Example 33, the title compound 68 and the hydrochloride thereof were obtained by using the compound 67 and benzoyl chloride.

Compound 68 (free base) $^1$H NMR (CDCl$_3$, 400 MHz): δ 0.01-0.18 (m, 2H), 0.40-0.60 (m, 2H), 0.82-1.02 (m, 1H), 1.02-1.18 (m, 1H), 1.39-1.53 (m, 1H), 1.67 (dd, J=6.8, 14.8 Hz, 0.8H), 1.72-2.01 (m, 3H), 2.03-2.16 (m, 1H), 2.20-2.38 (m, 1H), 2.42-2.73 (m, 2H), 2.91 (dd, J=6.4, 19.2 Hz, 1H), 3.00-3.20 (m, 1H), 3.43-3.75 (m, 3H), 3.88 (d, J=12.8 Hz, 1H), 4.10 (dd, J=5.9, 14.1 Hz, 0.2H), 4.18-4.32 (m, 0.2H), 4.91 (t, J=5.4 Hz, 0.8H), 5.00-5.09 (m, 1H), 6.58 (d, J=7.8 Hz, 1H), 6.62 (d, J=7.8 Hz, 0.2H), 6.67 (d, J=8.3 Hz, 0.8H), 6.82-6.94 (m, 1H), 7.16 (d, J=7.8 Hz, 0.4H), 7.25-7.29 (m, 0.2H), 7.36-7.54 (m, 4.2H), 7.79-7.84 (m, 0.2H), 8.68 (br s, 1H)

Example 62

Synthesis of (3-chlorophenyl)[(1S,3aR,5aS,6R,11bR,11cS)-14-(cyclopropylmethyl)-11-hydroxy-1,2,3a,4,5,6,7,11c-octahydro-3H-6,11b-(iminoethano)-1,5a-epoxynaphtho[1,2-e]indol-3-yl]methanone (69)

[Formula 93]

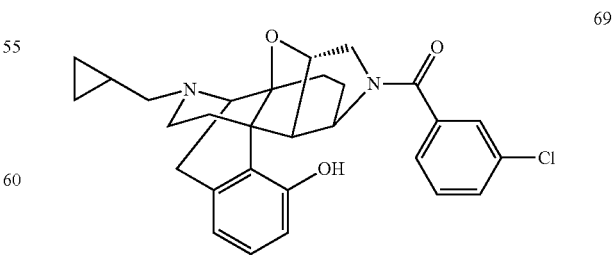

69

According to the method described in Example 33, the title compound 69 and the hydrochloride thereof were obtained by using the compound 67 and 3-chlorobenzoyl chloride.

Compound 69 (free base) $^1$H NMR (CDCl$_3$, 400 MHz): δ 0.04-0.19 (m, 2H), 0.42-0.61 (m, 2H), 0.85-1.17 (m, 2H), 1.41-1.53 (m, 1H), 1.63 (dd, J=6.8, 14.6 Hz, 0.8H), 1.68-2.02 (m, 3H), 2.03-2.30 (m, 2H), 2.45-2.72 (m, 2H), 2.92 (dd, J=5.9, 18.1 Hz, 1H), 3.02-3.20 (m, 1H), 3.52-3.76 (m, 3H), 3.84 (d, J=12.7 Hz, 1H), 4.14 (dd, J=6.3, 13.7 Hz, 0.2H), 4.20-4.34 (m, 0.2H), 4.94 (t, J=5.4 Hz, 0.8H), 4.99 (dd, J=5.4, 8.8 Hz, 0.8H), 5.05 (t, J=5.4 Hz, 0.2H), 6.56 (d, J=7.8 Hz, 0.2H), 6.61-6.66 (m, 1.8H), 6.91 (t, J=7.8 Hz, 1H), 7.12-7.32 (m, 0.8H), 7.33-7.48 (m, 3.2H)

Reference Example 9

Synthesis of (5R,6R,7S,9R,13S,14R)—N-benzyl-17-(cyclopropylmethyl)-4,5-epoxy-6-hydroxy-3-methoxy-6,14-ethenomorphinan-7-carboxamide (70)

[Formula 94]

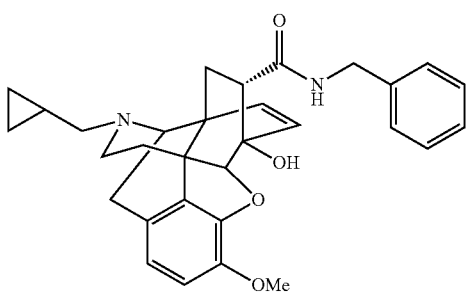

Under an argon atmosphere, (5R,6R,7S,9R,13S,14R)—N-benzyl-17-(cyclopropylmethyl)-4,5-epoxy-3,6-dimethoxy-6,14-ethenomorphinan-7-carboxamide [the compound described in Bioorg. Med. Chem. 2004, 12, 4133](402 mg, 0.83 mmol) was dissolved in DMF (10 mL), the solution was added with potassium carbonate (276 mg, 2.0 mmol), and methyl iodide (61.9 μL, 1.0 mmol), and the mixture was stirred at room temperature for 24 hours under light shielding. Then, the reaction mixture was added with methyl iodide (20.6 μL, 0.33 mmol), and the mixture was stirred for 6 hours. The reaction mixture was poured into distilled water, the mixture was extracted three times with ethyl acetate, and the organic layers were combined, washed two times with distilled water, and then with saturated brine, dried over anhydrous sodium sulfate, and then concentrated. The obtained crude product was purified by silica gel column chromatography to give the title compound 70 as white amorphous (379 mg, 92%).

$^1$H NMR (CDCl$_3$, 300 MHz): δ 0.06-0.21 (m, 2H), 0.43-0.57 (m, 2H), 0.76-0.90 (m, 1H), 1.65 (dd, J=6.0, 12.9 Hz, 1H), 1.83 (dd, J=2.4, 13.2 Hz, 1H), 2.00 (dt, J=5.7, 12.6 Hz, 1H), 2.27-2.48 (m, 4H), 2.57 (dd, J=6.0, 9.6 Hz, 1H), 2.71 (dd, J=4.8, 12.0 Hz, 1H), 3.03-3.17 (m, 2H), 3.56 (d, J=6.6 Hz, 1H), 3.69-3.88 (m, 1H), 3.81 (s, 3H), 4.33 (d, J=1.2 Hz, 1H), 4.43 (d, J=5.7 Hz, 1H), 5.47 (d, J=8.7 Hz, 1H), 5.76 (d, J=8.7 Hz, 1H), 6.46-6.56 (m, 2H), 6.62 (d, J=8.1 Hz, 1H), 7.19-7.35 (m, 5H)

Reference Example 10

Synthesis of (5R,6R,7S,9R,13S,14R)—N-benzyl-17-(cyclopropylmethyl)-4,5-epoxy-6-hydroxy-3-methoxy-6,14-ethanomorphinan-7-carboxamide (71)

[Formula 95]

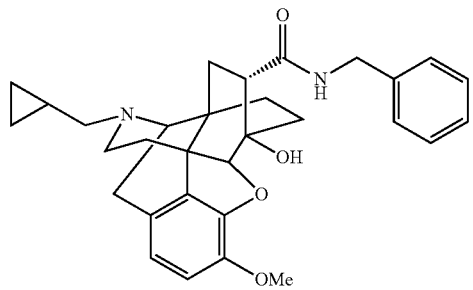

The compound 70 which was prepared in Reference Example 9 (99.7 mg, 0.20 mmol) was dissolved in methanol (15 mL), the solution was added with 10% palladium-activated carbon (21.3 mg, 0.020 mmol), and the mixture was stirred at 50° C. for 24 hours under a hydrogen atmosphere (0.5 MPa). The reaction mixture was filtered through Celite, and concentrated, and then the obtained crude product was purified by silica gel column chromatography to give the title compound 71 as colorless oil (89.6 mg, 90%).

$^1$H NMR (CDCl$_3$, 300 MHz): δ 0.05-0.14 (m, 2H), 0.42-0.53 (m, 2H), 0.59-0.86 (m, 2H), 1.22-1.37 (m, 2H), 1.63-1.74 (m, 1H), 2.01-2.40 (m, 6H), 2.46-2.69 (m, 3H), 2.87 (ddd, J=3.9, 11.4, 13.5 Hz, 1H), 3.00 (d, J=18.3 Hz, 1H), 3.11 (d, J=6.3 Hz, 1H), 3.88 (s, 3H), 4.25 (d, J=2.1 Hz, 1H), 4.49 (d, J=5.7 Hz, 2H), 6.53 (br t, J=5.7 Hz, 1H), 6.59 (d, J=8.1 Hz, 1H), 6.71 (d, J=8.1 Hz, 1H), 7.21-7.34 (m, 5H)

Reference Example 11

Synthesis of (1S,3aS,5aS,6R,11bS,11cS)-3-benzyl-14-(cyclopropylmethyl)-3a,11-dihydroxy-10-methoxy-1,3,3a,4,5,6,7,11c-octahydro-2H-6,11b-(iminoethano)-1,5a-methanonaphtho[1,2-e]indol-2-one (72)

[Formula 96]

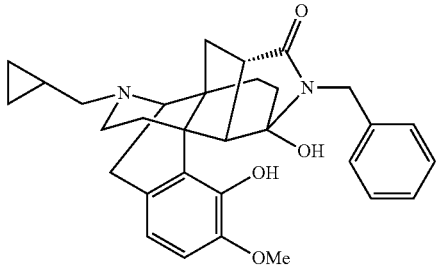

According to the method described in Reference Example 5, the title compound 72 (77%) was obtained by using the compound 71 which was prepared in Reference Example 10 instead of the compound 2b.

¹H NMR (CDCl₃, 300 MHz): δ 0.02-0.18 (m, 2H), 0.37-0.56 (m, 2H), 0.71-1.07 (m, 3H), 1.20-1.64 (m, 4H), 1.73 (dt, J=4.8, 12.6 Hz, 1H), 1.88-2.03 (m, 1H), 2.18-2.39 (m, 2H), 2.50-2.67 (m, 1H), 2.92 (d, J=2.7 Hz, 2H), 3.08-3.23 (m, 2H), 3.27-3.44 (m, 2H), 3.82 (s, 3H), 4.36 (d, J=15.0 Hz, 1H), 4.51 (d, J=15.0 Hz, 1H), 6.66 (s, 2H), 7.13-7.29 (m, 3H), 7.39 (d, J=6.9 Hz, 2H)

Example 63

Synthesis of (1S,3aR,5aS,6R,11bR,11cS)-3-benzyl-14-(cyclopropylmethyl)-10-methoxy-2,3,3a,4,5,6,7,11c-octahydro-1H-6,11b-(iminoethano)-1,5a-methanonaphtho[1,2-e]indol-11-ol (73)

[Formula 97]

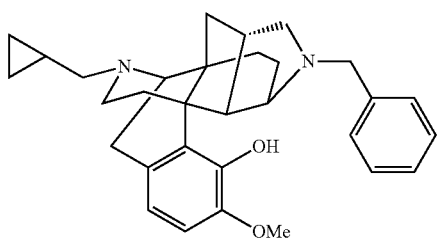

73

According to the method described in Example 1, the title compound 73 and the hydrochloride thereof were obtained from the compound 72.

Compound 73 (free base) ¹H NMR (CDCl₃, 400 MHz): δ 0.03-0.14 (m, 2H), 0.40-0.50 (m, 2H), 0.66-0.86 (m, 2H), 1.08-1.15 (m, 1H), 1.20-1.35 (m, 2H), 1.49-1.75 (m, 3H), 1.84-2.05 (m, 2H), 2.30 (d, J=5.9 Hz, 2H), 2.49-2.59 (m, 1H), 2.60-2.70 (m, 1H), 2.87-3.00 (m, 3H), 3.01-3.15 (m, 2H), 3.20-3.31 (m, 1H), 3.32-3.45 (m, 1H), 3.60-3.80 (m, 2H), 3.84 (s, 3H), 5.63 (br s, 1H), 6.61 (d, J=8.3 Hz, 1H), 6.63 (d, J=8.3 Hz, 1H), 7.16-7.40 (m, 5H)

Example 64

Synthesis of (1S,3aR,5aS,6R,11bR,11cS)-3-benzyl-14-(cyclopropylmethyl)-10-methoxy-11-phenoxy-2,3,3a,4,5,6,7,11c-octahydro-1H-6,11b-(iminoethano)-1,5a-methanonaphtho[1,2-e]indole (74)

[Formula 98]

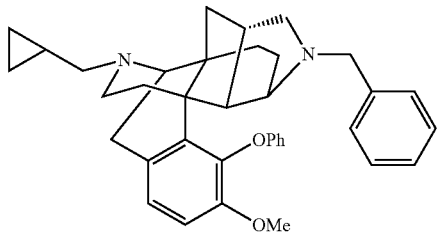

74

According to the method described in Example 2, the title compound 74 was obtained from the compound 73.

¹H NMR (CDCl₃, 400 MHz): δ 0.03-0.15 (m, 2H), 0.40-0.51 (m, 2H), 0.70-0.85 (m, 2H), 0.96-1.11 (m, 2H), 1.12-1.25 (m, 1H), 1.55-1.78 (m, 3H), 1.99 (dt, J=3.4, 12.2 Hz, 1H), 2.29 (d, J=5.9 Hz, 2H), 2.46 (dd, J=3.9, 11.2 Hz, 1H), 2.58-2.80 (m, 3H), 2.90-3.24 (m, 6H), 3.55-3.75 (m, 2H), 3.67 (s, 3H), 6.73-6.85 (m, 3H), 6.95 (d, J=8.3 Hz, 1H), 6.99 (d, J=8.3 Hz, 1H), 7.15-7.34 (m, 7H)

Example 65

Synthesis of (1S,3aR,5aS,6R,11bR,11cS)-3-benzyl-14-(cyclopropylmethyl)-10-methoxy-2,3,3a,4,5,6,7,11c-octahydro-1H-6,11b-(iminoethano)-1,5a-methanonaphtho[1,2-e]indole (75)

[Formula 99]

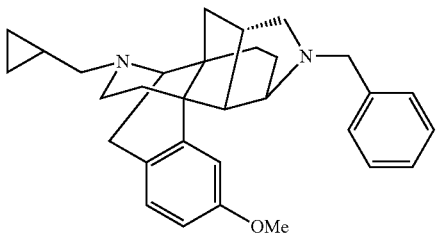

75

According to the method described in Example 3, the title compound 75 and the hydrochloride thereof were obtained from the compound 74.

Compound 75 (free base) ¹H NMR (CDCl₃, 400 MHz): δ 0.04-0.15 (m, 2H), 0.40-0.52 (m, 2H), 0.57-0.70 (m, 1H), 0.75-0.85 (m, 1H), 1.05-1.19 (m, 2H), 1.23-1.33 (m, 1H), 1.46-1.71 (m, 3H), 1.92-2.04 (m, 2H), 2.25-2.40 (m, 2H), 2.50-2.65 (m, 2H), 2.81-3.05 (m, 4H), 3.06-3.18 (m, 2H), 3.22-3.30 (m, 1H), 3.66 (d, J=13.7 Hz, 1H), 3.73 (d, J=13.7 Hz, 1H), 3.75 (s, 3H), 6.65 (dd, J=2.9, 8.3 Hz, 1H), 6.69 (d, J=2.9 Hz, 1H), 7.01 (d, J=8.3 Hz, 1H), 7.18-7.34 (m, 5H)

Example 66

Synthesis of (1S,3aR,5aS,6R,11bR,11cS)-3-benzyl-14-(cyclopropylmethyl)-2,3,3a,4,5,6,7,11c-octahydro-1H-6,11b-(iminoethano)-1,5a-methanonaphtho[1,2-e]indol-10-ol (76)

[Formula 100]

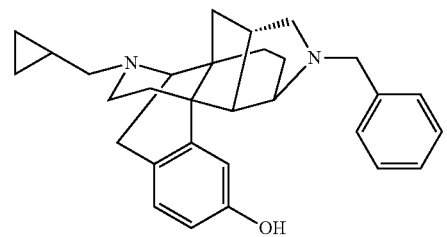

76

According to the method described in Example 6, the title compound 76 and the hydrochloride thereof were obtained from the compound 75.

Compound 76 (free base) ¹H NMR (CD₃OD, 400 MHz): δ 0.05-0.18 (m, 2H), 0.42-0.54 (m, 2H), 0.67-0.86 (m, 2H), 1.05-1.12 (m, 1H), 1.13-1.17 (m, 1H), 1.36-1.51 (m, 2H), 1.68-1.77 (m, 1H), 1.95 (dt, J=4.8, 12.4 Hz, 1H), 2.06 (dt, J=3.4, 12.4 Hz, 1H), 2.33 (dd, J=13.2, 19.5 Hz, 2H), 2.54 (dd, J=3.9, 11.2 Hz, 1H), 2.65 (dd, J=3.9, 9.8 Hz, 1H), 2.79-2.96

(m, 4H), 3.10-3.20 (m, 3H), 3.27 (d, J=6.3 Hz, 1H), 3.68 (d, J=13.2 Hz, 1H), 3.73 (d, J=13.2 Hz, 1H), 6.53 (dd, J=2.4, 8.3 Hz, 1H), 6.57 (d, J=2.4 Hz, 1H), 6.92 (d, J=8.3 Hz, 1H), 7.19-7.34 (m, 5H)

Example 67

Synthesis of (1S,3aR,5aS,6R,11bR,11cS)-14-(cyclopropylmethyl)-10-methoxy-2,3,3a,4,5,6,7,11c-octahydro-1H-6,11b-(iminoethano)-1,5a-methanonaphtho[1,2-e]indole (77)

[Formula 101]

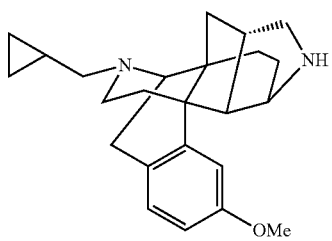

77

According to the method described in Example 4, the title compound 77 was obtained from the compound 75.

$^1$H NMR (CDCl$_3$, 400 MHz): δ 0.06-0.14 (m, 2H), 0.44-0.52 (m, 2H), 0.75-0.86 (m, 1H), 0.98-1.10 (m, 3H), 1.15 (d, J=8.8 Hz, 1H), 1.34-1.45 (m, 1H), 1.60-1.72 (m, 1H), 1.86-2.06 (m, 3H), 2.26-2.36 (m, 2H), 2.52-2.60 (m, 1H), 2.70-2.76 (m, 1H), 2.78-3.00 (m, 4H), 3.08 (d, J=5.9 Hz, 1H), 3.10-3.25 (m, 1H), 3.30 (dd, J=7.8, 11.2 Hz, 1H), 3.50-3.58 (m, 1H), 3.77 (s, 3H), 6.66 (dd, J=2.4, 8.3 Hz, 1H), 6.73 (d, J=2.4 Hz, 1H), 7.02 (d, J=8.3 Hz, 1H)

Example 68

Synthesis of [(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-methanonaphtho[1,2-e]indol-3-yl](phenyl)methanone (78)

[Formula 102]

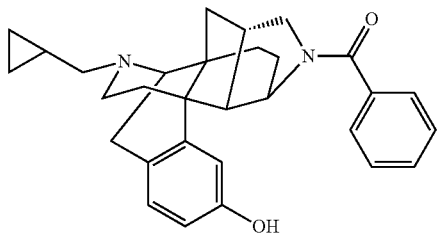

78

According to the method described in Example 32, the title compound 78 and the hydrochloride thereof were obtained by using the compound 77 and benzoyl chloride.

Compound 78 (free base) $^1$H NMR (CD$_3$OD, 400 MHz): δ 0.05-0.17 (m, 2H), 0.40-0.53 (m, 2H), 0.72-0.85 (m, 1H), 0.87-1.30 (m, 3H), 1.42-1.85 (m, 2.35H), 1.87-2.15 (m, 2.35H), 2.28-2.40 (m, 2H), 2.52-2.62 (m, 1H), 2.77-3.10 (m, 3.65H), 3.11-3.22 (m, 1.35H), 3.30-3.39 (m, 1.35H), 3.53-3.73 (m, 1.65H), 4.12-4.23 (m, 0.65H), 4.68 (t, J=6.3 Hz, 0.65H), 6.46 (d, J=2.4 Hz, 0.35H), 6.50 (dd, J=2.4, 8.3 Hz, 0.35H), 6.58 (dd, J=2.4, 8.3 Hz, 0.65H), 6.67 (d, J=2.4 Hz, 0.65H), 6.89 (d, J=8.3 Hz, 0.35H), 6.97 (d, J=8.3 Hz, 0.65H), 7.34-7.45 (m, 5H)

Example 69

Synthesis of (3-chlorophenyl)[(1S,3aR,5aS,6R,11bR,11cS)-14-(cyclopropylmethyl)-10-hydroxy-1,2,3a,4,5,6,7,11c-octahydro-3H-6,11b-(iminoethano)-1,5a-methanonaphtho[1,2-e]indol-3-yl]methanone (79)

[Formula 103]

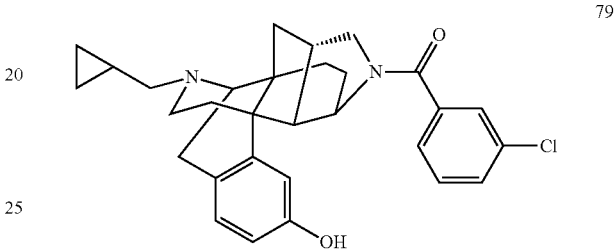

79

According to the method described in Example 32, the title compound 79 and the hydrochloride thereof were obtained by using the compound 77 and 3-chlorobenzoyl chloride.

Compound 79 (free base) $^1$H NMR (CD$_3$OD, 400 MHz): δ 0.08-0.18 (m, 2H), 0.43-0.54 (m, 2H), 0.75-1.32 (m, 4H), 1.45-1.61 (m, 1.35H), 1.67-1.85 (m, 1H), 1.88-2.20 (m, 2.35H), 2.30-2.44 (m, 2H), 2.56-2.64 (m, 1H), 2.80-3.12 (m, 3.65H), 3.13-3.40 (m, 2.7H), 3.54-3.62 (m, 1H), 3.66-3.73 (m, 0.65H), 4.12-4.22 (m, 0.65H), 4.67 (t, J=6.8 Hz, 0.65H), 6.48 (d, J=2.4 Hz, 0.35H), 6.52 (dd, J=2.4, 8.3 Hz, 0.35H), 6.60 (dd, J=2.4, 8.3 Hz, 0.65H), 6.67 (d, J=2.4 Hz, 0.65H), 6.91 (d, J=8.3 Hz, 0.35H), 6.98 (d, J=8.3 Hz, 0.65H), 7.28-7.50 (m, 4H)

Example 70

Synthesis of [(1S,3aR,5aS,6R,11bR,11cS)-14-(cyclopropylmethyl)-11-hydroxy-10-methoxy-1,2,3a,4,5,6,7,11c-octahydro-3H-6,11b-(iminoethano)-1,5a-epoxynaphtho[1,2-e]indol-3-yl](phenyl)methanone (80)

[Formula 104]

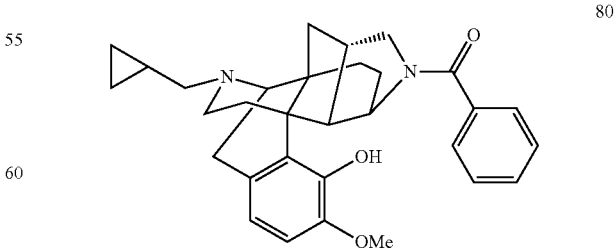

80

By using the compound 73 as a starting material, the title compound 80 and the hydrochloride thereof were obtained according to the methods described in Examples 4 and 33.

Compound 80 (free base) $^1$H NMR (CDCl$_3$, 400 MHz): δ 0.02-0.17 (m, 2H), 0.41-0.52 (m, 2H), 0.73-0.85 (m, 1H), 0.95-1.20 (m, 2H), 1.22-1.72 (m, 2H), 1.73-1.92 (m, 1.7H), 1.92-2.10 (m, 1H), 2.20-2.38 (m, 2H), 2.50-2.62 (m, 1H), 2.82-2.99 (m, 2.7H), 3.00-3.14 (m, 1.3H), 3.29 (t, J=10.7 Hz, 1H), 3.46-3.56 (m, 2H), 3.60-3.70 (m, 1H), 3.80 (s, 0.9H), 3.86 (s, 2.1H), 4.20 (dd, J=9.3, 12.7 Hz, 0.3H), 4.27 (t, J=7.3 Hz, 0.3H), 4.80 (dd, J=5.9, 8.3 Hz, 0.7H), 5.57 (s, 0.3H), 5.69 (s, 0.7H), 6.54-6.70 (m, 2H), 7.30-7.47 (m, 5H)

Example 71

Synthesis of [(1S,3aR,5aS,6R,11bR,11cS)-10-methoxy-1,2,3a,4,5,6,7,11c-octahydro-3H-6,11b-(iminoethano)-1,5a-methanonaphtho[1,2-e]indol-3-yl](phenyl)methanone (81)

[Formula 105]

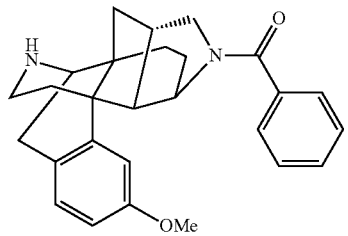

81

Under an argon atmosphere, [(1S,3aR,5aS,6R,11bR,11cS)-14-(cyclopropylmethyl)-10-methoxy-1,2,3a,4,5,6,7,11c-octahydro-3H-6,11b-(iminoethano)-1,5a-methanonaphtho[1,2-e]indol-3-yl](phenyl)methanone[O-methyl compound of the compound 78](30.0 mg, 0.064 mmol) was dissolved in benzene (2.0 mL), the solution was added with a 2.2 mol/L solution of diethyl azodicarboxylate in toluene (118.0 μL), and the mixture was refluxed for 5 hours by heating. The reaction mixture was left to cool, then concentrated under reduced pressure, and added with ethanol (2.0 mL), and pyridine hydrochloride (50.0 mg), and the mixture was stirred at room temperature for 17 hours. The reaction mixture was concentrated under reduced pressure, then the residue was added with 2 M hydrochloric acid, and the mixture was washed three times with diethyl ether. The aqueous layer was made basic with 25% aqueous ammonia, and extracted three times with chloroform. The organic layer was dried over anhydrous sodium sulfate, and then concentrated under reduced pressure. The obtained crude product was purified by preparative TLC to give the title compound 81 as brown amorphous (14.4 mg, 54%).

$^1$H NMR (CDCl$_3$, 400 MHz): δ 0.75-1.05 (m, 0.7H), 1.06-1.18 (m, 1H), 1.20-1.35 (m, 1H), 1.40-1.70 (m, 2H), 1.70-1.95 (m, 2H), 1.86 (br s, 1H), 2.58-2.76 (m, 2H), 2.80-3.08 (m, 4H), 3.10-3.23 (m, 1.3H), 3.35-3.60 (m, 1.7H), 3.65-3.70 (m, 1H), 3.68 (s, 0.9H), 3.78 (s, 2.1H), 4.17 (t, J=6.3 Hz, 0.3H), 4.28 (dd, J=9.3, 12.7 Hz, 0.3H), 4.80 (t, J=6.3 Hz, 0.7H), 6.53 (d, J=2.0 Hz, 0.3H), 6.64 (dd, J=2.0, 8.3 Hz, 0.3H), 6.70-6.78 (m, 1.4H), 7.01 (d, J=8.3 Hz, 0.3H), 7.06 (d, J=8.3 Hz, 0.7H), 7.31-7.47 (m, 5H)

Example 72

Synthesis of [(1S,3aR,5aS,6R,11bR,11cS)-10-hydroxy-14-methyl-1,2,3a,4,5,6,7,11c-octahydro-3H-6,11b-(iminoethano)-1,5a-methanonaphtho[1,2-e]indol-3-yl](phenyl)methanone (82)

[Formula 106]

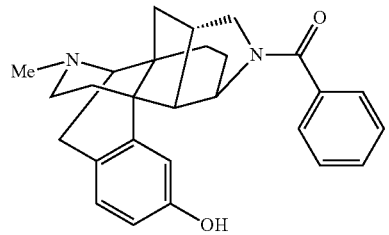

82

According to the method described in Example 8, the title compound 82 and the hydrochloride thereof were obtained from the compound 81.

Compound 82 (free base) $^1$H NMR (CD$_3$OD, 400 MHz): δ 0.75-1.05 (m, 1H), 1.05-1.35 (m, 3H), 1.44-1.64 (m, 1.6H), 1.65-1.85 (m, 1H), 1.90-2.03 (m, 1H), 2.05-2.20 (m, 1H), 2.33 (s, 1.2H), 2.35 (s, 1.8H), 2.38-2.44 (m, 1H), 2.80-3.25 (m, 5.8H), 3.58 (d, J=12.7 Hz, 1H), 3.62-3.72 (m, 0.6H), 4.15-4.24 (m, 0.6H), 4.69 (t, J=7.3H, 0.4H), 6.46 (d, J=2.9 Hz, 0.4H), 6.52 (dd, J=2.9, 8.3 Hz, 0.4H), 6.62 (dd, J=2.9, 8.3 Hz, 0.6H), 6.69 (d, J=2.9 Hz, 0.6H), 6.92 (d, J=8.3 Hz, 0.4H), 7.00 (d, J=8.3 Hz, 0.6H), 7.35-7.45 (m, 5H)

Example 73

Synthesis of [(1S,3aR,5aS,6R,11bR,11cS)-10-hydroxy-14-propyl-1,2,3a,4,5,6,7,11c-octahydro-3H-6,11b-(iminoethano)-1,5a-methanonaphtho[1,2-e]indol-3-yl](phenyl)methanone (83)

[Formula 107]

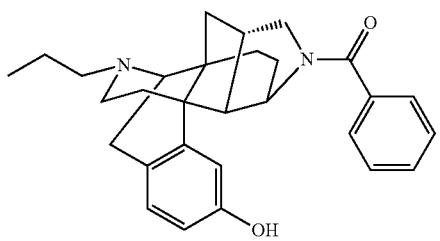

83

According to the method described in Example 10, the title compound 83 and the hydrochloride thereof were obtained by using the compound 81 and propyl bromide.

Compound 83 (free base) $^1$H NMR (CD$_3$OD, 400 MHz): δ 0.75-1.05 (m, 1H), 0.92 (t, J=7.3 Hz, 3H), 1.05-1.30 (m, 3H), 1.40-1.60 (m, 3.6H), 1.65-1.83 (m, 1H), 1.87-2.00 (m, 1H), 2.05-2.20 (m, 1H), 2.33-2.55 (m, 3H), 2.80-3.20 (m, 5.8H), 3.58 (d, J=10.7 Hz, 1H), 3.62-3.75 (m, 0.6H), 4.14-4.24 (m, 0.6H), 4.68 (t, J=6.8 Hz, 0.4H), 6.46 (d, J=2.4 Hz, 0.4H), 6.51 (dd, J=2.4, 8.3 Hz, 0.4H), 6.60 (dd, J=2.4, 8.3 Hz, 0.6H), 6.68 (d, J=2.4 Hz, 0.6H), 6.91 (d, J=8.3H, 0.4H), 6.98 (d, J=8.3 Hz, 0.6H), 7.34-7.46 (m, 5H)

Example 74

Synthesis of [(1S,3aR,5aS,6R,11bR,11cS)-14-(2-fluoroethyl)-10-hydroxy-1,2,3a,4,5,6,7,11c-octahydro-3H-6,11b-(iminoethano)-1,5a-methanonaphtho[1,2-e]indol-3-yl](phenyl)methanone (84)

[Formula 108]

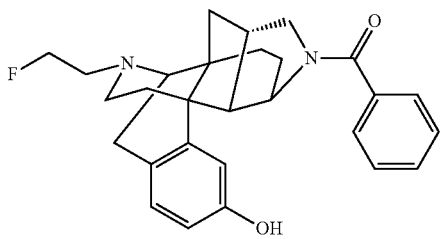

According to the method described in Example 10, the title compound 84 and the hydrochloride thereof were obtained by using the compound 81 and 1-bromo-2-fluoroethane.

Compound 84 (free base) $^1$H NMR (CD$_3$OD, 400 MHz): δ 0.75-1.05 (m, 1H), 1.05-1.35 (m, 3H), 1.42-1.60 (m, 1.6H), 1.62-1.82 (m, 1H), 1.90-2.02 (m, 1H), 2.14-2.28 (m, 1H), 2.50 (dd, J=4.9, 11.7 Hz, 1H), 2.56-2.88 (m, 2H), 2.90-3.20 (m, 5H), 3.35-3.39 (m, 3.59 (d, J=10.2 Hz, 1H), 3.62-3.72 (m, 0.6H), 4.15-4.25 (m, 0.6H), 4.46 (dt, J=4.9, 47.8 Hz, 2H), 4.68 (t, J=6.3 Hz, 0.4H), 6.46 (d, J=2.9 Hz, 0.4H), 6.52 (dd, J=2.9, 8.3 Hz, 0.4H), 6.60 (dd, J=2.9, 8.3 Hz, 0.6H), 6.68 (d, J=2.9 Hz, 0.6H), 6.92 (d, J=8.3 Hz, 0.4H), 6.99 (d, J=8.3 Hz, 0.6H), 7.34-7.46 (m, 5H)

Example 75

Synthesis of (1S,3aR,5aS,6R,11bR,11cS)-14-(cyclopropylmethyl)-3-(2,2,2-trifluoro-1-phenylethyl)-2,3,3a,4,5,6,7,11c-octahydro-1H-6,11b-(iminoethano)-1,5a-methanonaphtho[1,2-e]indol-10-ol (85)

[Formula 109]

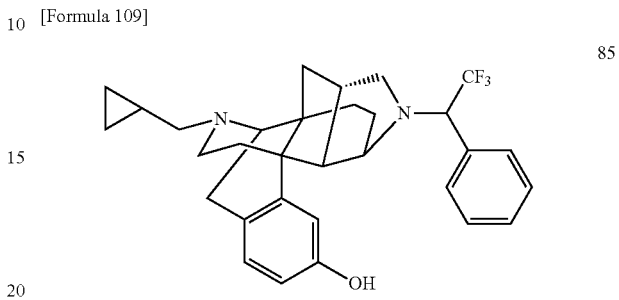

According to the method described in Example 58, the title compound 85 and the hydrochloride thereof were obtained by using the compound 77 and 2,2,2-trifluoro-1-phenylethyl trifluoromethanesulfonate.

Compound 85 (free base) $^1$H NMR (CDCl$_3$, 400 MHz): δ 0.05-0.19 (m, 2H), 0.40-0.55 (m, 2H), 0.56-0.90 (m, 2H), 1.00-1.42 (m, 5H), 1.52-1.70 (m, 1.5H), 1.85-2.10 (m, 2H), 2.22-2.42 (m, 1.5H), 2.45-2.65 (m, 1.5H), 2.76-2.94 (m, 4H), 3.00-3.25 (m, 3H), 3.62-3.70 (m, 0.5H), 4.13 (q, J=8.3 Hz, 0.5H), 4.21 (q, J=8.3 Hz, 0.5H), 6.51 (d, J=2.4 Hz, 0.5H), 6.55 (dd, J=2.4, 8.3Hz, 0.5H), 6.61 (dd, J=2.4, 8.3 Hz, 0.5H), 6.67 (d, J=2.4 Hz, 0.5H), 6.94 (d, J=8.3 Hz, 0.5H), 6.97 (d, J=8.3 Hz, 0.5H), 7.30-7.46 (m, 5H)

Examples 76 to 88

According to the method described in Example 32, the compounds of Examples 76 to 88 (free bases and the hydrochlorides thereof) were obtained by using the compound 77.

TABLE 1

| | Compound number | Structural formula | $^1$H NMR |
|---|---|---|---|
| Example 76 | 86 | (structure) | (Hydrochloride, CD$_3$OD) δ 0.40-0.60 (m, 2H), 0.70-0.85 (m, 2.3H), 0.85-1.00 (m, 0.7H), 1.05-1.20 (m, 1.3H), 1.50-1.60 (m, 1.7H), 1.65-1.80 (m, 2H), 1.80-1.90 (m, 0.3H), 1.90-2.00 (m, 0.7H), 2.00-2.20 (m, 1H), 2.70-2.80 (m, 2H), 2.95-3.10 (m, 1H), 3.10-3.75 (m, 8H), 4.10-4.25 (m, 1.3H), 4.68 (dd, J = 5.9, 8.8 Hz, 0.7H), 6.56 (d, J = 2.4 Hz, 0.3H), 6.63 (dd, J = 2.4, 8.3 Hz, 0.3H), 6.74 (dd, J = 2.4, 8.3 Hz, 0.7H), 6.77 (d, J = 2.4 Hz, 0.7H), 7.04 (d, J = 8.3 Hz, 0.3H), 7.14 (d, J = 8.3 Hz, 0.7H), 7.30-7.55 (m, 4H). |
| Example 77 | 87 | (structure) | (Hydrochloride, CD$_3$OD) δ 0.45-0.60 (m, 2H), 0.70-1.05 (m, 3H), 1.05-1.25 (m, 1H), 1.45-2.05 (m, 5H), 2.05-2.20 (m, 1H), 2.70-2.85 (m, 1H), 2.85-2.95 (m, 1H), 2.95-3.10 (m, 1H), 3.10-3.55 (m, 6H), 3.60-3.65 (m, 1.2H), 3.65-3.80 (m, 0.8H), 4.10-4.30 (m, 1.2H), 4.70-4.85 (m, 0.8H), 6.59 (d, J = 2.4 Hz, 0.2H), 6.65 (dd, J = 2.4, 8.3 Hz, 0.2H), 6.73 (dd, J = 2.4, 8.3 Hz, 0.8H), 6.77 (d, J = 2.4 Hz, 0.8H), 7.05 (d, J = 8.3 Hz, 0.2H), 7.12 (d, J = 8.3 Hz, 0.8H), 7.38-7.50 (m, 4H). |

TABLE 1-continued

| Compound number | | Structural formula | $^1$H NMR |
|---|---|---|---|
| Example 78 | 88 | | (Hydrochloride, CD$_3$OD)<br>δ 0.40-0.60 (m, 2H), 0.70-1.05 (m, 2.6H), 1.05-1.20 (m, 1.4H), 1.45-2.00 (m, 5H), 2.00-2.20 (m, 1H), 2.70-2.83 (m, 1H), 2.83-3.00 (m, 1H), 3.00-3.10 (m, 1H), 3.10-3.60 (m, 7H), 3.60-3.80 (m, 1H), 4.00-4.30 (m, 1.3H), 4.65-4.80 (m, 0.7H), 6.58 (d, J = 2.4 Hz, 0.3H), 6.64 (dd, J = 2.4, 8.3 Hz, 0.3H), 6.73 (dd, J = 2.4, 8.3 Hz, 0.7H), 6.78 (d, J = 2.4 Hz, 0.7H), 7.04 (d, J = 8.3 Hz, 0.3H), 7.12 (d, J = 8.3 Hz, 0.7H), 7.15-7.55 (m, 4H). |
| Example 79 | 89 | | (Hydrochloride, CD$_3$OD)<br>δ 0.40-0.60 (m, 2H), 0.70-0.90 (m, 2H), 0.90-1.05 (m, 0.6H), 1.05-1.25 (m, 1.4H), 1.50-2.00 (m, 5H), 2.00-2.20 (m, 1H), 2.70-2.86 (m, 1H), 2.86-2.98 (m, 1H), 2.98-3.10 (m, 1H), 3.10-3.60 (m, 5H), 3.60-3.70 (m, 1.3H), 3.70-3.80 (m, 0.7H), 4.10-4.30 (m, 2H), 4.70-4.80 (m, 0.7H), 4.80-5.10 (m, 0.3H), 6.59 (d, J = 2.4 Hz, 0.3H), 6.65 (dd, J = 2.4, 8.3 Hz, 0.3H), 6.74 (dd, J = 2.4, 8.3 Hz, 0.7H), 6.78 (d, J = 2.4 Hz, 0.7H), 7.05 (d, J = 8.3 Hz, 0.3H), 7.12 (d, J = 8.3 Hz, 0.7H), 7.15-7.35 (m, 2.8H), 7.40-7.75 (m, 1.2H). |
| Example 80 | 90 | | (Hydrochloride, CD$_3$OD)<br>δ 0.40-0.55 (m, 2H), 0.70-0.85 (m, 2H), 0.85-1.00 (m, 1H), 1.05-1.20 (m, 1H), 1.40-1.75 (m, 4H), 1.85-2.00 (m, 1H), 2.00-2.20 (m, 1H), 2.70-2.96 (m, 2H), 2.96-3.08 (m, 1H), 3.08-3.70 (m, 8H), 4.10-4.20 (m, 1H), 4.60-4.70 (m, 1H), 6.62 (d, J = 2.4 Hz, 0.2H), 6.74 (dd, J = 2.4, 8.3 Hz, 0.8H), 6.78 (d, J = 2.4 Hz, 1H), 7.04 (d, J = 8.3 Hz, 0.2H), 7.13 (d, J = 8.3 Hz, 0.8H), 7.48 (d, J = 7.8 Hz, 1H), 7.58-7.68 (m, 1H), 7.74 (t, J = 7.8 Hz, 1H), 7.79 (t, J = 7.8 Hz, 1H). |

TABLE 2

| Compound number | | Structural formula | $^1$H NMR |
|---|---|---|---|
| Example 81 | 91 | | (Hydrochloride, CD$_3$OD)<br>δ 0.40-0.60 (m, 2H), 0.70-1.05 (m, 2.4H), 1.05-1.25 (m, 1.6H), 1.45-2.00 (m, 5H), 2.00-2.25 (m, 1H), 2.70-2.85 (m, 1H), 2.85-2.95 (m, 1H), 2.95-3.10 (m, 1H), 3.10-3.60 (m, 6H), 3.60-3.85 (m, 1.8H), 4.10-4.35 (m, 1.2H), 4.50-4.70 (m, 0.8H), 4.70-4.80 (m, 0.2H), 6.57 (d, J = 2.4 Hz, 0.2H), 6.64 (dd, J = 2.4, 8.3 Hz, 0.2H), 6.74 (dd, J = 2.4, 8.3 Hz, 0.8H), 6.79 (d, J = 2.4 Hz, 0.8H), 7.05 (d, J = 8.3 Hz, 0.2H), 7.13 (d, J = 8.3 Hz, 0.8H), 7.60-7.82 (m, 4H). |
| Example 82 | 92 | | (Hydrochloride, CD$_3$OD)<br>δ 0.40-0.60 (m, 2H), 0.70-1.05 (m, 2.6H), 1.05-1.25 (m, 1.4H), 1.45-2.00 (m, 5H), 2.00-2.20 (m, 1H), 2.65-3.10 (m, 3H), 3.10-3.60 (m, 6H), 3.60-3.80 (m, 1.7H), 4.05-4.30 (m, 1.3H), 4.50-4.65 (m, 0.7H), 4.70-4.80 (m, 0.3H), 6.58 (d, J = 2.4 Hz, 0.3H), 6.64 (dd, J = 2.4, 8.3 Hz, 0.3H), 6.73 (dd, J = 2.4, 8.3 Hz, 0.7H), 6.78 (d, J = 2.4 Hz, 0.7H), 7.04 (d, J = 8.3 Hz, 0.3H), 7.13 (d, J = 8.3 Hz, 0.7H), 7.60 (d, J = 8.3 Hz, 0.6H), 7.67 (d, J = 8.3 Hz, 1.4H), 7.73 (d, J = 8.3 Hz, 0.6H), 7.78 (d, J = 8.3 Hz, 1.4H). |

TABLE 2-continued

| Compound number | | Structural formula | $^1$H NMR |
|---|---|---|---|
| Example 83 | 93 | | (Hydrochloride, CD$_3$OD) δ 0.40-0.60 (m, 2H), 0.60-0.85 (m, 2.2H), 0.85-1.00 (m, 0.8H), 1.00-1.25 (m, 1H), 1.45-2.00 (m, 5H), 2.00-2.20 (m, 1H), 2.70-2.85 (m, 1H), 2.85-2.98 (m, 1H), 2.98-3.10 (m, 1H), 3.10-3.80 (m, 8H), 4.10-4.25 (m, 1.2H), 4.64-4.70 (m, 0.8H), 6.59 (s, 0.2H), 6.65 (d, J = 8.3 Hz, 0.2H), 6.73 (d, J = 8.3 Hz, 0.8H), 6.77 (s, 0.8H), 6.80-7.00 (m, 2H), 7.00-7.30 (m, 3H). |
| Example 84 | 94 | | (Hydrochloride, CD$_3$OD) δ 0.45-0.55 (m, 2H), 0.70-0.90 (m, 2.3H), 0.90-1.08 (m, 0.7H), 1.08-1.25 (m, 1H), 1.45-1.70 (m, 3H), 1.70-1.85 (m, 1.3H), 1.85-2.00 (m, 0.7H), 2.10-2.20 (m, 1H), 2.70-2.96 (m, 2H), 2.96-3.10 (m, 1H), 3.10-3.60 (m, 7H), 3.60-3.85 (m, 1.7H), 4.10-4.30 (m, 1.3H), 6.58 (d, J = 2.4 Hz, 0.3H), 6.63 (dd, J = 2.4, 8.3 Hz, 0.3H), 6.74 (dd, J = 2.4, 8.3 Hz, 0.7H), 6.79 (d, J = 2.4 Hz, 0.7H), 7.04 (d, J = 8.3 Hz, 0.3H), 7.13 (d, J = 8.3 Hz, 0.7H), 7.50-7.70 (m, 2H), 7.85-8.00 (m, 2H). |
| Example 85 | 95 | | (Free base, CDCl$_3$) δ 0.02-0.13 (m, 2H), 0.38-0.51 (m, 2H), 0.70-0.84 (m, 1H), 0.99-1.17 (m, 3H), 1.38-1.63 (m, 1.2H), 1.74-1.95 (m, 3H), 1.97-2.09 (m, 0.8H), 2.20-2.37 (m, 2H), 2.43-2.58 (m, 1H), 2.67-3.43 (m, 7H), 3.48 (dd, J = 8.3, 11.2 Hz, 0.8H), 3.77-3.95 (m, 0.4H), 4.25-4.37 (m, 0.2H), 4.86-4.97 (m, 0.8H), 6.22-6.32 (m, 02.H), 6.40 (dd, J = 2.4, 8.3 Hz, 0.2H), 6.62 (dd, J = 2.4, 8.3 Hz, 0.8H), 6.71 (d, J = 2.4 Hz, 0.8H), 6.78 (d, J = 8.3 Hz, 0.2H), 6.90 (d, J = 8.3 Hz, 0.8H), 7.30-7.61 (m, 4H), 7.75-7.97 (m, 3H). |

TABLE 3

| Compound number | | Structural formula | $^1$H NMR |
|---|---|---|---|
| Example 86 | 96 | | (Hydrochloride, CD$_3$OD) δ 0.43-0.58 (m, 2H), 0.69-0.94 (m, 2.3H), 0.95-1.36 (m, 2H), 1.45-2.00 (m, 4.7H), 2.07-2.23 (m, 1H), 2.67-2.88 (m, 1H), 2.88-3.10 (m, 1.7H), 3.11-3.57 (m, 6.9H), 3.68-3.88 (m, 1.7H), 4.11-4.23 (m, 1H), 4.27-4.38 (m, 0.7H), 6.52-6.62 (m, 0.6H), 6.75 (dd, J = 2.4, 8.8 Hz, 0.7H), 6.81 (d, J = 2.4 Hz, 0.7H), 7.02 (d, J = 7.8 Hz, 0.3H), 7.14 (d, J = 8.8 Hz, 0.7H), 7.45-7.62 (m, 3H), 7.85-8.05 (m, 4H). |
| Example 87 | 97 | | (Hydrochloride, CD$_3$OD) δ 0.40-0.55 (m, 2H), 0.70-0.85 (m, 2.3H), 0.85-1.00 (m, 0.7H), 1.00-1.25 (m, 0.7H), 1.25-1.40 (m, 0.3H), 1.40-1.80 (m, 4H), 1.80-2.00 (m, 1H), 2.10-2.25 (m, 1H), 2.75-2.88 (m, 1H), 2.88-3.10 (m, 2H), 3.10-3.55 (m, 5.7H), 3.72 (d, J = 12.2 Hz, 0.3H), 4.10-4.22 (m, 2.3H), 4.28 (dd, J = 7.8, 12.2 Hz, 0.7H), 4.70-5.05 (m, 1H), 6.55 (s, 0.3H), 6.61 (s, 0.7H), 6.60-6.70 (m, 2H), 7.00-7.20 (m, 2H), 7.64 (s, 0.3H), 7.72 (s, 0.7H). |

TABLE 3-continued

| Compound number | | Structural formula | $^1$H NMR |
|---|---|---|---|
| Example 88 | 98 | (structure) | (Hydrochloride, CD$_3$OD) δ 0.42-0.54 (m, 2H), 0.70-0.86 (m, 2H), 0.88-1.02 (m, 1H), 1.06-1.18 (m, 1H), 1.38-1.48 (m, 1H), 1.50-1.62 (m, 2H), 1.66-1.80 (m, 1H), 1.80-1.92 (m, 1H), 1.96-2.10 (m, 1H), 2.66-2.80 (m, 1H), 2.80-2.96 (m, 2H), 2.97-3.55 (m, 7H), 3.55-3.68 (m, 1H), 4.02-4.20 (m, 2H), 6.59 (m, 1H), 6.71 (d, J = 8.3 Hz, 1H), 7.10 (d, J = 8.3 Hz, 1H), 7.72-7.84 (m, 1H), 8.34-8.44 (m, 1H), 8.82-8.96 (m, 1H), 9.00-9.14 (m, 1H). |

Example 89

([1,1'-Biphenyl]-2-yl) [(1S,5aS,6R,11bR)-14-(cyclopropylmethyl)-10-hydroxy-4,5,6,7-tetrahydro-1H-6,11b-(iminoethano)-1,5a-methanonaphtho[1,2-e]indol-3(2H,3aH,11cH)-yl]methanone (100)

(1) Synthesis of ([1,1'-biphenyl]-2-yl) [(1S,5aS,6R,11bR)-14-(cyclopropylmethyl)-10-methoxy-4,5,6,7-tetrahydro-1H-6,11b-(iminoethano)-1,5a-methanonaphtho[1,2-e]indol-3(2H,3aH,11cH)-yl]methanone (99)

[Formula 110]

Under an argon atmosphere, the compound 77 (20 mg, 0.055 mmol) was dissolved in DMF (1 mL), the solution was added with 2-phenylbenzoic acid (22 mg, 0.11 mmol), diisopropylethylamine (37 μL, 0.22 mmol), and O-(7-azabenzotriazol-1-yl)-N,N,N',N'-tetramethyluronium hexafluorophosphate (63 mg, 0.17 mmol), and the mixture was stirred at room temperature for 16 hours. The reaction mixture was diluted with ethyl acetate, and washed with saturated aqueous sodium hydrogencarbonate, water, and saturated brine. The organic layer was dried over anhydrous sodium sulfate, and then concentrated. The obtained crude product was purified by silica gel column chromatography to give the title compound 99 (30 mg, 100%).

(2) Synthesis of ([1,1'-biphenyl]-2-yl)[(1S,5aS,6R,11bR)-14-(cyclopropylmethyl)-10-hydroxy-4,5,6,7-tetrahydro-1H-6,11b-(iminoethano)-1,5a-methanonaphtho[1,2-e]indol-3(2H,3aH,11cH)-yl]methanone (100)

[Formula 111]

By using the compound 99 which was prepared in (1) mentioned above, the title compound 100 and the hydrochloride thereof (13 mg, 57%) were obtained according to the method described in Example 6.

Compound 100 (hydrochloride) $^1$H NMR (CD$_3$ OD, 400 MHz): δ 0.40-0.60 (m, 3H), 0.60-0.85 (m, 3H), 1.05-1.20 (m, 1H), 1.20-1.35 (m, 1H), 1.35-1.80 (m, 3H), 1.80-2.05 (m, 1H), 2.60-2.80 (m, 2H), 2.80-3.60 (m, 9H), 3.90-4.00 (m, 0.7H), 4.04 (d, J=6.3 Hz, 0.3H), 4.50-4.65 (m, 0.7H), 4.80-5.20 (m, 0.3H), 6.32 (d, J=2.4 Hz, 0.3H), 6.60-6.75 (m, 1.7H), 7.01 (d, J=8.3 Hz, 0.3H), 7.07 (d, J=8.3 Hz, 0.7H), 7.35-7.65 (m, 9H)

Examples 90 to 98

By using the compound 77, the compounds of Example 90 to 98 (free bases and the hydrochlorides thereof) were obtained according to the method described in Example 89.

TABLE 4

| Compound number | | Structural formula | $^1$H NMR |
|---|---|---|---|
| Example 90 | 101 | (structure) | (Hydrochloride, CD$_3$OD) δ 0.43-0.57 (m, 2H), 0.75-0.85 (m, 3H), 1.08-1.25 (m, 1H), 1.36-1.73 (m, 4H), 1.73-1.88 (m, 1H), 2.04-2.19 (m, 1H), 2.68-2.83 (m, 1H), 2.88-3.50 (m, 8H), 3.56-3.66 (m, 1H), 3.69-3.79 (m, 1H), 4.06-4.16 (m, 1H), 4.18-4.24 (m, 0.2H), 4.55-4.63 (m, 0.8H), 6.57-6.60 (m, 0.2H), 6.64-6.76 (m, 1.8H), 6.86-7.50 (m, 10H). |

TABLE 4-continued

| Compound number | | Structural formula | ¹H NMR |
|---|---|---|---|
| Example 91 | 102 | | (Hydrochloride, CD₃OD) δ 0.45-0.55 (m, 2H), 0.70-0.82 (m, 2H), 0.83-1.07 (m, 1H), 1.07-1.27 (m, 1H), 1.47-1.97 (m, 5H), 2.06-2.22 (m, 1H), 2.71-2.85 (m, 1H), 2.86-2.97 (m, 1H), 3.04 (dd, J = 7.8, 13.2 Hz, 1H), 3.10-3.55 (m, 7H), 3.62-3.87 (m, 1.7H), 4.10-4.35 (m, 1.3H), 6.59-6.82 (m, 2H), 6.95-7.23 (m, 6H), 7.34-7.57 (m, 4H). |
| Example 92 | 103 | | (Hydrochloride, CD₃OD) δ 0.45-0.55 (m, 2H), 0.70-0.84 (m, 2H), 0.84-1.00 (m, 0.7H), 1.00-1.20 (m, 1.3H), 1.45-1.75 (m, 4H), 1.75-2.00 (m, 1H), 2.10-2.25 (m, 1H), 2.76-2.90 (m, 1H), 2.90-3.10 (m, 2H), 3.10-3.60 (m, 7H), 3.60-3.70 (m, 0.3H), 3.90-4.04 (m, 0.7H), 4.14-4.26 (m, 2H), 6.20-6.30 (m, 1H), 6.70-6.85 (m, 3H), 6.90-7.00 (m, 1H), 7.12 (d, J = 8.3 Hz, 1H), 10.9 (br s, 1H). |
| Example 93 | 104 | | (Hydrochloride, CD₃OD) δ 0.45-0.55 (m, 2H), 0.70-0.85 (m, 2H), 0.85-1.05 (m, 1.3H), 1.05-1.25 (m, 1.7H), 1.50-1.70 (m, 2H), 1.70-1.85 (m, 1H), 1.85-2.00 (m, 1H), 2.10-2.25 (m, 1H), 2.70-2.85 (m, 1.3H), 2.90-3.10 (m, 2.7H), 3.10-3.60 (m, 5H), 3.75 (d, J = 13.7 Hz, 0.3H), 3.90-4.00 (m, 1.7H), 4.10-4.30 (m, 1.7H), 4.65-4.75 (m, 0.3H), 6.60-6.70 (m, 0.6H), 6.74 (dd, J = 2.4, 8.3 Hz, 0.7H), 6.79 (d, J = 2.4, 0.7H), 7.06 (d, J = 8.3 Hz, 0.3H), 7.13 (d, J = 8.3 Hz, 0.7H), 7.65-7.75 (m, 0.3H), 7.80-7.85 (m, 1H), 7.97 (d, J = 7.8 Hz, 0.7H), 8.03-8.10 (m, 0.3H), 8.20-8.30 (m, 0.7H), 8.61 (d, J = 4.9 Hz, 0.3H), 8.73 (d, J = 4.9 Hz, 0.7H). |
| Example 94 | 105 | | (Hydrochloride, CD₃OD) δ 0.45-0.60 (m, 2H), 0.70-0.90 (m, 2H), 0.90-1.10 (m, 1H), 1.10-1.20 (m, 1H), 1.35-1.45 (m, 0.3H), 1.50-1.60 (m, 0.7H), 1.60-1.75 (m, 2H), 1.75-1.90 (m, 1.3H), 1.90-2.00 (m, 0.7H), 2.10-2.15 (m, 1H), 2.70-2.90 (m, 2H), 3.10-3.60 (m, 7H), 3.79 (d, J = 13.7 Hz, 0.7H), 4.00-4.15 (m, 1.3H), 4.17 (dd, J = 6.3, 13.7 Hz, 0.7H), 4.32 (dd, J = 8.3, 13.4 Hz, 0.3H), 6.60-6.66 (m, 0.6H), 6.75 (dd, J = 2.4, 8.3 Hz, 0.7H), 6.82 (d, J = 2.4 Hz, 0.7H), 7.05 (d, J = 8.3 Hz, 0.3H), 7.14 (d, J = 8.3 Hz, 0.7H), 7.69 (t, J = 7.3 Hz, 0.3H), 7.76 (t, J = 7.3 Hz, 0.7H), 7.80-7.96 (m, 2H), 7.98 (d, J = 8.3 Hz, 0.3H), 7.99 (d, J = 8.3 Hz, 0.3H), 8.07 (d, J = 8.3 Hz, 0.7H), 8.15 (d, J = 8.3 Hz, 0.7H), 8.59 (d, J = 8.3 Hz, 0.3H), 8.62 (d, J = 8.3 Hz, 0.7H). |

TABLE 5

| Compound number | | Structural formula | ¹H NMR |
|---|---|---|---|
| Example 95 | 106 | | (Hydrochloride, CD₃OD) δ 0.45-0.55 (m, 2H), 0.70-0.80 (m, 2.7H), 1.10-1.75 (m, 5.3H), 1.75-2.00 (m, 1H), 2.00-2.25 (m, 1H), 2.70-2.85 (m, 1H), 2.85-3.10 (m, 1.7H), 3.10-3.60 (m, 8.3H), 3.72 (d, J = 11.2 Hz, 1H), 3.95 (dd, J = 7.8, 11.2 Hz, 1H), 4.10-4.20 (m, 1H), 4.15 (t, J = 5.8 Hz, 0.3H), 4.51 (t, J = 5.8 Hz, 0.7H), 6.70-6.80 (m, 2H), 7.05-7.15 (m, 1H). |

TABLE 5-continued

| Compound number | Structural formula | ¹H NMR |
|---|---|---|
| Example 96 | 107 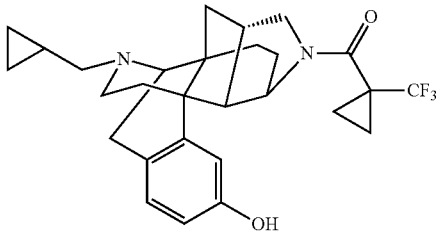 | (Hydrochloride, CD₃OD) δ 0.45-0.55 (m, 2H), 0.70-0.95 (m, 3H), 1.05-1.70 (m, 10H), 1.80-1.95 (m, 1H), 2.05-2.20 (m, 1H), 2.65-2.85 (m, 1H), 2.88-3.00 (m, 1H), 3.00-3.10 (m, 1H), 3.10-3.18 (m, 1H), 3.18-3.60 (m, 4H), 3.89 (d, J = 11.7 Hz, 1H), 4.15-4.20 (m, 2H), 4.50 (dd, J = 6.5, 8.8 Hz, 1H), 6.65-6.80 (m, 2H), 7.10 (d, J = 8.8 Hz, 1H). |
| Example 97 | 108 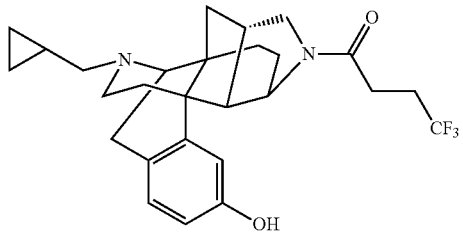 | (Hydrochloride, CD₃OD) δ 0.45-0.55 (m, 2H), 0.70-1.00 (m, 2.7H), 1.00-1.75 (m, 5.6H), 1.75-2.00 (m, 0.7H), 2.00-2.20 (m, 1H), 2.40-2.65 (m, 4H), 2.75-2.85 (m, 1H), 2.85-3.00 (m, 1H), 3.00-3.10 (m, 1H), 3.10-3.60 (m, 6H), 3.69 (d, J = 10.7 Hz, 1H), 3.90-4.00 (m, 1H), 4.10-4.20 (m, 1H), 4.20-4.30 (m, 0.3H), 4.30-4.45 (m, 0.7H), 6.70-6.80 (m, 2H), 7.05-7.15 (m, 1H). |
| Example 98 | 109 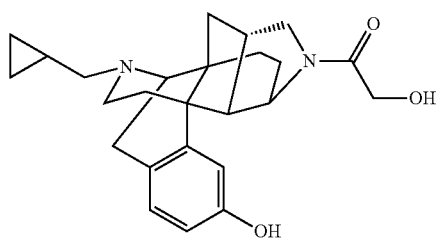 | (Hydrochloride, CD₃OD) δ 0.80-1.45 (m, 6H), 1.45-2.20 (m, 5H), 2.80-3.05 (m, 1.7H), 3.05-3.80 (m, 8.3H), 3.95-4.10 (m, 1H), 4.20-4.30 (m, 0.7H), 4.70-4.80 (m, 0.3H), 6.55-6.60 (m, 0.3H), 6.60-6.70 (m, 0.3H), 6.70-6.85 (m, 1.4H), 7.07 (d, J = 8.3 Hz, 0.3H), 7.15 (d, J = 8.3 Hz, 0.7H), 7.35-7.50 (m, 5H). |

Example 99

Synthesis of 1-[(1S,5aS,6R,11bR)-14-(cyclopropylmethyl)-10-hydroxy-4,5,6,7-tetrahydro-1H-6,11b-(iminoethano)-1,5a-methanonaphtho[1,2-e]indol-3(2H,3aH,11cH)-yl]-2,2,2-trifluoroethanone (110)

[Formula 112]

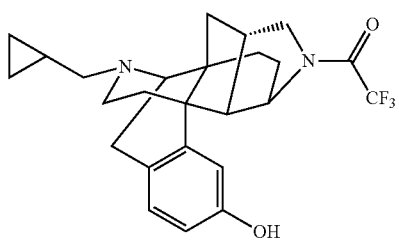

110

According to the method described in Example 5, the reactions and the treatments were performed by using the compound 77 and trifluoroacetic anhydride, and then according to the method described in Example 6, the title compound 110 and the hydrochloride thereof were obtained.

Compound 110 (hydrochloride) ¹H NMR (CD₃ OD, 400 MHz): δ 0.45-0.58 (m, 2H), 0.70-0.95 (m, 3H), 1.10-1.35 (m, 2H), 1.45 (dd, J=7.3, 15.1 Hz, 1H), 1.50-1.70 (m, 3H), 1.80-1.95 (m, 1H), 2.10-2.23 (m, 1H), 2.70-2.90 (m, 1H), 3.00-3.10 (m, 2H), 3.15-3.62 (m, 5.2H), 3.86 (d, J=11.7 Hz, 0.8H), 4.05-4.13 (m, 1H), 4.18 (d, J=5.9 Hz, 1H), 4.48-4.60 (m, 1H), 6.70-6.76 (m, 2H), 7.13 (d, J=8.3 Hz, 1H)

Reference Example 12

Synthesis of (4R,6S,7R,12bS)—N-benzyl-3-(cyclopropylmethyl)-7,9-dihydroxy-1,2,3,4,5,6,7,7a-octahydro-4a,7-ethano-4,12-methanobenzofuro[3,2-e]isoquinoline-6-carboxamide (111)

[Formula 113]

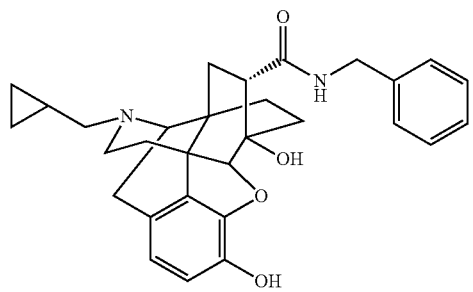

111

By using the compound 71 which was prepared in Reference Example 10 (2.03 g, 4.11 mmol), the title compound 111 (2 g, 100%) was obtained according to the method described in Example 6.

Compound 111 (free base) ¹H NMR (CDCl₃, 400 MHz): δ 0.05-0.20 (m, 2H), 0.40-0.60 (m, 2H), 0.63-0.85 (m, 2H), 1.20-1.45 (m, 2H), 1.60-1.90 (m, 2H), 1.92-2.10 (m, 2H), 2.20-2.40 (m, 4H), 2.40-2.55 (m, 1H), 2.60-2.70 (m, 1H), 2.85-3.00 (m, 1H), 2.95 (d, J=18.1 Hz, 1H), 3.07 (d, J=6.3 Hz, 1H), 3.95 (br s, 1H), 4.25 (d, J=2.0 Hz, 1H), 4.42 (dd, J=5.4, 14.6 Hz, 1H), 4.47 (dd, J=5.4, 14.6 Hz, 1H), 6.35 (t, J=5.4 Hz, 1H), 6.53 (d, J=7.8 Hz, 1H), 6.70 (d, J=7.8 Hz, 1H), 7.23-7.35 (m, 5H)

Reference Example 13

Synthesis of (4R,6S,7R,12bS)—N-benzyl-3-(cyclopropylmethyl)-7-hydroxy-9-[(1-phenyl-1H-tetrazol-5-yl)oxy]-1,2,3,4,5,6,7,7a-octahydro-4a,7-ethano-4,12-methanobenzofuro[3,2-e]isoquinoline-6-carboxamide (112)

[Formula 114]

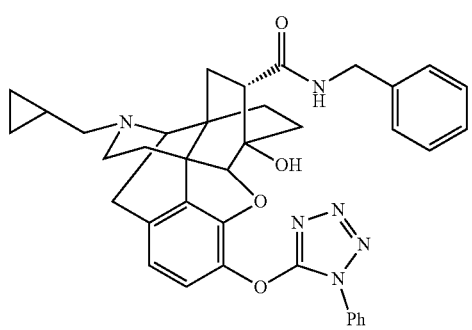

112

Under an argon atmosphere, the compound 111 (2 g, 4.11 mmol) was dissolved in DMF (40 mL), the solution was added with 5-chloro-1-phenyl-1H-tetrazole (891 mg, 4.93 mmol), and potassium carbonate (1.42 g, 10.3 mmol), and the mixture was stirred at room temperature for 16 hours. The reaction mixture was diluted with ethyl acetate, and washed with saturated aqueous sodium hydrogencarbonate, water, and saturated brine. The organic layer was dried over anhydrous sodium sulfate, and then concentrated. The obtained crude product was purified by silica gel column chromatography to give the title compound 112 (2.5 g, 96%).

$^1$H NMR (CDCl$_3$, 400 MHz): δ 0.05-0.15 (m, 2H), 0.45-0.55 (m, 2H), 0.65-0.75 (m, 2H), 1.25-1.40 (m, 1H), 1.40-1.55 (m, 1H), 1.70-1.85 (m, 2H), 2.00-2.15 (m, 2H), 2.20-2.40 (m, 4H), 2.40-2.55 (m, 1H), 2.68 (dd, J=4.9, 11.7 Hz, 1H), 2.80-2.95 (m, 1H), 3.05 (d, J=18.5 Hz, 1H), 3.15 (d, J=5.9 Hz, 1H), 4.26-4.30 (m, 1H), 4.46 (d, J=5.4 Hz, 2H), 6.69 (d, J=8.3 Hz, 1H), 6.78-7.00 (m, 1H), 7.05 (d, J=8.3 Hz, 1H), 7.20-7.35 (m, 5H), 7.50 (t, J=7.3 Hz, 1H), 7.58 (t, J=7.3 Hz, 2H), 7.83 (d, J=7.3 Hz, 2H)

Reference Example 14

Synthesis of (4R,6S,7R,12bS)—N-benzyl-3-(cyclopropylmethyl)-7-hydroxy-1,2,3,4,5,6,7,7a-octahydro-4a,7-ethano-4,12-methanobenzofuro[3,2-e]isoquinoline-6-carboxamide (113)

[Formula 115]

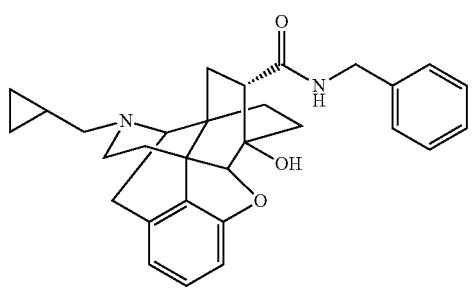

113

Under an argon atmosphere, the compound 112 (2.33 g, 3.69 mmol) was dissolved in ethanol (20 mL), benzene (36 mL), and water (10 mL), the solution was added with 10% palladium-carbon (2.3 g), and aqueous hydrazine (64 v/v %, 25 mL), and the mixture was stirred at 85° C. for 16 hours. The reaction mixture was diluted with ethyl acetate, and filtered through Celite. The organic layer was washed with water, and saturated brine, dried over anhydrous sodium sulfate, and then concentrated. The obtained crude product was purified by silica gel column chromatography to give the title compound 113 (650 mg, 37%).

$^1$H NMR (CDCl$_3$, 400 MHz): δ 0.06-0.14 (m, 2H), 0.44-0.52 (m, 2H), 0.58-0.70 (m, 1H), 0.80-0.92 (m, 3H), 1.60-1.85 (m, 2H), 2.00-2.10 (m, 2H), 2.20-2.40 (m, 4H), 2.45-2.55 (m, 1H), 2.60-2.70 (m, 1H), 2.85-3.00 (m, 1H), 3.04 (d, J=18.5 Hz, 1H), 3.10 (d, J=6.3 Hz, 1H), 4.20 (br s, 1H), 4.40-4.60 (m, 2H), 6.44 (br s, 1H), 6.59 (d, J=7.8 Hz, 1H), 6.62 (d, J=7.8 Hz, 1H), 7.05 (t, J=7.8 Hz, 1H), 7.20-7.36 (m, 5H)

Reference Example 15

Synthesis of (1S,5aS,6R,11bR)-3-benzyl-14-(cyclopropylmethyl)-3a,11-dihydroxy-3,3a, 4,5,6,7-hexahydro-1H-6,11b-(iminoethano)-1,5a-methanonaphtho[1,2-e]indol-2(11cH)-one (114)

[Formula 116]

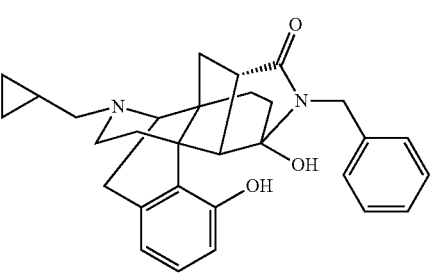

114

According to the method described in Reference Example 5, the title compound 114 (79 mg, 80%) was obtained by using the compound 113 (97 mg, 0.21 mmol). Compound 100 (free base) $^1$H NMR (CDCl$_3$, 400 MHz): δ 0.05-0.15 (m, 2H), 0.40-0.55 (m, 2H), 0.75-1.05 (m, 3H), 1.20-1.80 (m, 7H), 1.95-2.05 (m, 1H), 2.25-2.40 (m, 2H), 2.55-2.65 (m, 1H), 2.90-3.00 (m, 2H), 3.10-3.25 (m, 2H), 3.25-3.45 (m, 2H), 4.35 (d, J=14.6 Hz, 1H), 4.50 (d, J=14.6 Hz, 1H), 6.60 (d, J=7.8 Hz, 1H), 6.71 (d, J=7.8 Hz, 1H), 7.00 (t, J=7.8 Hz, 1H), 7.10-7.40 (m, 5H)

Example 100

Synthesis of (1S,5aS,6R,11bS)-3-benzyl-14-(cyclopropylmethyl)-2,3,3a,4,5,6,7,11c-octahydro-1H-6,11b-(iminoethano)-1,5a-methanonaphtho[1,2-e]indol-11-ol (115)

[Formula 117]

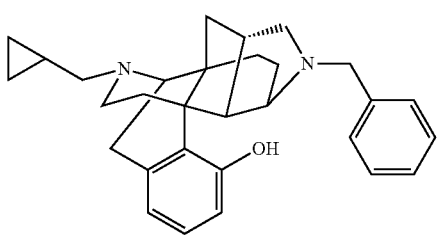

115

According to the method described in Example 1, the title compound 115 and the hydrochloride thereof (19 mg, 100%) were obtained by using the compound 114 (17 mg, 0.037 mmol).

Compound 115 (hydrochloride) $^1$H NMR (CD$_3$ OD, 400 MHz): δ 0.40-0.60 (m, 2H), 0.70-0.90 (m, 2H), 1.10-1.50 (m, 2H), 1.50-1.90 (m, 3H), 1.90-2.20 (m, 3H), 2.65-2.80 (m, 1H), 2.80-3.00 (m, 1H), 3.00-3.10 (m, 1H), 3.10-3.60 (m, 5H), 3.60-3.75 (m, 1H), 3.75-3.90 (m, 1H), 3.90-4.10 (m, 2H), 4.10-4.25 (m, 1H), 4.30-4.45 (m, 2H), 6.68 (d, J=7.8 Hz, 1H), 6.75-6.85 (m, 1H), 7.08 (t, J=7.8 Hz, 1H), 7.40-7.60 (m, 5H)

Example 101

Synthesis of (1S,5aS,6R,11bS)-14-(cyclopropylmethyl)-2,3,3a,4,5,6,7,11c-octahydro-1H-6,11b-(iminoethano)-1,5a-methanonaphtho[1,2-e]indol-11-ol (116)

[Formula 118]

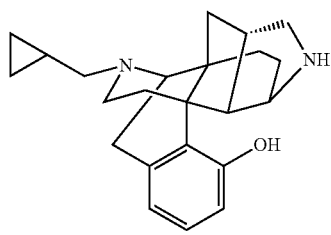

116

According to the method described in Example 4, the title compound 116 (170 mg, 97%) was obtained by using the compound 115 (220 mg, 0.50 mmol).

Compound 116 (hydrochloride) $^1$H NMR (CD$_3$ OD, 400 MHz): δ 0.05-0.15 (m, 2H), 0.40-0.50 (m, 2H), 0.75-0.85 (m, 1H), 1.00-1.10 (m, 2H), 1.20-1.50 (m, 3H), 1.70-1.90 (m, 2H), 1.95-2.10 (m, 1H), 2.25-2.35 (m, 2H), 2.50-2.60 (m, 1H), 2.85-3.00 (m, 3H), 3.00-3.20 (m, 3H), 3.45-3.60 (m, 2H), 3.60-3.70 (m, 1H), 6.44 (d, J=7.8 Hz, 1H), 6.57 (d, J=7.8 Hz, 1H), 6.89 (t, J=7.8 Hz, 1H)

Example 102

Synthesis of [(1S,5aS,6R,11bS)-14-(cyclopropylmethyl)-11-hydroxy-4,5,6,7-tetrahydro-1H-6,11b-(iminoethano)-1,5a-methanonaphtho[1,2-e]indol-3(2H,3aH,11cH)-yl](phenyl)methanone (117)

[Formula 119]

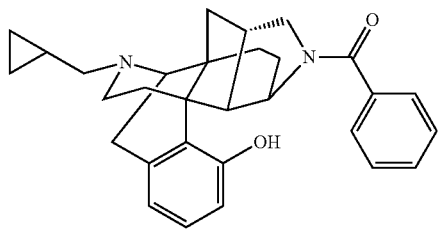

117

According to the method described in Example 33, the title compound 117 and the hydrochloride thereof (8 mg, 23%) were obtained by using the compound 116 (25 mg, 0.071 mmol) and benzoyl chloride (10 μL, 0.086 mmol).

Compound 117 (hydrochloride) $^1$H NMR (CD$_3$ OD, 400 MHz): δ 0.45-0.55 (m, 2H), 0.70-1.25 (m, 5H), 1.50-2.15 (m, 5H), 2.70-2.85 (m, 2H), 2.95-3.15 (m, 2H), 3.15-3.25 (m, 2H), 3.25-3.55 (m, 1H), 3.55-3.80 (m, 4H), 4.10-4.40 (m, 2H), 6.57 (d, J=7.8 Hz, 0.4H), 6.71 (d, J=7.8 Hz, 1H), 6.79 (d, J=7.8 Hz, 0.6H), 7.00 (t, J=7.8 Hz, 0.4H), 7.09 (t, J=7.8 Hz, 0.6H), 7.34-7.44 (m, 5H)

Example 103

[(1S,5aS,6R,11bR)-14-(Cyclobutylmethyl)-10-hydroxy-4,5,6,7-tetrahydro-1H-6,11b-(iminoethano)-1,5a-methanonaphtho[1,2-e]indol-3(2H,3aH,11cH)-yl](phenyl)methanone (119)

(1) Synthesis of [(1S,5aS,6R,11bR)-14-(cyclobutylmethyl)-10-methoxy-4,5,6,7-tetrahydro-1H-6,11b-(iminoethano)-1,5a-methanonaphtho[1,2-e]indol-3(2H,3aH,11cH)-yl](phenyl)methanone (118)

[Formula 120]

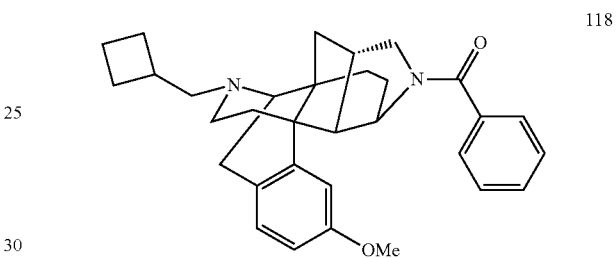

118

Under an argon atmosphere, the compound 81 (30 mg, 0.072 mmol) was dissolved in acetonitrile (1 mL), the solution was added with toluene-4-sulfonic acid cyclobutylmethyl ester (116 mg, 0.48 mmol), sodium iodide (86 mg, 0.58 mmol), and potassium carbonate (100 mg, 0.29 mmol), and the mixture was stirred at 80° C. for 16 hours. The reaction mixture was diluted with ethyl acetate, and washed with water and saturated brine. The organic layer was dried over anhydrous sodium sulfate, and then concentrated to give a crude product of the title compound 118.

(2) Synthesis of [(1S,5aS,6R,11bR)-14-(cyclobutylmethyl)-10-hydroxy-4,5,6,7-tetrahydro-1H-6,11b-(iminoethano)-1,5a-methanonaphtho[1,2-e]indol-3(2H,3aH,11cH)-yl](phenyl)methanone (119)

[Formula 121]

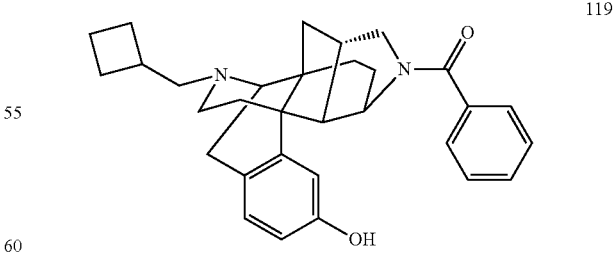

119

According to the method described in Example 6, the title compound 119 and the hydrochloride thereof (1.3 mg, 4%) were obtained by using the crude product which was prepared in (1) mentioned above.

Compound 119 (hydrochloride) $^1$H NMR (CD$_3$ OD, 400 MHz): δ 0.75-1.05 (m, 1.4H), 1.05-1.25 (m, 0.6H), 1.45-2.35

(m, 12H), 2.70-2.90 (m, 3H), 3.00-3.55 (m, 5.3H), 3.55-3.85 (m, 2.7H), 4.15-4.35 (m, 1H), 4.50-4.60 (m, 0.3H), 4.70-4.80 (m, 0.7H), 6.56 (d, J=2.4 Hz, 0.3H), 6.64 (dd, J=2.4, 8.3 Hz, 0.3H), 6.73 (dd, J=2.4, 8.3 Hz, 0.7H), 6.77 (d, J=2.4 Hz, 0.7H), 7.05 (d, J=8.3 Hz, 0.3H), 7.13 (d, J=8.3 Hz, 0.7H), 7.36-7.50 (m, 5H)

Example 104

[(1S,5aS,6R,11bR)-14-(3-Fluoropropyl)-10-hydroxy-4,5,6,7-tetrahydro-1H-6,11b-(iminoethano)-1,5a-methanonaphtho[1,2-e]indol-3(2H,3aH,11cH)-yl](phenyl)methanone (123)

(1) Synthesis of [(1S,5aS,6R,11bR)-10-[(t-butyldimethylsilyl)oxy]-14-(cyclopropylmethyl)-4,5,6,7-tetrahydro-1H-6,11b-(iminoethano)-1,5a-methanonaphtho[1,2-e]indol-3(2H,3aH,11cH)-yl](phenyl)methanone (120)

[Formula 122]

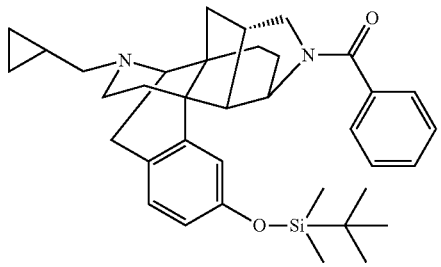

120

Under an argon atmosphere, the compound 78 (220 mg, 0.48 mmol) was dissolved in DMF (5 mL), the solution was added with imidazole (327 mg, 4.80 mmol), and t-butyldimethylchlorosilane (723 mg, 4.80 mmol), and the mixture was stirred at room temperature for 16 hours. The reaction mixture was diluted with ethyl acetate, and washed with water and saturated brine. The organic layer was dried over anhydrous sodium sulfate, and then concentrated. The obtained crude product was purified by silica gel column chromatography to give the title compound 120 as white amorphous (250 mg, 92%).

(2) Synthesis of [(1S,5aS,6R,11bR)-10-[(t-butyldimethylsilyl)oxy]-4,5,6,7-tetrahydro-1H-6,11b-(iminoethano)-1,5a-methanonaphtho[1,2-e]indol-3(2H,3aH,11cH)-yl](phenyl)methanone (121)

[Formula 123]

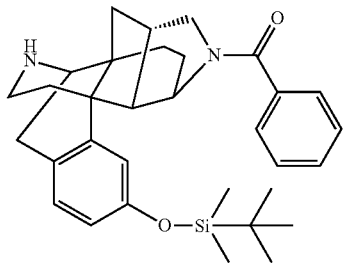

121

According to the method described in Example 71, the title compound 121 was obtained as white amorphous (50 mg, 23%) by using the compound 120 (250 mg, 0.44 mmol) which was prepared in (1) mentioned above.

(3) Synthesis of [(1S,5aS,6R,11bR)-10-[(t-butyldimethylsilyl)oxy]-14-(3-fluoropropyl)-4,5,6,7-tetrahydro-1H-6,11b-(iminoethano)-1,5a-methanonaphtho[1,2-e]indol-3(2H,3aH,11cH)-yl](phenyl)methanone (122)

[Formula 124]

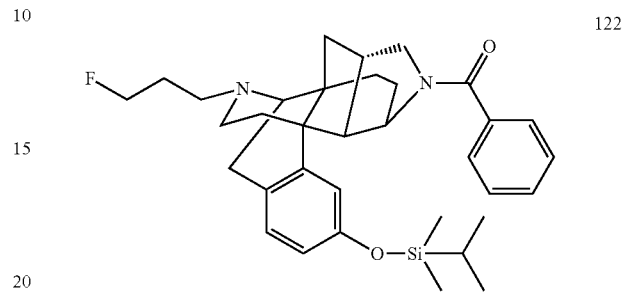

122

Under an argon atmosphere, the compound 121 (30 mg, 0.058 mmol) which was prepared in (2) mentioned above was dissolved in acetonitrile (0.5 mL), the solution was added with toluene-4-sulfonic acid 3-fluoropropyl ester (54 mg, 0.23 mmol), sodium iodide (35 mg, 0.23 mmol), and potassium carbonate (40 mg, 0.29 mmol), and the mixture was stirred at room temperature for 16 hours. The reaction mixture was diluted with ethyl acetate, and washed with water and saturated brine. The organic layer was dried over anhydrous sodium sulfate, and then concentrated to obtain a crude product of the title compound 122.

(4) Synthesis of [(1S,5aS,6R,11bR)-14-(3-fluoropropyl)-10-hydroxy-4,5,6,7-tetrahydro-1H-6,11b-(iminoethano)-1,5a-methanonaphtho[1,2-e]indol-3(2H,3aH,11cH)-yl](phenyl)methanone (123)

[Formula 125]

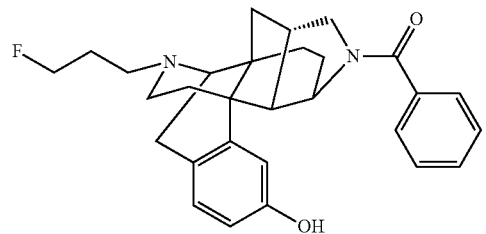

123

Under an argon atmosphere, the crude product which was prepared in (3) mentioned above was dissolved in THF (0.5 mL), the solution was added with a solution of tetrabutylammonium fluoride in THF (1.0 mol/L, 75 µL, 0.075 mmol) under ice cooling, and the mixture was stirred at room temperature for 2 hours. The reaction mixture was diluted with ethyl acetate, and washed with water and saturated brine. The organic layer was dried over anhydrous sodium sulfate, and then concentrated. The obtained crude product was purified by preparative TLC to give the title compound 123 and the hydrochloride thereof (1.4 mg, 5%).

Compound 123 (free base) $^1$H NMR (CDCl$_3$, 400 MHz): δ 0.80-0.96 (m, 1H), 0.96-1.45 (m, 3H), 1.45-1.70 (m, 3.3H), 1.70-1.90 (m, 1.7H), 1.90-2.15 (m, 2H), 2.40-2.55 (m, 0.7H), 2.65-2.85 (m, 1.6H), 2.90-3.05 (m, 1.7H), 3.35-3.75 (m, 2.4H), 3.75-3.85 (m, 0.3H), 3.90-4.00 (m, 0.3H), 4.15-4.35 (m, 2.7H), 4.35-4.40 (m, 0.3H), 4.40-4.65 (m, 2.3H), 4.80-4.95 (m, 0.7H), 6.52 (d, J=2.4 Hz, 0.3H), 6.57 (dd, J=2.4, 8.3

Hz, 0.3H), 6.66 (dd, J=2.4, 8.3 Hz, 0.7H), 6.74 (d, J=2.4 Hz, 0.7H), 6.88 (br s, 1H), 6.93 (d, J=8.3 Hz, 1H), 7.30-7.50 (m, 5H)

Example 105

[(1S,5aS,6R,11bR)-14-(3,3-Difluoropropyl)-10-hydroxy-4,5,6,7-tetrahydro-1H-6,11b-(iminoethano)-1,5a-methanonaphtho[1,2-e]indol-3(2H,3aH,11cH)-yl](phenyl)methanone (125)

(1) Synthesis of [(1S,5aS,6R,11bR)-10-[(t-butyldimethylsilyl)oxy]-14-(3,3-difluoropropyl)-4,5,6,7-tetrahydro-1H-6,11b-(iminoethano)-1,5a-methanonaphtho[1,2-e]indol-3(2H,3aH,11cH)-yl](phenyl)methanone (124)

[Formula 126]

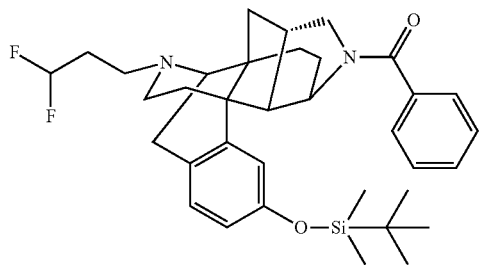

124

According to the method described in Example 104, (3), a crude product of the title compound 124 was obtained by using the compound 121 (50 mg, 0.1 mmol) and toluene-4-sulfonic acid 3,3-difluoropropyl ester (86 mg, 0.34 mmol).

(2) Synthesis of [(1S,5aS,6R,11bR)-14-(3,3-difluoropropyl)-10-hydroxy-4,5,6,7-tetrahydro-1H-6,11b-(iminoethano)-1,5a-methanonaphtho[1,2-e]indol-3(2H,3aH,11cH)-yl](phenyl)methanone (125)

[Formula 127]

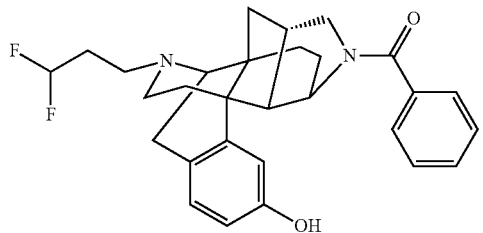

125

According to the method described in Example 104, (4), the title compound 125 and the hydrochloride thereof (1.9 mg, 4%) were obtained by using the crude product which was prepared in (1) mentioned above.

Compound 125 (free base) $^1$H NMR (CDCl$_3$, 400 MHz): δ 0.75-1.70 (m, 5H), 1.70-2.20 (m, 4H), 2.40-2.70 (m, 2.7H), 2.85-3.05 (m, 4.6H), 3.21 (t, J=12.2 Hz, 0.7H), 3.45-3.75 (m, 3H), 4.05-4.35 (m, 1.3H), 4.81 (t, J=12.2 Hz, 0.7H), 5.94 (tt, J=4.8, 57 Hz, 1H), 6.49 (d, J=2.4 Hz, 0.3H), 6.54 (dd, J=2.4, 8.3 Hz, 0.3H), 6.62 (dd, J=2.4, 8.3 Hz, 0.7H), 6.67 (d, J=2.4 Hz, 0.7H), 6.94 (d, J=8.3 Hz, 0.3H), 6.98 (d, J=8.3 Hz, 0.7H), 7.30-7.50 (m, 5H)

Example 106

[(1S,5aS,6R,11bR)-14-(2,2-Difluoro-2-phenylethyl)-10-hydroxy-4,5,6,7-tetrahydro-1H-6,11b-(iminoethano)-1,5a-methanonaphtho[1,2-e]indol-3(2H,3aH,11cH)-yl](phenyl)methanone (131)

(1) Synthesis of 2,2,2-trichloroethyl (1S,5aS,6R,11bR)-14-(cyclopropylmethyl)-10-methoxy-3a,4,5,6,7,11c-hexahydro-1H-6,11b-(iminoethano)-1,5a-methanonaphtho[1,2-e]indole-3(2H)-carboxylate (126)

[Formula 128]

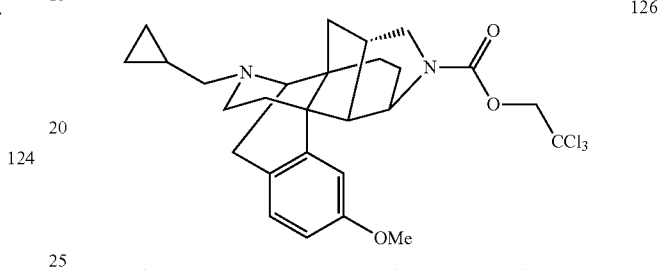

126

Under an argon atmosphere, the compound 77 (1 g, 2.74 mmol) was dissolved in dichloromethane (10 mL), the solution was cooled on ice, and then added with potassium carbonate (768 mg, 5.49 mmol), and 2,2,2-trichloroethyl chloroformate (406 µL, 3.02 mmol), and the mixture was stirred at room temperature for 1 hour. The reaction mixture was added with saturated aqueous sodium hydrogencarbonate, the mixture was extracted with chloroform, and then the organic layer was dried over anhydrous sodium sulfate, and concentrated. The obtained crude product was purified by silica gel column chromatography to give the title compound 126 (1.39 g, 94%).

Compound 126 (free base) $^1$H NMR (CDCl$_3$, 400 MHz): δ 0.05-0.20 (m, 2H), 0.40-0.55 (m, 2H), 0.70-0.92 (m, 2H), 1.10-1.20 (m, 2H), 1.35-1.60 (m, 2H), 1.65-1.75 (m, 1H), 1.85-2.05 (m, 2H), 2.24-2.36 (m, 2H), 2.55-2.60 (m, 1H), 2.85-2.95 (m, 2H), 3.00-3.15 (m, 3H), 3.32-3.45 (m, 1H), 3.50-3.63 (m, 1H), 3.74-3.86 (m, 4H), 4.28 (dd, J=5.4, 8.3 Hz, 1H), 4.57 (d, J=12.2 Hz, 0.5H), 4.66 (d, J=12.2 Hz, 0.5H), 4.78 (d, J=12.2 Hz, 0.5H), 4.87 (d, J=12.2 Hz, 0.5H), 6.64-6.72 (m, 2H), 7.02 (d, J=8.3 Hz, 0.5H), 7.03 (d, J=8.3 Hz, 0.5H)

(2) Synthesis of 2,2,2-trichloroethyl (1S,5aS,6R,11bR)-10-methoxy-3a,4,5,6,7,11c-hexahydro-1H-6,11b-(iminoethano)-1,5a-methanonaphtho[1,2-e]indole-3(2H)-carboxylate (127)

[Formula 129]

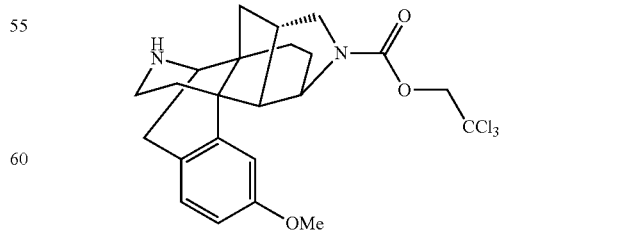

127

According to the method described in Example 71, the title compound 127 (1.6 g, 75%) was obtained as pale yellow amorphous by using the compound 126 (2.39 g, 4.4 mmol) which was prepared in (1) mentioned above.

¹H NMR (CDCl₃, 400 MHz): δ 0.70-0.90 (m, 1H), 1.30-1.60 (m, 4H), 1.60-1.80 (m, 1H), 1.95-2.10 (m, 1H), 2.75-2.85 (m, 1H), 3.00-3.30 (m, 5H), 3.50-3.85 (m, 4H), 3.78 (s, 1.5H), 3.80 (s, 1.5H), 4.25-4.40 (m, 1H), 4.57 (d, J=12.0 Hz, 0.5H), 4.65 (d, J=12.0 Hz, 0.5H), 4.79 (d, J=12.0 Hz, 0.5H), 4.87 (d, J=12.0 Hz, 0.5H), 6.65-6.73 (m, 1H), 6.73-6.85 (m, 1H), 7.11 (d, J=8.3 Hz, 0.5H), 7.12 (d, J=8.3 Hz, 0.5H)

(3) Synthesis of 2,2,2-trichloroethyl (1S,5aS,6R,11bR)-14-(2,2-difluoro-2-phenylacetyl)-10-methoxy-3a,4,5,6,7,11c-hexahydro-1H-6,11b-(iminoethano)-1,5a-methanonaphtho[1,2-e]indole-3(2H)-carboxylate (128)

[Formula 130]

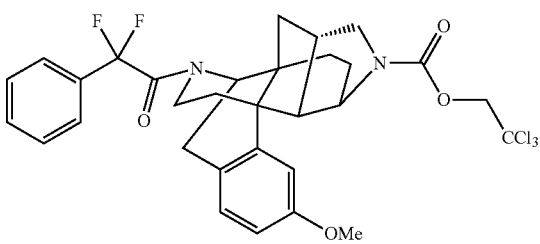

128

Under an argon atmosphere, the compound 127 (30 mg, 0.062 mmol) was dissolved in DMF (1 mL), the solution was added with 2,2-difluoro-2-phenylacetic acid (16 mg, 0.093 mmol), diisopropylethylamine (32 μL, 0.19 mmol), and O-(7-azabenzotriazol-1-yl)tetramethyluronium hexafluorophosphate (47 mg, 0.12 mmol), and the mixture was stirred at room temperature for 16 hours. The reaction mixture was diluted with ethyl acetate, and washed with saturated aqueous sodium hydrogencarbonate, water, and saturated brine. The organic layer was dried over anhydrous sodium sulfate, and then concentrated to obtain a crude product of the title compound 128.

(4) Synthesis of 2,2-difluoro-1-[(1S,5aS,6R,11bR)-10-methoxy-2,3,3a,4,5,6,7,11c-octahydro-1H-6,11b-(iminoethano)-1,5a-methanonaphtho[1,2-e]indol-14-yl]-2-phenylethanone (129)

[Formula 131]

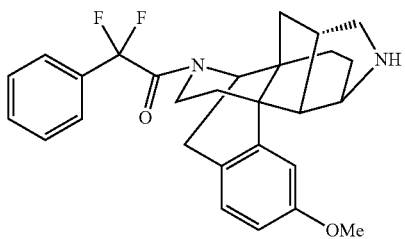

129

The crude product which was prepared in (3) mentioned above was dissolved in ethanol (1 mL), the solution was added with zinc (100 mg), and the mixture was stirred at 90° C. for 16 hours. The reaction mixture was filtered through Celite, and concentrated. The obtained residue was dissolved in ethyl acetate, and washed with water and saturated brine. The organic layer was dried over anhydrous sodium sulfate, and then concentrated to obtain a crude product of the title compound 129.

(5) Synthesis of (1S,5aS,6R,11bR)-14-(2,2-difluoro-2-phenylethyl)-10-methoxy-2,3,3a,4,5,6,7,11c-octahydro-1H-6,11b-(iminoethano)-1,5a-methanonaphtho[1,2-e]indole (130)

[Formula 132]

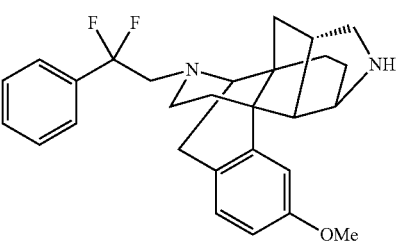

130

Under an argon atmosphere, the crude product which was prepared in (4) mentioned above was dissolved in THF (1 mL), the solution was added with a solution of borane-THF complex in THF (1.0 mol/L, 0.3 mL, 0.3 mmol), and the mixture was refluxed for 2 hours. The reaction mixture was concentrated, and added with 6 M hydrochloric acid (2 mL), and the mixture was refluxed for 1 hour. The reaction mixture was adjusted to pH 11 with potassium carbonate, and extracted three times with chloroform. The organic layers were combined, dried over anhydrous sodium sulfate, and then concentrated to obtain a crude product of the title compound 130.

(6) Synthesis of [(1S,5aS,6R,11bR)-14-(2,2-difluoro-2-phenylethyl)-10-hydroxy-4,5,6,7-tetrahydro-1H-6,11b-(iminoethano)-1,5a-methanonaphtho[1,2-e]indol-3(2H,3aH,11cH)-yl](phenyl)methanone (131)

[Formula 133]

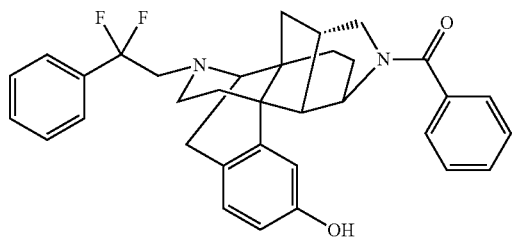

131

According to the method described in Example 32, the title compound 131 and the hydrochloride thereof (3.0 mg, 26%) were obtained by using the crude product (16 mg, 0.036 mmol) which was prepared in (5) mentioned above and benzoyl chloride (8 μL, 0.072 mmol).

Compound 131 (hydrochloride) ¹H NMR (CD₃OD, 400 MHz): δ 0.70-1.80 (m, 6H), 2.20-2.40 (m, 2H), 2.70-3.20 (m, 8H), 3.45-3.75 (m, 2.7H), 4.13 (t, J=6.8 Hz, 0.3H), 4.18-4.35

(m, 0.3H), 4.90 (t, J=6.8 Hz, 0.7H), 6.44 (d, J=2.4 Hz, 0.3H), 6.52 (dd, J=2.4, 8.2 Hz, 0.3H), 6.60 (dd, J=2.4, 8.2 Hz, 0.7H), 6.64 (d, J=2.4 Hz, 0.7H), 6.90-7.05 (m, 1H), 7.20-7.60 (m, 10H)

Example 107

Synthesis of [(1S,5aS,6R,11bR)-10-hydroxy-14-((R)-2-hydroxypropyl)-4,5,6,7-tetrahydro-1H-6,11b-(iminoethano)-1,5a-methanonaphtho[1,2-e]indol-3(2H,3aH,11cH)-yl](phenyl)methanone (132)

[Formula 134]

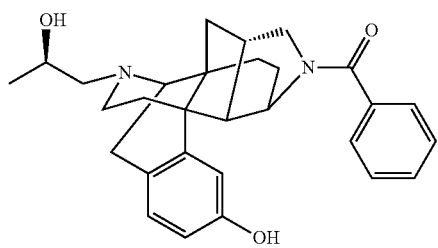

132

Under an argon atmosphere, the compound 81 (50 mg, 0.12 mmol) was dissolved in methanol (1 mL), the solution was added with each of three divided portions of (R)-(+)-propylene oxide (450 μL, 6.42 mmol) every 30 minutes, and the mixture was stirred under reflux for 2 hours and 30 minutes in total. The reaction mixture was left to cool, and then concentrated. By using the obtained crude product, the title compound 132 (48.0 mg, 88%) and the hydrochloride thereof were obtained according to the method described in Example 6.

Compound 132 (free base) $^1$H NMR (CD$_3$OD, 400 MHz): δ 0.71-1.35 (m, 4H), 1.15 (d, J=6.3 Hz, 3H), 1.42-1.62 (m, 2H), 1.62-1.81 (m, 1H), 1.90-2.05 (m, 1H), 2.20-2.35 (m, 2H), 2.40-2.50 (m, 2H), 2.90-3.21 (m, 5H), 3.59 (d, J=12.2 Hz, 1H), 3.65-3.72 (m, 0.6H), 3.74-3.82 (m, 1H), 4.15-4.25 (m, 0.8H), 4.65-4.72 (m, 0.6H), 6.47 (d, J=2.4 Hz, 0.4H), 6.51 (dd, J=2.4, 8.3 Hz, 0.4H), 6.60 (dd, J=2.4, 8.8 Hz, 0.6H), 6.68 (d, J=2.4 Hz, 0.6H), 6.92 (d, J=8.3 Hz, 0.4H), 7.00 (d, J=8.8 Hz, 0.6H), 7.34-7.45 (m, 5H)

Example 108

[(1S,5aS,6R,11bR)-10-Hydroxy-14-phenyl-4,5,6,7-tetrahydro-1H-6,11b-(iminoethano)-1,5a-methanonaphtho[1,2-e]indol-3(2H,3aH,11cH)-yl](phenyl)methanone (134)

(1) Synthesis of [(1S,5aS,6R,11bR)-10-[(t-butyldimethylsilyl)oxy]-14-phenyl-4,5,6,7-tetrahydro-1H-6,11b-(iminoethano)-1,5a-methanonaphtho[1,2-e]indol-3(2H,3aH,11cH)-yl](phenyl)methanone (133)

[Formula 135]

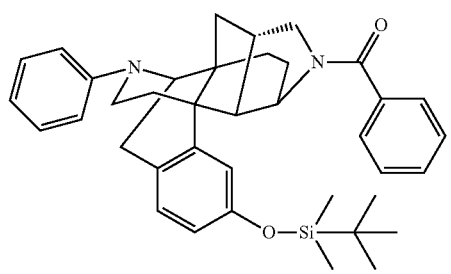

133

Under an argon atmosphere, the compound 121 (30 mg, 0.058 mmol) was dissolved in toluene (1 mL), the solution was added with tris(dibenzylideneacetone)dipalladium (5 mg, 6 mmol), 2,2'-bis(diphenylphosphino)-1,1'-binaphthyl (8 mg, 0.01 mmol), bromobenzene (9 μL, 0.09 mmol), and sodium t-butoxide (11 mg, 0.12 mmol), and the mixture was stirred at 80° C. for 16 hours. The reaction mixture was added with ethyl acetate (5 mL), and the mixture was filtered through Celite, and then concentrated to obtain a crude product of the title compound 133.

(2) Synthesis of [(1S,5aS,6R,11bR)-10-hydroxy-14-phenyl-4,5,6,7-tetrahydro-1H-6,11b-(iminoethano)-1,5a-methanonaphtho[1,2-e]indol-3(2H,3aH,11cH)-yl](phenyl)methanone (134)

[Formula 136]

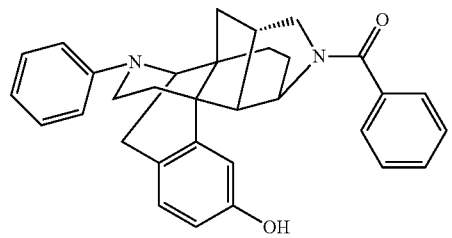

134

According to the method described in Example 104, (4), the title compound 134 and the hydrochloride thereof (3.0 mg, 22%) were obtained by using the crude product which was prepared in (1) mentioned above.

Compound 134 (hydrochloride) $^1$H NMR (CD$_3$OD, 400 MHz): δ 0.80-1.25 (m, 2H), 1.40-1.90 (m, 4H), 2.05-2.25 (m, 1H), 2.60-2.80 (m, 1H), 3.00-3.50 (m, 6.3H), 3.60-3.80 (m, 1.7H), 4.10-4.35 (m, 1.7H), 4.70-5.00 (m, 0.3H), 6.55-6.60 (m, 0.6H), 6.69 (dd, J=2.4, 8.3 Hz, 0.7H), 6.80 (d, J=2.4 Hz, 0.7H), 6.90 (d, J=8.3 Hz, 0.3H), 6.98 (d, J=8.3 Hz, 0.7H), 7.05-7.30 (m, 5H), 7.30-7.50 (m, 5H)

Examples 109 to 115

By using the compound 81 which was prepared in Example 71, the compounds of Example 109 to 115 (free bases and the hydrochlorides thereof) were obtained according to the methods mentioned in Tables 6 and 7.

TABLE 6

| Compound number | | Structural formula | ¹H NMR | Synthetic method |
|---|---|---|---|---|
| Example 109 | 135 | | (Free base, CDCl₃) δ 0.80-1.45 (m, 6H), 1.45-2.20 (m, 5H), 2.80-3.05 (m, 1.7H), 3.05-3.80 (m, 8.3H), 3.95-4.10 (m, 1H), 4.20-4.30 (m, 0.7H), 4.70-4.80 (m, 0.3H), 6.55-6.60 (m, 0.3H), 6.60-6.70 (m, 0.3H), 6.70-6.85 (m, 1.4H), 7.07 (d, J = 8.3 Hz, 0.3H), 7.15 (d, J = 8.3 Hz, 0.7H), 7.35-7.50 (m, 5H). | a |
| Example 110 | 136 | | (Hydrochloride, CD₃OD) δ 0.80-1.05 (m, 1.7H), 1.10-1.25 (m, 0.3H), 1.45-1.85 (m, 3.3H), 1.85-1.95 (m, 0.7H), 2.10-2.24 (m, 1H), 2.80-2.95 (m, 2H), 3.12-3.22 (m, 3H), 3.22-3.40 (m, 2.3H), 3.42-3.56 (m, 2H), 3.55-3.70 (m, 1H), 3.70-3.80 (m, 0.7H), 3.80-4.05 (m, 3H), 4.20-4.30 (m, 0.7H), 4.78-4.79 (m, 0.3H), 6.57 (d, J = 2.0 Hz, 0.3H), 6.65 (dd, J = 2.0, 8.8 Hz, 0.3H), 6.73 (dd, J = 2.0, 8.8 Hz, 0.7H), 6.78 (d, J = 2.0 Hz, 0.7H), 7.05 (d, J = 8.8 Hz, 0.3H), 7.13 (d, J = 8.8 Hz, 0.7H), 7.38-7.50 (m, 5H). | c |
| Example 111 | 137 | | (Free base, CD₃OD) δ 0.75-1.30 (m, 4H), 1.13 (d, J = 6.3 Hz, 3H), 1.43-1.60 (m, 2H), 1.62-1.82 (m, 1H), 1.90-2.05 (m, 1H), 2.10-2.25 (m, 1H), 2.30-2.40 (m, 2H), 2.45-2.55 (m, 1H), 2.85-3.20 (m, 5H), 3.60 (d, J = 12.2 Hz, 1H), 3.65-3.73 (m, 0.6H), 3.75-3.85 (m, 1H), 4.14-4.24 (m, 0.8H), 4.69 (t, J = 6.3 Hz, 0.6H), 6.47 (d, J = 2.4 Hz, 0.4H), 6.51 (dd, J = 2.4, 8.3 Hz, 0.4H), 6.60 (dd, J = 2.4, 8.3 Hz, 0.6H), 6.68 (d, J = 2.4 Hz, 0.6H), 6.91 (d, J = 8.3 Hz, 0.4H), 6.98 (d, J = 8.3 Hz, 0.6H), 7.34-7.46 (m, 5H). | b |
| Example 112 | 138 | | (Hydrochloride, CD₃OD) δ 0.70-1.39 (m, 4H), 1.40-1.60 (m, 2H), 1.62-1.83 (m, 1H), 1.84-2.00 (m, 1H), 2.08-2.21 (m, 1H), 2.22-2.39 (m, 2H), 2.42-2.51 (m, 1H), 2.52-2.65 (m, 1H), 2.66-2.79 (m, 1H), 2.86-3.18 (m, 5H), 3.54-3.62 (m, 1H), 3.64-3.72 (m, 0.6H), 4.13-4.24 (m, 0.8H), 4.68 (t, J = 6.5 Hz, 0.6H), 6.45 (d, J = 2.4 Hz, 0.4H), 6.50 (dd, J = 2.4, 8.3 Hz, 0.4H), 6.59 (dd, J = 2.4, 8.8 Hz, 0.6H), 6.67 (d, J = 2.4 Hz, 0.6H), 6.90 (d, J = 8.3 Hz, 0.4H), 6.98 (d, J = 8.8 Hz, 0.6H), 7.34-7.46 (m, 5H). | c |

TABLE 7

| Compound number | | Structural formula | ¹H NMR | Synthetic method |
|---|---|---|---|---|
| Example 113 | 139 | | (Hydrochloride, CD₃OD) δ 0.75-1.05 (m, 1.3H), 1.05-1.25 (m, 0.7H), 1.50-1.80 (m, 3.7H), 1.80-1.90 (m, 0.3H), 1.90 (s, 3H), 2.10-2.25 (m, 1H), 2.70-3.00 (m, 2H), 3.10-3.25 (m, 2H), 3.25-3.50 (m, 3H), 3.60-3.85 (m, 4H), 3.95-4.10 (m, 1H), 4.20-4.30 (m, 1H), 5.39 (br s, 2H), 6.58 (d, J = 2.4 Hz, 0.3H), 6.64 (dd, J = 2.4, 8.2 Hz, 0.3H), 6.74 (dd, J = 2.4, 8.2 Hz, 0.7H), 6.79 (d, J = 2.4 Hz, 0.7H), 7.06 (d, J = 8.2 Hz, 0.3H), 7.14 (d, J = 8.2 Hz, 0.7H), 7.36-7.50 (m, 5H). | c |

TABLE 7-continued

| Compound number | Structural formula | ¹H NMR | Synthetic method |
|---|---|---|---|
| Example 114 | 140 | (Hydrochloride, CD$_3$OD) δ 0.75-1.10 (m, 1.3H), 1.10-1.25 (m, 0.7H), 1.45-2.00 (m, 4H), 2.10-2.25 (m, 1H), 2.80-2.98 (m, 2H), 2.98-3.10 (m, 1H), 3.10-3.80 (m, 10H), 3.95-4.10 (m, 1H), 4.20-4.30 (m, 0.7H), 4.70-4.80 (m, 0.3H), 6.58 (d, J = 2.4 Hz, 0.3H), 6.64 (dd, J = 2.4, 8.3 Hz, 0.3H), 6.74 (dd, J = 2.4, 8.3 Hz, 0.7H), 6.79 (d, J = 2.4 Hz, 0.7H), 7.06 (d, J = 8.3 Hz, 0.3H), 7.14 (d, J = 8.3 Hz, 0.7H), 7.25-7.50 (m, 10H). | a |
| Example 115 | 141 | (Free base, CDCl$_3$) δ 0.75-1.20 (m, 3H), 1.40-1.95 (m, 3H), 1.95-2.20 (m, 1H), 2.40-2.55 (m, 1H), 2.55-2.75 (m, 4H), 2.80-3.15 (m, 5H), 3.15-3.25 (m, 1H), 3.50-3.70 (m, 2H), 4.10-4.35 (m, 1H), 4.81 (t, J = 7.3 Hz, 1H), 5.53 (br s, 1H), 6.48 (d, J = 2.4 Hz, 0.3H), 6.53 (dd, J = 2.4, 8.3 Hz, 0.3H), 6.61 (dd, J = 2.4, 8.3 Hz, 0.7H), 6.67 (d, J = 2.4 Hz, 0.7H), 6.90-7.00 (m, 3H), 7.10-7.20 (m, 2H), 7.30-7.50 (m, 5H). | c |

Synthesis Methods Mentioned in Tables

Method a: methods described in Examples 13 and 6

Method b: method described in Example 107

Method c: method described in Example 8, 10 or 11

Example 116

Synthesis of [(1S,5aS,6R,11bR)-10-hydroxy-14-((R)-2-hydroxypropyl)-4,5,6,7-tetrahydro-1H-6,11b-(iminoethano)-1,5a-epoxynaphtho[1,2-e]indol-3(2H,3aH,11cH)-yl](phenyl)methanone (142)

[Formula 137]

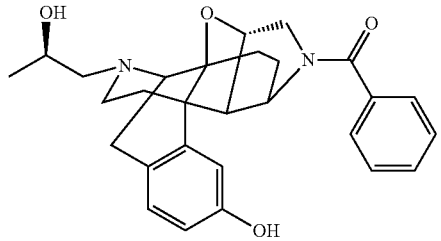

142

According to the method described in Example 107, the title compound 142 and the hydrochloride thereof were obtained by using the compound 11.

Compound 142 (hydrochloride) ¹H NMR (CD$_3$ OD, 400 MHz): δ 0.70-0.85 (m, 0.3H), 0.92-1.10 (m, 0.7H), 1.20-1.23 (m, 0.6H), 1.27 (d, J=6.3 Hz, 3H), 1.55-1.65 (m, 1.7H), 1.80-1.96 (m, 1.7H), 2.24-2.39 (m, 1H), 2.89-3.05 (m, 2H), 3.10-3.20 (m, 1H), 3.25-3.52 (m, 5H), 3.73-3.89 (m, 1.7H), 4.13-4.26 (m, 2H), 4.37-4.42 (m, 0.3H), 5.04 (t, J=5.4 Hz, 0.7H), 5.16 (t, J=5.9 Hz, 0.3H), 6.60 (d, J=2.4 Hz, 0.3H), 6.69 (dd, J=2.4, 8.3 Hz, 0.3H), 6.75-6.82 (m, 1.4H), 7.08 (d, J=8.3 Hz, 0.3H), 7.16 (d, J=8.3 Hz, 0.7H), 7.41-7.52 (m, 5H)

Example 117

Synthesis of [(1S,5aS,6R,11bR)-14-((S)-2-fluoropropyl)-10-hydroxy-4,5,6,7-tetrahydro-1H-6,11b-(iminoethano)-1,5a-epoxynaphtho[1,2-e]indol-3(2H,3aH,11cH)-yl](phenyl)methanone (143)

[Formula 138]

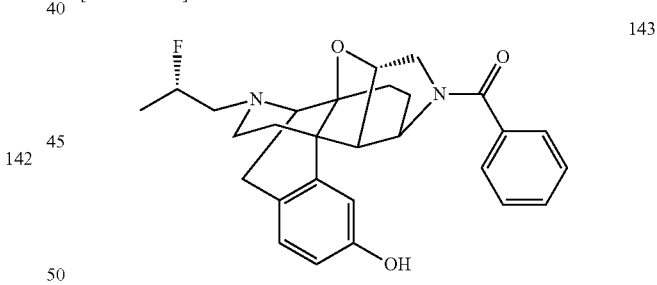

143

Under an argon atmosphere, the compound 142 (41 mg, 0.089 mmol) was dissolved in dichloromethane (1 mL), the solution was cooled to −78° C., and then added with bis(2-methoxyethyl)aminosulfur trifluoride (23 μL, 0.13 mmol), and the mixture was stirred at room temperature for 24 hours. The reaction mixture was added with saturated aqueous sodium hydrogencarbonate, the mixture was extracted with chloroform, and then the organic layer was dried over anhydrous sodium sulfate, and concentrated. The obtained crude product was purified by preparative TLC to give the title compound 143 as white amorphous (27.1 mg, 66%).

Compound 143 (hydrochloride) ¹H NMR (CD$_3$ OD, 400 MHz): δ 0.70-1.30 (m, 1.3H), 1.45 (dd, J=6.3, 23.9 Hz, 3H), 1.56-1.70 (m, 1.7H), 1.80-1.96 (m, 2H), 2.20-2.40 (m, 1H), 2.90-3.06 (m, 1H), 3.18-3.65 (m, 7H), 3.73-3.90 (m, 1.4H), 4.15-4.25 (m, 1.3H), 4.35-4.45 (m, 0.3H), 4.86-4.96 (m, 0.3H), 5.03 (t, J=5.9 Hz, 0.7H), 5.12-5.25 (m, 0.7H), 5.27-5.38 (m, 0.3H), 6.61 (d, J=2.4 Hz, 0.3H), 6.69 (dd, J=2.4, 8.3 Hz, 0.3H), 6.75-6.84 (m, 1.4H), 7.08 (d, J=8.3 Hz, 0.3H), 7.16 (d, J=8.3 Hz, 0.7H), 7.41-7.51 (m, 5H)

Examples 118 and 119

By using the compound 8, the compounds of Examples 118 and 119 (free bases and the hydrochlorides thereof) were obtained according to the method described in Example 74.

room temperature for 16 hours. The reaction mixture was concentrated, the obtained residue was dissolved in ethyl acetate, and the solution was washed with saturated aqueous sodium hydrogencarbonate, water, and saturated brine. The organic layer was dried over anhydrous sodium sulfate, and then concentrated. The obtained crude product was purified by silica gel column chromatography to give the title compound 146 (72 mg, 100%).

$^1$H NMR (CDCl$_3$, 400 MHz): δ 0.70-0.95 (m, 1H), 1.08-1.50 (m, 13H), 1.60-1.86 (m, 2H), 2.45-2.57 (m, 1H), 2.58-

TABLE 8

| | Compound number | Structural formula | $^1$H NMR |
|---|---|---|---|
| Example 118 | 144 | | (Free base, CDCl$_3$) δ 0.62-1.36 (m, 2.2H), 1.43-1.58 (m, 0.8H), 1.65-1.88 (m, 2H), 2.02 (dt, J = 5.1, 12.6 Hz, 1H), 2.17-2.42 (m, 1H), 2.48-2.62 (m, 1H), 2.72-3.13 (m, 4H), 3.14 (d, J = 18.6 Hz, 1H), 3.35-3.48 (m, 1H), 3.63 (dd, J = 6.0, 12.6 Hz, 0.8H), 3.87 (d, J = 12.6 Hz, 1H), 4.15-4.29 (m, 0.4H), 4.43-4.79 (m, 2H), 4.89-5.08 (m, 1.8H), 6.51 (d, J = 2.4 Hz, 0.2H), 6.59 (dd, J = 2.4, 8.4 Hz, 0.2H), 6.66 (dd, J = 2.4, 8.4 Hz, 0.8H), 6.72 (d, J = 2.4 Hz, 0.8H), 6.86-6.94 (m, 0.2H), 6.93 (d, J = 8.4 Hz, 0.8H), 7.28-7.55 (m, 5H). |
| Example 119 | 145 | | (Hydrochloride, CD$_3$OD) δ 0.67-1.20 (m, 2H), 1.54-1.60 (m, 2H), 1.80-1.96 (m, 2H), 2.05-2.37 (m, 2H), 2.86-3.02 (m, 1H), 3.15-3.24 (m, 1H), 3.25-3.53 (m, 5.2H), 3.73-3.90 (m, 2H), 4.08-4.17 (m, 1H), 4.19-4.27 (m, 0.4H), 4.36-4.42 (m, 0.4H), 4.48-4.72 (m, 2H), 5.00-5.06 (m, 0.6H), 5.12-5.18 (m, 0.4H), 6.60 (d, J = 2.4 Hz, 0.4H), 6.69 (dd, J = 2.4, 8.3 Hz, 0.4H), 6.74-6.82 (m, 1.2H), 7.09 (d, J = 8.3 Hz, 0.4H), 7.16 (d, J = 7.8 Hz, 0.6H), 7.41-7.53 (m, 5H). |

Example 120

[(1S,5aS,6R,11bR)-10-Hydroxy-14-methyl-4,5,6,7-tetrahydro-1H-6,11b-(iminoethano)-1,5a-methanonaphtho[1,2-e]indol-3(2H,3aH,11cH)-yl](pyridin-2-yl)methanone (150)

(1) Synthesis of 2,2,2-trichloroethyl (1S,5aS,6R,11bR)-14-t-butoxycarbonyl-10-methoxy-3a,4,5,6,7,11c-hexahydro-1H-6,11b-(iminoethano)-1,5a-methanonaphtho[1,2-e]indol-3(2H)-carboxylate (146)

[Formula 139]

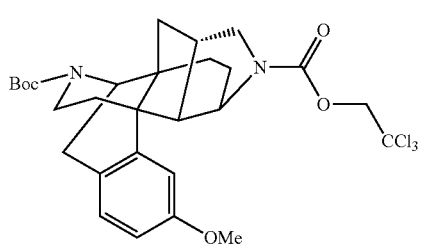

146

Under an argon atmosphere, the compound 127 (60 mg, 0.123 mmol) which was prepared in Example 106, (2) was dissolved in dichloromethane (1 mL), the solution was added with triethylamine (51 μL, 0.35 mmol), and di-t-butyl dicarbonate (42 μL, 0.19 mmol), and the mixture was stirred at 2.83 (m, 2H), 2.96-3.08 (m, 2H), 3.43-3.60 (m, 2H), 3.75-3.85 (m, 4.5H), 3.90-4.00 (m, 0.5H), 4.26-4.37 (m, 1.5H), 4.50-4.90 (m, 2.5H), 6.65-6.76 (m, 2H), 7.02-7.08 (m, 1H).

(2) Synthesis of t-butyl (1S,5aS,6R,11bR)-10-methoxy-2,3,3a,4,5,6,7,11c-octahydro-1H-6,11b-(iminoethano)-1,5a-methanonaphtho[1,2-e]indole-14-carboxylate (147)

[Formula 140]

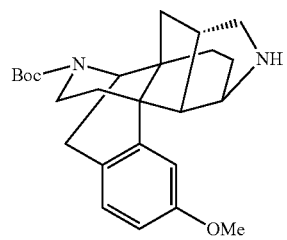

147

According to the method described in Example 106, (4), the title compound 147 (49 mg, 100%) was obtained as pale yellow amorphous by using the compound 146 (72 mg, 0.12 mmol) which was prepared in (1) mentioned above.

$^1$H NMR (CDCl$_3$, 400 MHz): δ 0.82-0.98 (m, 1H), 1.02-1.12 (m, 1H), 1.15-1.30 (m, 2H), 1.32-1.60 (m, 11H), 1.65-1.80 (m, 1H), 2.10-2.22 (m, 1H), 2.50-2.70 (m, 2H), 2.84-

3.04 (m, 4H), 3.10-3.90 (m, 3H), 3.73 (s, 3H), 4.15-4.40 (m, 2H), 6.72-6.77 (m, 2H), 7.05-7.10 (m, 1H).

(3) Synthesis of t-butyl (1S,5aS,6R,11bR)-10-methoxy-3-picolinoyl-2,3,3a,4,5,6,7,11c-octahydro-1H-6,11b-(iminoethano)-1,5a-methanonaphtho[1,2-e]indole-14-carboxylate (148)

[Formula 141]

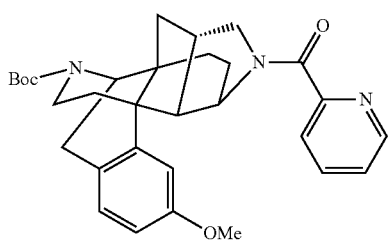

148

Under an argon atmosphere, the compound 147 (80 mg, 0.19 mmol) was dissolved in DMF (2 mL), the solution was added with pyridine-2-carboxylic acid (28 mg, 0.23 mmol), diisopropylethylamine (97 μL, 0.57 mmol), and O-(benzotriazol-1-yl)-N,N,N',N'-tetramethyluronium hexafluorophosphate (108 mg, 0.29 mmol), and the mixture was stirred at room temperature for 16 hours. The reaction mixture was diluted with ethyl acetate, and washed with saturated aqueous sodium hydrogencarbonate, water, and saturated brine. The organic layer was dried over anhydrous sodium sulfate, and then concentrated. The obtained crude product was purified by silica gel column chromatography to give the title compound 148 as white amorphous (70 mg, 72%).

(4) Synthesis of [(1S,5aS,6R,11bR)-10-methoxy-4,5,6,7-tetrahydro-1H-6,11b-(iminoethano)-1,5a-methanonaphtho[1,2-e]indol-3(2H,3aH,11cH) yl](pyridin-2-yl)methanone (149)

[Formula 142]

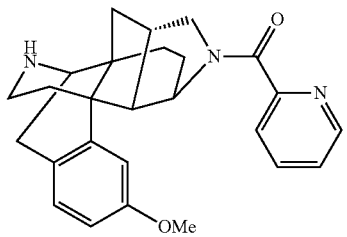

149

Under an argon atmosphere, the compound 148 (70 mg, 0.136 mmol) was dissolved in dichloromethane (0.70 mL), the solution was added with trifluoroacetic acid (0.70 mL), and the mixture was stirred at room temperature for 16 hours. The reaction mixture was concentrated, and the residue was dissolved in ethyl acetate. The organic layer was washed with saturated aqueous sodium hydrogencarbonate, water, and saturated brine, dried over anhydrous sodium sulfate, and then concentrated to give a crude product of the title compound 149.

(5) Synthesis of [(1S,5aS,6R,11bR)-10-hydroxy-14-methyl-4,5,6,7-tetrahydro-1H-6,11b-(iminoethano)-1,5a-methanonaphtho[1,2-e]indol-3(2H,3aH,11cH)-yl](pyridin-2-yl)methanone (150)

[Formula 143]

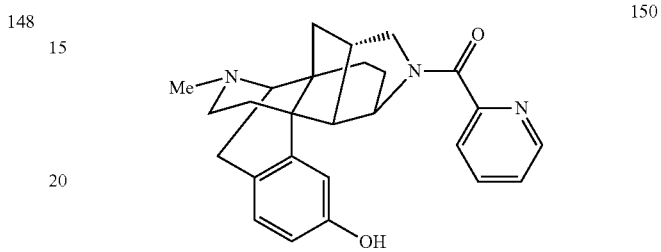

150

According to the method described in Example 8, the title compound 150 and the hydrochloride thereof (5 mg, 14%) were obtained by using the crude product which was prepared in (4) mentioned above.

Compound 150 (hydrochloride) $^1$H NMR (CD$_3$ OD, 400 MHz): δ 0.80-1.10 (m, 0.7H), 1.10-1.30 (m, 0.3H), 1.40-2.00 (m, 5H), 2.00-2.20 (m, 1H), 2.70-3.00 (m, 2H), 2.95 (s, 0.9H), 2.96 (s, 2.1H), 3.20-3.60 (m, 6H), 3.60-3.85 (m, 1.3H), 3.85-4.05 (m, 1.4H), 4.15-4.30 (m, 0.3H), 6.64 (s, 0.3H), 6.66 (d, J=8.3 Hz, 0.3H), 6.74 (d, J=8.3 Hz, 0.7H), 6.78 (s, 0.7H), 7.07 (d, J=8.3 Hz, 0.3H), 7.13 (d, J=8.3 Hz, 0.7H), 7.55-8.05 (m, 2H), 8.10 (t, J=7.3 Hz, 0.3H), 8.30 (t, J=7.3 Hz, 0.7H), 8.62 (s, 0.3H), 8.75 (s, 0.7H)

Example 121

[(1S,5aS,6R,11bR)-14-(2-Fluoroethyl)-10-hydroxy-4,5,6,7-tetrahydro-1H-6,11b-(iminoethano)-1,5a-methanonaphtho[1,2-e]indol-3(2H,3aH,11cH)-yl](pyridin-2-yl)methanone (152)

(1) Synthesis of [(1S,5aS,6R,11bR)-14-(2-fluoroethyl)-10-methoxy-4,5,6,7-tetrahydro-1H-6,11b-(iminoethano)-1,5a-methanonaphtho[1,2-e]indol-3 (2H,3aH,11cH)-yl](pyridin-2-yl)methanone (151)

[Formula 144]

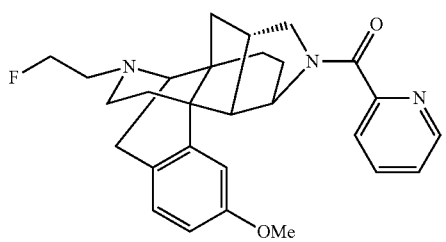

151

According to the method described in Example 104, (3), a crude product of the title compound 151 was obtained by using the compound 149 (36 mg, 0.087 mmol) and toluene-4-sulfonic acid 2-fluoroethyl ester (57 mg, 0.26 mmol).

(2) Synthesis of [(1S,5aS,6R,11bR)-14-(2-fluoroethyl)-10-hydroxy-4,5,6,7-tetrahydro-1H-6,11b-(iminoethano)-1,5a-methanonaphtho[1,2-e]indol-3(2H,3aH,11cH)-yl](pyridin-2-yl)methanone (152)

[Formula 145]

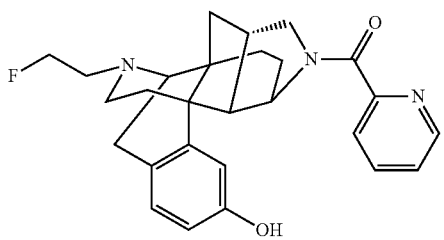

152

According to the method described in Example 6, the title compound 152 and the hydrochloride thereof (2.1 mg, 5%) were obtained by using the crude product which was prepared in (1) mentioned above.

Compound 152 (free base) $^1$H NMR (CD$_3$OD, 400 MHz): δ 0.75-1.10 (m, 2H), 1.50-2.00 (m, 4H), 2.10-2.25 (m, 1H), 2.85-3.00 (m, 2H), 3.15-3.58 (m, 5H), 3.58-3.85 (m, 3H), 3.85-4.10 (m, 2.6H), 4.10-4.35 (m, 0.4H), 4.90-5.10 (m, 2H), 6.65 (d, J=2.4 Hz, 0.4H), 6.67 (dd, J=2.4, 8.2 Hz, 0.4H), 6.75 (dd, J=2.4, 8.2 Hz, 0.6H), 6.79 (d, J=2.4 Hz, 0.6H), 7.07 (d, J=8.2 Hz, 0.4H), 7.13 (d, J=8.2 Hz, 0.6H), 7.45-7.90 (m, 2H), 7.90-8.20 (m, 1H), 8.50-8.75 (m, 1H)

Example 122

Synthesis of (1S,5aS,6R,11bR)-14-(cyclopropylmethyl)-10-hydroxy-N-phenyl-3a,4,5,6,7,11c-hexahydro-1H-6,11b-(iminoethano)-1,5a-methanonaphtho[1,2-e]indole-3(2H)-carboxamide (153)

[Formula 146]

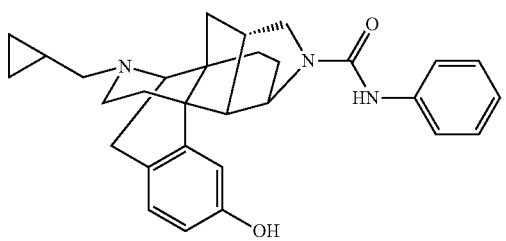

153

Under an argon atmosphere, the compound 77 (30 mg, 0.082 mmol) was dissolved in chloroform (3 mL), the solution was added with triethylamine (23 μL, 0.16 mmol), and phenyl isocyanate (17.8 μL, 0.16 mmol), and the mixture was stirred at room temperature for 10 minutes. The reaction mixture was added with saturated aqueous sodium hydrogencarbonate, the mixture was extracted with chloroform, and then the organic layer was dried over anhydrous sodium sulfate, and concentrated. By using the obtained crude product, the title compound 153 (39.9 mg, 100%) and the hydrochloride thereof were obtained according to the method described in Example 6.

Compound 153 (free base) $^1$H NMR (CDCl$_3$, 400 MHz): δ 0.13-0.22 (m, 2H), 0.47-0.56 (m, 2H), 0.82-0.98 (m, 2H), 1.15-1.40 (m, 4H), 1.45-1.60 (m, 1H), 1.70-1.82 (m, 1H), 1.95-2.05 (m, 1H), 2.10-2.25 (m, 1H), 2.35-2.53 (m, 2H), 2.60-2.75 (m, 1H), 2.93-3.20 (m, 4H), 3.25-3.45 (m, 3H), 3.60 (d, J=10.2 Hz, 1H), 3.80-3.95 (m, 1H), 4.35-4.45 (m, 1H), 6.58 (dd, J=2.4, 8.3 Hz, 1H), 6.66 (d, J=2.4 Hz, 1H), 6.94-7.02 (m, 2H), 7.22 (t, J=8.3 Hz, 2H), 7.36 (d, J=8.8 Hz, 2H)

Example 123

(1S,5aS,6R,11bR)—N-Benzyl-14-(cyclopropylmethyl)-10-hydroxy-N-isopropyl-3a,4,5,6,7,11c-hexahydro-1H-6,11b-(iminoethano)-1,5a-methanonaphtho[1,2-e]indole-3(2H)-carboxamide (155)

(1) Synthesis of (1S,5aS,6R,11bR)—N-benzyl-14-(cyclopropylmethyl)-N-isopropyl-10-methoxy-3a,4,5,6,7,11c-hexahydro-1,3-6,11b-(iminoethano)-1,5a-methanonaphtho[1,2-e]indole-3(2H)-carboxamide (154)

[Formula 147]

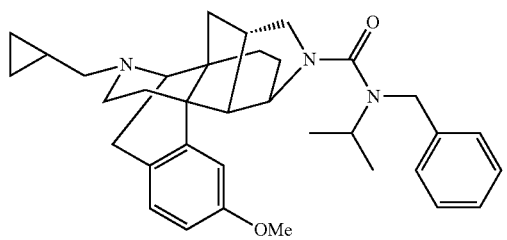

154

Under an argon atmosphere, the compound 77 (25 mg, 0.069 mmol) was dissolved in dichloromethane (1 mL), the solution was added with triethylamine (29 μL, 0.21 mmol), and 1-[benzyl(isopropyl)carbamoyl]-3-methyl-1H-imidazol-3-ium iodide (29 mg, 0.076 mmol; synthesized by the method described in Tetrahedron 2005, 61, 7153), and the mixture was stirred at room temperature for 24 hours. The reaction mixture was dissolved in ethyl acetate, and the solution was washed with water and saturated brine. The organic layer was dried over anhydrous sodium sulfate, and then concentrated to obtain a crude product of the title compound 154.

(2) Synthesis of (1S,5aS,6R,11bR)—N-benzyl-14-(cyclopropylmethyl)-10-hydroxy-N-isopropyl-3a,4,5,6,7,11c-hexahydro-1H-6,11b-(iminoethano)-1,5a-methanonaphtho[1,2-e]indole-3(2H)-carboxamide (155)

[Formula 148]

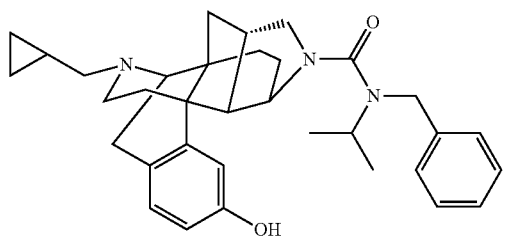

155

According to the method described in Example 6, the title compound 155 and the hydrochloride thereof (10 mg, 26%) were obtained by using the crude product which was prepared in (1) mentioned above.

Compound 155 (hydrochloride) $^1$H NMR (CD$_3$ OD, 400 MHz): δ 0.40-0.60 (m, 2H), 0.65-1.00 (m, 4H), 1.05-1.60 (m, 10H), 1.60-1.80 (m, 1H), 2.00-2.20 (m, 1H), 2.65-2.80 (m, 1H), 2.80-2.97 (m, 2H), 2.97-3.07 (m, 1H), 3.07-3.25 (m, 3H), 3.25-3.45 (m, 2H), 3.56 (d, J=11.2 Hz, 1H), 3.65-3.80 (m, 1H), 4.00-4.15 (m, 2H), 4.22 (d, J=16.0 Hz, 1H), 4.35-4.50 (m, 2H), 6.65-6.70 (m, 2H), 7.06 (d, J=9.3 Hz, 1H), 7.15-7.35 (m, 5H)

Example 124

(1S,5aS,6R,11bR)-14-(Cyclopropylmethyl)-10-hydroxy-N,N-dimethyl-3a,4,5,6,7,11c-hexahydro-1H-6,11b-(iminoethano)-1,5a-methanonaphtho[1,2-e]indole-3(2H)-carboxamide (157)

(1) Synthesis of (1S,5aS,6R,11bR)-14-(cyclopropylmethyl)-10-methoxy-N,N-dimethyl-3a,4,5,6,7,11c-hexahydro-1H-6,11b-(iminoethano)-1,5a-methanonaphtho[1,2-e]indole-3(2H)-carboxamide (156)

[Formula 149]

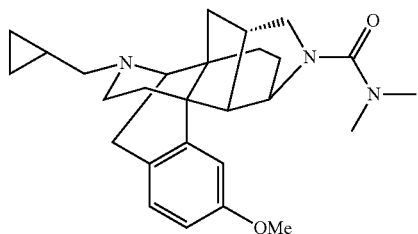

156

Under an argon atmosphere, the compound 77 (25 mg, 0.069 mmol) was dissolved in dichloromethane (1 mL), the solution was added with triethylamine (29 μL, 0.21 mmol), and dimethylcarbamoyl chloride (11 mg, 0.10 mmol), and the mixture was stirred at room temperature for 24 hours. The reaction mixture was diluted with ethyl acetate, and washed with water and saturated brine. The organic layer was dried over anhydrous sodium sulfate, and then concentrated to obtain a crude product of the title compound 156.

(2) Synthesis of (1S,5aS,6R,11bR)-14-(cyclopropylmethyl)-10-hydroxy-N,N-dimethyl-3a,4,5,6,7,11c-hexahydro-1H-6,11b-(iminoethano)-1,5a-methanonaphtho[1,2-e]indole-3(2H)-carboxamide (157)

[Formula 150]

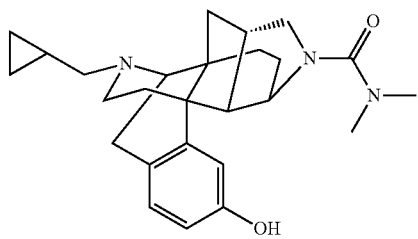

157

According to the method described in Example 6, the title compound 157 and the hydrochloride thereof (17 mg, 54%) were obtained by using the crude product which was prepared in (1) mentioned above.

Compound 157 (hydrochloride) $^1$H NMR (CD$_3$ OD, 400 MHz): δ 0.40-0.65 (m, 2H), 0.65-0.90 (m, 2H), 0.95-1.10 (m, 1H), 1.10-1.25 (m, 2H), 1.40-1.75 (m, 3H), 1.75-1.90 (m, 1H), 2.10-2.25 (m, 1H), 2.65-2.85 (m, 1H), 2.88 (s, 6H), 2.98-3.10 (m, 3H), 3.10-3.26 (m, 3H), 3.30-3.50 (m, 2H), 3.65-3.80 (m, 2H), 4.16 (d, J=5.9 Hz, 1H), 4.45-4.60 (m, 1H), 6.70 (dd, J=2.4, 8.3 Hz, 1H), 6.76 (d, J=2.4 Hz, 1H), 7.11 (d, J=8.3 Hz, 1H)

Example 125

Synthesis of (1S,5aS,6R,11bR)-14-(cyclopropylmethyl)-10-hydroxy-N-(2,2,2-trifluoroethyl)-3a,4,5,6,7,11c-hexahydro-1H-6,11b-(iminoethano)-1,5a-methanonaphtho[1,2-e]indole-3(2H)-carboxamide (158)

[Formula 151]

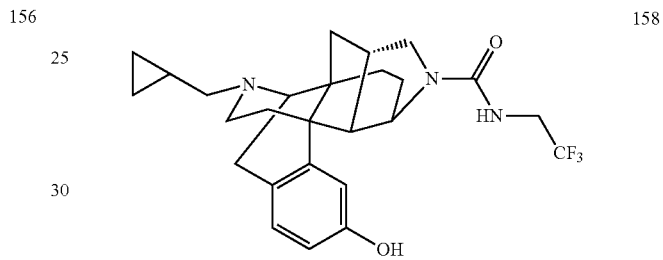

158

Under an argon atmosphere, carbonyldiimidazole (61 mg, 0.38 mmol) was dissolved in dichloromethane (1 mL), the solution was added with triethylamine (69 μL, 0.49 mmol), and 2,2,2-trifluoroethylamine (19 μL, 0.25 mmol), and the mixture was stirred at room temperature for 17 hours. This reaction mixture was added to a solution of the compound 77 (30 mg, 0.082 mmol) and triethylamine (34 μL, 0.25 mmol) in THF (3 mL), and the mixture was stirred at 60° C. for 1 hour and 30 minutes. The reaction mixture was added with saturated aqueous sodium hydrogencarbonate, and the mixture was extracted with chloroform, dried over anhydrous sodium sulfate, and then concentrated. By using the obtained crude product, the title compound 158 (59 mg, 100%) was obtained according to the method described in Example 6.

Compound 158 (hydrochloride) $^1$H NMR (CD$_3$ OD, 400 MHz): δ 0.45-0.56 (m, 2H), 0.70-0.95 (m, 3H), 1.10-1.25 (m, 1H), 1.27-1.45 (m, 1H), 1.45-1.70 (m, 3H), 1.80-1.92 (m, 1H), 2.10-2.22 (m, 1H), 2.70-2.85 (m, 1H), 2.90-3.10 (m, 2H), 3.15-3.30 (m, 4H), 3.30-3.40 (m, 2H), 3.43-3.54 (m, 2H), 3.65-3.93 (m, 3H), 4.15 (d, J=6.3 Hz, 1H), 4.25-4.37 (m, 1H), 6.70 (dd, J=2.4, 8.3 Hz, 1H), 6.73 (d, J=2.4 Hz, 1H), 7.10 (d, J=8.3 Hz, 1H)

Examples 126 to 137

By using the compound 77 which was prepared in Example 67, the compounds of Examples 126 to 137 (free bases and the hydrochlorides thereof) were obtained according to the methods mentioned in Tables 9 and 10.

TABLE 9

| Compound number | | Structural formula | ¹H NMR | Synthetic method |
|---|---|---|---|---|
| Example 126 | 159 | 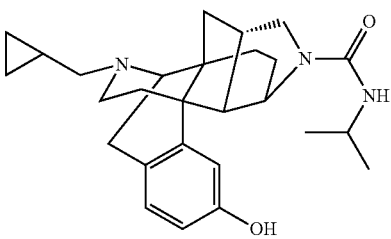 | (Hydrochloride, CD$_3$OD) δ 0.54-0.60 (m, 2H), 0.68-0.92 (m, 3H), 1.09-1.20 (m, 7H), 1.30-1.40 (m, 1H), 1.50-1.75 (m, 3H), 1.75-1.95 (m, 1H), 2.10-2.25 (m, 1H), 2.65-2.85 (m, 1H), 2.95-3.10 (m, 2H), 3.10-3.25 (m, 4H), 3.25-3.40 (m, 1H), 3.40-3.55 (m, 2H), 3.65-3.80 (m, 1H), 3.80-3.95 (m, 1H), 4.15 (d, J = 5.9 Hz, 1H), 4.25-4.40 (m, 1H), 6.65-6.75 (m, 2H), 7.10 (d, J = 8.3 Hz, 1H). | e |
| Example 127 | 160 | 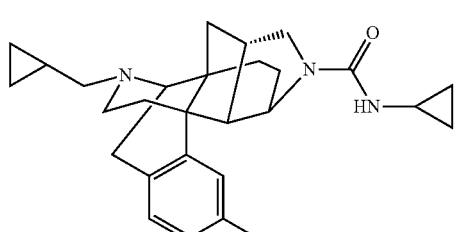 | (Hydrochloride, CD$_3$OD) δ 0.40-0.56 (m, 4H), 0.60-0.70 (m, 2H), 0.70-0.96 (m, 3H), 1.08-1.22 (m, 1H), 1.26-1.44 (m, 1H), 1.46-1.70 (m, 3H), 1.79-1.92 (m, 1H), 2.08-2.21 (m, 1H), 2.46-2.59 (m, 1H), 2.71-2.88 (m, 1H), 2.88-2.99 (m, 1H), 3.04 (dd, J = 7.3, 13.7 Hz, 1H), 3.10-3.60 (m, 7H), 3.62-3.75 (m, 1H), 4.14 (d, J = 6.3 Hz, 1H), 4.24-4.37 (m, 1H), 6.70 (dd, J = 2.4, 8.3 Hz, 1H), 6.72 (d, J = 2.4 Hz, 1H), 7.10 (d, J = 8.3 Hz, 1H). | f |
| Example 128 | 161 | 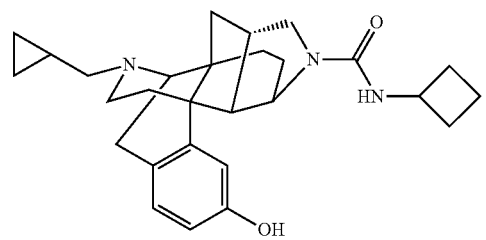 | (Hydrochloride, CD$_3$OD) δ 0.45-0.55 (m, 2H), 0.70-0.94 (m, 3H), 1.07-1.20 (m, 1H), 1.28-1.39 (m, 1H), 1.47-1.71 (m, 5H), 1.78-2.02 (m, 3H), 2.07-2.30 (m, 3H), 2.72-2.84 (m, 1H), 2.87-2.98 (m, 1H), 3.02 (dd, J = 7.3, 13.6 Hz, 1H), 3.10-3.52 (m, 7H), 3.65-3.75 (m, 1H), 4.10-4.25 (m, 2H), 4.25-4.30 (m, 1H), 6.70 (dd, J = 2.4, 8.3 Hz, 1H), 6.75 (d, J = 2.4 Hz, 1H), 7.10 (d, J = 8.3 Hz, 1H). | f |
| Example 129 | 162 | 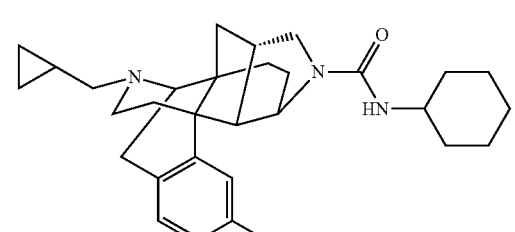 | (Hydrochloride, CD$_3$OD) δ 0.44-0.56 (m, 2H), 0.70-0.90 (m, 3H), 1.28-1.40 (m, 7H), 1.48-1.62 (m, 4H), 1.70-1.90 (m, 5H), 2.08-2.22 (m, 1H), 2.72-2.84 (m, 1H), 2.92-3.08 (m, 2H), 3.10-3.23 (m, 4H), 3.25-3.40 (m, 1H), 3.42-3.56 (m, 3H), 3.66-3.75 (m, 1H), 4.14 (d, J = 6.3 Hz, 1H), 4.26-4.36 (m, 1H), 6.70 (dd, J = 2.4, 8.3 Hz, 1H), 6.72 (d, J = 2.4 Hz, 1H, ), 7.09 (d, J = 8.3 Hz, 1H). | e |
| Example 130 | 163 | 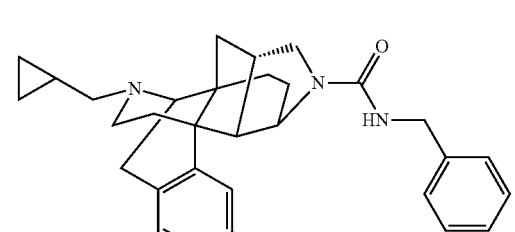 | (Hydrochloride, CD$_3$OD) δ 0.45-0.60 (m, 2H), 0.70-0.95 (m, 3H), 1.10-1.20 (m, 1H), 1.33-1.45 (m, 1H), 1.45-1.70 (m, 3H), 1.80-1.90 (m, 1H), 2.10-2.25 (m, 1H), 2.70-2.85 (m, 1H), 2.95-3.10 (m, 2H), 3.10-3.25 (m, 4H), 3.25-3.40 (m, 1H), 3.40-3.55 (m, 2H), 3.70-3.80 (m, 1H), 4.15 (d, J = 6.3 Hz, 1H), 4.24-4.41 (m, 3H), 6.69 (dd, J = 2.4, 8.3 Hz, 1H), 6.73 (d, J = 2.4 Hz, 1H), 7.10 (d, J = 8.3 Hz, 1H), 7.16-7.30 (m, 5H). | e |
| Example 131 | 164 | 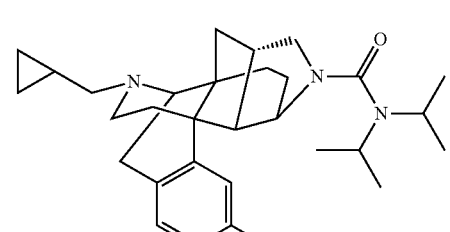 | (Hydrochloride, CD$_3$OD) δ 0.45-0.55 (m, 2H), 0.70-0.85 (m, 2H), 0.95-1.40 (m, 15H), 1.45-1.70 (m, 3H), 1.80-1.90 (m, 1H), 2.10-2.20 (m, 1H), 2.72-3.26 (m, 6H), 3.26-3.85 (m, 7H), 4.13 (d, J = 6.3 Hz, 1H), 4.35-4.50 (m, 1H), 6.70 (dd, J = 2.4, 8.3 Hz, 1H), 6.76 (d, J = 2.4 Hz, 1H), 7.10 (d, J = 8.3 Hz, 1H). | g |

TABLE 10

| | Compound number | Structural formula | ¹H NMR | Synthetic method |
|---|---|---|---|---|
| Example 132 | 165 | | (Hydrochloride, CD$_3$OD) δ 0.45-0.55 (m, 2H), 0.70-0.85 (m, 2H), 0.85-1.00 (m, 1H), 1.00-1.20 (m, 2H), 1.35-1.55 (m, 3H), 1.70-1.80 (m, 1H), 2.05-2.20 (m, 1H), 2.70-2.90 (m, 2H), 2.95-3.10 (m, 2H), 3.10-3.25 (m, 3H), 3.25-3.55 (m, 2H), 3.64 (d, J = 10.7 Hz, 1H), 3.85 (dd, J = 8.8, 10.7 Hz, 1H), 4.08 (d, J = 5.9 Hz, 1H), 4.26 (d, J = 16.1 Hz, 2H), 4.50-4.65 (m, 3H), 6.67-6.73 (m, 2H), 7.08 (d, J = 8.3 Hz, 1H), 7.21-7.35 (m, 10H). | f |
| Example 133 | 166 | | (Hydrochloride, CD$_3$OD) δ 0.45-0.55 (m, 1H), 0.60-0.70 (m, 1H), 0.70-0.90 (m, 2H), 0.95-1.10 (m, 1H), 1.10-1.35 (m, 2H), 1.45-1.75 (m, 3H), 1.75-1.90 (m, 3H), 1.90-2.05 (m, 2H), 2.15-2.30 (m, 1H), 2.70-2.82 (m, 1H), 3.02-3.14 (m, 2H), 3.14-3.40 (m, 5H), 3.40-3.60 (m, 5H), 3.70-3.95 (m, 2H), 4.10-4.25 (m, 1H), 4.55-4.65 (m, 1H), 6.70-6.80 (m, 2H), 7.10 (d, J = 8.3 Hz, 1H). | f |
| Example 134 | 167 | | (Hydrochloride, CD$_3$OD) δ 0.45-0.60 (m, 2H), 0.70-0.90 (m, 2H), 0.95-1.10 (m, 1H), 1.10-1.25 (m, 2H), 1.45-1.70 (m, 9H), 1.80-1.90 (m, 1H), 2.10-2.25 (m, 1H), 2.70-2.84 (m, 1H), 2.88-3.10 (m, 3H), 3.10-3.26 (m, 5H), 3.26-3.50 (m, 4H), 3.61 (d, J = 10.7 Hz, 1H), 3.76 (dd, J = 8.3, 10.7 Hz, 1H), 4.14 (d, J = 5.9 Hz, 1H), 4.45-4.55 (m, 1H), 6.70 (dd, J = 2.4, 8.3 Hz, 1H), 6.76 (d, J = 2.4 Hz, 1H), 7.10 (d, J = 8.3 Hz, 1H). | f |
| Example 135 | 168 | | (Hydrochloride, CD$_3$OD) δ 0.40-0.60 (m, 2H), 0.70-0.90 (m, 2H), 0.95-1.25 (m, 3H), 1.40-1.90 (m, 12H), 2.10-2.25 (m, 1H), 2.70-2.85 (m, 1H), 2.85-2.95 (m, 1H), 2.95-3.10 (m, 2H), 3.10-3.25 (m, 3H), 3.25-3.55 (m, 6H), 3.63 (d, J = 9.3 Hz, 1H), 3.65-3.80 (m, 1H), 4.13 (d, J = 5.9 Hz, 1H), 4.52 (t, J = 7.3 Hz, 1H), 6.70 (dd, J = 2.4, 8.3 Hz, 1H), 6.76 (d, J = 2.4 Hz, 1H), 7.09 (d, J = 8.3 Hz, 1H). | f |
| Example 136 | 169 | | (Hydrochloride, CD$_3$OD) δ 0.40-0.55 (m, 2H), 0.70-0.90 (m, 2H), 0.95-1.25 (m, 3H), 1.45-1.70 (m, 3H), 1.80-1.90 (m, 1H), 2.05-2.20 (m, 1H), 2.70-2.90 (m, 2H), 2.96-3.06 (m, 2H), 3.10-3.26 (m, 5H), 3.26-3.50 (m, 4H), 3.58-3.74 (m, 5H), 3.80 (dd, J = 8.9, 11.2 Hz, 1H), 4.13 (d, J = 5.9 Hz, 1H), 4.50-4.57 (m, 1H), 6.71 (dd, J = 2.4, 8.3 Hz, 1H), 6.76 (d, J = 2.4 Hz, 1H), 7.10 (d, J = 8.3 Hz, 1H). | f |
| Example 137 | 170 | | (Hydrochloride, CD$_3$OD) δ 0.40-0.55 (m, 2H), 0.70-0.85 (m, 2H), 0.95-1.25 (m, 3H), 1.45-1.70 (m, 3H), 1.80-1.90 (m, 1H), 2.05-2.20 (m, 1H), 2.50-2.70 (m, 4H), 2.70-2.90 (m, 2H), 2.95-3.10 (m, 2H), 3.10-3.65 (m, 10H), 3.76 (dd, J = 8.9, 11.2 Hz, 1H), 4.12 (d, J = 6.3 Hz, 1H), 4.51 (t, J = 6.3 Hz, 1H), 6.70 (dd, J = 2.4, 8.3 Hz, 1H), 6.76 (d, J = 2.4 Hz, 1H), 7.09 (d, J = 8.3 Hz, 1H). | f |

Synthesis Methods Mentioned in Tables
Method e: method described in Example 122
Method f: method described in Example 123
Method g: method described in Example 124

Example 138

[(1S,5aS,6R,11bR)-14-(Cyclopropylmethyl)-10-hydroxy-4,5,6,7-tetrahydro-1H-6,11b-(iminoethano)-1,5a-methanonaphtho[1,2-e]indol-3(2H,3aH,11cH)-yl](piperazin-1-yl)methanone (173)

(1) Synthesis of t-butyl 4-[(1S,5aS,6R,11bR)-14-(cyclopropylmethyl)-10-methoxy-2,3,3a,4,5,6,7,11c-octahydro-1H-6,11b-(iminoethano)-1,5a-methanonaphtho[1,2-e]indole-3-carbonyl]piperazine-1-carboxylate (171)

[Formula 152]

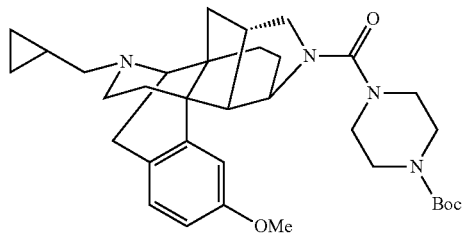

According to the method described in Example 123, (1), a crude product of the title compound 171 was obtained by using the compound 77 (90 mg, 0.25 mmol) and 1-[4-t-butoxycarbonylpiperazine-1-carbonyl]-3-methyl-1H-imidazol-3-ium iodide (209 mg, 0.49 mmol).

(2) Synthesis of [(1S,5aS,6R,11bR)-14-(cyclopropylmethyl)-10-methoxy-4,5,6,7-tetrahydro-1H-6,11b-(iminoethano)-1,5a-methanonaphtho[1,2-e]indol-3(2H,3aH,11cH)-yl](piperazin-1-yl)methanone (172)

[Formula 153]

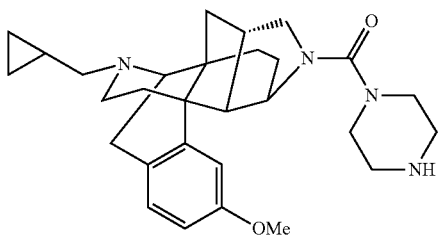

Under an argon atmosphere, the crude product which was prepared in (1) mentioned above was dissolved in dichloromethane (1.5 mL), the solution was added with trifluoroacetic acid (1.5 mL), and the mixture was stirred at room temperature for 2 hours. The reaction mixture was concentrated, and the residue was diluted with ethyl acetate. The organic layer was washed with saturated aqueous sodium hydrogencarbonate, water, and saturated brine, dried over anhydrous sodium sulfate, and then concentrated to obtain a crude product of the title compound 172.

(3) Synthesis of [(1S,5aS,6R,11bR)-14-(cyclopropylmethyl)-10-hydroxy-4,5,6,7-tetrahydro-1H-6,11b-(iminoethano)-1,5a-methanonaphtho[1,2-e]indol-3(2H,3aH,11cH)-yl](piperazin-1-yl)methanone (173)

[Formula 154]

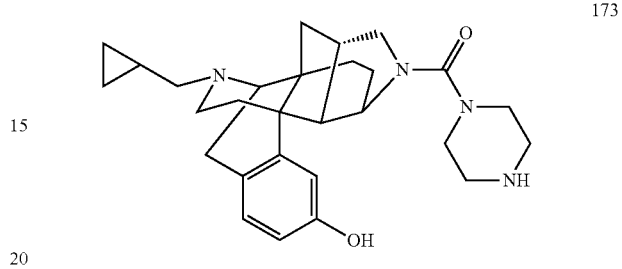

According to the method described in Example 6, the title compound 173 and the hydrochloride thereof (10 mg, 19%) were obtained by using the crude product (48 mg, 0.1 mmol) which was prepared in (2) mentioned above.

Compound 173 (hydrochloride) $^1$H NMR (CD$_3$ OD, 400 MHz): δ 0.40-0.65 (m, 2H), 0.65-0.90 (m, 2H), 0.90-1.10 (m, 1H), 1.10-1.30 (m, 2H), 1.40-1.75 (m, 3H), 1.75-1.90 (m, 1H), 2.10-2.25 (m, 1H), 2.70-2.85 (m, 1H), 2.95-3.10 (m, 3H), 3.10-3.70 (m, 14H), 3.70-3.90 (m, 1H), 4.15 (d, J=6.3 Hz, 1H), 4.54 (t, J=6.3 Hz, 1H), 6.70 (d, J=2.4, 8.3 Hz, 1H), 6.76 (d, J=2.4 Hz, 1H), 7.10 (d, J=8.3 Hz, 1H)

Example 139

1-[4-[(1S,5aS,6R,11bR)-14-(Cyclopropylmethyl)-10-hydroxy-2,3,3a,4,5,6,7,11c-octahydro-1H-6,11b-(iminoethano)-1,5a-methanonaphtho[1,2-e]indole-3-carbonyl]piperazin-1-yl]ethanone (175)

(1) Synthesis of 1-[4-[(1S,5aS,6R,11bR)-14-(cyclopropylmethyl)-10-methoxy-2,3,3a,4,5,6,7,11c-octahydro-1H-6,11b-(iminoethano)-1,5a-methanonaphtho[1,2-e]indole-3-carbonyl]piperazin-1-yl]ethanone (174)

[Formula 155]

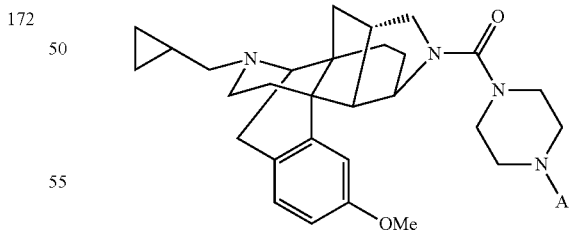

Under an argon atmosphere, the compound 172 (50 mg, 0.11 mmol) was dissolved in dichloromethane (1.5 mL), the solution was cooled on ice, and then added with triethylamine (73 μL, 0.53 mmol), and acetyl chloride (22 μL, 0.32 mmol), and the mixture was stirred at room temperature for 16 hours. The reaction mixture was diluted with ethyl acetate, the organic layer was washed with saturated aqueous sodium hydrogencarbonate, water, and saturated brine, dried over anhydrous sodium sulfate, and then concentrated to obtain a crude product of the title compound 174.

(2) Synthesis of 1-[4-[(1S,5aS,6R,11bR)-14-(cyclopropylmethyl)-10-hydroxy-2,3,3a,4,5,6,7,11c-octahydro-1H-6,11b-(iminoethano)-1,5a-methanonaphtho[1,2-e]indole-3-carbonyl]piperazin-1-yl]ethanone (175)

[Formula 156]

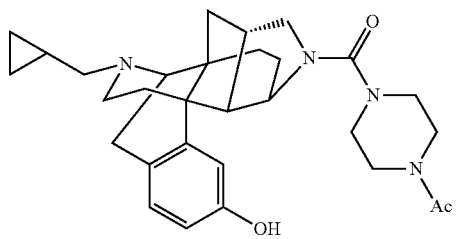

175

According to the method described in Example 6, the title compound 175 and the hydrochloride thereof (4.5 mg, 8%) were obtained by using the crude product which was prepared in (1) mentioned above.

Compound 175 (hydrochloride) $^1$H NMR (CD$_3$OD, 400 MHz): δ 0.45-0.65 (m, 2H), 0.65-0.90 (m, 2H), 0.90-1.10 (m, 1H), 1.10-1.25 (m, 2H), 1.45-1.75 (m, 3H), 1.75-1.90 (m, 1H), 2.10-2.24 (m, 1H), 2.15 (s, 3H), 2.70-2.85 (m, 1H), 2.95-3.10 (m, 3H), 3.10-3.50 (m, 9H), 3.50-3.70 (m, 5H), 3.81 (dd, J=8.9, 11.2 Hz, 1H), 4.15 (d, J=6.3 Hz, 1H), 4.54 (t, J=7.3 Hz, 1H), 6.70 (dd, J=2.4, 8.3 Hz, 1H), 6.76 (d, J=2.4 Hz, 1H), 7.10 (d, J=8.3 Hz, 1H)

Example 140

[(1S,5aS,6R,11bR)-14-(Cyclopropylmethyl)-10-hydroxy-4,5,6,7-tetrahydro-1H-6,11b-(iminoethano)-1,5a-methanonaphtho[1,2-e]indol-3(2H,3aH,11cH)-yl](4-methylpiperazin-1-yl)methanone (177)

(1) Synthesis of [(1S,5aS,6R,11bR)-14-(cyclopropylmethyl)-10-methoxy-4,5,6,7-tetrahydro-1H-6,11b-(iminoethano)-1,5a-methanonaphtho[1,2-e]indol-3(2H,3aH,11cH)-yl](4-methylpiperazin-1-yl)methanone (176)

[Formula 157]

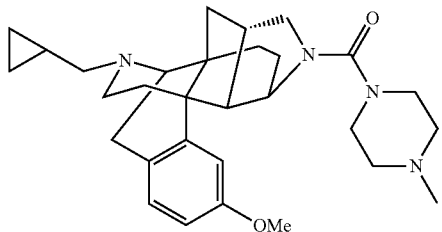

176

Under an argon atmosphere, the compound 172 (50 mg, 0.11 mmol) which was prepared in Example 138, (2) was dissolved in methanol (1 mL), the solution was added with zinc chloride (7.0 mg, 0.055 mmol), and aqueous formaldehyde (37%, 39 μL, 0.5 mmol), and the mixture was stirred at 0° C. for 10 minutes. The reaction mixture was added with sodium cyanoborohydride (13 mg, 0.21 mmol), and the mixture was stirred at room temperature for 16 hours. The reaction mixture was diluted with ethyl acetate, and washed with water and saturated brine. The organic layer was dried over anhydrous sodium sulfate, and then concentrated to obtain a crude product of the title compound 176.

(2) Synthesis of [(1S,5aS,6R,11bR)-14-(cyclopropylmethyl)-10-hydroxy-4,5,6,7-tetrahydro-1H-6,11b-(iminoethano)-1,5a-methanonaphtho[1,2-e]indol-3(2H,3aH,11cH)-yl](4-methylpiperazin-1-yl)methanone (177)

[Formula 158]

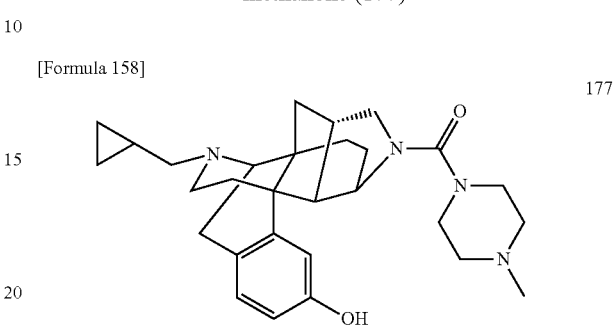

177

According to the method described in Example 6, the title compound 177 and the hydrochloride thereof (8.0 mg, 16%) were obtained by using the crude product (44 mg, 0.09 mmol) which was prepared in (1) mentioned above.

Compound 177 (hydrochloride) $^1$H NMR (CD$_3$OD, 400 MHz): δ 0.40-0.65 (m, 2H), 0.65-0.90 (m, 2H), 0.90-1.10 (m, 1H), 1.10-1.30 (m, 2H), 1.45-1.75 (m, 3H), 1.75-1.95 (m, 1H), 2.10-2.25 (m, 1H), 2.70-2.84 (m, 1H), 2.92 (s, 3H), 2.96-3.60 (m, 14H), 3.65 (d, J=10.7 Hz, 1H), 3.75-3.90 (m, 2H), 3.93 (d, J=13.2 Hz, 1H), 4.15 (d, J=6.3 Hz, 1H), 4.54 (t, J=6.8 Hz, 1H), 6.70 (dd, J=2.4, 8.3 Hz, 1H), 6.76 (d, J=2.4 Hz, 1H), 7.10 (d, J=8.3 Hz, 1H)

Example 141

4-[(1S,5aS,6R,11bR)-14-(Cyclopropylmethyl)-10-hydroxy-2,3,3a,4,5,6,7,11c-octahydro-1H-6,11b-(iminoethano)-1,5a-methanonaphtho[1,2-e]indole-3-carbonyl]piperazin-2-one (179)

(1) Synthesis of 4-[(1S,5aS,6R,11bR)-14-(cyclopropylmethyl)-10-methoxy-2,3,3a,4,5,6,7,11c-octahydro-1H-6,11b-(iminoethano)-1,5a-methanonaphtho[1,2-e]indole-3-carbonyl]piperazin-2-one (178)

[Formula 159]

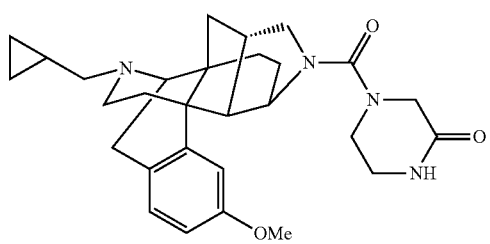

178

According to the method described in Example 123, (1), a crude product of the title compound 178 was obtained by using the compound 77 (30 mg, 0.082 mmol) and 3-methyl-1-(3-oxypiperazine-1-carbonyl)-1H-imidazol-3-ium iodide (50 mg, 0.155 mmol).

(2) Synthesis of 4-[(1S,5aS,6R,11bR)-14-(cyclopropylmethyl)-10-hydroxy-2,3,3a,4,5,6,7,11c-octahydro-1H-6,11b-(iminoethano)-1,5a-methanonaphtho[1,2-e]indole-3-carbonyl]piperazin-2-one (179)

[Formula 160]

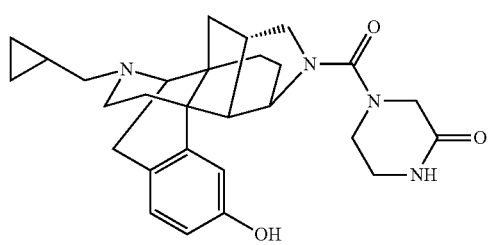

179

According to the method described in Example 6, the title compound 179 and the hydrochloride thereof (10 mg, 26%) were obtained by using the crude product which was prepared in (1) mentioned above.

Compound 179 (free base) $^1$H NMR (CDCl$_3$, 400 MHz): δ 0.05-0.20 (m, 2H), 0.40-0.60 (m, 2H), 0.70-0.90 (m, 1H), 0.90-1.20 (m, 4H), 1.30-1.50 (m, 2H), 1.80-1.95 (m, 1H), 1.95-2.10 (m, 1H), 2.20-2.40 (m, 2H), 2.50-2.60 (m, 1H), 2.75-2.95 (m, 3H), 2.95-3.15 (m, 2H), 3.15-3.40 (m, 3H), 3.40-3.65 (m, 3H), 3.65-3.80 (m, 2H), 3.94 (d, J=17.1 Hz, 1H), 4.02 (d, J=17.1 Hz, 1H), 4.45-4.55 (m, 1H), 6.15-6.40 (m, 1H), 6.61 (d, J=8.3 Hz, 1H), 6.72 (s, 1H), 6.94 (d, J=8.3 Hz, 1H)

Example 142

(1S,5aS,6R,11bR)-14-(Cyclopropylmethyl)-10-hydroxy-N-(2-hydroxyethyl)-3a,4,5,6,7,11c-hexahydro-1H-6,11b-(iminoethano)-1,5a-methanonaphtho[1,2-e]indole-3(2H)-carboxamide (182)

(1) Synthesis of [(1S,5aS,6R,11bR)-14-(cyclopropylmethyl)-10-methoxy-4,5,6,7-tetrahydro-1H-6,11b-(iminoethano)-1,5a-methanonaphtho[1,2-e]indol-3(2H,3aH,11cH)-yl](1H-imidazol-1-yl)methanone (180)

[Formula 161]

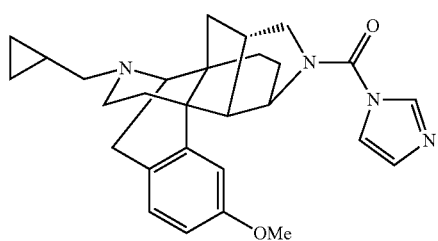

180

Under an argon atmosphere, the compound 77 (200 mg, 0.55 mmol) and triethylamine (140 µL, 0.82 mmol) were dissolved in dichloromethane (5 mL), the solution was added with carbonyldiimidazole (140 mg, 0.82 mmol), and the mixture was stirred at room temperature for 2 hours. The reaction mixture was added with saturated aqueous sodium hydrogencarbonate, the mixture was extracted four times with chloroform, and then the organic layers were combined, and washed with saturated brine. The organic layer was dried over anhydrous sodium sulfate, and then concentrated. The obtained crude product was purified by silica gel column chromatography to give the title compound 180 (252 mg, 100%).

$^1$H NMR (CDCl$_3$, 400 MHz): δ 0.04-0.17 (m, 2H), 0.41-0.56 (m, 2H), 0.74-0.86 (m, 1H), 0.92-1.06 (m, 1H), 1.13-1.24 (m, 2H), 1.29-1.42 (m, 1H), 1.42-1.54 (m, 1H), 1.72-1.83 (m, 1H), 1.84-1.97 (m, 1H), 1.97-2.09 (m, 1H), 2.25-2.39 (m, 2H), 2.52-2.63 (m, 1H), 2.88-2.95 (m, 2H), 3.02 (t, J=7.8 Hz, 1H), 3.09-3.20 (m, 2H), 3.42 (t, J=12.2 Hz, 1H), 3.69-3.82 (m, 4H), 3.90-4.12 (m, 1H), 4.54-4.80 (m, 1H), 6.60-6.74 (m, 2H), 7.01-7.10 (m, 2H), 7.30-7.39 (m, 11n, 7.93-8.03 (m, 1H)

(2) Synthesis of (1S,5aS,6R,11bR)-14-(cyclopropylmethyl)-10-methoxy-N-(2-methoxyethyl)-3a,4,5,6,7,11c-hexahydro-1H-6,11b-(iminoethano)-1,5a-methanonaphtho[1,2-e]indole-3(2H)-carboxamide (181)

[Formula 162]

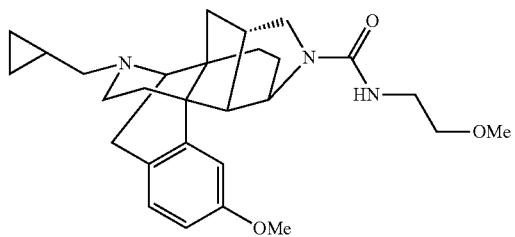

181

Under an argon atmosphere, the compound 180 (30 mg, 0.065 mmol) which was prepared in (1) mentioned above was dissolved in acetonitrile (1 mL), the solution was added with methyl iodide (244 µL, 3.92 mmol), and the mixture was stirred at room temperature for 21 hours. The reaction mixture was concentrated, then the residue was dissolved in THF (1 mL), the solution was added with 2-methoxyethylamine (17 µL, 0.20 mmol), and the mixture was stirred at 60° C. for 3 hours. The reaction mixture was added with saturated aqueous sodium hydrogencarbonate, the mixture was extracted three times with chloroform, and then the organic layers were combined, and washed with saturated brine. The organic layer was dried over anhydrous sodium sulfate, and then concentrated. The obtained crude product was purified by preparative TLC to give the title compound 181 (27 mg, 88%).

$^1$H NMR (CDCl$_3$, 400 MHz): δ 0.04-0.21 (m, 2H), 0.37-0.58 (m, 2H), 0.63-0.98 (m, 2H), 1.05-1.55 (m, 4H), 1.56-1.75 (m, 1H), 1.80-2.12 (m, 2H), 2.19-2.42 (m, 2H), 2.48-2.65 (m, 1H), 2.84-3.20 (m, 5H), 3.28-3.52 (m, 9H), 3.62-3.74 (m, 1H), 3.76 (s, 3H), 4.11-4.33 (m, 1H), 4.48-4.61 (m, 1H), 6.61-6.74 (m, 2H), 6.98-7.08 (m, 1H)

(3) Synthesis of (1S,5aS,6R,11bR)-14-(cyclopropylmethyl)-10-hydroxy-N-(2-hydroxyethyl)-3a,4,5,6,7,11c-hexahydro-1H-6,11b-(iminoethano)-1,5a-methanonaphtho[1,2-e]indole-3(2H)-carboxamide (182)

[Formula 163]

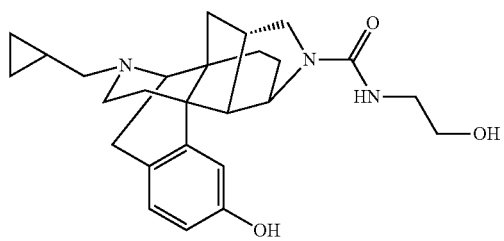

According to the method described in Example 6, the title compound 182 and the hydrochloride thereof (7 mg, 26%) were obtained by using the compound 181 (26.7 mg, 0.057 mmol) which was prepared in (2) mentioned above.

Compound 182 (hydrochloride) $^1$H NMR (CD$_3$OD, 400 MHz): δ 0.44-0.57 (m, 2H), 0.70-0.93 (m, 3H), 1.07-1.22 (m, 1H), 1.32-1.43 (m, 1H), 1.46-1.71 (m, 3H), 1.79-1.91 (m, 1H), 2.08-2.22 (m, 1H), 2.75-2.85 (m, 1H), 2.91-3.08 (m, 2H), 3.10-3.81 (m, 12H), 4.15 (d, J=6.1 Hz, 1H), 4.26-4.37 (m, 1H), 6.65-6.77 (m, 2H), 7.10 (d, J=8.5 Hz, 1H)

Example 143

(1S,5aS,6R,11bR)-10-Hydroxy-14-(2-hydroxyethyl)-N-isopropyl-3a,4,5,6,7,11c-hexahydro-1H-6,11b-(iminoethano)-1,5a-methanonaphtho[1,2-e]indole-3(2H)-carboxamide (187)

(1) Synthesis of 2,2,2-trichloroethyl[1S,5aS,6R,11bR]-14-(2-hydroxyethyl)-10-methoxy-3a,4,5,6,7,11c-hexahydro-1H-6,11b-(iminoethano)-1,5a-methanonaphtho[1,2-e]indole-3(2H)-carboxylate (183)

[Formula 164]

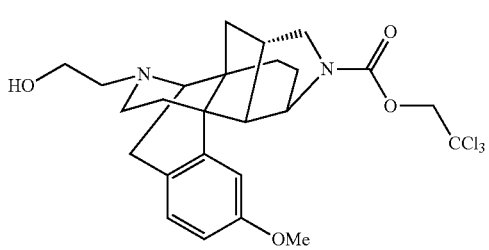

According to the method described in Example 104, (3), a crude product of the title compound 183 was obtained by using the compound 127 (60 mg, 0.123 mmol) and 2-bromoethanol (13 μL, 0.185 mmol).

(2) Synthesis of 2,2,2-trichloroethyl (1S,5aS,6R,11bR)-14-[2-[(t-butyldimethylsilyl)oxy]ethyl]-10-methoxy-3a,4,5,6,7,11c-hexahydro-1H-6,11b-(iminoethano)-1,5a-methanonaphtho[1,2-e]indole-3(2H)-carboxylate (184)

[Formula 165]

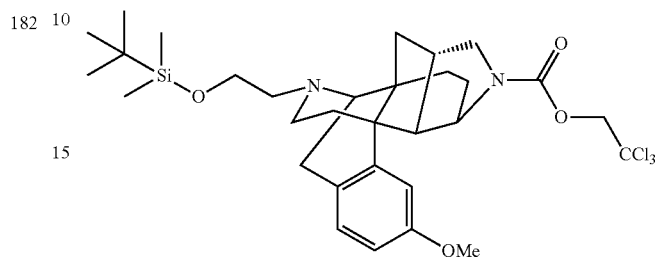

Under an argon atmosphere, the crude product which was prepared in (1) mentioned above was dissolved in DMF (5 mL), the solution was added with imidazole (50 mg, 0.74 mmol), and t-butyldimethylchlorosilane (93 mg, 0.62 mmol), and the mixture was stirred at room temperature for 16 hours. The reaction mixture was diluted with ethyl acetate, and washed with water and saturated brine. The organic layer was dried over anhydrous sodium sulfate, and then concentrated. The obtained crude product was purified by silica gel column chromatography to give the title compound 184 (74 mg, 93%).

$^1$H NMR (CDCl$_3$, 400 MHz): δ 0.06 (s, 6H), 0.70-1.00 (m, 10H), 1.00-1.20 (m, 2H), 1.35-1.50 (m, 2H), 1.60-1.80 (m, 1H), 1.80-1.95 (m, 1H), 2.10-2.25 (m, 1H), 2.40-2.55 (m, 2H), 2.55-2.70 (m, 1H), 2.90-3.10 (m, 5H), 3.36 (t, J=11.7 Hz, 1H), 3.55 (t, J=11.7 Hz, 1H), 3.60-3.75 (m, 2H), 3.75-3.85 (m, 1H), 3.77 (s, 1.5H), 3.78 (s, 1.5H), 4.25-4.35 (m, 1H), 4.57 (d, J=12.2 Hz, 0.5H), 4.65 (d, J=12.2 Hz, 0.5H), 4.79 (d, J=12.2 Hz, 0.5H), 4.88 (d, J=12.2 Hz, 0.5H), 6.60-6.75 (m, 2H), 7.04 (d, J=8.3 Hz, 0.5H), 7.05 (d, J=8.3 Hz, 0.5H)

(3) Synthesis of (1S,5aS,6R,11bR)-14-[2-[(t-butyldimethylsilyl)oxy]ethyl]-10-methoxy-2,3,3a,4,5,6,7,11c-octahydro-1H-6,11b-(iminoethano)-1,5a-methanonaphtho[1,2-e]indole (185)

[Formula 166]

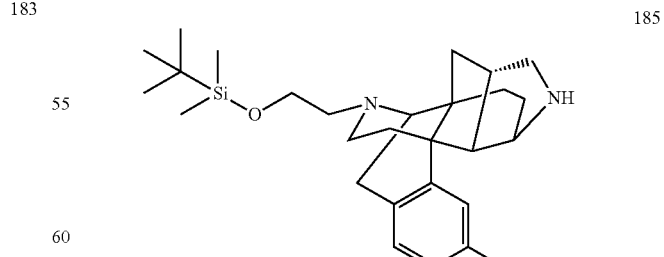

According to the method described in Example 106, (4), a crude product of the title compound 185 was obtained by using the compound 184 (74 mg, 0.11 mmol) which was prepared in (2) mentioned above.

(4) Synthesis of (1S,5aS,6R,11bR)-14-[2-[(t-butyldimethylsilyl)oxy]ethyl]-N-isopropyl-10-methoxy-3a,4,5,6,7,11c-hexahydro-1H-6,11b-(iminoethano)-1,5a-methanonaphtho[1,2-e]indole-3(2H)-carboxamide (186)

[Formula 167]

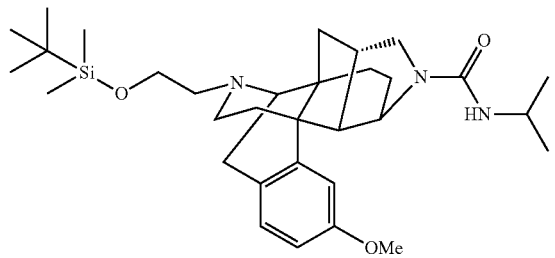

Under an argon atmosphere, a solution of the crude product which was prepared in (3) mentioned above in chloroform (1 mL) was added with triethylamine (48 µL, 0.35 mmol), and isopropyl isocyanate (17 µL, 0.17 mmol), and the mixture was stirred at room temperature for 16 hours. The reaction mixture was added with saturated aqueous sodium hydrogencarbonate, the mixture was extracted with chloroform, and then the organic layer was dried over anhydrous sodium sulfate, and concentrated to obtain a crude product of the title compound 186.

(5) Synthesis of (1S,5aS,6R,11bR)-10-hydroxy-14-(2-hydroxyethyl)-N-isopropyl-3a,4,5,6,7,11c-hexahydro-1H-6,11b-(iminoethano)-1,5a-methanonaphtho[1,2-e]indole-3(2H)-carboxamide (187)

[Formula 168]

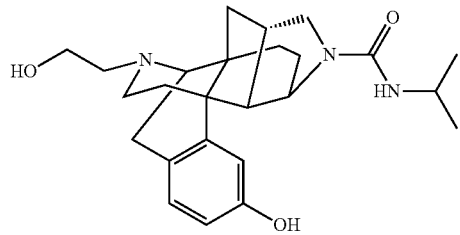

Under an argon atmosphere, a solution of the crude product which was prepared in (4) mentioned above in THF (1 mL) was added with a solution of tetrabutylammonium fluoride in THF (1.0 mol/L, 140 µL, 0.14 mmol) under ice cooling, and the mixture was stirred at room temperature for 2 hours. The reaction mixture was diluted with ethyl acetate, and washed with water and saturated brine, and the organic layer was dried over anhydrous sodium sulfate, and concentrated. Then, by using the obtained crude product, the title compound 187 and the hydrochloride thereof (3.8 mg, 27%) were obtained according to the method described in Example 6.

Compound 187 (hydrochloride) $^1$H NMR (CD$_3$OD, 400 MHz): δ 0.80-0.94 (m, 1H), 1.11 (d, J=6.3 Hz, 3H), 1.12 (d, J=6.3 Hz, 3H), 1.30-1.40 (m, 1H), 1.45-1.70 (m, 3H), 1.75-1.90 (m, 1H), 2.10-2.25 (m, 1H), 2.80-3.00 (m, 2H), 3.10-3.30 (m, 4H), 3.30-3.40 (m, 1H), 3.40-3.60 (m, 3H), 3.71 (dd, J=7.3, 10.2 Hz, 1H), 3.80-4.00 (m, 4H), 4.25-4.35 (m, 1H), 6.70 (dd, J=2.4, 8.3 Hz, 1H), 6.73 (d, J=2.4 Hz, 1H), 7.10 (d, J=8.3 Hz, 1H)

Example 144

(1S,5aS,6R,11bR)-10-Hydroxy-14-((R)-2-hydroxypropyl)-N-isopropyl-3a,4,5,6,7,11c-hexahydro-1H-6,11b-(iminoethano)-1,5a-methanonaphtho[1,2-e]indole-3(2H)-carboxamide (190)

(1) Synthesis of 2,2,2-trichloroethyl (1S,5aS,6R,11bR)-14-((R)-2-hydroxypropyl)-10-methoxy-3a,4,5,6,7,11c-hexahydro-1H-6,11b-(iminoethano)-1,5a-methanonaphtho[1,2-e]indole-3(2H)-carboxylate (188)

[Formula 169]

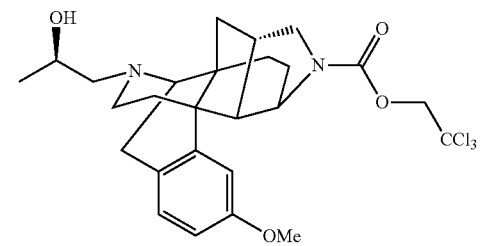

According to the method described in Example 107, a crude product of the title compound 188 was obtained by using the compound 127 (60 mg, 0.123 mmol).

(2) Synthesis of (2R)-1-[(1S,5aS,6R,11bR)-10-methoxy-2,3,3a,4,5,6,7,11c-octahydro-1H-6,11b-(iminoethano)-1,5a-methanonaphtho[1,2-e]indol-14-yl]propan-2-ol (189)

[Formula 170]

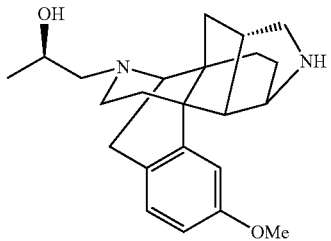

According to the method described in Example 106, (4), a crude product of the title compound 189 was obtained by using the crude product which was prepared in (1) mentioned above.

(3) Synthesis of (1S,5aS,6R,11bR)-10-hydroxy-14-((R)-2-hydroxypropyl)-N-isopropyl-3a,4,5,6,7,11c-hexahydro-1H-6,11b-(iminoethano)-1,5a-methanonaphtho[1,2-e]indole-3(2H)-carboxamide (190)

[Formula 171]

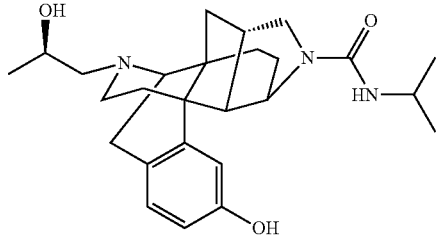

According to the method described in Example 122, the title compound 190 and the hydrochloride thereof (4 mg, 37%) were obtained by using the crude product which was prepared in (2) mentioned above and isopropyl isocyanate.

Compound 190 (hydrochloride) $^1$H NMR (CD$_3$ OD, 400 MHz): δ 0.80-0.94 (m, 1H), 1.12 (d, J=6.3 Hz, 3H), 1.13 (d, J=6.3 Hz, 3H), 1.26 (d, J=6.3 Hz, 3H), 1.40-1.60 (m, 1H), 1.60-1.70 (m, 3H), 1.70-1.90 (m, 1H), 2.10-2.30 (m, 1H), 2.80-3.00 (m, 3H), 3.00-3.30 (m, 3.40-3.60 (m, 3H), 3.70 (dd, J=7.8, 10.7 Hz, 1H), 3.80-3.95 (m, 1H), 3.98 (d, J=6.3 Hz, 1H), 4.10-4.25 (m, 1H), 4.25-4.48 (m, 1H), 6.70 (dd, J=2.4, 8.3 Hz, 1H), 6.73 (d, J=2.4 Hz, 1H), 7.10 (d, J=8.3 Hz, 1H)

Example 145

3-[(1S,5aS,6R,11bR)-14-(Cyclopropylmethyl)-10-methoxy-4,5,6,7-tetrahydro-1H-6,11b-(iminoethano)-1,5a-methanonaphtho[1,2-e]indol-3(2H,3aH,11cH)-yl]-2,2-dimethyl-3-oxopropanoic acid (193)

(1) Synthesis of ethyl 3-[(1S,5aS,6R,11bR)-14-(cyclopropylmethyl)-10-methoxy-4,5,6,7-tetrahydro-1H-6,11b-(iminoethano)-1,5a-methanonaphtho[1,2-e]indol-3(2H,3aH,11cH)-yl]-3-oxopropanoate (191)

[Formula 172]

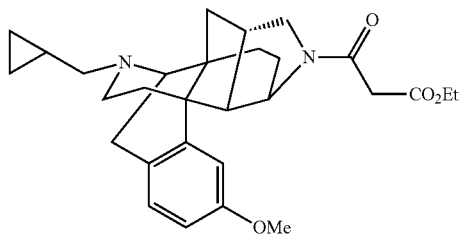

191

According to the method described in Example 33, the title compound 191 (47 mg, 90%) was obtained by using the compound 77 (40 mg, 0.11 mmol) and ethyl malonyl chloride (20 µL, 0.15 mmol).

$^1$H NMR (CDCl$_3$, 400 MHz): δ 0.05-0.14 (m, 2H), 0.38-0.54 (m, 2H), 0.70-1.01 (m, 2H), 1.05-1.50 (m, 7H), 1.63-1.77 (m, 1H), 1.82-2.08 (m, 2H), 2.24-2.39 (m, 2H), 2.51-2.62 (m, 1H), 2.83-3.19 (m, 5H), 3.24-3.58 (m, 4H), 3.68-3.88 (m, 4H), 4.09-4.39 (m, 2.3H), 4.47-4.58 (m, 0.7H), 6.61-6.72 (m, 2H), 6.98-7.07 (m, 1H)

(2) Synthesis of ethyl 3-[(1S,5aS,6R,11bR)-14-(cyclopropylmethyl)-10-methoxy-4,5,6,7-tetrahydro-1H-6,11b-(iminoethano)-1,5a-methanonaphtho[1,2-e]indol-3(2H,3aH,11cH)-yl]-2,2-dimethyl-3-oxopropanoate (192)

[Formula 173]

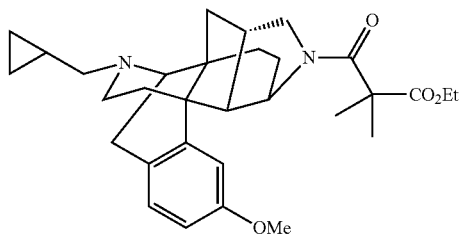

192

Under an argon atmosphere, the compound 191 (47 mg, 0.099 mmol) which was prepared in (1) mentioned above was dissolved in DMF (1 mL), the solution was added with sodium hydride (40 mg, 0.99 mol), and methyl iodide (25 µL, 0.40 mmol), and the mixture was stirred at room temperature for 24 hours. The reaction mixture was added with ice water at 0° C., the mixture was extracted three times with chloroform, and then the organic layers were combined, and washed with saturated brine. The organic layer was dried over anhydrous sodium sulfate, and then concentrated to obtain a crude product of the title compound 192.

(3) Synthesis of 3-[(1S,5aS,6R,11bR)-14-(cyclopropylmethyl)-10-methoxy-4,5,6,7-tetrahydro-1H-6,11b-(iminoethano)-1,5a-methanonaphtho[1,2-e]indol-3(2H,3aH,11cH)-yl]-2,2-dimethyl-3-oxopropanoic acid (193)

[Formula 174]

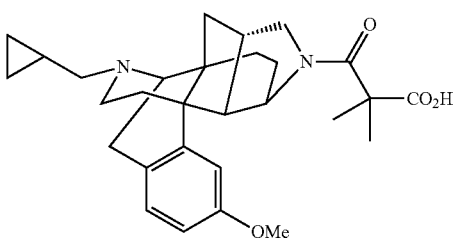

193

Under an argon atmosphere, the crude product (5.4 mg, 0.011 mmol) which was prepared in (2) mentioned above was dissolved in THF (1 mL), water (1 mL), and methanol (0.1 mL), the solution was added with potassium hydroxide (60 mg, 1.07 mmol), and the mixture was stirred at room temperature for 4 days. The reaction mixture was made acidic by adding 1 M hydrochloric acid, and then neutralized by adding sodium hydrogencarbonate. The reaction mixture was extracted three times with ethyl acetate, and then the organic layers were combined, and washed with saturated brine. The organic layer was dried over anhydrous sodium sulfate, and then concentrated. The obtained crude product was purified by preparative TLC to give the title compound 193 and the hydrochloride thereof (4.0 mg, 71%).

Compound 193 (hydrochloride) $^1$H NMR (CD$_3$ OD, 400 MHz): δ 0.42-0.55 (m, 2H), 0.68-0.87 (m, 3H), 1.07-1.19 (m, 1H), 1.25-1.67 (m, 10H), 1.75-1.90 (m, 1H), 2.06-2.22 (m, 1H), 2.69-2.84 (m, 1H), 2.84-2.95 (m, 1H), 2.97-3.08 (m, 1H), 3.11-3.66 (m, 8H), 3.75-3.95 (m, 4H), 4.08-4.12 (m, 1H), 6.80-6.91 (m, 2H), 7.15-7.24 (m, 1H)

Example 146

Synthesis of 2,2,2-trichloroethyl (1S,5aS,6R,11bR)-14-(cyclopropylmethyl)-10-hydroxy-3a,4,5,6,7,11c-hexahydro-1H-6,11b-(iminoethano)-1,5a-methanonaphtho[1,2-e]indole-3(2H)-carboxylate (194)

[Formula 175]

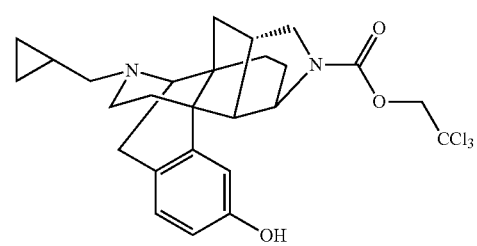

194

According to the method described in Example 6, the title compound 194 and the hydrochloride thereof were obtained by using the compound 126.

Compound 194 (hydrochloride) $^1$H NMR (CD$_3$OD, 400 MHz): δ 0.43-0.55 (m, 2H), 0.66-0.96 (m, 3H), 1.05-1.20 (m, 1H), 1.40-1.70 (m, 4H), 1.80-1.92 (m, 1H), 2.06-2.20 (m, 1H), 2.70-2.85 (m, 1H), 2.86-3.09 (m, 2H), 3.10-3.40 (m, 4.3H), 3.40-3.70 (m, 2.4H), 3.75-3.95 (m, 1H), 4.05-4.20 (m, 1H), 4.20-4.40 (m, 1H), 4.46-4.60 (m, 0.3H), 4.62-4.94 (m, 2H), 6.60-6.80 (m, 2H), 7.04-7.14 (m, Examples 147 and 148

According to the methods described in Example 106, (1) and Example 6, the compounds of Examples 147 and 148 (free bases and the hydrochlorides thereof) were obtained.

TABLE 11

| Compound number | | Structural formula | $^1$H NMR |
|---|---|---|---|
| Example 147 | 195 | | (Hydrochloride, CD$_3$OD) δ 0.46-0.56 (m, 2H), 0.70-1.05 (m, 3H), 1.10-1.20 (m, 1H), 1.40-1.80 (m, 4H), 1.85-2.00 (m, 1H), 2.15-2.25 (m, 1H), 2.75-2.86 (m, 1H), 2.90-3.10 (m, 2H), 3.18-3.42 (m, 5H), 3.43-3.65 (m, 1.5H), 3.71 (d, J = 11.2 Hz, 0.5H), 3.83-3.90 (m, 0.5H), 3.95-4.05 (m, 0.5H), 4.14-4.23 (m, 1H), 4.27-4.35 (m, 0.5H), 4.45-4.50 (m, 0.5H), 6.68-6.78 (m, 2H), 7.02-7.14 (m, 3H), 7.15-7.24 (m, 1H), 7.30-7.40 (m, 2H). |
| Example 148 | 196 | | (Hydrochloride, CD$_3$OD) δ 0.45-0.55 (m, 2H), 0.70-0.85 (m, 3H), 0.89 (d, J = 6.8 Hz, 3H), 0.95 (d, J = 6.8 Hz, 3H), 1.10-1.20 (m, 1H), 1.35-1.45 (m, 1H), 1.45-1.70 (m, 3H), 1.80-2.00 (m, 2H), 2.05-2.20 (m, 1H), 2.70-2.85 (m, 1H), 2.85-3.10 (m, 2H), 3.10-3.25 (m, 3H), 3.40-3.70 (m, 3H), 3.70-3.95 (m, 3H), 4.05-4.20 (m, 1H), 4.20-4.30 (m, 1H), 4.50-4.60 (m, 1H), 6.65-6.80 (m, 2H), 7.10 (d, J = 7.3 Hz, 1H). |

Example 149

Phenyl (1S,5aS,6R,11bR)-10-hydroxy-14-methyl-3a, 4,5,6,7,11e-hexahydro-1H-6,11b-(iminoethano)-1, 5a-methanonaphtho[1,2-e]indole-3(2H)-carboxylate (199)

(1) Synthesis of phenyl (1S,5aS,6R,11bR)-14-t-butoxycarbonyl-10-methoxy-3a,4,5,6,7,11c-hexahydro-1H-6,11b-(iminoethano)-1,5a-methanonaphtho[1,2-e]indole-3(2H)-carboxylate (197)

[Formula 176]

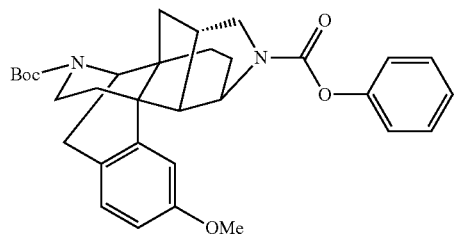

197

According to the method described in Example 106, (1), the title compound 197 (81 mg, 79%) was obtained by using the compound 147 (80 mg, 0.19 mmol) and phenyl chloroformate (36 μL, 0.29 mmol).

(2) Synthesis of phenyl (1S,5aS,6R,11bR)-10-methoxy-3a,4,5,6,7,11c-hexahydro-1H-6,11b-(iminoethano)-1,5a-methanonaphtho[1,2-e]indole-3(2H)-carboxylate (198)

[Formula 177]

198

According to the method described in Example 120, (4), a crude product of the title compound 198 was obtained by using the compound 197 (32 mg, 0.075 mmol) which was prepared in (1) mentioned above.

(3) Synthesis of phenyl (1S,5aS,6R,11bR)-10-hydroxy-14-methyl-3a,4,5,6,7,11c-hexahydro-1H-6, 11b-(iminoethano)-1,5a-methanonaphtho[1,2-e]indole-3(2H)-carboxylate (199)

[Formula 178]

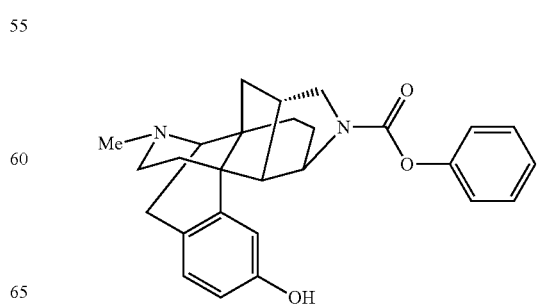

199

According to the method described in Example 8, the title compound 199 and the hydrochloride thereof (5 mg, 14%) were obtained by using the crude product which was prepared in (2) mentioned above.

Compound 199 (hydrochloride) $^1$H NMR (CD$_3$ OD, 400 MHz): δ 0.75-1.10 (m, 1H), 1.40-1.80 (m, 4H), 1.80-2.00 (m, 1H), 2.00-2.25 (m, 1H), 2.75-2.95 (m, 2H), 2.97 (s, 3H), 3.10-3.45 (m, 3H), 3.45-3.70 (m, 2H), 3.70-4.10 (m, 3H), 4.20-4.60 (m, 1H), 6.70-6.80 (m, 2H), 7.00-7.25 (m, 4H), 7.25-7.45 (m, 2H)

Example 150

Phenyl (1S,5aS,6R,11bR)-14-(2-fluoroethyl)-10-hydroxy-3a,4,5,6,7,11c-hexahydro-1H-6,11b-(iminoethano)-1,5a-methanonaphtho[1,2-e]indole-3(2H)-carboxylate (201)

(1) Synthesis of phenyl (1S,5aS,6R,11bR)-14-(2-fluoroethyl)-10-methoxy-3a,4,5,6,7,11c-hexahydro-1H-6,11b-(iminoethano)-1,5a-methanonaphtho[1,2-e]indole-3(2H)-carboxylate (200)

[Formula 179]

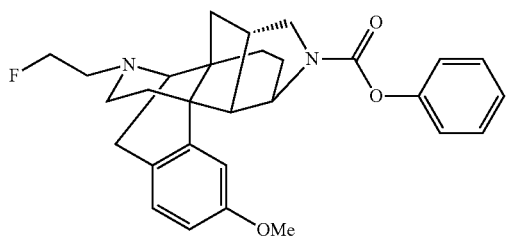

200

According to the method described in Example 121, a crude product of the title compound 200 was obtained by using the compound 198 (32 mg, 0.075 mmol).

(2) Synthesis of phenyl (1S,5aS,6R,11bR)-14-(2-fluoroethyl)-10-hydroxy-3a,4,5,6,7,11c-hexahydro-1H-6,11b-(iminoethano)-1,5a-methanonaphtho[1,2-e]indole-3(2H)-carboxylate (201)

[Formula 180]

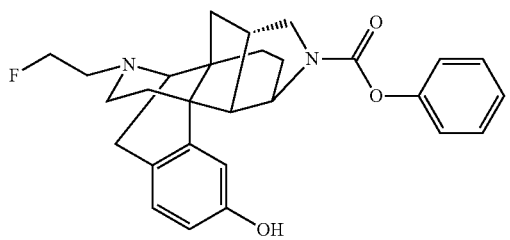

201

According to the method described in Example 6, the title compound 201 and the hydrochloride thereof (2 mg, 5%) were obtained by using the crude product which was prepared in (1) mentioned above.

Compound 201 (hydrochloride) $^1$H NMR (CD$_3$ OD, 400 MHz): δ 0.75-1.10 (m, 2H), 1.40-2.00 (m, 4H), 2.00-2.30 (m, 1H), 2.80-3.10 (m, 2H), 3.20-3.95 (m, 8H), 3.95-4.10 (m, 2H), 4.25-4.55 (m, 1H), 4.90-5.10 (m, 2H), 6.70-6.80 (m, 2H), 7.00-7.25 (m, 4H), 7.25-7.45 (m, 2H)

Example 151

(1S,5aS,6R,11bR)-3-(Cyclohexylmethyl)-14-(cyclopropylmethyl)-2,3,3a,4,5,6,7,11c-octahydro-1H-6,11b-(iminoethano)-1,5a-methanonaphtho[1,2-e]indol-10-ol (204)

(1) Synthesis of cyclohexyl[(1S,5aS,6R,11bR)-14-(cyclopropylmethyl)-10-methoxy-4,5,6,7-tetrahydro-1H-6,11b-(iminoethano)-1,5a-methanonaphtho[1,2-e]indol-3(2H,3aH,11cH)-yl]methanone (202)

[Formula 181]

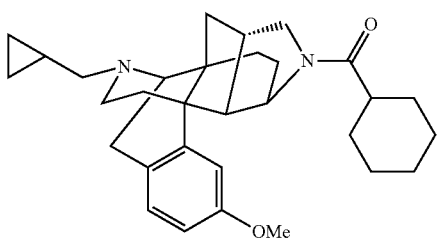

202

According to the method described in Example 33, a crude product of the title compound 202 was obtained by using the compound 77 (25 mg, 0.069 mmol) and cyclohexanecarbonyl chloride (19 μL, 0.14 mmol).

(2) Synthesis of (1S,5aS,6R,11bR)-3-(cyclohexylmethyl)-14-(cyclopropylmethyl)-10-methoxy-2,3,3a,4,5,6,7,11c-octahydro-1H-6,11b-(iminoethano)-1,5a-methanonaphtho[1,2-e]indole (203)

[Formula 182]

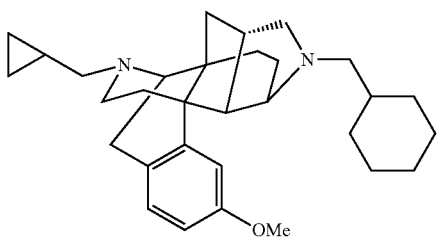

203

Under an argon atmosphere, the crude product which was prepared in (1) mentioned above was dissolved in THF (1 mL), the solution was added with a solution of borane-THF complex in THF (1.0 mol/L, 0.36 mL, 0.36 mmol), and the mixture was stirred under reflux for 2 hours. The reaction mixture was cooled to room temperature, then concentrated under reduced pressure, and added with 6 M hydrochloric acid (5 mL), and the mixture was refluxed for 1 hour. The reaction mixture was cooled again, then adjusted to pH 11 with potassium carbonate, and extracted three times with chloroform. The organic layers were combined, dried over anhydrous sodium sulfate, and then concentrated to obtain a crude product of the title compound 203.

(3) Synthesis of (1S,5aS,6R,11bR)-3-(cyclohexylmethyl)-14-(cyclopropylmethyl)-2,3,3a,4,5,6,7,11c-octahydro-1H-6,11b-(iminoethano)-1,5a-methanonaphtho[1,2-e]indol-10-ol (204)

[Formula 183]

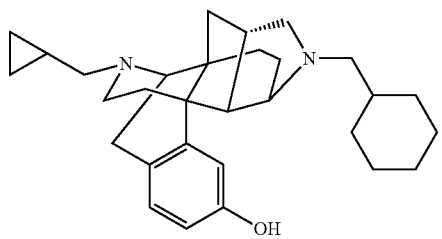

204

According to the method described in Example 6, the title compound 204 and the hydrochloride thereof (18 mg, 51%) were obtained by using the crude product which was prepared in (2) mentioned above.

Compound 204 (hydrochloride) $^1$H NMR (CD$_3$OD, 400 MHz): δ 0.45-0.60 (m, 2H), 0.70-0.85 (m, 2H), 0.95-2.00 (m, 18H), 2.10-2.25 (m, 1H), 2.70-2.85 (m, 1H), 2.95-3.10 (m, 3H), 3.10-3.55 (m, 7H), 3.71 (d, J=6.8 Hz, 1H), 4.00-4.10 (m, 2H), 4.18 (dd, J=6.3, 17.1 Hz, 1H), 6.72-6.78 (m, 2H), 7.08 (d, J=8.8 Hz, 1H)

Examples 152 to 162

By using the compound 77, the compounds of Examples 152 to 162 (free bases and the hydrochlorides thereof) were obtained according to the methods mentioned in Tables 12 and 13.

TABLE 12

| | Compound number | Structural formula | $^1$H NMR | Synthetic method |
|---|---|---|---|---|
| Example 152 | 205 | | (Hydrochloride, CD$_3$OD) δ 0.45-0.53 (m, 1H), 0.54-0.62 (m, 1H), 0.70-0.85 (m, 2H), 1.13-1.23 (m, 1H), 1.26-1.45 (m, 1H), 1.71-1.76 (m, 4H), 1.77-2.00 (m, 1H), 2.14-2.24 (m, 1H), 2.74-2.83 (m, 1H), 3.07 (dd, J = 7.3, 13.2 Hz, 2H), 3.23-3.43 (m, 6H), 3.52-3.66 (m, 1H), 4.02-4.12 (m, 1H), 4.15-4.23 (m, 2H), 4.24-4.34 (m, 2H), 6.72-6.77 (m, 2H), 7.13 (d, J = 8.8 Hz, 1H). | h |
| Example 153 | 206 | | (Hydrochloride, CD$_3$OD) δ 0.45-0.60 (m, 2H), 0.70-0.85 (m, 2H), 1.10-1.25 (m, 1H), 1.25-1.45 (m, 1H), 1.50-1.75 (m, 4H), 1.85-2.00 (m, 1H), 2.10-2.25 (m, 1H), 2.72-2.90 (m, 3H), 2.90-3.10 (m, 2H), 3.20-3.85 (m, 9H), 4.00-4.25 (m, 3H), 6.72-6.76 (m, 2H), 7.13 (d, J = 8.8 Hz, 1H). | h |
| Example 154 | 207 | | (Hydrochloride, CD$_3$OD) δ 0.45-0.60 (m, 2H), 0.70-0.90 (m, 2H), 1.00-1.20 (m, 1H), 1.20-1.40 (m, 1H), 1.50-1.80 (m, 3H), 1.80-2.20 (m, 3H), 2.20-2.40 (m, 2H), 2.72-2.85 (m, 1H), 2.85-3.10 (m, 2H), 3.20-3.75 (m, 11H), 4.00-4.20 (m, 3H), 6.70-6.78 (m, 2H), 7.13 (d, J = 8.3 Hz, 1H). | h |
| Example 155 | 208 | | (Hydrochloride, CD$_3$OD) δ 0.45-0.65 (m, 2H), 0.65-0.90 (m, 2H), 1.10-1.50 (m, 6H), 1.50-1.80 (m, 4H), 1.80-2.00 (m, 1H), 2.10-2.20 (m, 1H), 2.60-2.85 (m, 1H), 2.95-3.15 (m, 2H), 3.20-3.55 (m, 6H), 3.58 (s, 2H), 3.70-3.95 (m, 2H), 4.10-4.30 (m, 2H), 6.70-6.80 (m, 2H), 7.14 (d, J = 8.3 Hz, 1H). | h |

TABLE 12-continued

| Compound number | | Structural formula | ¹H NMR | Synthetic method |
|---|---|---|---|---|
| Example 156 | 209 | | (Hydrochloride, CD₃OD) δ 0.40-0.60 (m, 2H), 0.70-1.00 (m, 3H), 1.00-1.30 (m, 1H), 1.40-1.85 (m, 4H), 1.85-2.00 (m, 1H), 2.00-2.30 (m, 1H), 2.70-2.90 (m, 1H), 2.90-3.10 (m, 2H), 3.20-3.70 (m, 7H), 3.70-3.80 (m, 1H), 3.80-4.10 (m, 1H), 4.19 (d, J = 6.3 Hz, 1H), 4.41 (s, 2H), 6.70-6.80 (m, 2H), 7.08 (d, J = 7.8 Hz, 1H). | i |
| Example 157 | 210 | | (Hydrochloride, OD₃OD) δ 0.40-0.60 (m, 2H), 0.70-0.85 (m, 2H), 0.85-2.00 (m, 18H), 2.10-2.20 (m, 1H), 2.72-2.90 (m, 1H), 2.90-3.55 (m, 10H), 3.55-3.75 (m, 1H), 3.95-4.25 (m, 3H), 6.60-6.80 (m, 2H), 7.13 (d, J = 9.2 Hz, 1H). | h |

TABLE 13

| Compound number | | Structural formula | ¹H NMR | Synthetic method |
|---|---|---|---|---|
| Example 158 | 211 | | (Hydrochloride, CD₃OD) δ 0.40-0.55 (m, 2H), 0.65-0.85 (m, 2H), 0.85-1.00 (m, 1H), 1.00-1.20 (m, 1H), 1.40-1.55 (m, 1H), 1.55-1.85 (m, 4H), 2.05-2.20 (m, 1H), 2.65-2.80 (m, 1H), 2.80-2.95 (m, 1H), 2.95-3.20 (m, 2H), 3.20-3.60 (m, 7H), 3.60-3.80 (m, 1H), 4.13 (d, J = 5.9 Hz, 1H), 4.90-5.20 (m, 1H), 6.53 (d, J = 2.4 Hz, 1H), 6.65 (dd, J = 2.4, 8.3 Hz, 1H), 7.06 (d, J = 8.3 Hz, 1H), 7.40-7.50 (m, 5H). | i |
| Example 159 | 212 | | (Hydrochloride, CD₃OD) δ 0.40-0.60 (m, 2H), 0.60-0.90 (m, 2H), 1.00-1.40 (m, 2H), 1.40-2.00 (m, 5H), 2.00-2.20 (m, 1H), 2.70-2.90 (m, 2H), 2.90-3.20 (m, 3H), 3.20-3.50 (m, 6H), 4.00-4.20 (m, 2H), 5.00-5.20 (m, 1H), 6.60-6.80 (m, 2H), 7.12 (d, J = 8.3 Hz, 1H), 7.40-7.70 (m, 5H). | i |
| Example 160 | 213 | | (Hydrochloride, CD₃OD) δ 0.45-0.60 (m, 2H), 0.70-0.85 (m, 2H), 1.10-1.20 (m, 2H), 1.50-2.00 (m, 5H), 2.10-2.25 (m, 1H), 2.74-2.86 (m, 1H), 2.90-3.10 (m, 2H), 3.20-3.75 (m, 9H), 3.75-4.40 (m, 3H), 6.70-6.76 (m, 2H), 7.13 (d, J = 8.3 Hz, 1H), 7.48-7.66 (m, 5H). | h |

TABLE 13-continued

| Compound number | Structural formula | ¹H NMR | Synthetic method |
|---|---|---|---|
| Example 161 | 214 | (Free base, CD₃OD) δ 0.10-0.20 (m, 2H), 0.43-0.58 (m, 3H), 0.75-0.93 (m, 1H), 1.05-1.30 (m, 2H), 1.35-1.58 (m, 2H), 1.63-1.75 (m, 1H), 1.90-2.05 (m, 1H), 2.06-2.20 (m, 1H), 2.30-2.52 (m, 3H), 2.55-2.65 (m, 1H), 2.75-3.06 (m, 5H), 3.08-3.15 (m, 1H), 3.20-3.40 (m, 2H), 4.66 (s, 1H), 6.44-6.54 (m, 2H), 6.89 (d, J = 7.8 Hz, 1H), 7.08-7.26 (m, 6H), 7.36-7.48 (m, 4H). | i |
| Example 162 | 215 | (Hydrochloride, CD₃OD) δ 0.42-0.58 (m, 2H), 0.68-0.85 (m, 2H), 1.18-1.88 (m, 7H), 2.04-2.20 (m, 1H), 2.69-2.81 (m, 1H), 2.85-3.09 (m, 2H), 3.09-3.52 (m, 7.6H), 3.64 (d, J = 6.3 Hz, 0.7H), 3.76 (dd, J = 8.8, 12.2 Hz, 0.7H), 3.89-4.06 (m, 3H), 4.10-4.19 (m, 1H), 4.51 (t, J = 7.3 Hz, 0.7H), 4.58 (t, J = 6.8 Hz, 0.3H), 6.55 (d, J = 2.4 Hz, 0.3H), 6.61 (d, J = 2.4 Hz, 0.7H), 6.68-6.68 (m, 1H), 7.05-7.15 (m, 1H), 7.19-7.53 (m, 9H). | h |

Synthesis Methods Mentioned in Tables

Method h: method described in Example 151

Method i: method described in Example 58

Example 163

(1S,5aS,6R,11bR)-14-Methyl-3-(2,2,2-trifluoroethyl)-2,3,3a,4,5,6,7,11c-octahydro-1H-6,11b-(iminoethano)-1,5a-methanonaphtho[1,2-e]indol-10-ol (219)

(1) Synthesis of t-butyl (1S,5aS,6R,11bR)-10-methoxy-3-(2,2,2-trifluoroacetyl)-2,3,3a,4,5,6,7,11c-octahydro-1H-6,11b-(iminoethano)-1,5a-methanonaphtho[1,2-e]indole-14-carboxylate (216)

[Formula 184]

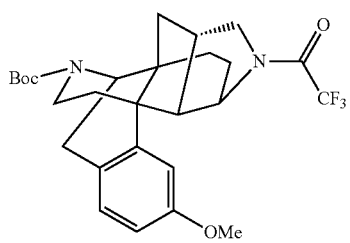

216

According to the method described in Example 5, the title compound 216 (68 mg, 79%) was obtained by using the compound 147 (68 mg, 0.17 mmol) and trifluoroacetic anhydride (71 μL, 0.51 mmol).

(2) Synthesis of 2,2,2-trifluoro-1-[(1S,5aS,6R,11bR)-10-methoxy-4,5,6,7-tetrahydro-1H-6,11b-(iminoethano)-1,5a-methanonaphtho[1,2-e]indol-3(2H,3aH,11cH)-yl]ethanone (217)

[Formula 185]

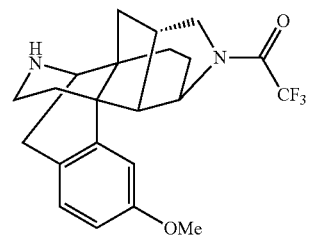

217

According to the method described in Example 120, (4), a crude product of the title compound 217 was obtained by using the compound 216 (68 mg, 0.13 mmol) which was prepared in (1) mentioned above.

(3) Synthesis of (1S,5aS,6R,11bR)-10-methoxy-3-(2,2,2-trifluoroethyl)-2,3,3a,4,5,6,7,11c-octahydro-1H-6,11b-(iminoethano)-1,5a-methanonaphtho[1,2-e]indole (218)

[Formula 186]

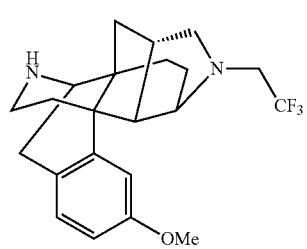

218

According to the method described in Example 151, (2), a crude product of the title compound 218 was obtained by using the crude product which was prepared in (2) mentioned above.

(4) Synthesis of (1S,5aS,6R,11bR)-14-methyl-3-(2,2,2-trifluoroethyl)-2,3,3a,4,5,6,7,11c-octahydro-1H-6,11b-(iminoethano)-1,5a-methanonaphtho[1,2-e]indol-10-ol (219)

[Formula 187]

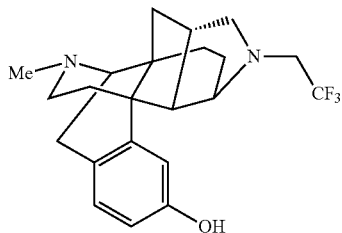

219

According to the method described in Example 8, the title compound 219 and the hydrochloride thereof (5 mg, 39%) were obtained by using the crude product which was prepared in (3) mentioned above.

Compound 219 (hydrochloride) $^1$H NMR (CD$_3$ OD, 400 MHz): δ 1.10-1.25 (m, 1H), 1.45-1.75 (m, 4H), 1.75-1.95 (m, 1H), 2.10-2.25 (m, 1H), 2.75-2.90 (m, 2H), 2.96 (s, 3H), 3.10-3.50 (m, 6H), 3.75-4.05 (m, 5H), 6.65-6.80 (m, 2H), 7.13 (d, J=8.3 Hz, 1H)

Example 164

(1S,5aS,6R,11bR)-14-(Cyclopropylmethyl)-3-(pyridin-2-yl)-2,3,3a,4,5,6,7,11c-octahydro-1H-6,11b-(iminoethano)-1,5a-methanonaphtho[1,2-e]indol-10-ol (221)

(1) Synthesis of (1S,5aS,6R,11bR)-14-(cyclopropylmethyl)-10-methoxy-3-(pyridin-2-yl)-2,3,3a,4,5,6,7,11c-octahydro-1H-6,11b-(iminoethano)-1,5a-methanonaphtho[1,2-e]indole (220)

[Formula 188]

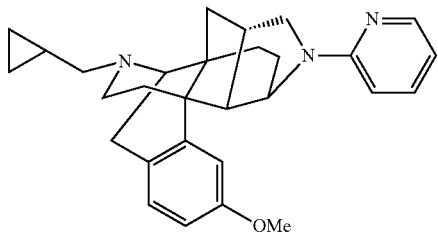

220

Under an argon atmosphere, the compound 77 (30 mg, 0.082 mmol) was dissolved in toluene (1 mL), the solution was added with palladium acetate (2 mg, 8.2 μmol), 4,5-bis(diphenylphosphino)-9,9-dimethylxanthene (9 mg, 0.016 mmol), 2-bromopyridine (16 μL, 0.16 mmol), and sodium t-butoxide (24 mg, 0.25 mmol), and the mixture was stirred at 110° C. for 16 hours. The reaction mixture was diluted with ethyl acetate, filtered through Celite, and then concentrated to obtain a crude product of the title compound 220.

(2) Synthesis of (1S,5aS,6R,11bR)-14-(cyclopropylmethyl)-3-(pyridin-2-yl)-2,3,3a,4,5,6,7,11c-octahydro-1H-6,11b-(iminoethano)-1,5a-methanonaphtho[1,2-e]indol-10-ol (221)

[Formula 189]

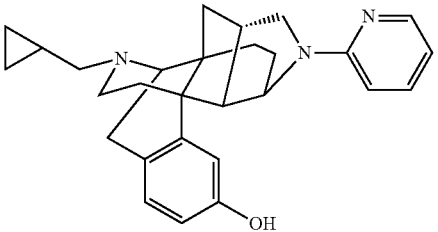

221

According to the method described in Example 6, the title compound 221 and the hydrochloride thereof (5 mg, 12%) were obtained by using the crude product which was prepared in (1) mentioned above.

Compound 221 (hydrochloride) $^1$H NMR (CD$_3$ OD, 400 MHz): δ 0.40-0.60 (m, 2H), 0.70-0.90 (m, 2H), 1.00-1.10 (m, 1H), 1.10-1.20 (m, 1H), 1.20-1.50 (m, 2H), 1.50-1.80 (m, 3H), 1.90-2.00 (m, 1H), 2.10-2.30 (m, 1H), 2.70-2.90 (m, 1H), 3.00-3.20 (m, 2H), 3.20-3.60 (m, 5H), 3.80 (d, J=10.7 Hz, 1H), 3.90-4.00 (m, 1H), 4.20 (d, J=6.3 Hz, 1H), 4.50-4.60 (m, 1H), 6.75 (dd, J=2.4, 8.3 Hz, 1H), 6.80 (d, J=2.4 Hz, 1H), 6.85-6.95 (m, 1H), 6.95-7.10 (m, 1H), 7.14 (d, J=8.3 Hz, 1H), 7.80-8.00 (m, 2H)

Example 165

Synthesis of (1S,5aS,6R,11bR)-14-(cyclopropylmethyl)-3-(4,6-dimethylpyrimidin-2-yl)-10-methoxy-2,3,3a,4,5,6,7,11c-octahydro-1H-6,11b-(iminoethano)-1,5a-methanonaphtho[1,2-e]indole (222)

[Formula 190]

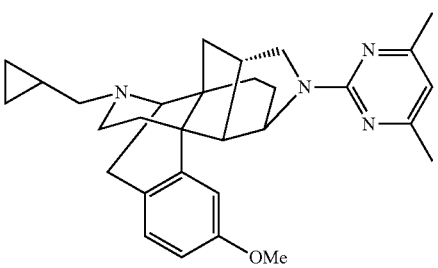

222

Under an argon atmosphere, the compound 77 (23 mg, 0.06 mmol) was dissolved in acetonitrile (4 mL), the solution was added with potassium carbonate (27 mg, 0.20 mol), and 2-chloro-4,6-dimethylpyrimidine (14 mg, 0.10 mmol), and the mixture was stirred at 85° C. for 16 hours. The reaction mixture was diluted with ethyl acetate, and washed with water and saturated brine. The organic layer was dried over anhydrous sodium sulfate, and then concentrated. The obtained crude product was purified by silica gel column chromatography to give the title compound 222 and the hydrochloride thereof.

Compound 222 (free base) $^1$H NMR (CDCl$_3$, 400 MHz): δ 0.05-0.15 (m, 2H), 0.43-0.53 (m, 2H), 0.76-0.88 (m, 2H), 1.10-1.30 (m, 2H), 1.37-1.55 (m, 2H), 1.60-1.73 (m, 1H), 1.94-2.06 (m, 2H), 2.10-2.38 (m, 8H), 2.52-2.63 (m, 1H), 2.92 (d, J=2.9 Hz, 2H), 3.00-3.16 (m, 3H), 3.38 (t, J=11.7 Hz, 1H), 3.67 (d, J=11.7 Hz, 1H), 3.81 (s, 3H), 3.86 (dd, J=7.8, 11.7 Hz, 1H), 4.57 (dd, J=5.4, 8.3 Hz, 1H), 6.20 (s, 1H), 6.68 (dd, J=2.4, 8.3 Hz, 1H), 6.74 (d, J=2.4 Hz, 1H), 7.03 (d, J=8.3 Hz, 1H)

Example 166

Synthesis of (1S,5aS,6R,11bR)-14-(cyclopropylmethyl)-3-(4,6-dimethylpyrimidin-2-yl)-2,3,3a,4,5,6,7,11c-octahydro-1H-6,11b-(iminoethano)-1,5a-methanonaphtho[1,2-e]indol-10-ol (223)

[Formula 191]

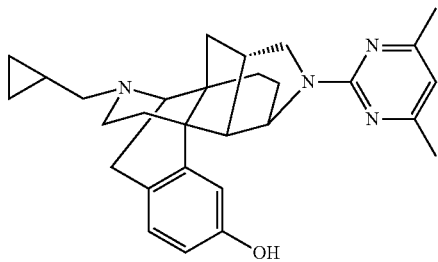

223

According to the method described in Example 6, the title compound 223 and the hydrochloride thereof were obtained by using the compound 222.

Compound 223 (free base) ¹H NMR (CDCl₃, 400 MHz): δ 0.05-0.14 (m, 2H), 0.42-0.53 (m, 2H), 0.76-0.90 (m, 2H), 1.08-1.28 (m, 2H), 1.37-1.72 (m, 3H), 1.93-2.07 (m, 2H), 2.17-2.37 (m, 8H), 2.55-2.61 (m, 1H), 2.86-2.92 (m, 2H), 2.96-3.14 (m, 3H), 3.32-3.43 (m, 1H), 3.67 (d, J=11.7 Hz, 1H), 3.88 (dd, J=7.8 Hz, 11.7 Hz, 1H), 4.60 (dd, J=5.7, 8.3 Hz, 1H), 6.21 (s, 1H), 6.59 (dd, J=2.9, 8.3 Hz, 1H), 6.69 (d, J=2.9 Hz, 1H), 6.96 (d, J=8.3 Hz, 1H)

Example 167

(1S,5aS,6R,11bR)-3-(1H-Benzo[d]imidazol-2-yl)-14-(cyclopropylmethyl)-2,3,3a,4,5,6,7,11c-octahydro-1H-6,11b-(iminoethano)-1,5a-methanonaphtho[1,2-e]indol-10-ol (225)

(1) Synthesis of (1S,5aS,6R,11bR)-3-(1H-benzo[d]imidazol-2-yl)-14-(cyclopropylmethyl)-10-methoxy-2,3,3a,4,5,6,7,11c-octahydro-1H-6,11b-(iminoethano)-1,5a-methanonaphtho[1,2-e]indole (224)

[Formula 192]

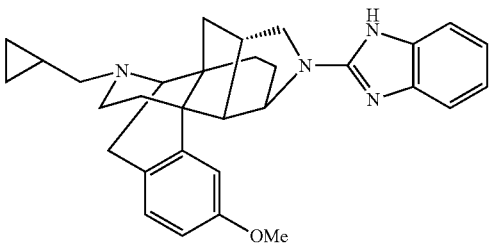

224

Under an argon atmosphere, a solution of the compound 77 (30 mg, 0.08 mmol) in 1,4-dioxane (1 mL) was added with 2-chloro-1H-benzoimidazole (25 mg, 0.16 mmol), diisopropylethylamine (0.07 mL, 0.4 mmol) and copper(I) iodide (1 mg, 1 μmol), and the mixture was stirred at 120° C. for 20 hours. The reaction mixture was cooled to room temperature, then diluted with chloroform, and washed with saturated brine. The organic layer was dried over anhydrous sodium sulfate, and concentrated. The obtained crude product was purified by preparative TLC to give the title compound 224 (30 mg, 76%) as brown oil.

¹H NMR (CDCl₃, 400 MHz): δ 0.09-0.19 (m, 2H), 0.45-0.53 (m, 2H), 0.78-0.94 (m, 2H), 1.17-1.28 (m, 2H), 1.40-1.53 (m, 2H), 1.65-1.77 (m, 1H), 1.90-2.13 (m, 2H), 2.30-2.45 (m, 2H), 2.58-2.68 (m, 1H), 2.90-2.98 (m, 2H), 3.05-3.25 (m, 3H), 3.40-3.51 (m, 2H), 3.80 (s, 3H), 3.84-3.92 (m, 1H), 4.31-4.38 (m, 1H), 6.68 (s, 1H), 6.71 (dd, J=2.9, 7.8 Hz, 1H), 7.02 (dd, J=3.4, 5.8 Hz, 2H), 7.06 (d, J=7.8 Hz, 1H), 7.22-7.32 (m, 2H)

(2) Synthesis of (1S,5aS,6R,11bR)-3-(1H-benzo[d]imidazol-2-yl)-14-(cyclopropylmethyl)-2,3,3a,4,5,6,7,11c-octahydro-1H-6,11b-(iminoethano)-1,5a-methanonaphtho[1,2-e]indol-10-ol (225)

[Formula 193]

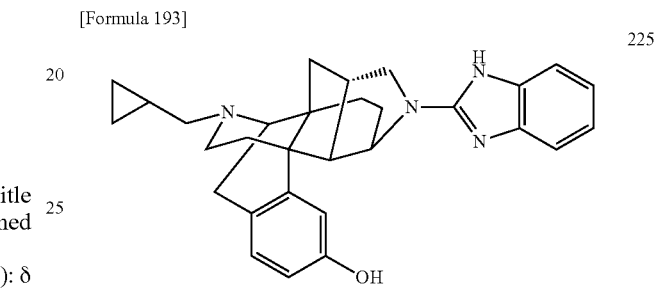

225

According to the method described in Example 6, the title compound 225 and the hydrochloride thereof were obtained by using the compound 224 which was prepared in (1) mentioned above.

Compound 225 (hydrochloride) ¹H NMR (CD₃ OD, 400 MHz): δ 0.45-0.60 (m, 2H), 0.70-0.87 (m, 2H), 1.00-1.21 (m, 2H), 1.44 (dd, J=6.8, 14.6 Hz, 1H), 1.60-1.80 (m, 1H), 1.62 (d, J=11.7 Hz, 1H), 1.69 (d, J=14.1 Hz, 1H), 1.90-2.00 (m, 1H), 2.18-2.30 (m, 1H), 2.77-2.88 (m, 1H), 3.08 (dd, J=7.8, 13.8 Hz, 1H), 3.15-3.56 (m, 7H), 3.86 (d, J=10.7 Hz, 1H), 4.00-4.10 (m, 1H), 4.22 (d, J=6.3 Hz, 1H), 4.47-4.57 (m, 1H), 6.75 (dd, J=2.4, 8.8 Hz, 1H), 6.80 (d, J=2.4 Hz, 1H), 7.15 (d, J=8.3 Hz, 1H), 7.25-7.30 (m, 2H), 7.32-7.40 (m, 2H)

Example 168

Synthesis of (1S,5aS,6R,11bR)-3-(4-aminopyrimidin-2-yl)-14-(cyclopropylmethyl)-2,3,3a,4,5,6,7,11c-octahydro-1H-6,11b-(iminoethano)-1,5a-methanonaphtho[1,2-e]indol-10-ol (226)

[Formula 194]

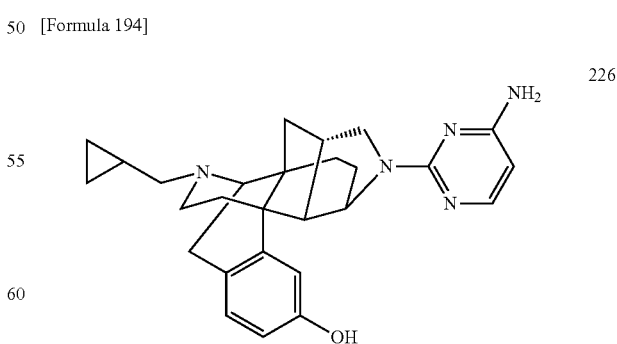

226

Under an argon atmosphere, a solution of the compound 77 (30 mg, 0.08 mmol) in THF (2 mL) was added with 4-amino-2-chloropyrimidine (19 mg, 0.15 mmol) and diisopropylethylamine (0.04 mL, 0.25 mmol), and the mixture was stirred under reflux for 20 hours. The reaction mixture was cooled to room temperature, and then added with water, and the mixture was extracted with ethyl acetate. The organic layers were combined, washed with saturated brine, then dried over anhydrous sodium sulfate, and concentrated. By using the obtained crude product, the title compound 226 and the hydrochloride thereof were obtained according to the method described in Example 6.

Compound 226 (free base) $^1$H NMR (CDCl$_3$, 400 MHz): δ 0.05-0.15 (m, 2H), 0.40-0.50 (m, 2H), 0.72-0.90 (m, 2H), 1.10-1.30 (m, 2H), 1.32-1.50 (m, 2H), 1.58-1.70 (m, 1H), 1.85-1.98 (m, 1H), 1.98-2.10 (m, 1H), 2.22-2.38 (m, 2H), 2.50-2.59 (m, 1H), 2.73-2.90 (m, 2H), 2.92-3.10 (m, 3H), 3.37 (t, J=11.7 Hz, 1H), 3.61 (d, J=11.7 Hz, 1H), 3.69-3.77 (m, 1H), 3.80-3.90 (m, 1H), 4.64 (br s, 2H), 5.69 (d, J=5.4 Hz, 1H), 6.55 (d, J=7.8 Hz, 1H), 6.70 (s, 1H), 6.81 (br s, 1H), 7.84 (br s, 1H)

Examples 169 to 200

By using the compound 77, the compounds of Examples 169 to 200 (free bases and the hydrochlorides thereof) were obtained according to the methods mentioned in Tables 14 to 19.

TABLE 14

| | Compound number | Structural formula | $^1$H NMR | Synthetic method |
|---|---|---|---|---|
| Example 169 | 227 | | (Hydrochloride, CD$_3$OD) δ 0.40-0.55 (m, 2H), 0.70-1.00 (m, 3H), 1.10-1.20 (m, 1H), 1.35-1.50 (m, 1H), 1.50-1.70 (m, 3H), 1.80-1.90 (m, 1H), 2.15-2.30 (m, 1H), 2.70-2.90 (m, 1H), 2.90-3.10 (m, 2H), 3.20-3.60 (m, 7H), 3.65-3.75 (m, 1H), 4.15 (d, J = 6.3 Hz, 1H), 4.20-4.25 (m, 1H), 6.64 (d, J = 8.3 Hz, 2H), 6.65-6.75 (m, 2H), 6.80 (d, J = 2.4 Hz, 1H), 7.12 (d, J = 8.3 Hz, 1H), 7.19 (d, J = 7.8 Hz, 2H). | k |
| Example 170 | 228 | | (Hydrochloride, CD$_3$OD) δ 0.40-0.60 (m, 2H), 0.70-0.90 (m, 2H), 1.10-1.30 (m, 2H), 1.40-1.70 (m, 2H), 1.70-2.00 (m, 3H), 2.10-2.20 (m, 1H), 2.45 (s, 3H), 2.75-2.85 (m, 1H), 2.95-3.15 (m, 2H), 3.20-3.70 (m, 6H), 3.90-4.30 (m, 4H), 6.60-6.70 (m, 1H), 6.70 (dd, J = 2.4, 8.3 Hz, 1H), 7.11 (d, J = 8.3 Hz, 1H), 7.20-7.60 (m, 4H). | k |
| Example 171 | 229 | | (Hydrochloride, CD$_3$OD) δ 0.40-0.60 (m, 2H), 0.70-1.00 (m, 4H), 1.00-1.30 (m, 2H), 1.50-1.70 (m, 3H), 1.70-1.90 (m, 1H), 2.10-2.30 (m, 1H), 2.70-2.85 (m, 1H), 2.85-3.00 (m, 1H), 3.00-3.10 (m, 1H), 3.15-3.70 (m, 6H), 3.70-3.90 (m, 1H), 4.13 (d, J = 6.3 Hz, 1H), 4.45-4.55 (m, 1H), 6.65-6.80 (m, 3H), 6.82 (d, J = 2.4 Hz, 1H), 6.90-7.05 (m, 2H), 7.11 (d, J = 8.3 Hz, 1H). | k |
| Example 172 | 230 | | (Hydrochloride, CD$_3$OD) δ 0.40-0.60 (m, 2H), 0.70-1.00 (m, 3H), 1.00-1.40 (m, 2H), 1.50-1.80 (m, 3H), 1.80-1.90 (m, 1H), 2.10-2.30 (m, 1H), 2.75-2.95 (m, 2H), 3.00-3.10 (m, 1H), 3.15-3.60 (m, 8H), 4.14 (d, J = 5.9 Hz, 1H), 4.30-4.40 (m, 1H), 6.72 (dd, J = 2.4, 8.3 Hz, 1H), 6.75-6.90 (m, 2H), 7.05 (d, J = 8.3 Hz, 1H), 7.10 (d, J = 8.3 Hz, 1H), 7.39 (t, J = 8.3 Hz, 1H), 7.57 (d, J = 8.3 Hz, 1H). | k |

TABLE 14-continued

| Compound number | | Structural formula | ¹H NMR | Synthetic method |
|---|---|---|---|---|
| Example 173 | 231 | | (Hydrochloride, CD$_3$OD) δ 0.40-0.60 (m, 2H), 0.70-0.90 (m, 2H), 0.90-1.10 (m, 1H), 1.10-1.25 (m, 1H), 1.40-1.55 (m, 1H), 1.55-1.60 (m, 1H), 1.60-1.80 (m, 2H), 1.80-2.00 (m, 1H), 2.15-2.30 (m, 1H), 2.76-2.86 (m, 1H), 3.00-3.10 (m, 2H), 3.20-3.50 (m, 6H), 3.70-3.85 (m, 1H), 3.85-4.00 (m, 1H), 4.18 (d, J = 6.3 Hz, 1H), 4.25-4.40 (m, 1H), 6.73 (dd, J = 2.4, 8.3 Hz, 1H), 6.79 (d, J = 2.4 Hz, 1H), 6.95-7.10 (m, 2H), 7.12 (d, J = 8.3 Hz, 1H), 7.46-7.54 (m, 2H), 7.54-7.60 (m, 1H), 7.64-7.72 (m, 2H), 7.91 (d, J = 7.3 Hz, 2H). | m |
| Example 174 | 232 | | (Hydrochloride, CD$_3$OD) δ 0.40-0.60 (m, 2H), 0.70-0.90 (m, 2H), 1.05-1.25 (m, 2H), 1.50-1.65 (m, 2H), 1.80-2.05 (m, 3H), 2.20-2.30 (m, 1H), 2.74-2.86 (m, 1H), 3.00-3.12 (m, 2H), 3.18-3.70 (m, 6H), 4.00-4.12 (m, 1H), 4.12-4.30 (m, 2H), 4.30-4.40 (m, 1H), 6.60-6.65 (m, 1H), 6.67 (dd, J = 2.9, 8.3 Hz, 1H), 7.09 (d, J = 8.3 Hz, 1H), 7.50-7.75 (m, 4H), 7.91 (d, J = 7.8 Hz, 1H), 8.00 (d, J = 7.8 Hz, 1H), 8.07 (d, J = 7.8 Hz, 1H). | m |

TABLE 15

| Compound number | | Structural formula | ¹H NMR | Synthetic method |
|---|---|---|---|---|
| Example 175 | 233 | | (Hydrochloride, CD$_3$OD) δ 0.40-0.60 (m, 2H), 0.70-1.00 (m, 4H), 1.10-1.25 (m, 1H), 1.40-1.75 (m, 4H), 1.75-1.95 (m, 1H), 2.15-2.30 (m, 1H), 2.70-2.90 (m, 1H), 2.95-3.10 (m, 2H), 3.20-3.55 (m, 5H), 3.65 (d, J = 10.2 Hz, 1H), 3.85 (dd, J = 7.8, 10.2 Hz, 1H), 4.16 (d, J = 6.3 Hz, 1H), 4.35-4.45 (m, 1H), 6.75 (dd, J = 2.4, 8.3 Hz, 1H), 6.84 (d, J = 2.4 Hz, 1H), 7.04 (d, J = 8.3 Hz, 1H), 7.10-7.20 (m, 2H), 7.31 (t, J = 7.3 Hz, 1H), 7.60-7.75 (m, 4H). | k |
| Example 176 | 234 | | (Hydrochloride, CD$_3$OD) δ 0.40-0.60 (m, 2H), 0.70-1.05 (m, 3H), 1.10-1.25 (m, 1H), 1.25-1.40 (m, 2H), 1.50-1.80 (m, 3H), 1.80-2.00 (m, 1H), 2.15-2.30 (m, 1H), 2.75-2.90 (m, 1H), 3.00-3.20 (m, 2H), 3.20-3.55 (m, 5H), 3.62 (d, J = 11.2 Hz, 1H), 3.70-3.85 (m, 1H), 4.19 (d, J = 5.9 Hz, 1H), 4.30-4.40 (m, 1H), 6.75 (dd, J = 2.4, 8.3 Hz, 1H), 6.81 (d, J = 2.4 Hz, 1H), 7.14 (d, J = 8.3 Hz, 1H), 7.60-7.70 (m, 1H), 7.72 (dd, J = 5.4, 9.2 Hz, 1H), 7.85-8.00 (m, 2H). | k |
| Example 177 | 235 | | (Hydrochloride, CD$_3$OD) δ 0.40-0.60 (m, 2H), 0.70-0.90 (m, 2H), 1.00-1.25 (m, 2H), 1.25-1.50 (m, 1H), 1.50-1.80 (m, 3H), 1.90-2.00 (m, 1H), 2.10-2.30 (m, 1H), 2.70-2.90 (m, 1H), 3.00-3.20 (m, 2H), 3.20-3.60 (m, 6H), 3.78 (d, J = 12.2 Hz, 1H), 3.90-4.00 (m, 1H), 4.19 (d, J = 6.3 Hz, 1H), 4.50-4.60 (m, 1H), 6.75 (dd, J = 2.4, 8.3 Hz, 1H), 6.80 (d, J = 2.4 Hz, 1H), 6.82 (dd, J = 2.4, 7.3 Hz, 1H), 6.88 (dd, J = 2.4, 7.3 Hz, 1H), 7.14 (d, J = 8.3 Hz, 1H), 8.03 (d, J = 7.3 Hz, 1H), 8.12 (d, J = 7.3 Hz, 1H). | k |

TABLE 15-continued

| Compound number | | Structural formula | ¹H NMR | Synthetic method |
|---|---|---|---|---|
| Example 178 | 236 | 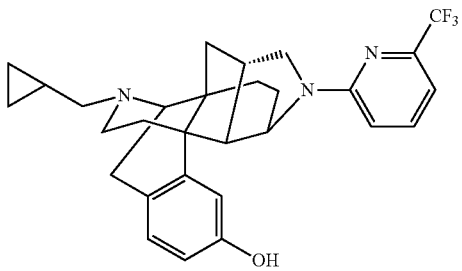 | (Hydrochloride, CD₃OD)<br>δ 0.40-0.55 (m, 2H), 0.70-1.00 (m, 3H), 1.10-1.20 (m, 1H), 1.40-1.70 (m, 4H), 1.80-1.90 (m, 1H), 2.10-2.30 (m, 1H), 2.70-2.90 (m, 1H), 2.90-3.10 (m, 2H), 3.15-3.55 (m, 5H), 3.60-3.70 (m, 1H), 3.75-3.85 (m, 1H), 4.10-4.20 (m, 1H), 4.45-4.60 (m, 2H), 6.61 (d, J = 8.8 Hz, 1H), 6.73 (dd, J = 2.4, 8.3 Hz, 1H), 6.81 (d, J = 2.4 Hz, 1H), 6.87 (d, J = 7.3 Hz, 1H), 7.12 (d, J = 8.3 Hz, 1H), 7.55-7.63 (m, 1H). | m |
| Example 179 | 237 | 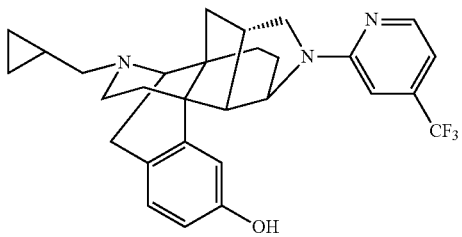 | (Hydrochloride, CD₃OD)<br>δ 0.40-0.60 (m, 2H), 0.70-0.85 (m, 2H), 0.95-1.10 (m, 1H), 1.10-1.25 (m, 1H), 1.35-1.45 (m, 1H), 1.55-1.70 (m, 3H), 1.85-1.95 (m, 1H), 2.15-2.30 (m, 1H), 2.75-2.90 (m, 1H), 3.00-3.20 (m, 2H), 3.20-3.55 (m, 6H), 3.80 (d, J = 10.7 Hz, 1H), 3.90-4.00 (m, 1H), 4.19 (d, J = 6.3 Hz, 1H), 4.60-4.65 (m, 1H), 6.75 (dd, J = 2.4, 8.3 Hz, 1H), 6.80 (d, J = 2.4 Hz, 1H), 6.96 (d, J = 6.3 Hz, 1H), 7.05-7.10 (m, 1H), 7.14 (d, J = 8.3 Hz, 1H), 8.11 (d, J = 5.9 Hz, 1H). | m |

TABLE 16

| Compound number | | Structural formula | ¹H NMR | Synthetic method |
|---|---|---|---|---|
| Example 180 | 238 | 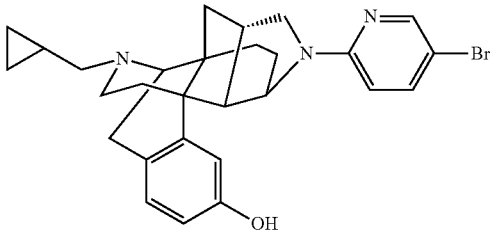 | (Hydrochloride, CD₃OD)<br>δ 0.45-0.60 (m, 2H), 0.70-0.85 (m, 2H), 0.95-1.10 (m, 1H), 1.10-1.25 (m, 1H), 1.25-1.40 (m, 1H), 1.55-1.75 (m, 3H), 1.90-2.00 (m, 1H), 2.15-2.30 (m, 1H), 2.75-2.85 (m, 1H), 3.00-3.20 (m, 2H), 3.20-3.55 (m, 6H), 3.79 (d, J = 11.7 Hz, 1H), 3.95 (dd, J = 7.8, 11.7 Hz, 1H), 4.20 (d, J = 6.3 Hz, 1H), 4.50-4.60 (m, 1H), 6.74 (dd, J = 2.4, 8.3 Hz, 1H), 6.79 (d, J = 2.4 Hz, 1H), 7.01 (d, J = 9.8 Hz, 1H), 7.14 (d, J = 8.3 Hz, 1H), 7.97-8.05 (m, 2H). | k |
| Example 181 | 239 | 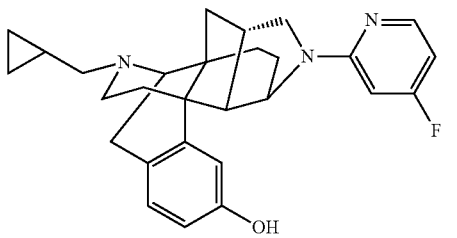 | (Hydrochloride, CD₃OD)<br>δ 0.45-0.55 (m, 1H), 0.55-0.68 (m, 1H), 0.68-0.90 (m, 2H), 0.95-1.15 (m, 1H), 1.15-1.25 (m, 1H), 1.25-1.45 (m, 1H), 1.50-1.75 (m, 3H), 1.85-2.05 (m, 1H), 2.20-2.35 (m, 1H), 2.75-2.85 (m, 1H), 3.00-3.15 (m, 1H), 3.15-3.68 (m, 7H), 3.82 (d, J = 10.7 Hz, 1H), 3.90-4.05 (m, 1H), 4.15-4.30 (m, 1H), 4.50-4.60 (m, 1H), 6.74 (d, J = 8.3 Hz, 1H), 6.78-6.95 (m, 3H), 7.15 (d, J = 8.3 Hz, 1H), 7.99 (br s, 1H). | m |
| Example 182 | 240 | 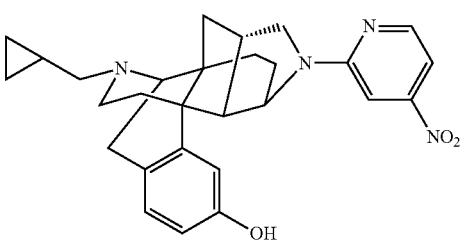 | (Hydrochloride, CD₃OD)<br>δ 0.45-0.60 (m, 2H), 0.70-0.90 (m, 2H), 1.00-1.25 (m, 2H), 1.35-1.45 (m, 1H), 1.55-1.75 (m, 3H), 1.90-2.00 (m, 1H), 2.15-2.30 (m, 1H), 2.75-2.90 (m, 1H), 3.05-3.10 (m, 1H), 3.10-3.60 (m, 7H), 3.80-4.00 (m, 1H), 4.00-4.15 (m, 1H), 4.15-4.25 (m, 1H), 4.65-4.75 (m, 1H), 6.76 (dd, J = 2.4, 8.3 Hz, 1H), 6.81 (d, J = 2.4 Hz, 1H), 7.15 (d, J = 8.3 Hz, 1H), 7.40-7.50 (m, 1H), 7.65-7.75 (m, 1H), 8.10-8.20 (m, 1H). | m |

TABLE 16-continued

| Compound number | | Structural formula | ¹H NMR | Synthetic method |
|---|---|---|---|---|
| Example 183 | 241 | | (Hydrochloride, CD₃OD) δ 0.40-0.60 (m, 2H), 0.70-0.85 (m, 2H), 0.90-1.05 (m, 1H), 1.10-1.25 (m, 1H), 1.40-1.55 (m, 1H), 1.55-1.75 (m, 3H), 1.90-2.00 (m, 1H), 2.10-2.25 (m, 1H), 2.75-2.85 (m, 1H), 3.00-3.60 (m, 8H), 3.81 (d, J = 11.7 Hz, 1H), 3.90-4.00 (m, 1H), 4.21 (d, J = 5.9, Hz, 1H), 4.35-4.50 (m, 1H), 6.70-6.80 (m, 2H), 6.99 (d, J = 4.4 Hz, 1H), 7.14 (d, J = 7.8 Hz, 1H), 7.34 (d, J = 4.4 Hz, 1H). | m |
| Example 184 | 242 | | (Hydrochloride, CD₃OD) δ 0.40-0.55 (m, 2H), 0.65-0.90 (m, 2H), 0.90-1.10 (m, 1H), 1.10-1.25 (m, 1H), 1.50-1.65 (m, 2H), 1.65-1.80 (m, 2H), 1.90-2.10 (m, 1H), 2.10-2.30 (m, 1H), 2.75-2.90 (m, 1H), 3.05-3.15 (m, 1H), 3.15-3.60 (m, 7H), 3.87 (d, J = 11.7 Hz, 1H), 4.00-4.10 (m, 1H), 4.22 (d, J = 5.9, Hz, 1H), 4.50-4.60 (m, 1H), 6.75 (dd, J = 2.4, 8.3 Hz, 1H), 6.78 (d, J = 2.4 Hz, 1H), 7.02 (s, 1H), 7.45-7.55 (m, 3H), 7.14 (d, J = 8.3 Hz, 1H), 7.60-7.70 (m, 2H). | m |
| Example 185 | 243 | | (Hydrochloride, CD₃OD) δ 0.45-0.65 (m, 2H), 0.70-0.90 (m, 2H), 1.10-1.25 (m, 2H), 1.40-1.50 (m, 1H), 1.55-1.80 (m, 3H), 1.90-2.00 (m, 1H), 2.20-2.35 (m, 1H), 2.75-2.90 (m, 1H), 3.05-3.15 (m, 1H), 3.15-3.60 (m, 7H), 4.00-4.10 (m, 1H), 4.15-4.25 (m, 2H), 4.70-5.00 (m, 1H), 6.77 (d, J = 8.3 Hz, 1H), 6.80-6.90 (m, 1H), 7.16 (d, J = 8.3 Hz, 1H), 7.16-7.30 (m, 1H), 7.52 (t, J = 8.3 Hz, 1H), 7.70-7.85 (m, 1H), 7.99 (d, J = 8.3 Hz, 1H), 7.99-8.10 (m, 1H), 8.25-8.45 (m, 1H). | m |

TABLE 17

| Compound number | | Structural formula | ¹H NMR | Synthetic method |
|---|---|---|---|---|
| Example 186 | 244 | | (Hydrochloride, CD₃OD) δ 0.40-0.55 (m, 2H), 0.60-0.90 (m, 2H), 0.90-1.10 (m, 1H), 1.10-1.30 (m, 1H), 1.40-1.85 (m, 4H), 1.85-2.00 (m, 1H), 2.10-2.30 (m, 1H), 2.75-2.90 (m, 1H), 3.00-3.15 (m, 1H), 3.15-3.60 (m, 7H), 3.84 (d, J = 11.7 Hz, 1H), 4.00-4.15 (m, 1H), 4.21 (d, J = 5.4 Hz, 1H), 4.70-4.80 (m, 1H), 6.70-6.85 (m, 2H), 6.95 (d, J = 4.9 Hz, 1H), 7.14 (d, J = 8.3 Hz, 1H), 8.55 (br s, 2H). | n |
| Example 187 | 245 | | (Free base, CDCl₃) δ 0.05-0.15 (m, 2H), 0.42-0.53 (m, 2H), 0.75-0.93 (m, 2H), 1.10-1.30 (m, 2H), 1.30-1.50 (m, 2H), 1.60-1.73 (m, 1H), 1.88-2.11 (m, 2H), 2.25-2.38 (m, 2H), 2.54-2.62 (m, 1H), 2.80-2.96 (m, 2H), 3.00-3.16 (m, 3H), 3.42 (t, J = 11.7 Hz, 1H), 3.63 (d, J = 11.2 Hz, 1H), 3.85 (dd, J = 7.8, 11.2 Hz, 1H), 4.54 (dd, J = 5.9, 7.8 Hz, 1H), 6.56 (dd, J = 2.4, 7.8 Hz, 1H), 6.68 (d, J = 2.4 Hz, 1H), 6.92 (d, J = 7.8 Hz, 1H), 8.24 (br s, 2H). | n |

TABLE 17-continued

| Compound number | | Structural formula | $^1$H NMR | Synthetic method |
|---|---|---|---|---|
| Example 188 | 246 | | (Hydrochloride, CD$_3$OD) δ 0.45-0.60 (m, 2H), 0.70-0.85 (m, 2H), 0.85-1.05 (m, 1H), 1.10-1.25 (m, 1H), 1.40-1.55 (m, 1H), 1.55-1.75 (m, 3H), 1.85-1.95 (m, 1H), 2.10-2.30 (m, 1H), 2.75-2.90 (m, 1H), 3.00-3.10 (m, 1H), 3.10-3.55 (m, 7H), 3.79 (d, J = 11.7 Hz, 1H), 4.00 (dd, J = 7.8, 11.7 Hz, 1H), 4.20 (d, J = 5.9 Hz, 1H), 4.60-4.70 (m, 1H), 6.74 (dd, J = 2.4, 8.3 Hz, 1H), 6.77 (d, J = 2.4 Hz, 1H), 7.13 (d, J = 8.3 Hz, 1H), 8.54 (br s, 2H). | n |
| Example 189 | 247 | | (Hydrochloride, CD$_3$OD) δ 0.44-0.61 (m, 2H), 0.69-0.88 (m, 2H), 0.89-1.05 (m, 1H), 1.10-1.14 (m, 1H), 1.45 (dd, J = 7.3, 14.6 Hz, 1H), 1.54-1.75 (m, 3H), 1.85-1.97 (m, 1H), 2.15-2.30 (m, 1H), 2.75-2.88 (m, 1H), 3.00-3.48 (m, 8H), 3.80 (d, J = 11.7 Hz, 1H), 3.87 (s, 3H), 4.00 (dd, J = 7.3, 11.2 Hz, 1H), 4.20 (d, J = 6.3 Hz, 1H), 4.62-4.70 (m, 1H), 6.70-6.82 (m, 2H), 7.14 (d, J = 8.3 Hz, 1H), 8.30 (s, 2H). | n |
| Example 190 | 248 | | (Hydrochloride, CD$_3$OD) δ 0.45-0.56 (m, 2H), 0.70-0.97 (m, 3H), 1.09-1.22 (m, 1H), 1.45-1.68 (m, 4H), 1.81-1.93 (m, 1H), 2.13-2.26 (m, 1H), 2.77-2.88 (m, 1H), 2.93-3.10 (m, 2H), 3.18-3.42 (m, 5H), 3.49 (dd, J = 6.3, 19.5 Hz, 1H), 3.76 (d, J = 12.7 Hz, 1H), 3.95-4.05 (m, 1H), 4.16 (d, J = 5.9 Hz, 1H), 4.64-4.72 (m, 1H), 6.73 (dd, J = 2.4, 8.3 Hz, 1H), 6.78 (d, J = 2.4 Hz, 1H), 7.12 (d, J = 8.3 Hz, 1H), 8.50 (s, 1H), 8.56 (s, 1H). | n |
| Example 191 | 249 | | (Hydrochloride, CD$_3$OD) δ 0.45-0.56 (m, 2H), 0.70-0.97 (m, 3H), 1.07-1.21 (m, 1H), 1.44-1.68 (m, 4H), 1.82-1.93 (m, 1H), 2.14-2.26 (m, 1H), 2.74-2.90 (m, 1H), 2.95-3.10 (m, 2H), 3.18-3.42 (m, 5H), 3.49 (dd, J = 6.3, 19.5 Hz, 1H), 3.77 (d, J = 12.7 Hz, 1H), 4.00 (dd, J = 7.8, 12.7 Hz, 1H), 4.16 (d, J = 6.3 Hz, 1H), 4.68 (t, J = 6.3 Hz, 1H), 6.73 (dd, J = 2.4, 8.3 Hz, 1H), 6.78 (d, J = 2.4 Hz, 1H), 7.14 (d, J = 8.3 Hz, 1H), 8.53 (d, J = 2.9 Hz, 1H), 8.60 (d, J = 2.9 Hz, 1H). | n |

TABLE 18

| Compound number | | Structural formula | $^1$H NMR | Synthetic method |
|---|---|---|---|---|
| Example 192 | 250 | | (Hydrochloride, CD$_3$OD) δ 0.48-0.58 (m, 2H), 0.73-0.86 (m, 2H), 0.85-1.02 (m, 1H), 1.09-2.00 (m, 1H), 1.48-1.70 (m, 4H), 1.82-1.95 (m, 1H), 2.16-2.23 (m, 1H), 2.77-2.90 (m, 1H), 2.95-3.10 (m, 2H), 3.18-3.55 (m, 6H), 3.84 (d, J = 13.2 Hz, 1H), 4.09 (dd, J = 8.3, 11.2 Hz, 1H), 4.17 (d, J = 6.3 Hz, 1H), 4.70-4.90 (m, 1H), 6.73 (dd, J = 2.0, 8.3 Hz, 1H), 6.77 (d, J = 2.0 Hz, 1H), 7.12 (d, J = 8.3 Hz, 1H), 9.04 (d, J = 3.4 Hz, 1H), 9.10 (d, J = 3.4 Hz, 1H). | n |

TABLE 18-continued

| Compound number | Structural formula | ¹H NMR | Synthetic method |
|---|---|---|---|
| Example 193 | 251 | (Hydrochloride, CD₃OD) δ 0.45-0.62 (m, 2H), 0.70-0.88 (m, 2H), 0.92-1.09 (m, 1H), 1.12-1.23 (m, 1H), 1.50 (dd, J = 6.8, 15.1 Hz, 1H), 1.58 (d, J = 14.6 Hz, 1H), 1.60-1.72 (m, 1H), 1.67 (d, J = 12.7 Hz, 1H), 1.87-1.98 (m, 1H), 2.15-2.30 (m, 1H), 2.75-2.85 (m, 1H), 3.07 (dd, J = 7.8, 13.2 Hz, 1H), 3.15-3.53 (m, 7H), 3.88 (d, J = 12.2 Hz, 1H), 4.10 (dd, J = 7.8, 12.2 Hz, 1H), 4.21 (d, J = 5.9 Hz, 1H), 4.70-5.00 (m, 1H), 6.74 (dd, J = 2.4, 8.3 Hz, 1H), 6.78 (d, J = 2.4 Hz, 1H), 7.13 (d, J = 8.3 Hz, 1H), 8.94 (d, J = 8.8 Hz, 2H). | n |
| Example 194 | 252 | (Free base, CDCl₃) δ 0.03-0.17 (m, 2H), 0.35-0.55 (m, 2H), 0.75-0.93 (m, 2H), 1.12-1.27 (m, 5H), 1.35-1.42 (m, 2H), 1.60-1.72 (m, 1H), 1.88-2.14 (m, 2H), 2.23-2.37 (m, 2H), 2.42 (q, J = 7.3 Hz, 2H), 2.53-2.63 (m, 1H), 2.76-2.94 (m, 2H), 3.04-3.17 (m, 3H), 3.37-3.48 (m, 1H), 3.69 (d, J = 11.7 Hz, 1H), 3.89 (dd, J = 7.8, 11.7 Hz, 1H), 4.61-4.70 (m, 1H), 6.57 (dd, J = 2.4, 8.3 Hz, 1H), 6.73 (d, J = 2.4, 1H), 6.84 (d, J = 8.3 Hz, 1H), 8.19 (br s, 2H). | n |
| Example 195 | 253 | (Hydrochloride, CD₃OD) δ 0.48-0.60 (m, 2H), 0.70-1.00 (m, 3H), 1.10-1.20 (m, 2H), 1.28 (d, J = 6.8 Hz, 6H), 1.40-1.50 (m, 1H), 1.56-1.70 (m, 3H), 1.85-1.95 (m, 1H), 2.15-2.28 (m, 1H), 2.72-2.88 (m, 1H), 2.88-2.99 (m, 1H), 3.02-3.17 (m, 2H), 3.20-3.70 (m, 5H), 3.78-3.85 (m, 1H), 3.82 (s, 3H), 3.95-4.08 (m, 1H), 4.20 (d, J = 6.3 Hz, 1H), 4.65-4.75 (m, 1H), 7.85-7.95 (m, 1H), 6.90 (s, 1H), 7.24 (d, J = 8.3 Hz, 1H), 8.41 (br s, 2H). | n |
| Example 196 | 254 | (Hydrochloride, CD₃OD) δ 0.45-0.60 (m, 2H), 0.70-0.83 (m, 2H), 0.91-1.05 (m, 1H), 1.10-1.22 (m, 1H), 1.28 (d, J = 6.8 Hz, 6H), 1.40-1.52 (m, 1H), 1.52-1.71 (m, 3H), 1.83-2.02 (m, 2H), 2.13-2.30 (m, 1H), 2.75-2.85 (m, 1H), 2.90-3.00 (m, 1H), 3.00-3.10 (m, 1H), 3.10-3.70 (m, 6H), 3.81 (d, J = 11.7 Hz, 1H), 3.95-4.05 (m, 1H), 4.19 (d, J = 5.4 Hz, 1H), 4.65-4.78 (m, 1H), 6.74 (dd, J = 2.0, 8.3 Hz, 1H), 6.77 (d, J = 2.0 Hz, 1H), 7.13 (d, J = 8.3 Hz, 1H), 8.42 (br s, 2H). | n |

TABLE 19

| Compound number | Structural formula | ¹H NMR | Synthetic method |
|---|---|---|---|
| Example 197 | 255 | (Hydrochloride, CD₃OD) δ 0.45-0.62 (m, 2H), 0.68-0.88 (m, 2H), 0.88-1.07 (m, 4H), 1.12-1.24 (m, 1H), 1.30-1.52 (m, 5H), 1.55-1.75 (m, 5H), 1.85-1.97 (m, 1H), 2.22 (dt, J = 4.9, 14.1 Hz, 1H), 2.59 (t, J = 7.8 Hz, 2H), 2.75-2.88 (m, 1H), 3.04-3.56 (m, 8H), 3.83 (d, J = 11.7 Hz, 1H), 3.97-4.09 (m, 1H), 4.19 (d, J = 6.3 Hz, 1H), 4.68-4.75 (m, 1H), 6.75 (dd, J = 2.4, 8.3 Hz, 1H), 6.78 (d, J = 8.3 Hz, 1H), 7.14 (d, J = 8.3 Hz, 1H), 8.44 (br s, 2H). | n |

TABLE 19-continued

| Compound number | Structural formula | ¹H NMR | Synthetic method |
|---|---|---|---|
| Example 198 — 256 | | (Hydrochloride, CD$_3$OD) δ 0.45-0.64 (m, 2H), 0.69-0.88 (m, 2H), 0.94-1.12 (m, 1H), 1.12-1.25 (m, 1H), 1.27-1.40 (m, 0.4H), 1.54-1.76 (m, 3.6H), 1.85-2.03 (m, 1H), 2.16-2.30 (m, 1H), 2.73-2.87 (m, 1H), 3.02-3.12 (m, 1H), 3.15-3.56 (m, 7.6H), 3.76 (d, J = 11.2 Hz, 0.6H), 3.87-4.03 (m, 2.8H), 4.07 (s, 1.2H), 4.20-4.26 (m, 1.4 H), 4.46-4.54 (m, 0.4H), 6.37-6.45 (m, 1H), 6.70-6.83 (m, 2H), 7.14 (dd, J = 3.9, 8.3 Hz, 1H), 7.89 (d, J = 6.8 Hz, 0.4H), 8.01 (d, J = 7.3 Hz, 0.6H). | n |
| Example 199 — 257 | | (Hydrochloride, CD$_3$OD) δ 0.45-0.60 (m, 2H), 0.70-0.95 (m, 2H), 0.95-1.10 (m, 1H), 1.10-1.25 (m, 1H), 1.35-1.50 (m, 1H), 1.55-1.75 (m, 3H), 1.85-2.00 (m, 1H), 2.10-2.30 (m, 1H), 2.75-2.90 (m, 1H), 3.03-3.13 (m, 1H), 3.13-3.55 (m, 7H), 3.84 (d, J = 11.7 Hz, 1H), 3.99 (dd, J = 7.8, 11.7 Hz, 1H), 4.20 (d, J = 6.3 Hz, 1H), 4.60-4.70 (m, 1H), 6.75 (dd, J = 2.4, 8.3 Hz, 1H), 6.80 (d, J = 2.4 Hz, 1H), 7.14 (d, J = 8.3 Hz, 1H), 7.90 (d, J = 3.4 Hz, 1H), 8.24 (d, J = 3.4 Hz, 1H), 8.32 (br s, 1H). | m |
| Example 200 — 258 | | (Hydrochloride, CD$_3$OD) δ 0.45-0.60 (m, 2H), 0.70-0.90 (m, 2H), 0.90-1.05 (m, 1H), 1.10-1.22 (m, 1H), 1.23-1.40 (m, 2H), 1.51-1.61 (m, 1H), 1.61-1.72 (m, 2H), 1.83-1.95 (m, 1H), 2.12-2.30 (m, 1H), 2.45 (s, 3H), 3.04 (s, 3H), 2.76-2.85 (m, 1H), 3.00-3.18 (m, 2H), 3.20-3.52 (m, 5H), 4.12-4.20 (m, 2H), 4.26 (dd, J = 8.3, 11.2 Hz, 1H), 4.96 (t, J = 7.3 Hz, 1H), 6.74 (dd, J = 2.0, 8.3 Hz, 1H), 6.79 (d, J = 2.0 Hz, 1H), 7.12 (d, J = 8.3 Hz, 1H), 7.60 (s, 1H). | m |

Synthesis Methods Mentioned in Tables
Method k: methods described in Examples 26 and 6
Method m: method described in Example 164
Method n: methods described in Examples 165 and 166

Example 201

(1S,5aS,6R,11bR)-3-(2-Aminophenyl)-14-(cyclopropylmethyl)-2,3,3a,4,5,6,7,11c-octahydro-1H-6,11b-(iminoethano)-1,5a-methanonaphtho[1,2-e]indol-10-ol (260)

(1) Synthesis of 2-[(1S,5aS,6R,11bR)-14-(cyclopropylmethyl)-10-methoxy-4,5,6,7-tetrahydro-1H-6,11b-(iminoethano)-1,5a-methanonaphtho[1,2-e]indol-3(2H,3aH,11cH)-yl]aniline (259)

[Formula 195]

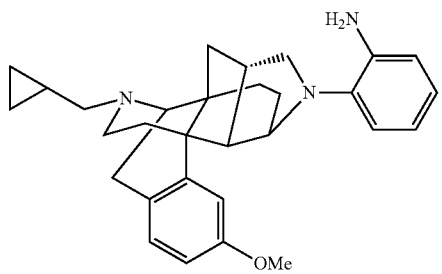

259

The compound 230 (120 mg, 0.25 mmol) which was prepared in Example 172 was dissolved in ethanol (2 mL) and water (0.5 mL), the solution was added with zinc (480 mg) and calcium chloride (19 mg, 0.17 mmol), and the mixture was stirred at 90° C. for 16 hours. The reaction mixture was filtered through Celite, and concentrated. The obtained residue was dissolved in ethyl acetate, and the solution was washed with water and saturated brine. The organic layer was dried over anhydrous sodium sulfate, and then concentrated to obtain a crude product of the title compound 259.

(2) Synthesis of (1S,5aS,6R,11bR)-3-(2-aminophenyl)-14-(cyclopropylmethyl)-2,3,3a,4,5,6,7,11c-octahydro-1H-6,11b-(iminoethano)-1,5a-methanonaphtho[1,2-e]indol-10-ol (260)

[Formula 196]

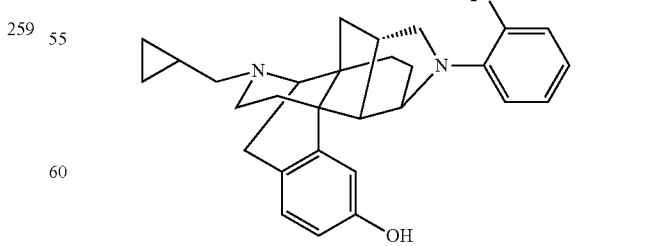

260

According to the method described in Example 6, the title compound 260 and the hydrochloride thereof (10 mg, 44%) were obtained by using the crude product which was prepared in (1) mentioned above.

Compound 260 (hydrochloride) ¹H NMR (CD₃ OD, 400 MHz): δ 0.40-0.60 (m, 2H), 0.70-1.00 (m, 3H), 1.10-1.40 (m, 2H), 1.50-1.65 (m, 1H), 1.70-1.80 (m, 2H), 1.80-2.00 (m, 1H), 2.20-2.30 (m, 1H), 2.70-2.88 (m, 1H), 2.88-3.00 (m, 1H), 3.00-3.15 (m, 1H), 3.20-3.55 (m, 6H), 3.60-3.75 (m, 2H), 3.85-3.95 (m, 1H), 4.17 (d, J=6.3 Hz, 1H), 6.69 (dd, J=2.4, 8.3 Hz, 1H), 6.79 (d, J=2.4 Hz, 1H), 7.09 (d, J=8.3 Hz, 1H), 7.15-7.25 (m, 1H), 7.30 (d, J=7.3 Hz, 1H), 7.35-7.40 (m, 1H), 7.44 (d, J=6.8 Hz, 1H)

Example 202

(1S,5aS,6R,11bR)-14-(Cyclopropylmethyl)-3-[2-(dimethylamino)phenyl]-2,3,3a,4,5,6,7,11c-octahydro-1H-6,11b-(iminoethano)-1,5a-methanonaphtho[1,2-e]indol-10-ol (262)

(1) Synthesis of 2-[(1S,5aS,6R,11bR)-14-(cyclopropylmethyl)-10-methoxy-4,5,6,7-tetrahydro-1H-6,11b-(iminoethano)-1,5a-methanonaphtho[1,2-e]indol-3(2H,3aH,11cH)-yl]-N,N-dimethylaniline (261)

[Formula 197]

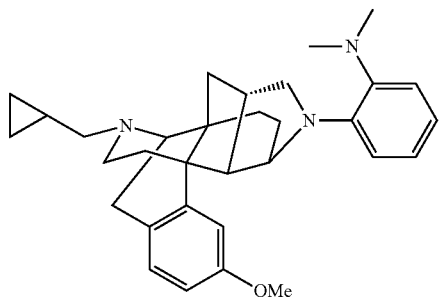

261

A solution of the compound 259 (50 mg, 0.11 mmol) which was prepared in Example 201, (1) in methanol (1 mL) was added with zinc chloride (7 mg, 0.06 mmol), and aqueous formaldehyde (37%, 37 µL, 0.5 mmol), and the mixture was stirred at 0° C. for 10 minutes. The reaction mixture was added with sodium cyanoborohydride (8 mg, 0.13 mmol), and the mixture was stirred at room temperature for 16 hours. The reaction mixture was diluted with ethyl acetate, and washed with water and saturated brine. The organic layer was dried over anhydrous sodium sulfate, and then concentrated to obtain a crude product of the title compound 261.

(2) Synthesis of (1S,5aS,6R,11bR)-14-(cyclopropylmethyl)-3-[2-(dimethylamino)phenyl]-2,3,3a,4,5,6,7,11c-octahydro-1H-6,11b-(iminoethano)-1,5a-methanonaphtho[1,2-e]indol-10-ol (262)

[Formula 198]

262

According to the method described in Example 6, the title compound 262 and the hydrochloride thereof (12 mg, 36%) were obtained by using the compound 261 (30 mg, 0.06 mmol) which was prepared in (1) mentioned above.

Compound 262 (hydrochloride) ¹H NMR (CD₃ OD, 400 MHz): δ 0.40-0.65 (m, 2H), 0.70-0.95 (m, 3H), 1.10-1.25 (m, 1H), 1.25-1.40 (m, 1H), 1.55-1.65 (m, 1H), 1.70-1.80 (m, 1H), 1.90-1.95 (m, 2H), 2.20-2.35 (m, 1H), 2.74-2.86 (m, 1H), 2.94-3.12 (m, 2H), 3.12-3.55 (m, 5H), 3.26 (s, 6H), 3.55-3.75 (m, 4H), 4.21 (d, J=6.3 Hz, 1H), 6.67 (dd, J=2.4, 8.7 Hz, 1H), 6.98 (d, J=2.4 Hz, 1H), 7.09 (d, J=8.7 Hz, 1H), 7.47 (t, J=7.3 Hz, 1H), 7.58 (t, J=7.3 Hz, 1H), 7.66 (d, J=7.3 Hz, 1H), 7.77 (d, J=7.3 Hz, 1H)

Examples 203 and 204

According to the method described in Example 201, the compounds of Examples 203 and 204 (free bases and the hydrochlorides thereof) were obtained.

TABLE 20

| | Compound number | Structural formula | ¹H NMR |
|---|---|---|---|
| Example 203 | 263 | (structure shown) | (Hydrochloride, CD₃OD) δ 0.40-0.65 (m, 2H), 0.70-0.95 (m, 3H), 1.10-1.25 (m, 1H), 1.35-1.45 (m, 1H), 1.50-1.65 (m, 3H), 1.80-1.90 (m, 1H), 2.20-2.35 (m, 1H), 2.75-2.85 (m, 1H), 3.00-3.18 (m, 2H), 3.20-3.43 (m, 5H), 3.43-3.60 (m, 2H), 3.60-3.70 (m, 1H), 4.17 (d, J = 5.9 Hz, 1H), 4.20-4.28 (m, 1H), 6.62 (d, J = 8.8 Hz, 2H), 6.73 (dd, J = 2.4, 8.3 Hz, 1H), 6.80 (d, J = 2.4 Hz, 1H), 7.12 (d, J = 8.3 Hz, 1H), 7.16 (d, J = 8.8 Hz, 2H). |

| Compound number | Structural formula | ¹H NMR |
|---|---|---|
| Example 204 | 264 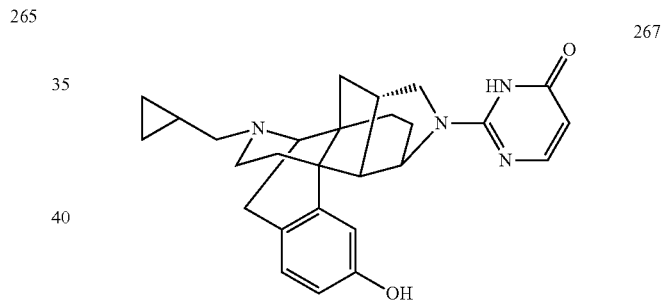 | (Hydrochloride, CD₃OD) δ 0.45-0.60 (m, 2H), 0.70-0.85 (m, 2H), 0.90-1.05 (m, 1H), 1.10-1.25 (m, 1H), 1.25-1.35 (m, 1H), 1.55-1.75 (m, 3H), 1.85-2.00 (m, 1H), 2.15-2.30 (m, 1H), 2.74-2.86 (m, 1H), 3.00-3.20 (m, 2H), 3.20-3.55 (m, 6H), 3.63 (d, J = 10.7 Hz, 1H), 3.82 (dd, J = 7.8, 10.7 Hz, 1H), 4.15-4.25 (m, 1H), 4.30-4.40 (m, 1H), 5.76 (d, J = 2.0 Hz, 1H), 6.23 (dd, J = 2.0, 7.3 Hz, 1H), 6.73 (dd, J = 2.4, 8.3 Hz, 1H), 6.78 (d, J = 2.4 Hz, 1H), 7.13 (d, J = 8.3 Hz, 1H), 7.40 (d, J = 7.3 Hz, 1H). |

Example 205

2-[(1S,5aS,6R,11bR)-14-(Cyclopropylmethyl)-10-hydroxy-4,5,6,7-tetrahydro-1H-6,11b-(iminoethano)-1,5a-methanonaphtho[1,2-e]indol-3(2H,3aH,11cH)-yl]pyrimidin-4(3H)-one (267)

(1) Synthesis of (1S,5aS,6R,11bR)-14-(cyclopropylmethyl)-10-methoxy-3-(4-methoxypyrimidin-2-yl)-2,3,3a,4,5,6,7,11c-octahydro-1H-6,11b-(iminoethano)-1,5a-methanonaphtho[1,2-e]indole (265)

[Formula 199]

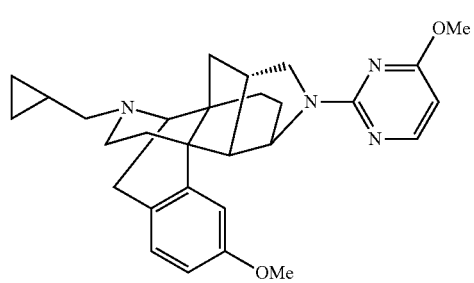

According to the method described in Example 165, a crude product of the title compound 265 was obtained by using the compound 77 (30 mg, 0.08 mmol) and 2-chloro-4-methoxypyrimidine (18 mg, 0.12 mmol).

(2) Synthesis of (1S,5aS,6R,11bR)-14-(cyclopropylmethyl)-3-(4-methoxypyrimidin-2-yl)-2,3,3a,4,5,6,7,11c-octahydro-1H-6,11b-(iminoethano)-1,5a-methanonaphtho[1,2-e]indol-10-ol (266)

[Formula 200]

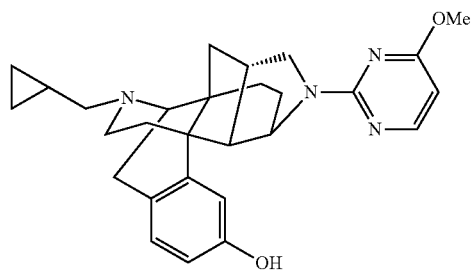

According to the method described in Example 6, a crude product of the title compound 266 was obtained by using the crude product which was prepared in (1) mentioned above.

(3) Synthesis of 2-[(1S,5aS,6R,11bR)-14-(cyclopropylmethyl)-10-hydroxy-4,5,6,7-tetrahydro-1H-6,11b-(iminoethano)-1,5a-methanonaphtho[1,2-e]indol-3(2H,3aH,11cH)-yl]pyrimidin-4(3H)-one (267)

[Formula 201]

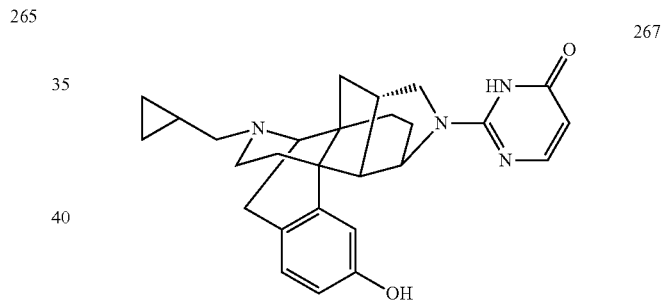

The crude product which was prepared in (2) mentioned above was dissolved in 6 M hydrochloric acid, and the solution was stirred at 110° C. for 3 hours. The reaction mixture was left to cool to room temperature, and adjusted to pH 10 with 6% aqueous ammonia. The aqueous layer was extracted three times with ethyl acetate, and the organic layers were combined, dried over anhydrous sodium sulfate, and then concentrated. The obtained crude product was purified by preparative TLC to give the title compound 267 and the hydrochloride thereof (11 mg, 28%).

Compound 267 (hydrochloride) ¹H NMR (CD₃ OD, 400 MHz): δ 0.45-0.63 (m, 2H), 0.70-0.78 (m, 2H), 0.78-1.10 (m, 1H), 1.10-1.25 (m, 1H), 1.27-1.52 (m, 1H), 1.54-1.75 (m, 3H), 1.85-2.00 (m, 1H), 2.14-2.30 (m, 1H), 2.76-2.87 (m, 1H), 3.05-3.12 (m, 1H), 3.12-3.55 (m, 7H), 3.72-3.88 (m, 1H), 3.92-4.12 (m, 1H), 4.21 (d, J=5.9 Hz, 1H), 4.45-5.02 (m, 1H), 6.06-6.26 (m, 1H), 6.71-6.80 (m, 2H), 7.14 (d, J=8.3 Hz, 1H), 7.60-7.93 (m, 1H)

Example 206

(1S,5aS,6R,11bR)-3-(4,6-Dimethylpyrimidin-2-yl)-14-methyl-2,3,3a,4,5,6,7,11c-octahydro-1H-6,11b-(iminoethano)-1,5a-methanonaphtho[1,2-e]indol-10-ol (269)

(1) Synthesis of (1S,5aS,6R,11bR)-3-(4,6-dimethylpyrimidin-2-yl)-10-methoxy-2,3,3a,4,5,6,7,11c-octahydro-1H-6,11b-(iminoethano)-1,5a-methanonaphtho[1,2-e]indole (268)

[Formula 202]

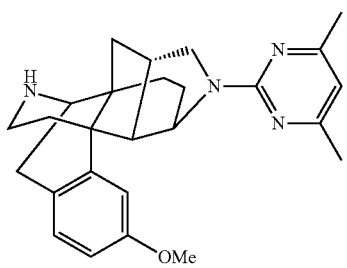

268

According to the method described in Example 71, the title compound 268 (91 mg, 52%) was obtained by using the compound 222 (198 mg, 0.42 mmol). $^1$H NMR (CDCl$_3$, 400 MHz): δ 0.75-0.90 (m, 1H), 1.10-1.20 (m, 1H), 1.25-1.35 (m, 1H), 1.35-1.55 (m, 2H), 1.60-1.85 (m, 2H), 2.24 (br s, 6H), 2.60-2.75 (m, 2H), 2.85 (d, J=18.5 Hz, 1H), 2.95-3.20 (m, 4H), 3.51 (dd, J=6.8, 18.5 Hz, 1H), 3.68 (d, J=11.7 Hz, 1H), 3.82 (s, 3H), 3.88 (dd, J=7.8, 11.7 Hz, 1H), 4.59 (dd, J=5.4, 8.8 Hz, 1H), 6.20 (s, 1H), 6.71 (dd, J=2.4, 8.3 Hz, 1H), 6.75 (d, J=2.4 Hz, 1H), 7.06 (d, J=8.3 Hz, 1H)

(2) Synthesis of (1S,5aS,6R,11bR)-3-(4,6-dimethylpyrimidin-2-yl)-10-methoxy-14-methyl-2,3,3a,4,5,6,7,11e-octahydro-1H-6,11b-(iminoethano)-1,5a-methanonaphtho[1,2-e]indole (269)

[Formula 203]

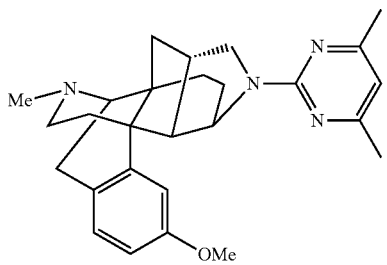

269

Under an argon atmosphere, the compound 268 (18 mg, 0.04 mmol) which was prepared in (1) mentioned above was dissolved in acetonitrile (0.5 mL), the solution was added with methyl iodide (5.0 µL, 0.09 mmol), and potassium carbonate (18 mg, 0.13 mmol), and the mixture was stirred at room temperature for 16 hours. The reaction mixture was poured into water, and the mixture was extracted three times with chloroform. The organic layers were combined, dried over anhydrous sodium sulfate, and then concentrated. The obtained crude product was purified by preparative TLC to give the title compound 269 and the hydrochloride thereof (11 mg, 55%).

Compound 269 (hydrochloride) $^1$H NMR (CD$_3$ OD, 400 MHz): δ 0.85-1.00 (m, 1H), 1.40-1.50 (m, 1H), 1.55-1.70 (m, 3H), 1.85-1.95 (m, 1H), 2.10-2.25 (m, 1H), 2.45 (br s, 3H), 2.52 (br s, 3H), 2.75-2.85 (m, 1H), 2.98 (s, 3H), 3.00-3.12 (m, 1H), 3.16-3.26 (m, 1H), 3.26-3.60 (m, 5H), 3.82 (s, 3H), 3.84-3.90 (m, 2H), 4.00-4.10 (m, 1H), 6.77 (s, 1H), 6.85-6.95 (m, 2H), 7.25 (d, J=9.3 Hz, 1H)

Example 207

Synthesis of (1S,5aS,6R,11bR)-3-(4,6-dimethylpyrimidin-2-yl)-14-methyl-2,3,3a,4,5,6,7,11c-octahydro-1H-6,11b-(iminoethano)-1,5a-methanonaphtho[1,2-e]indol-10-ol (270)

[Formula 204]

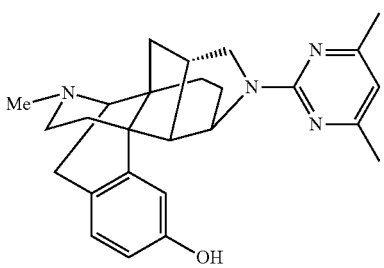

270

According to the method described in Example 6, the title compound 270 and the hydrochloride thereof (13.4 mg, 95%) were obtained by using the compound 269 (13 mg, 0.03 mmol).

Compound 270 (hydrochloride) $^1$H NMR (CD$_3$ OD, 400 MHz): δ 0.92-1.07 (m, 1H), 1.37-1.52 (m, 1H), 1.53-1.71 (m, 3H), 1.83-1.95 (m, 1H), 2.12-2.24 (m, 1H), 2.45 (br s, 3H), 2.52 (br s, 3H), 2.78-2.89 (m, 1H), 2.98 (s, 3H), 3.03-3.14 (m, 1H), 3.15-3.55 (m, 6H), 3.80-3.90 (m, 2H), 3.99-4.13 (m, 1H), 6.72-6.82 (m, 3H), 7.14 (d, J=8.3 Hz, 1H)

Example 208

(1S,5aS,6R,11bR)-3-(4,6-Dimethylpyrimidin-2-yl)-14-[(1-methylcyclopropyl)methyl]-2,3,3a,4,5,6,7,11c-octahydro-1H-6,11b-(iminoethano)-1,5a-methanonaphtho[1,2-e]indol-10-ol (273)

(1) Synthesis of [(1S,5aS,6R,11bR)-3-(4,6-dimethylpyrimidin-2-yl)-10-methoxy-2,3,3a,4,5,6,7,11c-octahydro-1H-6,11b-(iminoethano)-1,5a-methanonaphtho[1,2-e]indol-14-yl](1-methylcyclopropyl)methanone (271)

[Formula 205]

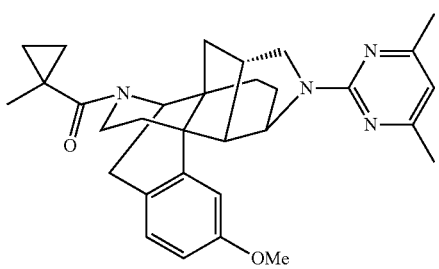

271

According to the method described in Example 106, (3), a crude product of the title compound 271 was obtained by using the compound 268 (18 mg, 0.04 mmol) which was prepared in Example 206, (1) and 1-methylcyclopropanecarboxylic acid (6 mg, 0.07 mmol).

(2) Synthesis of (1S,5aS,6R,11bR)-3-(4,6-dimethylpyrimidin-2-yl)-10-methoxy-14-[(1-methylcyclopropyl)methyl]-2,3,3a,4,5,6,7,11c-octahydro-1H-6,11b-(iminoethano)-1,5a-methanonaphtho[1,2-e]indole (272)

[Formula 206]

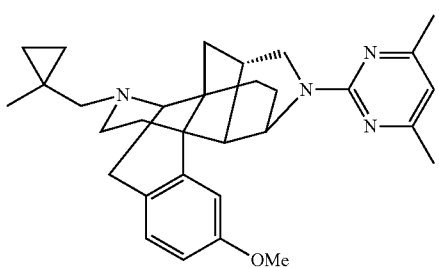

According to the method described in Example 106, (5), a crude product of the title compound 272 was obtained by using the crude product which was prepared in (1) mentioned above.

(3) Synthesis of (1S,5aS,6R,11bR)-3-(4,6-dimethylpyrimidin-2-yl)-14-[(1-methylcyclopropyl)methyl]-2,3,3a,4,5,6,7,11c-octahydro-1H-6,11b-(iminoethano)-1,5a-methanonaphtho[1,2-e]indol-10-ol (273)

[Formula 207]

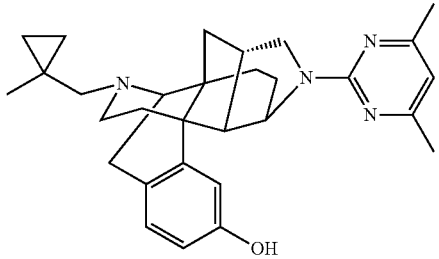

According to the method described in Example 6, the title compound 273 and the hydrochloride thereof (12 mg, 56%) were obtained by using the crude product which was prepared in (2) mentioned above.

Compound 273 (hydrochloride) $^1$H NMR (CD$_3$OD, 400 MHz): δ 0.50-0.60 (m, 1H), 0.60-0.75 (m, 2H), 0.75-0.85 (m, 1H), 0.90-1.10 (m, 1H), 1.25 (s, 3H), 1.40-1.55 (m, 1H), 1.55-1.80 (m, 3H), 1.85-2.00 (m, 1H), 2.20-2.40 (m, 1H), 2.48 (br s, 6H), 2.82-2.92 (m, 1H), 3.00-3.26 (m, 4H), 3.30-3.55 (m, 5H), 3.87 (d, J=11.7 Hz, 1H), 4.00-4.10 (m, 1H), 4.21 (d, J=6.3 Hz, 1H), 6.70-6.80 (m, 3H), 7.14 (d, J=8.3 Hz, 1H)

Example 209

(1S,5aS,6R,11bR)-3-(4,6-Dimethylpyrimidin-2-yl)-14-phenethyl-2,3,3a,4,5,6,7,11c-octahydro-1H-6,11b-(iminoethano)-1,5a-methanonaphtho[1,2-e]indol-10-ol (275)

(1) Synthesis of (1S,5aS,6R,11bR)-3-(4,6-dimethylpyrimidin-2-yl)-10-methoxy-14-phenethyl-2,3,3a,4,5,6,7,11c-octahydro-1H-6,11b-(iminoethano)-1,5a-methanonaphtho[1,2-e]indole (274)

[Formula 208]

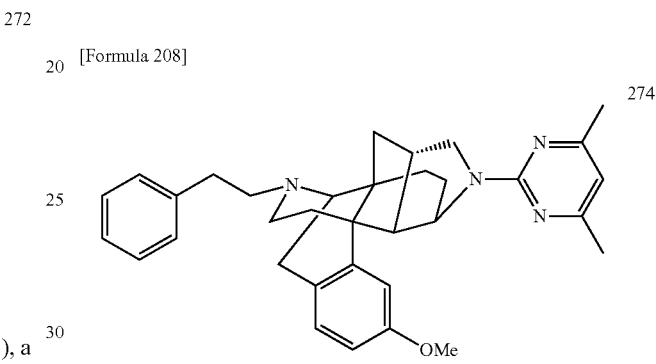

Under an argon atmosphere, a solution of the compound 268 (18 mg, 0.04 mmol) which was prepared in Example 206, (1) in dichloromethane (0.5 mL) was added with phenylacetaldehyde (15 mg, 0.13 mol), and sodium triacetoxyborohydride (27 mg, 0.13 mmol), and the mixture was stirred at room temperature for 16 hours. The reaction mixture was added with 6 M aqueous ammonia (5 mL) under ice cooling, and the mixture was stirred at room temperature for 30 minutes, and extracted three times with chloroform. The organic layers were combined, dried over anhydrous sodium sulfate, and then concentrated to obtain a crude product of the title compound 274.

(2) Synthesis of (1S,5aS,6R,11bR)-3-(4,6-dimethylpyrimidin-2-yl)-14-phenethyl-2,3,3a,4,5,6,7,11c-octahydro-1H-6,11b-(iminoethano)-1,5a-methanonaphtho[1,2-e]indol-10-ol (275)

[Formula 209]

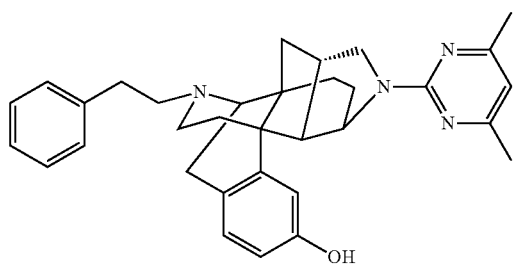

According to the method described in Example 6, the title compound 275 and the hydrochloride thereof (12 mg, 54%) were obtained by using the compound 274 (22 mg, 0.04 mmol) which was prepared in (1) mentioned above.

Compound 275 (hydrochloride) $^1$H NMR (CD$_3$OD, 400 MHz): δ 0.95-1.10 (m, 1H), 1.40-1.50 (m, 1H), 1.55-1.75 (m, 3H), 1.85-1.95 (m, 1H), 2.15-2.30 (m, 1H), 2.48 (br s, 6H), 2.85-2.95 (m, 1H), 3.00-3.25 (m, 3H), 3.25-3.65 (m, 9H), 3.85 (d, J=11.7 Hz, 1H), 4.05 (d, J=5.9 Hz, 1H), 6.73-6.80 (m, 3H), 7.15 (d, J=8.3 Hz, 1H), 7.24-7.38 (m, 5H)

Examples 210 to 221

By using the compound 268 which was prepared in Example 206, (1), the compounds of Examples 210 to 221 (free bases and the hydrochlorides thereof) were obtained according to the methods mentioned in Tables 21 and 22.

TABLE 21

| | Compound number | Structural formula | $^1$H NMR | Synthetic method |
|---|---|---|---|---|
| Example 210 | 276 | | (Free base, CDCl$_3$) δ 0.80-0.97 (m, 2H), 1.28 (s, 9H), 1.10-1.60 (m, 6H), 1.63-1.75 (m, 1H), 1.87-2.00 (m, 1H), 2.22 (s, 6H), 2.41-2.60 (m, 1H), 2.62-2.74 (m, 1H), 3.01-3.18 (m, 2H), 3.35 (s, 3H), 3.42-3.88 (m, 3H), 3.80-3.90 (m, 1H), 4.00-4.30 (m, 1H), 4.56-4.67 (m, 1H), 6.31 (s, 1H), 6.65 (dd, J = 2.4, 8.3 Hz, 1H), 6.75 (d, J = 2.4 Hz, 1H), 7.01 (d, J = 8.3 Hz, 1H). | o |
| Example 211 | 277 Diastereomer A | | (Free base, CDCl$_3$) δ 0.74-0.92 (m, 1H), 0.97-1.08 (m, 1H), 1.14-1.25 (m, 2H), 1.35-1.78 (m, 5H), 1.88-2.10 (m, 2H), 2.25 (br s, 6H), 2.45-2.64 (m, 3H), 2.87-3.14 (m, 5H), 3.34 (t, J = 11.2 Hz, 1H), 3.67 (d, J = 11.2 Hz, 1H), 3.81 (s, 3H), 3.86 (dd, J = 7.3, 11.7 Hz, 1H), 4.54-4.62 (m, 1H), 6.21 (s, 1H), 6.69 (dd, J = 2.4, 8.3 Hz, 1H), 6.75 (d, J = 2.4 Hz, 1H), 7.04 (d, J = 8.3 Hz, 1H). | o |
| Example 212 | 278 Diastereomer A | | (Hydrochloride, CD$_3$OD) δ 0.92-1.08 (m, 1H), 1.37-1.57 (m, 2H), 1.57-1.75 (m, 3H), 1.78-1.96 (m, 2H), 2.17-2.33 (m, 2H), 2.46 (br s, H), 2.52 (br s, 3H), 2.73-2.85 (m, 1H), 3.15-3.58 (m, 9H), 3.86 (d, J = 12.2 Hz, 1H), 4.00-4.13 (m, 2H), 6.73-6.82 (m, 3H), 7.14 (d, J = 8.3 Hz, 1H). | o |
| Example 213 | 279 Diastereomer B | | (Hydrochloride, OD$_3$OD) δ 0.93-1.10 (m, 1H), 1.39-1.53 (m, 1H), 1.56-1.74 (m, 4H), 1.75-1.98 (m, 2H), 2.12-2.21 (m, 2H), 2.46 (br s, 3H), 2.51 (br s, 3H), 2.83-2.96 (m, 1H), 3.10-3.55 (m, 8H), 3.63 (dd, J = 7.3, 13.7 Hz, 1H), 3.85 (d, J = 12.9 Hz, 1H), 3.95-4.13 (m, 2H), 6.72-6.82 (m, 3H), 7.14 (d, J = 8.3 Hz, 1H). | o |

TABLE 21-continued

| Compound number | | Structural formula | ¹H NMR | Synthetic method |
|---|---|---|---|---|
| Example 214 | 280 | | (Hydrochloride, CD$_3$OD) δ 0.90-1.10 (m, 1H), 1.35-1.50 (m, 1H), 1.50-1.70 (m, 3H), 1.80-2.10 (m, 6H), 2.10-2.30 (m, 3H), 2.45 (br s, 3H), 2.52 (br s, 3H), 2.75-2.90 (m, 2H), 3.00-3.20 (m, 2H), 3.20-3.50 (m, 6H), 3.78 (d, J = 5.9 Hz, 1H), 3.84 (d, J = 11.7 Hz, 1H), 4.00-4.15 (m, 1H), 6.72-6.80 (m, 3H), 7.15 (d, J = 8.3 Hz, 1H). | q |
| Example 215 | 281 | | (Hydrochloride, Cd$_3$OD) δ 0.95-1.10 (m, 1H), 1.40-1.55 (m, 1H), 1.55-1.75 (m, 3H), 1.85-2.00 (m, 1H), 2.15-2.30 (m, 1H), 2.46 (br s, 3H), 2.53 (br s, 3H), 2.86-2.96 (m, 1H), 3.06-3.20 (m, 2H), 3.20-3.65 (m, 9H), 3.86 (d, J = 11.7 Hz, 1H), 4.00-4.15 (m, 2H), 6.72-6.80 (m, 3H), 7.10-7.24 (m, 3H), 7.30-7.38 (m, 1H), 7.38-7.40 (m, 1H). | o |

TABLE 22

| Compound number | | Structural formula | ¹H NMR | Synthetic method |
|---|---|---|---|---|
| Example 216 | 282 | | (Hydrochloride, CD$_3$OD) δ 0.95-1.10 (m, 1H), 1.40-1.50 (m, 1H), 1.55-1.75 (m, 3H), 1.85-1.95 (m, 1H), 2.15-2.30 (m, 1H), 2.46 (br s, 3H), 2.52 (br s, 3H), 2.94-3.00 (m, 1H), 3.00-3.20 (m, 1H), 3.20-3.70 (m, 10H), 3.86 (d, J = 11.7 Hz, 1H), 4.00-4.10 (m, 2H), 6.70-6.80 (m, 3H), 7.00 (dd, J = 3.4, 5.4 Hz, 1H), 7.05 (d, J = 3.4 Hz, 1H), 7.14 (d, J = 8.3 Hz, 1H), 7.33 (d, J = 5.4 Hz, 1H). | q |
| Example 217 | 283 | | (Free base, CDCl$_3$) 0.70-0.95 (m, 2H), 0.95-1.15 (m, 1H), 1.20-1.55 (m, 3H), 1.75-1.85 (m, 1H), 2.25 (br s, 6H), 2.25-2.35 (m, 2H), 2.70-3.15 (m, 8H), 3.62 (d, J = 11.7 Hz, 1H), 3.86 (dd, J = 7.3, 11.7 Hz, 1H), 4.57-4.65 (m, 1H), 6.20 (s, 1H), 6.54 (s, 1H), 6.64 (dd, J = 2.9, 8.3 Hz, 1H), 6.89 (d, J = 8.3 Hz, 1H) 7.38-7.54 (m, 5H). | o |
| Example 218 | 284 | | (Hydrochloride, CD$_3$OD) δ 0.95-1.10 (m, 1H), 1.40-1.55 (m, 1H), 1.55-1.70 (m, 3H), 1.85-1.95 (m, 1H), 2.15-2.30 (m, 1H), 2.46 (br s, 3H), 2.52 (br s, 3H), 2.86-2.98 (m, 1H), 3.00-3.10 (m, 1H), 3.18-3.56 (m, 8H), 3.80-4.00 (m, 3H), 4.06 (d, J = 5.9 Hz, 2H), 6.70-6.80 (m, 3H), 7.14 (d, J = 8.3 Hz, 1H). | q |

TABLE 22-continued

| Compound number | Structural formula | $^1$H NMR | Synthetic method |
|---|---|---|---|
| Example 219 | 285 | (Hydrochloride, CD$_3$OD) δ 0.92-1.08 (m, 1H), 1.27 (d, J = 6.3 Hz, 3H), 1.40-1.50 (m, 1H), 1.55-1.75 (m, 3H), 1.80-1.95 (m, 1H), 2.20-2.35 (m, 1H), 2.45 (br s, 3H), 2.52 (br s, 3H), 2.85-3.00 (m, 1H), 3.00-3.15 (m, 1H), 3.15-3.60 (m, 8H), 3.86 (d, J = 11.7 Hz, 1H), 4.00-4.10 (m, 1H), 4.12 (d, J = 6.3 Hz, 1H), 4.20-4.30 (m, 1H), 6.70-6.80 (m, 3H), 7.15 (d, J = 8.3 Hz, 1H). | p |
| Example 220 | 286 | (Hydrochloride, CD$_3$OD) δ 0.92-1.08 (m, 1H), 1.37 (s, 3H), 1.42 (s, 3H), 1.35-1.50 (m, 1H), 1.52-1.75 (m, 3H), 1.80-1.90 (m, 1H), 2.29-2.45 (m, 1H), 2.45 (s, 3H), 2.52 (s, 3H), 2.95-3.55 (m, 9H), 3.87 (d, J = 12.2 Hz, 1H), 4.00-4.10 (m, 1H), 4.28 (d, J = 6.3 Hz, 1H), 4.80-5.00 (m, 1H), 6.77 (s, 1H), 6.72-6.89 (m, 2H), 7.15 (d, J = 8.3 Hz, 1H). | p |
| Example 221 | 287 | (Hydrochloride, CD$_3$OD) δ 0.95-1.10 (m, 1H), 1.40-1.50 (m, 1H), 1.55-1.75 (m, 3H), 1.85-1.95 (m, 1H), 2.15-2.30 (m, 1H), 2.46 (br s, 3H), 2.52 (br s, 3H), 2.88-3.00 (m, 1H), 3.06-3.18 (m, 1H), 3.20-3.95 (m, 9H), 4.07 (d, J = 5.9 Hz, 2H), 4.90-5.10 (m, 2H), 6.70-6.80 (m, 3H), 7.15 (d, J = 8.3 Hz, 1H). | q |

Synthesis Methods Mentioned in Tables
Method o: method described in Example 106
Method p: method described in Example 107
Method q: method described in Example 11 or Example 103

Example 222

Synthesis of (1S,5aS,6R,11bR)-14-(cyclopropylmethyl)-3-(4,6-dimethylpyrimidin-2-yl)-10-methoxy-2,3,3a,4,5,6,7,11c-octahydro-1H-6,11b-(iminoethano)-1,5a-epoxynaphtho[1,2-e]indole (288)

[Formula 210]

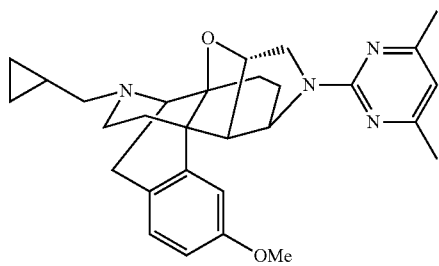

288

According to the method described in Example 165, the title compound 288 (297 mg, 61%) and the hydrochloride thereof were obtained by using the compound 8 (487 mg, 1.03 mmol).

Compound 288 (hydrochloride) $^1$H NMR (CD$_3$ OD, 400 MHz): δ 0.46-0.60 (m, 2H), 0.73-0.90 (m, 2H), 0.90-1.05 (m, 1H), 1.10-1.24 (m, 1H), 1.45-1.55 (m, HD, 1.69-1.77 (m, 1H), 1.78-2.00 (m, 2H), 2.35 (dt, J=5.4, 14.1 Hz, 1H), 2.49 (br s, 3H), 2.54 (br s, 3H), 2.85-2.97 (m, 1H), 3.07 (dd, J=7.3, 13.7 Hz, 1H), 3.17-3.41 (m, 2H), 3.43-3.49 (m, 2H), 3.65-3.69 (m, 1H), 3.85 (s, 3H), 4.03 (d, J=13.2 Hz, 1H), 4.14 (dd, J=5.4, 13.2 Hz, 1I0, 4.37 (d, J=5.4 Hz, 1H), 4.96-5.05 (m, 1H), 5.27-5.34 (m, 1H), 6.81 (s, 1H), 6.90-6.97 (m, 2H), 7.26 (d, J=8.3 Hz, 1H)

Example 223

Synthesis of (1S,5aS,6R,11bR)-14-(cyclopropylmethyl)-3-(4,6-dimethylpyrimidin-2-yl)-2,3,3a,4,5,6,7,11c-octahydro-1H-6,11b-(iminoethano)-1,5a-epoxynaphtho[1,2-e]indol-10-ol (289)

[Formula 211]

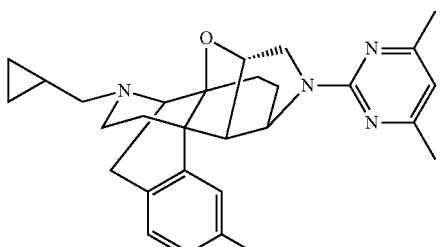

289

According to the method described in Example 6, the title compound 289 and the hydrochloride thereof (14.5 mg, 94%) were obtained by using the compound 288 (15.8 mg, 0.03 mmol) which was prepared in Example 222.

Compound 289 (hydrochloride) $^1$H NMR (CD$_3$ OD, 400 MHz): δ 0.44-0.60 (m, 2H), 0.70-0.92 (m, 2H), 0.95-1.10 (m, 1H), 1.10-1.25 (m, 1H), 1.45-1.57 (m, 1H), 1.66-1.76 (m, 1H), 1.76-2.00 (m, 2H), 2.33 (dd, J=5.9, 12.1 Hz, 1H), 2.49 (br s, 3H), 2.53 (br s, 3H), 2.87-2.99 (m, 1H), 3.01-3.11 (m, 1H), 3.17-3.50 (m, 4H), 3.54-3.62 (m, 1H), 4.02 (d, J=4.9 Hz, 1H), 4.08-4.19 (m, 1H), 4.35 (d, J=4.9 Hz, 1H), 4.96-5.03 (m, 1H), 5.24-5.34 (m, 1H), 6.75-6.85 (m, 3H), 7.16 (d, J=7.8 Hz, 1H)

Example 224

(1S,5aS,6R,11bS)-14-(Cyclopropylmethyl)-3-(4,6-dimethylpyrimidin-2-yl)-11-methoxy-2,3,3a,4,5,6,7,11c-octahydro-11b-(iminoethano)-1,5a-methanonaphtho[1,2-e]indole (293)

(1) Synthesis of t-butyl (1S,5aS,6R,11bS)-14-(cyclopropylmethyl)-11-methoxy-3a,4,5,6,7,11c-hexahydro-1H-6,11b-(iminoethano)-1,5a-methanonaphtho[1,2-e]indole-3(2H)-carboxylate (290)

[Formula 212]

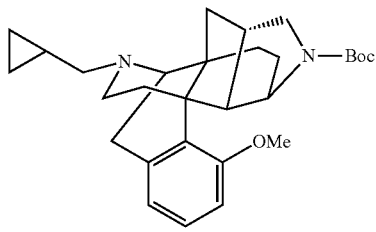

290

Under an argon atmosphere, a solution of the compound 116 (100 mg, 0.29 mmol) which was prepared in Example 101 in dichloromethane (3 mL) was added with triethylamine (162 μL, 1.20 mmol), and di-t-butyl dicarbonate (167 μL, 0.73 mmol), and the mixture was stirred at room temperature for 16 hours. The reaction mixture was diluted with ethyl acetate, and washed with saturated aqueous sodium hydrogencarbonate, water, and saturated brine. The organic layer was dried over anhydrous sodium sulfate, and then concentrated. Under an argon atmosphere, a solution of the obtained crude product in DMF (3 mL) was added with methyl iodide (54 μL, 0.87 mmol), and potassium carbonate (200 mg, 1.45 mmol), and the mixture was stirred at room temperature for 16 hours. The reaction mixture was diluted with ethyl acetate, and washed with saturated aqueous sodium hydrogencarbonate, water, and saturated brine. The organic layer was dried over anhydrous sodium sulfate, and then concentrated. The obtained crude product was purified by silica gel column chromatography to give the title compound 290 (134 mg, 100%).

(2) Synthesis of (1S,5aS,6R,11bS)-14-(cyclopropylmethyl)-11-methoxy-2,3,3a,4,5,6,7,11c-octahydro-1H-6,11b-(iminoethano)-1,5a-methanonaphtho[1,2-e]indole (291)

[Formula 213]

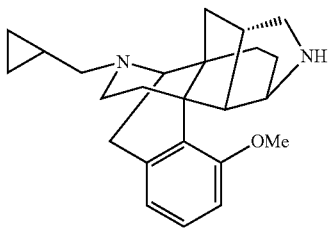

291

Under an argon atmosphere, a solution of the compound 290 (134 mg, 0.29 mmol) which was prepared in (1) mentioned above in dichloromethane (1.5 mL) was added with trifluoroacetic acid (1.5 mL), and the mixture was stirred at room temperature for 2 hours. The reaction mixture was concentrated, and the residue was dissolved in ethyl acetate. The organic layer was washed with saturated aqueous sodium hydrogencarbonate, water, and saturated brine, dried over anhydrous sodium sulfate, and then concentrated to obtain a crude product of the title compound 291.

(3) Synthesis of (1S,5aS,6R,11bS)-14-(cyclopropylmethyl)-3-(4,6-dimethylpyrimidin-2-yl)-11-methoxy-2,3,3a,4,5,6,7,11c-octahydro-1H-6,11b-(iminoethano)-1,5a-methanonaphtho[1,2-e]indole (292)

[Formula 214]

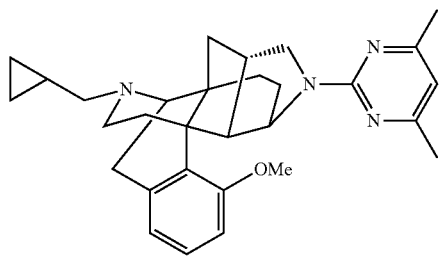

292

According to the method described in Example 165, the title compound 292 and the hydrochloride thereof (2 mg, 67%) were obtained by using the compound 291 (2 mg, 5.5 μmol) which was prepared in (2) mentioned above.

Compound 292 (hydrochloride) $^1$H NMR (CD$_3$ OD, 400 MHz): δ 0.40-0.65 (m, 2H), 0.70-0.90 (m, 2H), 0.90-1.05 (m, 1H), 1.10-1.25 (m, 1H), 1.40-1.55 (m, 1H), 1.55-1.70 (m, 2H), 1.70-1.80 (m, 1H), 1.90-2.00 (m, 1H), 2.10-2.20 (m, 1H), 2.45 (br s, 3H), 2.52 (br s, 3H), 2.75-2.80 (m, 1H), 3.00-3.15 (m, 2H), 3.20-3.50 (m, 4H), 3.66 (dd, J=6.8, 20.0 Hz, 1H), 3.75-3.90 (m, 2H), 3.88 (s, 3H), 3.95-4.20 (m, 1H), 4.21 (d, J=6.3 Hz, 1H), 4.65-4.80 (m, 1H), 6.76 (s, 1H), 6.93 (d, J=7.8 Hz, 2H), 7.28 (t, J=7.8 Hz, 1H)

Example 225

Synthesis of (1S,5aS,6R,11bS)-14-(cyclopropylmethyl)-3-(4,6-dimethylpyrimidin-2-yl)-2,3,3a,4,5,6,7,11c-octahydro-1H-6,11b-(iminoethano)-1,5a-methanonaphtho[1,2-e]indol-11-ol (293)

[Formula 215]

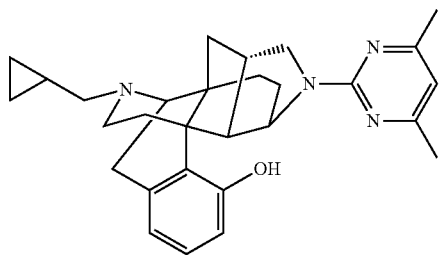

293

According to the method described in Example 6, the title compound 293 and the hydrochloride thereof (10 mg, 30%) were obtained by using the compound 292 (24 mg, 0.05 mmol) which was prepared in Example 224.

Compound 293 (hydrochloride) $^1$H NMR (CD$_3$OD, 400 MHz): δ 0.40-0.65 (m, 2H), 0.70-0.90 (m, 2H), 1.00-1.25 (m, 2H), 1.40-1.70 (m, 3H), 1.75-1.85 (m, 1H), 1.85-2.00 (m, 1H), 2.10-2.25 (m, 1H), 2.45 (br s, 3H), 2.52 (br s, 3H), 2.72-2.82 (m, 1H), 3.00-3.10 (m, 1H), 3.10-3.20 (m, 1H), 3.20-3.50 (m, 4H), 3.62 (dd, J=6.3, 20.0 Hz, 1H), 3.80-3.95 (m, 2H), 3.95-4.10 (m, 1H), 4.21 (d, J=6.3 Hz, 1H), 4.80-5.00 (m, 1H), 6.72 (d, J=7.8 Hz, 1H), 6.75 (s, 1H), 6.80 (d, J=7.8 Hz, 1H), 7.10 (t, J=7.8 Hz, 1H)

Example 226

Synthesis of (1S,5aS,6R,11bS)-3-(4,6-dimethylpyrimidin-2-yl)-14-methyl-2,3,3a,4,5,6,7,11c-octahydro-1H-6,11b-(iminoethano)-1,5a-methanonaphtho[1,2-e]indol-11-ol (294)

[Formula 216]

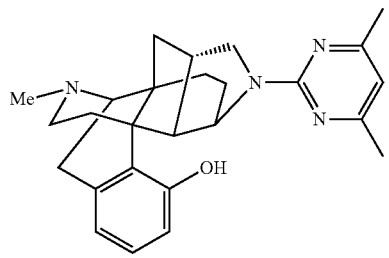

294

According to the methods described in Examples 71, 8 and 6, the title compound 294 and the hydrochloride thereof were obtained by using the compound 292 which was prepared in Example 224, (3).

Compound 294 (hydrochloride) $^1$H NMR (CD$_3$OD, 400 MHz): δ 1.00-1.15 (m, 1H), 1.40-1.65 (m, 3H), 1.75-1.85 (m, 1H), 1.88-2.00 (m, 1H), 2.02-2.15 (m, 1H), 2.44 (br s, 6H), 2.75-2.95 (m, 2H), 2.96 (s, 3H), 3.17-3.40 (m, 4H), 3.55-3.70 (m, 1H), 3.75-3.90 (m, 3H), 3.95-4.10 (m, 1H), 6.69 (s, 1H), 6.73 (d, J=8.3 Hz, 1H), 6.81 (d, J=8.3 Hz, 1H), 7.10 (t, J=8.3 Hz, 1H)

Example 227

(1S,5aS,6R,11bR)-3-Benzyl-14-(cyclopropylmethyl)-2,3,3a,4,5,6,7,11c-octahydro-1H-6,11b-(iminoethano)-1,5a-methanonaphtho[1,2-e]indole (296)

(1) Synthesis of (1S,5aS,6R,11bR)-3-benzyl-14-(cyclopropylmethyl)-2,3,3a,4,5,6,7,11c-octahydro-1H-6,11b-(iminoethano)-1,5a-methanonaphtho[1,2-e]indol-10-yl trifluoromethanesulfonate (295)

[Formula 217]

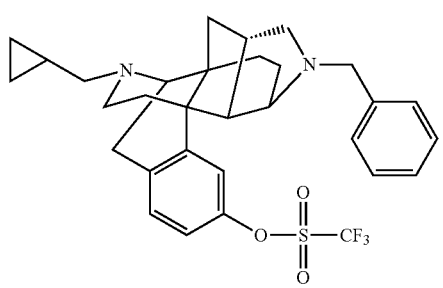

295

A solution of the compound 76 (570.7 mg, 1.30 mmol) in dichloromethane (6 mL) was added with triethylamine (361 μL, 2.59 mmol), and N-phenylbis(trifluoromethanesulfonimide) (509 mg, 1.42 mmol), and the mixture was stirred at room temperature for 3 hours. The reaction mixture was added with saturated aqueous sodium hydrogencarbonate, the mixture was extracted with chloroform, and then the organic layer was dried over anhydrous sodium sulfate, and concentrated. The obtained crude product was purified by silica gel column chromatography to give the title compound 295 (537 mg, 72%).

$^1$H NMR (CDCl$_3$, 400 MHz): δ 0.05-0.15 (m, 2H), 0.40-0.52 (m, 2H), 0.60-0.82 (m, 2H), 0.95-1.10 (m, 1H), 1.15-1.25 (m, 1H), 1.35-1.65 (m, 3H), 1.86-1.96 (m, 2H), 2.24-2.36 (m, 2H), 2.45-2.75 (m, 1H), 2.80-2.93 (m, 3H), 2.95-3.07 (m, 2H), 3.10-3.25 (m, 2H), 3.34-3.42 (m, 1H), 3.44-3.52 (m, 1H), 3.88 (d, J=11.4 Hz, 1H), 4.02 (d, J=11.4 Hz, 1H), 6.80 (d, J=2.4 Hz, 1H), 6.98 (dd, J=2.4, 8.0 Hz, 1H), 7.05-7.46 (m, 6H)

(2) Synthesis of (1S,5aS,6R,11bR)-3-benzyl-14-(cyclopropylmethyl)-2,3,3a,4,5,6,7,11c-octahydro-1H-6,11b-(iminoethano)-1,5a-methanonaphtho[1,2-e]indole (296)

[Formula 218]

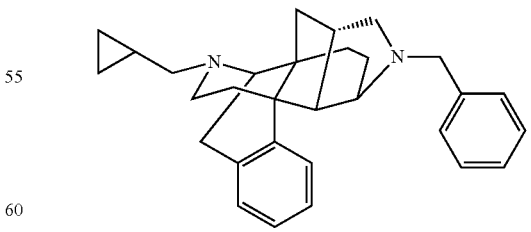

296

A solution of the compound 295 (250 mg, 0.44 mmol) which was prepared in (1) mentioned above in DMF (5 mL) was added with palladium acetate (10 mg, 0.04 mmol), 1,3-bis(diphenylphosphino)propane (36 mg, 0.09 mmol), and triethylsilane (174 μL, 1.09 mmol), and the mixture was stirred at 60° C. for 2 hours and 30 minutes. The reaction mixture was cooled to room temperature, and then added with saturated aqueous sodium hydrogencarbonate. The mixture was extracted with chloroform, and the organic layer was dried over anhydrous sodium sulfate, and then concentrated under reduced pressure. The obtained crude product was purified by silica gel column chromatography to give the title compound 296 (70 mg, 38%).

Compound 296 (free base) $^1$H NMR (CDCl$_3$, 400 MHz): δ 0.04-0.14 (m, 2H), 0.40-0.62 (m, 3H), 0.78-0.86 (m, 1H), 1.14-1.19 (m, 2H), 1.20-1.25 (m, 1H), 1.46-1.56 (m, 1H), 1.60-1.70 (m, 1H), 1.92-2.04 (m, 2H), 2.26-2.36 (m, 2H), 2.47-2.58 (m, 1H), 2.58-2.64 (m, HD, 2.85-3.05 (m, 5H), 3.10-3.20 (m, 2H), 3.20-3.27 (m, 1H), 3.65 (d, J=13.2 Hz, 1H), 3.72 (d, J=13.2 Hz, 1H), 7.05-7.35 (m, 9H)

Example 228

[(1S,5aS,6R,11bR)-14-(Cyclopropylmethyl)-4,5,6,7-tetrahydro-1H-6,11b-(iminoethano)-1,5a-methanonaphtho[1,2-e]indol-3(2H,3aH,11cH)-yl](phenyl)methanone (298)

(1) Synthesis of (1S,5aS,6R,11bR)-14-(cyclopropylmethyl)-2,3,3a,4,5,6,7,11c-octahydro-1H-6,11b-(iminoethano)-1,5a-methanonaphtho[1,2-e]indole (297)

[Formula 219]

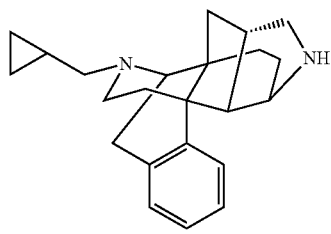

297

According to the method described in Example 4, a crude product of the title compound 297 was obtained by using the compound 296 (59 mg, 0.14 mmol).

(2) Synthesis of [(1S,5aS,6R,11bR)-14-(cyclopropylmethyl)-4,5,6,7-tetrahydro-1H-6,11b-(iminoethano)-1,5a-methanonaphtho[1,2-e]indol-3(2H,3aH,11cH)-yl](phenyl)methanone (298)

[Formula 220]

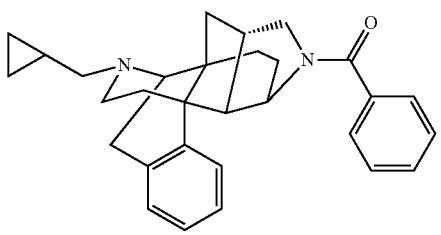

298

According to the method described in Example 33, the title compound 298 and the hydrochloride thereof were obtained by using the compound 297 which was prepared in (1) mentioned above.

Compound 298 (hydrochloride) $^1$H NMR (CD$_3$ OD, 400 MHz): δ 0.43-0.60 (m, 2H), 0.61-0.80 (m, 3H), 1.07-1.23 (m, 1.3H), 1.44-1.82 (m, 4H), 1.85-2.00 (m, 0.7H), 2.10-2.23 (m, 1H), 2.63-2.80 (m, 1H), 2.90-3.10 (m, 2H), 3.15-3.43 (m, 5.3H), 3.45-3.82 (m, 2.7H), 4.15-4.28 (m, 1.7H), 4.65-4.90 (m, 0.3H), 7.15-7.50 (m, 9H)

Examples 229 and 230

By using the compound 297 obtained in Example 228, (1), the compounds of Examples 229 and 230 were synthesized according to the methods of Examples 122 and 165, respectively.

TABLE 23

| Compound number | | Structural formula | $^1$H NMR |
|---|---|---|---|
| Example 229 | 299 | 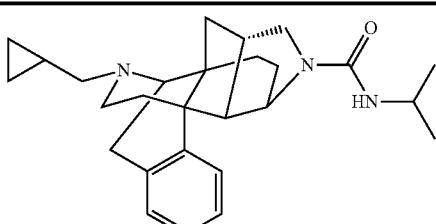 | (Hydrochloride, CD$_3$OD) δ 0.45-0.60 (m, 2H), 0.65-0.88 (m, 3H), 1.14 (d, J = 7.3 Hz, 6H), 1.10-1.25 (m, 1H), 1.27-1.37 (m, 1H), 1.47-1.58 (m, 2H), 1.58-1.70 (m, 1H), 1.80-1.90 (m, 1H), 2.13-2.25 (m, 1H), 2.67-2.78 (m, 1H), 3.06 (dd, J = 7.8, 13.2 Hz, 2H), 3.18-3.42 (m, 4H), 3.48 (d, J = 10.2 Hz, 1H), 3.53-3.65 (m, 1H), 3.67-3.75 (m, 1H), 3.78-3.92 (m, 2H), 4.20 (d, J = 5.9 Hz, 1H), 4.27-4.35 (m, 1H), 7.20-7.36 (m, 4H). |
| Example 230 | 300 | 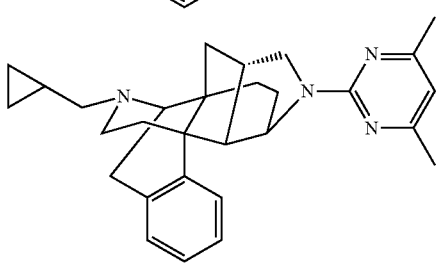 | (Hydrochloride, CD$_3$OD) δ 0.45-0.64 (m, 2H), 0.70-0.93 (m, 3H), 1.10-1.50 (m, 3H), 1.52-1.70 (m, 3H), 1.84-1.96 (m, 1H), 2.26 (ddd, J = 5.4, 8.8, 13.7 Hz, 1H), 2.44 (br s, 3H), 2.52 (br s, 3H), 2.70-2.82 (m, 1H), 3.09 (dd, J = 7.8, 13.2 Hz, 1H), 3.20-3.50 (m, 6H), 3.60 (dd, J = 6.3, 11.7 Hz, 1H), 3.86 (d, J = 11.7 Hz, 1H), 3.92-4.18 (m, 1H), 4.24 (d, J = 6.3 Hz, 1H), 6.76 (s, 1H), 7.25-7.42 (m, 4H). |

Example 231

(1S,5aS,6R,11bR)-14-(Cyclopropylmethyl)-3-(4,6-dimethylpyrimidin-2-yl)-2,3,3a,4,5,6,7,11c-octahydro-1H-6,11b-(iminoethano)-1,5a-epoxynaphtho[1,2-e]indole (302)

(1) Synthesis of (1S,5aS,6R,11bR)-14-(cyclopropylmethyl)-3-(4,6-dimethylpyrimidin-2-yl)-2,3,3a,4,5,6,7,11c-octahydro-1H-6,11b-(iminoethano)-1,5a-epoxynaphtho[1,2-e]indol-10-yl trifluoromethanesulfonate (301)

[Formula 221]

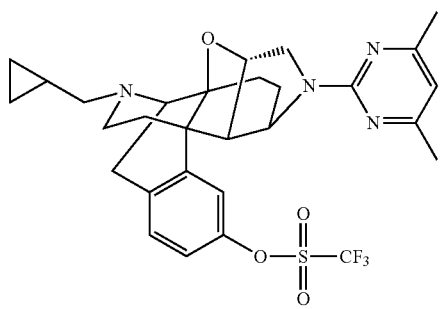

301

According to the method described in Example 227, (1), the title compound 301 was obtained by using the compound 289 which was prepared in Example 223.

(2) Synthesis of (1S,5aS,6R,11bR)-14-(cyclopropylmethyl)-3-(4,6-dimethylpyrimidin-2-yl)-2,3,3a,4,5,6,7,11c-octahydro-1H-6,11b-(iminoethano) 1,5a-epoxynaphtho[1,2-e]indole (302)

[Formula 222]

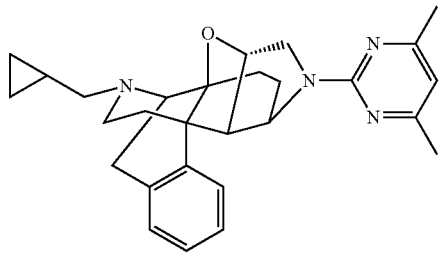

302

According to the method described in Example 227, (2), the title compound 302 and the hydrochloride thereof were obtained by using the compound 301 which was prepared in (1) mentioned above.

Compound 302 (hydrochloride) $^1$H NMR (CD$_3$ OD, 400 MHz): δ 0.48-0.62 (m, 2H), 0.72-0.95 (m, 3H), 1.10-1.25 (m, 1H), 1.43-1.56 (m, 1H), 1.65-1.75 (m, 1H), 1.77-1.95 (m, 2H), 2.30-2.60 (m, 1H), 2.47 (br s, 6H), 2.85-2.95 (m, 1H), 3.08 (dd, J=6.3, 13.7 Hz, 1H), 3.20-3.40 (m, 2H), 3.46-3.68 (m, 3H), 4.01 (d, J=13.7 Hz, 1H), 4.10 (dd, J=5.4, 13.7 Hz, 1H), 4.40 (d, J=5.4 Hz, 1H), 4.80-5.10 (m, 1H), 5.25-5.35 (m, 1H), 6.75 (s, 1H), 7.30-7.45 (m, 4H)

Example 232

Synthesis of (1S,5aS,6R,11bR)-3-benzyl-14-(cyclopropylmethyl)-10-phenoxy-2,3,3a,4,5,6,7,11c-octahydro-1H-6,11b-(iminoethano)-1,5a-methanonaphtho[1,2-e]indole (303)

[Formula 223]

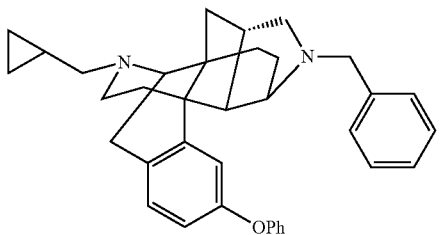

303

A solution of the compound 76 (86 mg, 0.20 mmol) in pyridine (3 mL) was added with metal copper powder (12 mg, 0.20 mmol), potassium carbonate (135 mg, 0.98 mmol), and bromobenzene (103 μL, 0.98 mmol), and the mixture was stirred under reflux for 18 hours and 30 minutes. The reaction mixture was cooled to room temperature, then filtered through Celite, and concentrated. The obtained crude product was purified by silica gel column chromatography to give the title compound 303 (84 mg, 84%).

Compound 303 (hydrochloride) $^1$H NMR (CD$_3$ OD, 400 MHz): δ 0.43-0.65 (m, 2H), 0.70-0.90 (m, 2H), 1.10-1.25 (m, 1H), 1.35-1.49 (m, 1H), 1.50-1.70 (m, 1H), 1.70-2.10 (m, 4H), 2.10-2.30 (m, 1H), 2.70-2.85 (m, 1H), 3.00-3.20 (m, 2H), 3.20-3.55 (m, 7H), 3.60-3.77 (m, J), 3.80-4.00 (m, 1H), 4.20-4.28 (m, 1H), 4.30-4.45 (m, 2H), 6.80-7.00 (m, 4H), 7.05-7.20 (m, 1H), 7.20-7.40 (m, 3H), 7.40-7.62 (m, 5H)

Example 233

(1S,5aS,6R,11bR)-3-Benzoyl-14-(cyclopropylmethyl)-2,3,3a,4,5,6,7,11c-octahydro-1H-6,11b-(iminoethano)-1,5a-epoxynaphtho[1,2-e]indole-10-carbonitrile (305)

(1) Synthesis of (1S,5aS,6R,11bR)-3-benzoyl-14-(cyclopropylmethyl)-2,3,3a,4,5,6,7,11c-octahydro-1H-6,11b-(iminoethano)-1,5a-epoxynaphtho[1,2-e]indol-10-yl trifluoromethanesulfonate (304)

[Formula 224]

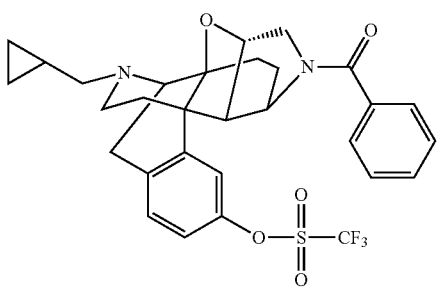

304

According to the method described in Example 227, (1), the title compound 304 (275 mg, 68%) was obtained by using the compound 10 (315 mg, 0.69 mmol).

(2) Synthesis of (1S,5aS,6R,11bR)-3-benzoyl-14-(cyclopropylmethyl)-2,3,3a,4,5,6,7,11c-octahydro-1H-6,11b-(iminoethano)-1,5a-epoxynaphtho[1,2-e]indole-10-carbonitrile (305)

[Formula 224]

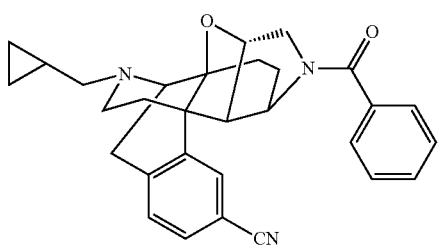

305

Under an argon atmosphere, a solution of the compound 304 (205 mg, 0.35 mmol) which was prepared in (1) mentioned above in DMF (3 mL) was added with tetrakis(triphenylphosphine)palladium (117 mg, 0.10 mol), and zinc cyanide (82 mg, 0.70 mmol), and the mixture was stirred at 120° C. for 22 hours. The reaction mixture was diluted with ethyl acetate, filtered through Celite, and then washed with water, and saturated brine. The organic layer was dried over anhydrous sodium sulfate, and then concentrated. The obtained crude product was purified by silica gel column chromatography to give the title compound 305 (31 mg, 19%) and the hydrochloride thereof.

Compound 305 (hydrochloride) $^1$H NMR (CD$_3$ OD, 400 MHz): δ 0.43-0.61 (m, 2H), 0.70-1.31 (m, 4H), 1.57-2.06 (m, 4H), 2.22-2.39 (m, 1H), 2.70-2.88 (m, 1H), 3.04 (dd, J=7.3, 13.2 Hz, 1H), 3.15-3.97 (m, 7H), 4.17-4.27 (m, 0.4H), 4.35-4.53 (m, 1H), 4.91-5.23 (m, 1.6H), 7.37-7.79 (m, 7.4H), 7.89 (s, 0.6H)

Example 234

Synthesis of (1S,5aS,6R,11bR)-3-benzoyl-14-(cyclopropylmethyl)-2,3,3a,4,5,6,7,11c-octahydro-1H-6,11b-(iminoethano)-1,5a-epoxynaphtho[1,2-e]indole-10-carboxamide (306)

[Formula 226]

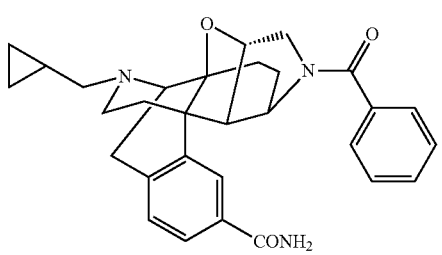

306

Under an argon atmosphere, a solution of the compound 305 (25 mg, 0.05 mmol) which was prepared in Example 233 in toluene (3 mL) was added with palladium acetate (2 mg, 9 μmol), triphenylphosphine (3 mg, 0.01 mmol), and acetaldoxime (7 μL, 0.11 mmol), and the mixture was stirred at 80° C. for 1 hour. The reaction mixture was concentrated, and the obtained crude product was purified by preparative TLC to give the title compound 306 and the hydrochloride thereof (22 mg, 83%).

Compound 306 (hydrochloride) $^1$H NMR (CD$_3$ OD, 400 MHz): δ 0.43-0.65 (m, 2.3H), 0.70-0.92 (m, 2.7H), 1.09-1.25 (m, 1.3H), 1.55-1.75 (m, 1.7H), 1.80-2.05 (m, 2H), 2.23-2.40 (m, 1H), 3.04 (dd, J=7.3, 13.7 Hz, 1H), 3.15-3.45 (m, 3.3H), 3.45-3.72 (m, 2.7H), 3.80 (dd, J=5.9, 12.7 Hz, 0.7H), 3.89 (d, J=12.7 Hz, 1H), 4.23 (dd, J=6.3, 14.6 Hz, 0.3H), 4.41 (d, J=4.9 Hz, 1H), 4.46-4.55 (m, 0.3H), 4.98-5.03 (m, 0.7H), 5.07-5.14 (m, 0.7H), 5.18-5.25 (m, 0.3H), 7.35-7.53 (m, 6H), 7.72-7.80 (m, 0.6H), 7.84 (dd, J=1.5, 7.8 Hz, 0.7H), 7.94 (d, J=1.5 Hz, 0.7H)

Example 235

[(1S,5aS,6R,11bR)-10-Amino-14-(cyclopropylmethyl)-4,5,6,7-tetrahydro-1H-6,11b-(iminoethano)-1,5a-epoxynaphtho[1,2-e]indol-3(2H,3aH,11cH)-yl](phenyl)methanone (308)

(1) Synthesis of [(1S,5aS,6R,11bR)-14-(cyclopropylmethyl)-10-[(diphenylmethylene)amino]-4,5,6,7-tetrahydro-1H-6,11b-(iminoethano)-1,5a-epoxynaphtho[1,2-e]indol-3(2H,3aH,11cH)-yl](phenyl)methanone (307)

[Formula 227]

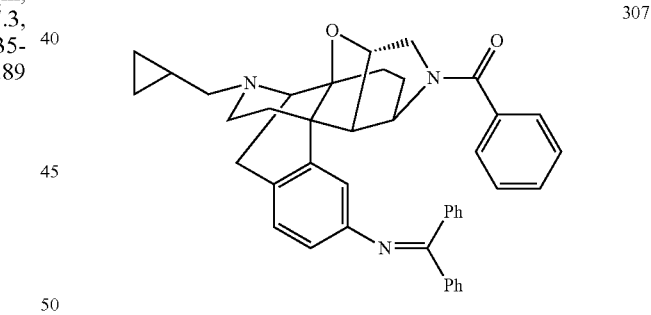

307

Under an argon atmosphere, a solution of the compound 304 (275 mg, 0.47 mmol) which was prepared in Example 233 in THF (9 mL) was added with palladium acetate (6 mg, 0.03 mmol), 2,2'-bis(diphenylphosphino)-1,1'-binaphthyl (17 mg, 0.03 mmol), benzophenonimine (119 mg, 0.66 mmol), cesium carbonate (213 mg, 0.65 mmol) and 4,7,13,16,21,24-hexaoxa-1,10-diazabicyclo[8.8.8]hexacosane (25 mg, 0.07), and the mixture was stirred at 70° C. for 16 hours. The reaction mixture was concentrated, and then dissolved in ethyl acetate, and the solution was washed with water and saturated brine. The organic layer was dried over anhydrous sodium sulfate, and then concentrated. The obtained crude product was purified by silica gel column chromatography to give the title compound 307 (66 mg, 23%).

(2) Synthesis of [(1S,5aS,6R,11bR)-10-amino-14-(cyclopropylmethyl)-4,5,6,7-tetrahydro-1H-6,11b-(iminoethano)-1,5a-epoxynaphtho[1,2-e]indol-3(2H,3aH,11cH)-yl](phenyl)methanone (308)

[Formula 228]

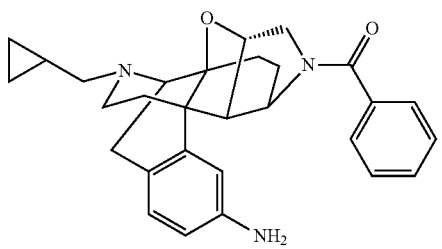
308

A solution of the compound 307 (66 mg, 0.11 mmol) which was prepared in (2) mentioned above in methanol (2 mL) was added with 2 M hydrochloric acid (0.5 mL), and the mixture was stirred at room temperature for 20 minutes. The reaction mixture was adjusted to pH 10 with sodium carbonate, and extracted twice with ethyl acetate. The organic layers were combined, dried over anhydrous sodium sulfate, and then concentrated. The obtained crude product was purified by silica gel column chromatography to give the title compound 308 and the hydrochloride thereof (22 mg, 39%).

Compound 308 (free base) $^1$H NMR (CDCl$_3$, 400 MHz): δ 0.03-0.16 (m, 2H), 0.43-0.59 (m, 2H), 0.89-1.38 (m, 3H), 1.46-1.55 (m, 1H), 1.73-1.92 (m, 1H), 1.98-2.35 (m, 3H), 2.45-2.70 (m, 2H), 2.70-2.90 (m, 1H), 2.95-3.14 (m, 2H), 3.40-3.77 (m, 2.7H), 3.80-3.90 (m, 1H), 4.19-4.32 (m, 0.6H), 4.92-5.02 (m, 1.4H), 5.05-5.12 (m, 0.3H), 6.33 (d, J=2.4 Hz, 0.3H), 6.42-6.60 (m, 1.7H), 6.87 (d, J=8.8 Hz, 0.3H), 6.92 (d, J=8.4 Hz, 0.7H), 7.33-7.50 (m, 5H)

Example 236

Synthesis of N-[(1S,5aS,6R,11bR)-3-benzoyl-14-(cyclopropylmethyl)-2,3,3a,4,5,6,7,11c-octahydro-1H-6,11b-(iminoethano)-1,5a-epoxynaphtho[1,2-e]indol-10-yl]acetamide (309)

[Formula 229]

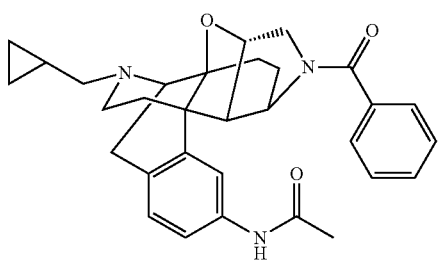
309

Under an argon atmosphere, a solution of the compound 308 (8 mg, 0.02 mmol) which was prepared in Example 235 in dichloromethane (2 mL) was added with acetic anhydride (4 μL, 0.04 mmol), and pyridine (10 μL, 0.12 mmol), and the mixture was stirred at room temperature for 15 hours. The reaction mixture was concentrated, and the obtained crude product was purified by preparative TLC to give the title compound 309 and the hydrochloride thereof (7.2 mg, 80%).

Compound 309 (hydrochloride) $^1$H NMR (CD$_3$ OD, 400 MHz): δ 0.42-0.57 (m, 2H), 0.61-1.00 (m, 3H), 1.07-1.13 (m, 2H), 1.54-1.74 (m, 1H), 1.81-1.99 (m, 1H), 2.08 (s, 0.9H), 2.15 (s, 2.1H), 2.20-2.35 (m, 1H), 2.78-2.95 (m, 1H), 2.98-3.08 (m, 1H), 3.14-3.56 (m, 3H), 3.74-3.91 (m, 2H), 4.18-4.46 (m, 2H), 5.04-5.11 (m, 0.7H), 5.16-5.22 (m, 0.3H), 7.25-7.55 (m, 7.3H), 7.68-7.74 (m, 0.7H)

Example 237

(1S,5aS,6R,11bR)-14-(Cyclopropylmethyl)-3-(4,6-dimethylpyrimidin-2-yl)-10-methoxy-2,3,3a,4,5,6,7,11c-octahydro-1H-6,11b-(iminoethano)-1,5a-methanonaphtho[1,2-e]indol-9-amine (312)

(1) Synthesis of (1S,5aS,6R,11bR)-14-(cyclopropylmethyl)-10-methoxy-9-nitro-2,3,3a,4,5,6,7,11c-octahydro-1H-6,11b-(iminoethano)-1,5a-methanonaphtho[1,2-e]indole (310)

[Formula 230]

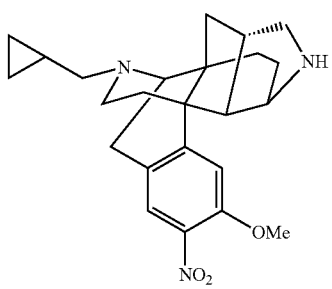
310

A solution of the compound 77 (105 mg, 0.29 mmol) in acetic acid (1 mL) was added with concentrated nitric acid (specific gravity, 1.42; 1 mL), and the mixture was stirred at 50° C. for 24 hours. The reaction mixture was diluted with ice water, and adjusted to pH 11 with potassium carbonate, and the mixture was extracted three times with chloroform. The organic layers were combined, dried over anhydrous sodium sulfate, and then concentrated to obtain a crude product of the title compound 310.

(2) Synthesis of (1S,5aS,6R,11bR)-14-(cyclopropylmethyl)-3-(4,6-dimethylpyrimidin-2-yl)-10-methoxy-9-nitro-2,3,3a,4,5,6,7,11c-octahydro-1H-6,11b-(iminoethano)-1,5a-methanonaphtho[1,2-e]indole (311)

[Formula 231]

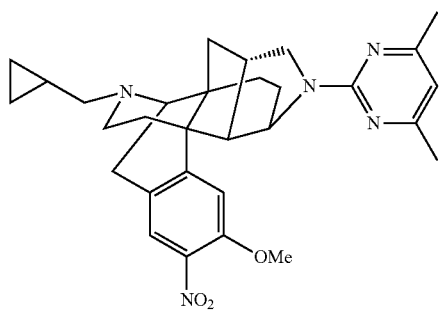
311

According to the method described in Example 165, the title compound 311 (90 mg, 60%) was obtained by using the crude product which was prepared in (1) mentioned above.

$^1$H NMR (CDCl$_3$, 400 MHz): δ 0.05-0.20 (m, 2H), 0.45-0.60 (m, 2H), 0.65-0.95 (m, 2H), 1.10-1.35 (m, 3H), 1.40-1.70 (m, 3H), 1.92-2.14 (m, 2H), 2.20-2.40 (m, 2H), 2.26 (br s, 6H), 2.60-2.75 (m, 1H), 2.90-3.25 (m, 4H), 3.41 (d, J=11.7

Hz, 1H), 3.68 (d, J=11.7 Hz, 1H), 3.88 (dd, J=7.8, 11.7 Hz, 1H), 3.97 (s, 3H), 4.57 (dd, J=5.4, 8.3 Hz, 1H), 6.23 (s, 1H), 6.89 (s, 1H), 7.69 (s, 1H)

(3) Synthesis of (1S,5aS,6R,11bR)-14-(cyclopropylmethyl)-3-(4,6-dimethylpyrimidin-2-yl)-10-methoxy-2,3,3a,4,5,6,7,11c-octahydro-1H-6,11b-(iminoethano)-1,5a-methanonaphtho[1,2-e]indol-9-amine (312)

[Formula 232]

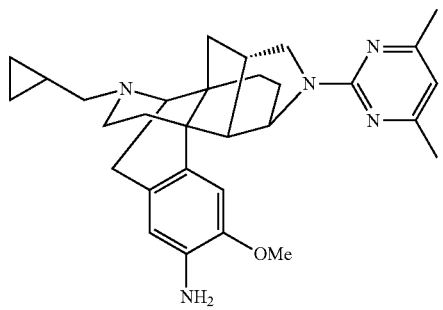

312

According to the method described in Example 201, the title compound 312 and the hydrochloride thereof (9.7 mg, 16%) were obtained by using the compound 311 (54 mg, 0.11 mmol) which was prepared in (2) mentioned above.

Compound 312 (hydrochloride) $^1$H NMR (CD$_3$ OD, 400 MHz): δ 0.45-0.70 (m, 2H), 0.70-1.00 (m, 3H), 1.10-1.30 (m, 1H), 1.45-1.80 (m, 4H), 1.80-2.00 (m, 1H), 2.20-2.35 (m, 1H), 2.47 (br s, 3H), 2.53 (br s, 3H), 2.70-2.85 (m, 1H), 3.05-3.20 (m, 1H), 3.20-3.75 (m, 8H), 3.88 (d, J=11.7 Hz, 1H), 4.00-4.15 (m, 1H), 4.04 (s, 3H), 4.26 (d, J=6.3 Hz, 1H), 6.79 (s, 1H), 7.19 (s, 1H), 7.35 (s, 1H)

Example 238

Synthesis of (1S,5aS,6R,11bR)-14-(cyclopropylmethyl)-3-(4,6-dimethylpyrimidin-2-yl)-9-nitro-2,3,3a,4,5,6,7,11c-octahydro-1H-6,11b-(iminoethano)-1,5a-methanon aphtho[1,2-e]indol-10-ol (313)

[Formula 233]

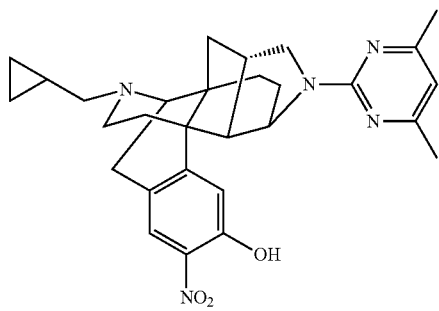

313

According to the method described in Example 6, the title compound 313 and the hydrochloride thereof were obtained by using the compound 311 which was prepared in Example 237, (2).

Compound 313 (hydrochloride) $^1$H NMR (CD$_3$ OD, 400 MHz): δ 0.45-0.65 (m, 2H), 0.65-0.90 (m, 2H), 0.90-1.05 (m, 1H), 1.10-1.25 (m, 1H), 1.50-1.80 (m, 4H), 1.90-2.00 (m, 1H), 2.20-2.35 (m, 1H), 2.46 (br s, 3H), 2.53 (br s, 3H), 2.70-2.85 (m, 1H), 3.10 (dd, J=7.8, 13.2 Hz, 1H), 3.20-3.55 (m, 7H), 3.63 (dd, J=6.3, 20.0 Hz, 1H), 3.88 (d, J=12.2 Hz, 1H), 4.00-4.15 (m, 1H), 4.28 (d, J=6.3 Hz, 1H), 6.79 (s, 1H), 7.22 (s, 1H), 8.10 (s, 1H)

Example 239

(1S,5aS,6R,11bR)-9-Amino-14-(cyclopropylmethyl)-3-(4,6-dimethylpyrimidin-2-yl)-2,3,3a,4,5,6,7,11c-octahydro-1H-6,11b-(iminoethano)-1,5a-methanonaphtho[1,2-e]indole-10-carboxamide (316)

(1) Synthesis of (1S,5aS,6R,11bR)-14-(cyclopropylmethyl)-3-(4,6-dimethylpyrimidin-2-yl)-9-nitro-2,3,3a,4,5,6,7,11c-octahydro-1H-6,11b-(iminoethano)-1,5a-methanonaphtho[1,2-e]indol-10-yl trifluoromethanesulfonate (314)

[Formula 234]

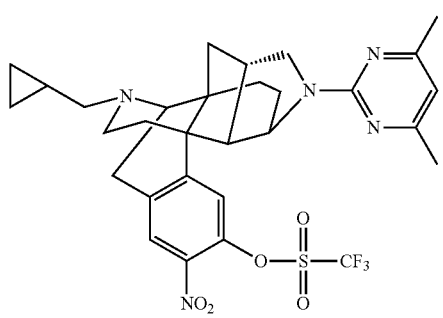

314

According to the method described in Example 227, (1), the title compound 314 (538 mg, 79%) was obtained by using the compound 313 (542 mg, 1.08 mmol) which was prepared in Example 238.

(2) Synthesis of (1S,5aS,6R,11bR)-14-(cyclopropylmethyl)-3-(4,6-dimethylpyrimidin-2-yl)-9-nitro-2,3,3a,5,6,7,11c-octahydro-1H-6,11b-(iminoethano)-1,5a-methanonaphtho[1,2-e]indole-10-carbonitrile (315)

[Formula 235]

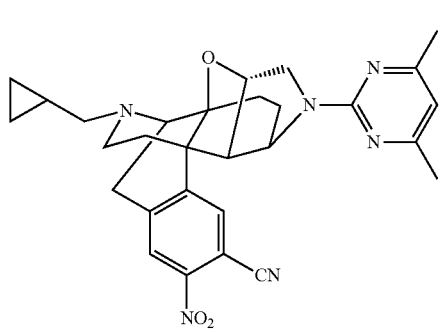

315

According to the method described in Example 233, (2), the title compound 315 (350 mg, 82%) was obtained by using the compound 314 (538 mg, 0.85 mmol) which was prepared in (1) mentioned above.

(3) Synthesis of (1S,5aS,6R,11bR)-9-amino-14-(cyclopropylmethyl)-3-(4,6-dimethylpyrimidin-2-yl)-2,3,3a,4,5,6,7,11c-octahydro-1H-6,11b-(iminoethano)-1,5a-methanonaphtho[1,2-e]indole-10-carboxamide (316)

[Formula 236]

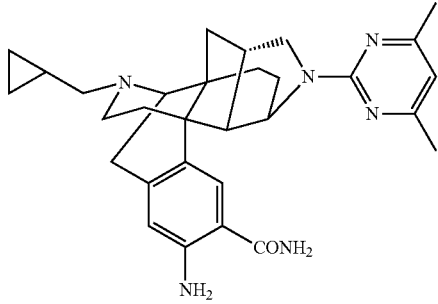

The compound 315 (29 mg, 1.08 mmol) which was prepared in (2) mentioned above was dissolved in ethanol (1 mL) and water (0.3 mL), the solution was added with zinc (112 mg, 1.71 mmol) and calcium chloride (4 mg, 0.04 mmol), and the mixture was stirred at 90° C. for 16 hours. The reaction mixture was filtered through Celite, and concentrated. The obtained residue was dissolved in ethyl acetate, and the solution was washed with water and saturated brine. The organic layer was dried over anhydrous sodium sulfate, and then concentrated. The obtained crude product was purified by preparative TLC to give the title compound 316 (3 mg, 8%). Compound 316 (hydrochloride) $^1$H NMR (CD$_3$OD, 400 MHz): δ 0.50-0.70 (m, 2H), 0.70-0.95 (m, 3H), 1.15-1.30 (m, 1H), 1.45-1.65 (m, 3H), 1.65-1.80 (m, 1H), 1.80-2.00 (m, 1H), 2.25-2.40 (m, 1H), 2.45 (br s, 3H), 2.53 (br s, 3H), 2.65-2.80 (m, 1H), 3.12 (dd, J=7.8, 13.7 Hz, 1H), 3.20-3.60 (m, 7H), 3.73 (dd, J=6.8, 21.0 Hz, 1H), 3.89 (d, J=11.7 Hz, 1H), 4.10-4.15 (m, 1H), 4.31 (d, J=6.3 Hz, 1H), 6.78 (s, 1H), 7.40 (s, 1H), 8.01 (s, 1H)

Example 240

Synthesis of (1S,5aS,6R,11bR)-14-(cyclopropylmethyl)-10-hydroxy-N-isopropyl-3a,4,5,6,7,11c-hexahydro-1H-6,11b-(iminoethano)-1,5a-methanonaphtho[1,2-e]indole-3(2H)-carbothioamide (317)

[Formula 237]

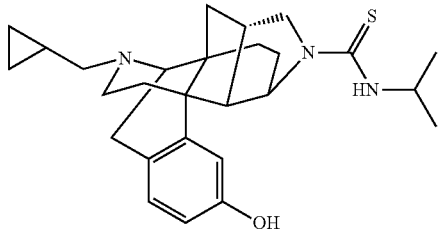

According to the method described in Example 122, the title compound 317 and the hydrochloride thereof were obtained by using the compound 77 and isopropyl isothiocyanate.

Compound 317 (hydrochloride) $^1$H NMR (CD$_3$OD, 400 MHz): δ 0.40-0.60 (m, 2H), 0.65-1.00 (m, 3H), 1.10-1.25 (m, 6H), 1.45-1.68 (m, 4H), 1.80-1.95 (m, 1H), 2.10-2.25 (m, 1H), 2.70-2.84 (m, 1H), 2.96-3.12 (m, 2H), 3.15-3.40 (m, 8H), 3.43-3.55 (m, 1H), 3.60-3.75 (m, 1H), 3.85-4.00 (m, 1H), 4.15 (d, J=5.9 Hz, 1H), 4.57-4.68 (m, 1H), 6.71 (dd, J=2.4, 8.3 Hz, 1H), 6.73 (d, J=2.4 Hz, 1H), 7.10 (d, J=8.3 Hz, 1H)

Example 241

(1S,5aS,6R,11bR)-14-(Cyclopropylmethyl)-3-[3,3,3-trifluoro-2-hydroxy-2-(trifluoromethyl)propyl]-2,3,3a,4,5,6,7,11c-octahydro-1H-6,11b-(iminoethano)-1,5a-methanonaphtho[1,2-e]indol-10-ol (319)

(1) Synthesis of 2-[[(1S,5aS,6R,11bR)-14-(cyclopropylmethyl)-10-methoxy-4,5,6,7-tetrahydro-1H-6,11b-(iminoethano)-1,5a-methanonaphtho[1,2-e]indol-3(2H,3aH,11cH)-yl]methyl]-1,1,1,3,3,3-hexafluoropropan-2-ol (318)

[Formula 238]

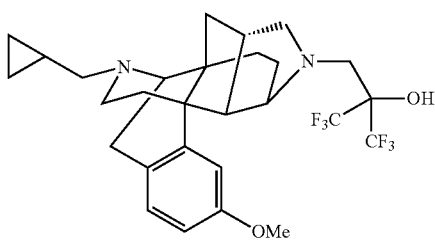

Under an argon atmosphere, the compound 77 (542 mg, 1.08 mmol) which was prepared in Example 67 was dissolved in methanol (1 mL), the solution was added with 2,2-bis(trifluoromethyl)oxirane (0.25 mL), and the mixture was stirred at 60° C. for 24 hours. The reaction mixture was concentrated to obtain a crude product of the title compound 318.

(2) Synthesis of (1S,5aS,6R,11bR)-14-(cyclopropylmethyl)-3-(3,3,3-trifluoro-2-hydroxy-2-(trifluoromethyl)propyl)-2,3,3a,4,5,6,7,11c-octahydro-1H-6,11b-(iminoethano)-1,5a-methanonaphtho[1,2-e]indol-10-ol (319)

[Formula 239]

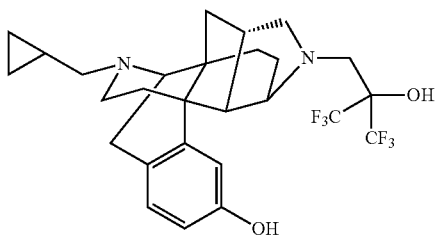

According to the method described in Example 6, the title compound 319 and the hydrochloride thereof (12 mg, 29%) were obtained by using the crude product which was prepared in (1) mentioned above.

Compound 319 (hydrochloride) $^1$H NMR (CD$_3$OD, 400 MHz): δ 0.45-0.70 (m, 2H), 0.70-0.90 (m, 2H), 1.10-1.25 (m, 1H), 1.30-1.50 (m, 1H), 1.50-1.65 (m, 1H), 1.65-1.85 (m, 3H), 1.85-2.00 (m, 1H), 2.10-2.30 (m, 1H), 2.70-2.80 (m, 1H), 3.00-3.15 (m, 2H), 3.15-3.75 (m, 7H), 3.90-4.05 (m, 2H), 4.05-4.30 (m, 3H), 6.70-6.80 (m, 2H), 7.14 (d, J=7.8 Hz, 1H)

Example 242

Synthesis of [(1S,5aS,6R,11bR)-10-hydroxy-14-neopentyl-4,5,6,7-tetrahydro-1H-6,11b-(iminoethano)-1,5a-methanonaphtho[1,2-e]indol-3(2H,3aH,11cH)-yl](phenyl)methanone (320)

[Formula 240]

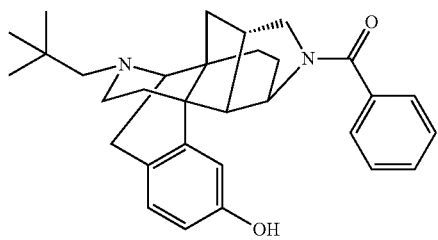

320

According to the method described in Example 106, the title compound 320 and the hydrochloride thereof were obtained by using the compound 127 which was prepared in Example 106, (2) and pivalic acid.

Compound 320 (hydrochloride) $^1$H NMR (CD$_3$OD, 400 MHz): δ 0.78-0.91 (m, 0.3H), 0.91-1.05 (m, 0.7H), 1.10-2.00 (m, 5.7H), 1.19 (s, 9H), 2.20-2.35 (m, 1H), 2.42-2.56 (m, 0.3H), 2.84-3.03 (m, 3.3H), 3.11-3.57 (m, 4.3H), 3.67 (d, J=11.7 Hz, 1H), 3.70-3.78 (m, 0.7H), 4.01-4.10 (m, 1H), 4.20-4.30 (m, 0.7H), 4.70-5.00 (m, 1H), 6.57 (d, J=2.4 Hz, 0.3H), 6.65 (dd, J=2.4, 8.3 Hz, 0.3H), 6.74 (dd, J=2.4, 8.3 Hz, 0.7H), 6.78 (d, J=2.4 Hz, 0.7H), 7.07 (d, J=8.3 Hz, 0.3H), 7.15 (d, J=8.3 Hz, 0.7H), 7.37-7.49 (m, 5H)

Example 243

[(1S,3aR,5aS,6R,11bS,11cS)-12,12-Difluoro-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl](phenyl)methanone (323)

(1) Synthesis of [(1S,3aR,5aS,6R,11bR,11cS)-14-(cyclopropylmethyl)-10-methoxy-1,2,3a,4,5,6,7,11c-octahydro-3H-6,11b-(iminoetheno)-1,5a-epoxynaphtho[1,2-e]indol-3-yl](phenyl)methanone (321)

[Formula 241]

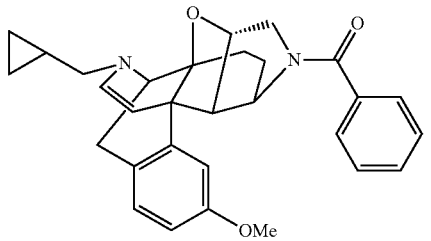

321

Under an argon atmosphere, the compound 9 (471 mg, 1.0 mmol) which was prepared in Example 5 was dissolved in acetic acid (4 mL) and water (40 mL), the solution was added with mercury(II) acetate (1.6 g, 5.0 mmol), and the mixture was stirred under reflux for 1 hour. The reaction mixture was returned to room temperature, and added with sodium thiosulfate pentahydrate (5 g, 20 mmol), and the mixture was stirred at room temperature for 1 hour. The reaction mixture was filtered through Celite, then adjusted to pH 11 with potassium carbonate, and extracted three times with chloroform. The organic layers were combined, filtered through Celite, then washed with water, dried over anhydrous sodium sulfate, and then concentrated. The obtained crude product was purified by silica gel column chromatography to give the compound 321 as white amorphous (90 mg, 19%).

(2) Synthesis of [(1S,3aR,5aS,6R,11bS,11cS)-12,12-difluoro-14-(cyclopropylmethyl)-10-methoxy-1,2,3a,4,5,6,7,11c-octahydro-3H-6,11b-(iminoethano)-1,5a-epoxynaphtho[1,2-e]indol-3-yl](phenyl)methanone (322)

[Formula 242]

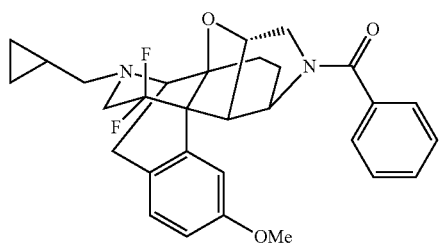

322

Under an argon atmosphere, the compound 321 (70 mg, 0.15 mmol) which was prepared in (1) mentioned above was dissolved in THF (3 mL), the solution was added with N-fluorobenzenesulfonimide (142 mg, 0.45 mmol) under ice cooling, and the mixture was stirred at room temperature for 30 minutes. The reaction mixture was added with methanol (5 mL), and sodium borohydride (57 mg, 1.5 mmol), and the mixture was stirred at room temperature for 30 minutes. The reaction mixture was added with saturated aqueous sodium hydrogencarbonate (20 mL), and the mixture was extracted three times with chloroform. The organic layers were combined, dried over anhydrous sodium sulfate, and then concentrated. The obtained crude product was purified by preparative TLC to give the title compound 322 as colorless oil (20 mg, 26%).

$^1$H NMR (CDCl$_3$, 300 MHz): δ 0.02-0.20 (m, 2H), 0.49-1.05 (m, 4H), 1.12-2.03 (m, 3H), 2.37-2.64 (m, 3H), 2.97-3.20 (m, 3H), 3.46-3.90 (m, 4.6H), 3.82 (s, 2.1H), 4.32 (t, J=6.6 Hz, 0.3H), 4.42 (dd, J=7.8, 14.4 Hz, 0.3H), 5.06-5.17 (m, 0.7H), 5.23-5.39 (m, 1H), 6.62 (br s, 0.3H), 6.75 (dd, J=2.7, 8.7 Hz, 0.3H), 6.77-6.90 (m, 1.4H), 7.03 (d, J=8.4 Hz, 0.3H), 7.08 (d, J=8.1 Hz, 0.7H), 7.31-7.52 (m, 5H)

(3) Synthesis of [(1S,3aR,5aS,6R,11bS,11cS)-12,12-difluoro-14-(cyclopropylmethyl)-10-hydroxy-1,2,3a,4,5,6,7,11c-octahydro-3H-6,11b-(iminoethano)-1,5a-epoxynaphtho[1,2-e]indol-3-yl](phenyl)methanone (323)

[Formula 243]

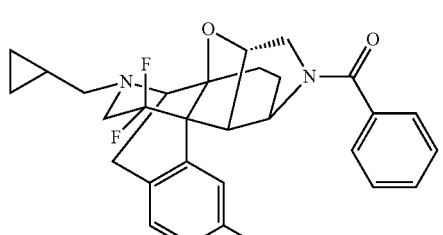

323

According to the method described in Example 6, the title compound 323 (9 mg, 48%) and the hydrochloride thereof were obtained by using the compound 322 (20 mg, 0.04 mmol) which was prepared in (2) mentioned above.

Compound 323 (free base) $^1$H NMR (CDCl$_3$, 300 MHz): δ 0.04-0.20 (m, 2H), 0.48-0.63 (m, 2H), 0.80-1.12 (m, 2H), 1.41 (dd, J=7.2, 15.3 Hz, 1H), 1.60-2.04 (m, 2H), 2.45-2.68 (m, 3H), 2.96-3.18 (m, 3H), 3.45-3.60 (m, 1H), 3.61-3.95 (m, 3H), 4.28-4.49 (m, 0.4H), 5.20-5.36 (m, 1.6H), 6.60-6.72 (m, 0.4H), 6.72 (dd, J=2.4, 8.4 Hz, 0.8H), 6.93-7.02 (m, 1.8H), 7.32-7.53 (m, 5H)

Example 244

(1S,3aR,5aS,6R,11bR,11cS,12S)-3-Benzyl-14-(cyclopropylmethyl)-1,2,3a,4,5,6,7,11c-octahydro-1H-6,11b-(iminoethano)-1,5a-epoxynaphtho[1,2-e]indole-10,12-diol (325)

(1) Synthesis of (1S,3aR,5aS,6R,11bR,11cS,12S)-3-benzyl-14-(cyclopropylmethyl)-10-methoxy-1,2,3a,4,5,6,7,11c-octahydro-1H-6,11b-(iminoethano)-1,5a-epoxynaphtho[1,2-e]indol-12-ol (324)

[Formula 244]

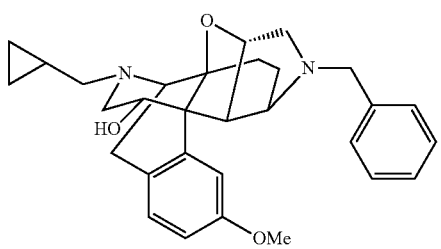

324

Under an argon atmosphere, the compound 321 (107 mg, 0.23 mmol) which was prepared in Example 243, (1) was dissolved in THF (3 mL), the solution was added with a solution of borane-THF complex in THF (0.9 mol/L, 1.3 mL, 1.2 mmol), and the mixture was refluxed for 1 hour. The reaction mixture was added with water (4 mL), and sodium perborate tetrahydrate (702 mg, 4.6 mmol), and the mixture was stirred at room temperature for 4 hours. The reaction mixture was added with saturated aqueous sodium hydrogencarbonate (10 mL), and the mixture was extracted three times with chloroform. The organic layers were combined, dried over anhydrous sodium sulfate, and then concentrated. The obtained crude product was purified by preparative TLC to give the title compound 324 as white amorphous (47 mg, 43%).

$^1$H NMR (CDCl$_3$, 300 MHz): δ 0.02-0.16 (m, 2H), 0.37-0.59 (m, 3H), 0.83-1.02 (m, 1H), 1.51 (dd, J=7.2, 15.3 Hz, 1H), 1.63-1.87 (m, 3H), 2.34 (dd, J=6.9, 12.3 Hz, 1H), 2.52 (dd, J=6.0, 12.6 Hz, 1H), 2.76-2.93 (m, 2H), 2.88 (dd, J=5.4, 15.6 Hz, 1H), 3.08 (d, J=18.6 Hz, 1H), 3.31 (dd, J=6.9, 10.8 Hz, 1H), 3.43-3.53 (m, 2H), 3.58 (d, J=6.0 Hz, 1H), 3.68 (d, J=13.2 Hz, 1H), 3.73-3.84 (m, 1H), 3.77 (s, 3H), 3.98 (dd, J=5.7, 10.8 Hz, 1H), 4.94-5.03 (m, 1H), 6.70-6.79 (m, 2H), 7.10 (d, J=8.4 Hz, 1H), 7.19-7.34 (m, 5H)

(2) Synthesis of (1S,3aR,5aS,6R,11bR,11cS,12S)-3-benzyl-14-(cyclopropylmethyl)-1,2,3a,4,5,6,7,11c-octahydro-1H-6,11b-(iminoethano)-1,5a-epoxynaphtho[1,2-e]indole-10,12-diol (325)

[Formula 245]

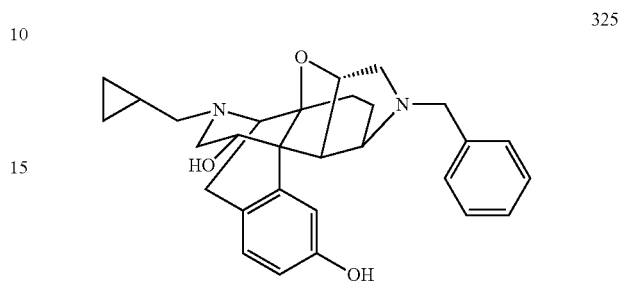

325

According to the method described in Example 6, the title compound 325 (17 mg, 74%) and the hydrochloride thereof were obtained by using the compound 324 (24 mg, 0.051 mmol) which was prepared in (1) mentioned above.

Compound 325 (free base) $^1$H NMR (CDCl$_3$, 300 MHz): δ −0.06-0.14 (m, 2H), 0.37-0.63 (m, 3H), 0.79-0.97 (m, 1H), 1.50-1.89 (m, 4H), 2.07-2.20 (m, 1H), 2.50-2.80 (m, 3H), 2.81 (dd, J=6.0, 18.3 Hz, 1H), 3.03 (d, J=18.6 Hz, 1H), 3.07 (br s, 1H), 3.32 (dd, J=7.5, 14.1 Hz, 1H), 3.43 (t, J=6.6 Hz, 1H), 3.56-3.79 (m, 4H), 4.71-4.85 (m, 1H), 6.56-6.69 (m, 2H), 6.94 (d, J=8.7 Hz, 1H), 7.12-7.29 (m, 5H)

Example 245

Synthesis of (1S,3aR,5aS,6R,11bS,11cS,12S)-3-benzyl-14-(cyclopropylmethyl)-12-fluoro-1,2,3a,4,5,6,7,11c-octahydro-1H-6,11b-(iminoethano)-1,5a-epoxynaphtho[1,2-e]indol-10-ol (326)

[Formula 246]

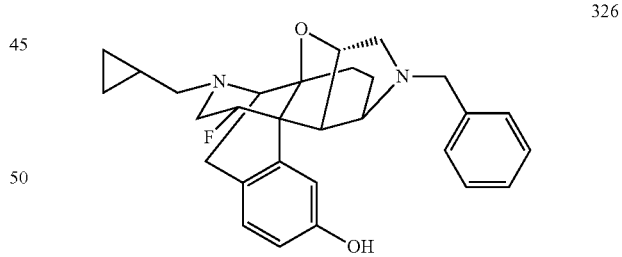

326

Under an argon atmosphere, the compound 325 (18 mg, 0.04 mmol) which was prepared in Example 244, (2) was dissolved in THF (2 mL), the solution was added with a solution of bis(2-methoxyethyl)aminosulfur trifluoride in THF (50%, 51 μL, 0.12 mmol) under ice cooling, and the mixture was stirred at 0° C. for 1 hour. The reaction mixture was added with saturated aqueous sodium hydrogencarbonate (10 mL), and the mixture was extracted three times with chloroform. The organic layers were combined, dried over anhydrous sodium sulfate, and then concentrated. The obtained crude product was purified by preparative TLC to give the title compound 326 (13 mg, 71%) as colorless oily substance and the hydrochloride thereof.

Compound 326 (free base) $^1$H NMR (CDCl$_3$, 300 MHz): δ 0.02-0.16 (m, 2H), 0.41-0.64 (m, 3H), 0.81-0.97 (m, 1H), 1.50-1.90 (m, 3H), 2.03-2.18 (m, 1H), 2.39 (dd, J=6.9, 12.3 Hz, 1H), 2.49 (dd, J=6.3, 12.6 Hz, 1H), 2.78-3.03 (m, 3H), 3.08 (d, J=18.3, 1H), 3.38 (dd, J=7.2, 11.1 Hz, 1H), 3.41-3.60 (m, 3H), 3.62-3.79 (m, 2H), 4.81 (ddd, J=6.0, 10.5, 50.1 Hz, 1H), 4.89-5.02 (m, 1H), 6.61-6.72 (m, 2H), 6.93-7.02 (m, 1H), 7.13-7.32 (m, 5H)

Example 246

(1S,3aR,5aS,6R,11bS,11cS,12R)-3-Benzyl-14-(cyclopropylmethyl)-1,2,3a,4,5,6,7,11c-octahydro-1H-6,11b-(iminoethano)-1,5a-epoxynaphtho[1,2-e]indole-10,12-diol (329)

(1) Synthesis of (1S,3aR,5aS,6R,11bS,11cS)-3-benzyl-14-(cyclopropylmethyl)-10-methoxy-1,2,3a,4,5,6,7,11c-octahydro-1H-6,11b-(iminoethano)-1,5a-epoxynaphtho[1,2-e]indol-12-one (327)

[Formula 247]

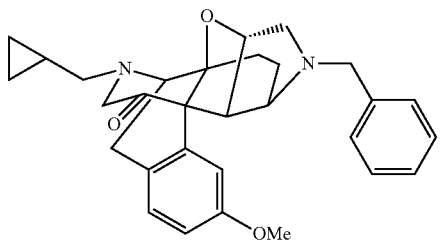

327

Under an argon atmosphere, oxalyl chloride (51 µL, 0.60 mmol) was dissolved in dichloromethane (2 mL), the solution was slowly added dropwise with dimethyl sulfoxide (64 µL, 0.90 mmol) with cooling to −78° C., and the mixture was stirred for 5 minutes. The reaction mixture was added with a solution of the compound 324 (95 mg, 0.20 mmol) which was prepared in Example 244, (1) in dichloromethane (1.5 mL), and the mixture was stirred at −78° C. for 2 hours. The reaction mixture was added with triethylamine (251 µL, 1.8 mmol) at once, and the mixture was maintained at −78° C. for 10 minutes, and then gradually warmed to room temperature. The reaction mixture was diluted by adding dichloromethane (20 mL), and washed with saturated aqueous sodium hydrogencarbonate. The organic layer was dried over anhydrous sodium sulfate, and then concentrated. The obtained crude product was purified by preparative TLC to give the title compound 327 as white amorphous (68 mg, 70%).

$^1$H NMR (CDCl$_3$, 300 MHz): δ 0.03-0.19 (m, 2H), 0.47-0.66 (m, 3H), 0.85-1.04 (m, 1H), 1.37-1.49 (m, 1H), 1.76-1.89 (m, 2H), 2.42-2.57 (m, 2H), 2.89 (dd, J=2.1, 11.1 Hz, 1H), 2.95 (d, J=16.2 Hz, 1H), 3.03-3.17 (m, 2H), 3.29 (d, J=18.9 Hz, 1H), 3.34 (d, J=16.5 Hz, 1H), 3.51 (dd, J=5.1, 8.4 Hz, 1H), 3.68-3.86 (m, 3H), 3.74 (s, 3H), 3.94 (dd, J=5.4, 8.1 Hz, 1H), 4.62-4.70 (m, 1H), 6.70 (d, J=2.7 Hz, 1H), 6.74 (dd, J=2.7, 8.4 Hz, 1H), 7.09 (d, J=8.4 Hz, 1H), 7.18-7.36 (m, 5H)

(2) Synthesis of (1S,3aR,5aS,6R,11bS,11cS,12R)-3-benzyl-14-(cyclopropylmethyl)-10-methoxy-1,2,3a,4,5,6,7,11c-octahydro-1H-6,11b-(iminoethano)-1,5a-epoxynaphtho[1,2-e]indol-12-ol (328)

[Formula 248]

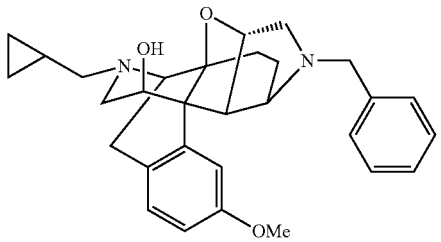

328

Under an argon atmosphere, the compound 327 (24 mg, 0.05 mmol) which was prepared in (1) mentioned above was dissolved in methanol (2 mL), the solution was added with sodium borohydride (10 mg, 0.25 mmol), and the mixture was stirred at room temperature for 1 hour. The reaction mixture was added with saturated aqueous sodium hydrogencarbonate (10 mL), and the mixture was extracted three times with chloroform. The organic layers were combined, dried over anhydrous sodium sulfate, and then concentrated. The obtained crude product was purified by preparative TLC to give the title compound 328 (11 mg, 45%) and the compound 324 (4 mg, 18%) as colorless oil.

$^1$H NMR (CDCl$_3$, 300 MHz): δ 0.03-0.17 (m, 2H), 0.36-0.58 (m, 3H), 0.81-0.96 (m, 1H), 1.46-1.69 (m, 2H), 1.78-1.92 (m, 1H), 2.26-2.56 (m, 3H), 2.66-2.78 (m, 2H), 2.94 (dd, J=6.0, 18.3 Hz, 1H), 3.07 (d, J=18.3 Hz, 1H), 3.26-3.41 (m, 3H), 3.43-3.55 (m, 2H), 3.61-3.82 (m, 3H), 3.75 (s, 3H), 5.23-5.34 (m, 1H), 6.69 (dd, J=2.7, 8.4 Hz, 1H), 6.73 (d, J=2.7 Hz, Hp), 7.02 (d, J=8.4 Hz, 1H), 7.18-7.34 (m, 5H)

(3) Synthesis of (1S,3aR,5aS,6R,11bS,11cS,12R)-3-benzyl-14-(cyclopropylmethyl)-1,2,3a,4,5,6,7,11c-octahydro-1H-6,11b-(iminoethano)-1,5a-epoxynaphtho[1,2-e]indole-10,12-diol (329)

[Formula 249]

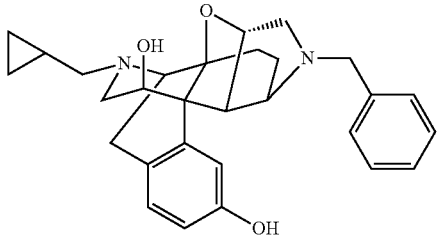

329

According to the method described in Example 22, the title compound 329 (4 mg, 39%) and the hydrochloride thereof were obtained by using the compound 328 (10 mg, 0.022 mmol) which was prepared in (2) mentioned above.

Compound 329 (free base) $^1$H NMR (CDCl$_3$, 300 MHz): δ 0.03-0.17 (m, 2H), 0.41-0.63 (m, 3H), 0.78-0.96 (m, 1H), 1.53-1.71 (m, 2H), 1.91 (dd, J=9.9, 13.8 Hz, 1H), 2.25-2.58 (m, 3H), 2.63-2.80 (m, 2H), 2.94 (dd, J=6.0, 18.3 Hz, 1H), 3.06 (d, J=18.3 Hz, 1H), 3.20 (t, J=6.6 Hz, 1H), 3.31-3.48 (m, 3H), 3.53 (d, J=5.1 Hz, 1H), 3.60-3.74 (m, 2H), 5.20-5.29 (m, 1H), 6.53 (d, J=2.4 Hz, 1H), 6.64 (dd, J=2.4, 8.4 Hz, 1H), 6.98 (d, J=8.4 Hz, 1H), 7.12-7.33 (m, 5H)

Example 247

[(1S,2R,3aR,5aS,6R,11bS,11cS)-14-(Cyclopropylmethyl)-10-hydroxy-2-methyl-1,2,3a,4,5,6,7,11c-octahydro-3H-6,11b-(iminoethano)-1,5a-methanonaphtho[1,2-e]indol-3-yl](phenyl)methanone (332)

(1) Synthesis of (1S,3aR,5aS,6R,11bS,11cS)-14-(cyclopropylmethyl)-10-methoxy-3a,4,5,6,7,11c-hexahydro-1H-6,11b-(iminoethano)-1,5a-methanonaphtho[1,2-e]indole (330)

[Formula 250]

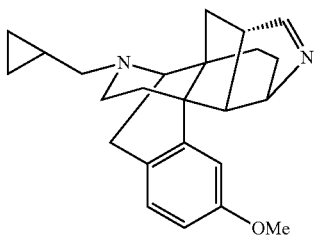

330

Under an argon atmosphere, the compound 77 (146 mg, 0.40 mmol) was dissolved in dichloromethane (3 mL), the solution was added with iodosobenzene (97 mg, 0.44 mmol), and the mixture was stirred at room temperature for 1 hour. The reaction mixture was added with saturated aqueous sodium hydrogencarbonate (15 mL), and the mixture was extracted three times with chloroform. The organic layers were combined, dried over anhydrous sodium sulfate, and then concentrated. The obtained crude product was purified by preparative TLC to give the title compound 330 as colorless oil (108 mg, 74%).

$^1$H NMR (CDCl$_3$, 400 MHz): δ 0.03-0.15 (m, 2H), 0.41-0.53 (m, 2H), 0.73-0.89 (m, 2H), 1.07-1.30 (m, 4H), 1.52-1.63 (m, 1H), 1.83 (dt, J=5.2, 12.8 Hz, 1H), 1.96-2.08 (m, 1H), 2.22-2.38 (m, 2H), 2.51-2.63 (m, 1H), 2.84-2.98 (m, 3H), 3.06-3.21 (m, 2H), 3.25-3.34 (m, 1H), 3.79 (s, 3H), 4.36-4.44 (m, 1H), 6.65-6.74 (m, 2H), 7.03 (d, J=8.8 Hz, 1H), 7.63 (d, J=1.2 Hz, 1H)

(2) Synthesis of (1S,2R,3aR,5aS,6R,11bS,11cS)-14-(cyclopropylmethyl)-2-methyl-10-methoxy-1,2,3a,4,5,6,7,11c-octahydro-1H-6,11b-(iminoethano)-1,5a-methanonaphtho[1,2-e]indole (331)

[Formula 251]

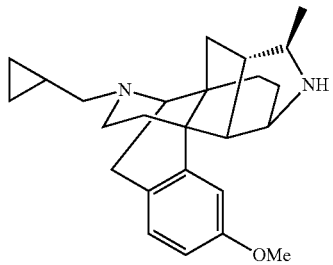

331

Under an argon atmosphere, the compound 330 (36 mg, 0.10 mmol) which was prepared in (1) mentioned above was dissolved in THF (2 mL), the solution was cooled to −78° C., and added with a solution of methyllithium in diethyl ether (1.0 mol/L, 0.5 mL, 0.5 mmol), and the mixture was stirred at −78° C. for 2 hours. The reaction mixture was added with saturated aqueous sodium hydrogencarbonate (5 mL), and the mixture was extracted three times with chloroform. The organic layers were combined, dried over anhydrous sodium sulfate, and then concentrated. The obtained crude product was purified by preparative TLC to give the title compound 331 as colorless oil (22 mg, 58%).

$^1$H NMR (CDCl$_3$, 300 MHz): δ 0.03-0.16 (m, 2H), 0.40-0.53 (m, 2H), 0.72-0.86 (m, 1H), 0.97-1.18 (m, 4H), 1.25 (d, J=6.3 Hz, 3H), 1.34-1.49 (m, 1H), 1.60-1.74 (m, 1H), 1.83-2.06 (m, 2H), 2.21 (dd, J=6.3, 12.6 Hz, 1H), 2.30 (dd, J=6.3, 12.6 Hz, 1H), 2.38-2.59 (m, 2.75-2.97 (m, 4H), 3.06-3.21 (m, 2H), 3.27-3.38 (m, 1H), 3.59 (dt, J=2.7, 6.6 Hz, 1H), 3.76 (s, 3H), 6.66 (dd, J=2.7, 8.4 Hz, 1H), 6.71 (d, J=2.7 Hz, 1H), 7.01 (d, J=8.4 Hz, 1H)

(3) Synthesis of [(1S,2R,3aR,5aS,6R,11bS,11cS)-14-(cyclopropylmethyl)-10-hydroxy-2-methyl-1,2,3a,4,5,6,7,11c-octahydro-3H-6,11b-(iminoethano)-1,5a-methanonaphtho[1,2-e]indol-3-yl](phenyl)methanone (332)

[Formula 252]

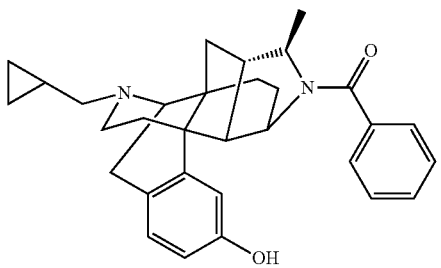

332

According to the methods described in Examples 5 and 6, the title compound 332 (8 mg, 21%) and the hydrochloride thereof were obtained by using the compound 331 (29 mg, 0.078 mmol) which was prepared in (2) mentioned above.

Compound 332 (free base) $^1$H NMR (CDCl$_3$, 300 MHz): δ 0.02-0.17 (m, 2H), 0.40-0.53 (m, 2H), 0.71-0.95 (m, 2H), 0.96 (d, J=6.3, 2.25H), 1.05-2.12 (m, 7.75H), 2.25-2.38 (m, 2H), 2.48-2.73 (m, 2H), 2.76-2.94 (m, 2H), 3.09 (dd, J=6.6, 9.0 Hz, 1H), 3.11-3.22 (m, 1H), 3.27-3.49 (m, 1H), 4.13 (dd, J=6.6, 12.9 Hz, 0.75H), 4.37-4.50 (m, 0.5H), 4.75 (dd, J=7.5, 9.3 Hz, 0.75H), 6.51 (dd, J=2.7, 8.4 Hz, 0.25H), 6.57 (d, J=2.7 Hz, 0.25H), 6.59-6.69 (m, 1.5H), 6.87 (d, J=8.1 Hz, 0.25H), 6.88 (d, J=8.1 Hz, 0.75H), 7.22-7.57 (m, 5H)

Example 248

[(1S,2S,3aR,5aS,6R,11bS,11cS)-14-(Cyclopropylmethyl)-10-hydroxy-2-methyl-1,2,3a,4,5,6,7,11c-octahydro-3H-6,11b-(iminoethano)-1,5a-methanonaphtho[1,2-e]indol-3-yl](phenyl)methanone (334)

(1) Synthesis of (1S,2S,3aR,5aS,6R,11bS,11cS)-14-(cyclopropylmethyl)-2-methyl-10-methoxy-1,2,3a,4,5,6,7,11c-octahydro-1H-6,11b-(iminoethano)-1,5a-methanonaphtho[1,2-e]indole (333)

[Formula 253]

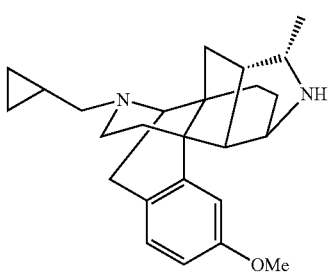

333

Under an argon atmosphere, the compound 331 (35 mg, 0.093 mmol) which was prepared in Example 247, (2) was dissolved in dichloromethane (2 mL), the solution was added with iodosobenzene (33 mg, 0.15 mmol), and the mixture was stirred at room temperature for 30 minutes. The reaction mixture was added with methanol (3 mL), and sodium borohydride (19 mg, 0.50 mmol), and the mixture was stirred at room temperature for 30 minutes. The reaction mixture was added with saturated aqueous sodium hydrogencarbonate (5 mL), and the mixture was extracted three times with chloroform. The organic layers were combined, dried over anhydrous sodium sulfate, and then concentrated. The obtained crude product was purified by preparative TLC to give the title compound 333 as colorless oil (20 mg, 56%).

$^1$H NMR (CDCl$_3$, 300 MHz): δ 0.03-0.17 (m, 2H), 0.41-0.56 (m, 2H), 0.67-0.89 (m, 2H), 1.03 (dd, J=7.2, 15.0 Hz, 1H), 1.11-1.32 (m, 2H), 1.24 (d, J=6.6 Hz, 3H), 1.45-1.73 (m, 2H), 1.90-2.06 (m, 2H), 2.31 (d, J=6.3 Hz, 2H), 2.45-2.58 (m, 1H), 2.66-2.79 (m, 1H), 2.82-3.00 (m, 4H), 3.11-3.19 (m, 1H), 3.37 (br s, 1H), 3.40-3.54 (m, 1H), 3.61-3.71 (m, 1H), 3.76 (s, 3H), 6.62-6.69 (m, 2H), 7.02 (d, J=8.4 Hz, 1H)

(2) Synthesis of [(1S,2S,3aR,5aS,6R,11bS,11cS)-14-(cyclopropylmethyl)-10-hydroxy-2-methyl-1,2,3a,4,5,6,7,11c-octahydro-3H-6,11b-(iminoethano)-1,5a-methanonaphtho[1,2-e]indol-3-yl](phenyl)methanone (334)

[Formula 254]

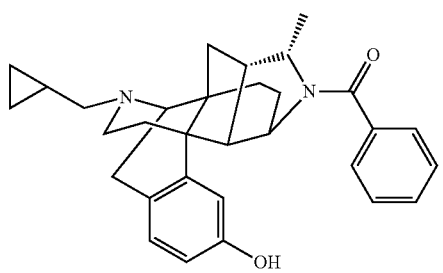

According to the methods described in Example 5 and 6, the title compound 334 (13 mg, 54%) and the hydrochloride thereof were obtained by using the compound 333 (20 mg, 0.052 mmol) which was prepared in (1) mentioned above.

Compound 334 (free base) $^1$H NMR (CDCl$_3$, 300 MHz): δ 0.03-0.19 (m, 2H), 0.40-0.58 (m, 2H), 0.71-1.81 (m, 11H), 1.83-2.12 (m, 2H), 2.21-2.41 (m, 2H), 2.47-2.62 (m, 1H), 2.70-3.00 (m, 3H), 3.02-3.22 (m, 2H), 3.80-4.06 (m, 0.5H), 4.22-4.80 (m, 1.5H), 6.31-6.72 (m, 2H), 6.91 (d, J=8.4 Hz, 1H), 7.21-7.50 (m, 5H)

Example 249

(1S,2S,3aR,5aS,6R,11bS,11cS)-14-(Cyclopropylmethyl)-10-methoxy-3-methyl-2-(naphthalen-2-yl)-1,2,3a,4,5,6,7,11c-octahydro-1H-6,11b-(iminoethano)-1,5a-methanonaphtho[1,2-e]indole (337)

(1) Synthesis of (1S,2R,3aR,5aS,6R,11bS,11cS)-14-(cyclopropylmethyl)-10-methoxy-2-(naphthalen-2-yl)-1,2,3a,4,5,6,7,11c-octahydro-1H-6,11b-(iminoethano)-1,5a-methanonaphtho[1,2-e]indole (335)

[Formula 255]

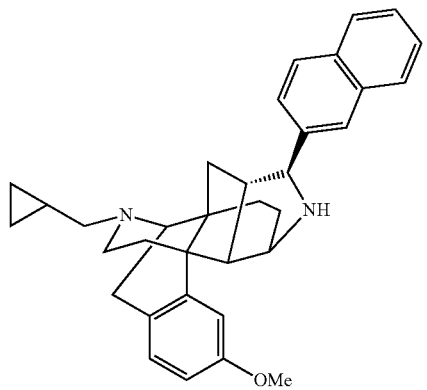

Under an argon atmosphere, 2-bromonaphthalene (249 mg, 1.2 mmol) was dissolved in THF (1 mL), the solution was cooled to −78° C., and added with a solution of n-butyllithium in hexane (1.63 mol/L, 613 µL, 1.0 mmol), and the mixture was stirred at −78° C. for 5 minutes. The reaction mixture was cooled to −78° C., and added with a solution of the compound 330 (73 mg, 0.20 mmol) which was prepared in Example 247, (1) in THF (2 mL), and the mixture was stirred at −78° C. for 2 hours. The reaction mixture was added with saturated aqueous sodium hydrogencarbonate (10 mL), and the mixture was extracted three times with chloroform. The organic layers were combined, dried over anhydrous sodium sulfate, and then concentrated. The obtained crude product was purified by preparative TLC to give the title compound 335 as colorless oil (23 mg, 23%).

$^1$H NMR (CDCl$_3$, 300 MHz): δ 0.02-0.18 (m, 2H), 0.38-0.54 (m, 2H), 0.72-0.90 (m, 1H), 0.96-1.32 (m, 3H), 1.42 (d, J=13.5 Hz, 1H), 1.50-1.67 (m, 1H), 1.69-1.97 (m, 2H), 2.01 (dt, J=3.0, 12.3 Hz, 1H), 2.22-2.40 (m, 2H), 2.54 (dd, J=4.2, 11.4 Hz, 1H), 2.79-3.00 (m, 4H), 3.06 (t, J=7.5 Hz, 1H), 3.17 (d, J=4.2 Hz, 1H), 3.33 (t, J=11.4 Hz, 1H), 3.78 (s, 3H), 3.93 (t, J=6.6 Hz, 1H), 4.52 (d, J=3.0 Hz, 1H), 6.69 (dd, J=2.7, 8.4 Hz, 1H), 6.76 (d, J=2.7 Hz, 1H), 7.03 (d, J=8.1 Hz, 1H), 7.36-7.52 (m, 2H), 7.56 (d, J=8.7 Hz, 1H), 7.72-7.91 (m, 4H)

(2) Synthesis of (1S,2S,3aR,5aS,6R,11bS,11cS)-14-(cyclopropylmethyl)-10-methoxy-2-(naphthalen-2-1,2,3a,4,5,6,7,11c-octahydro-1H-6,11b-(iminoethano)-1,5a-methanonaphtho[1,2-e]indole (336)

[Formula 256]

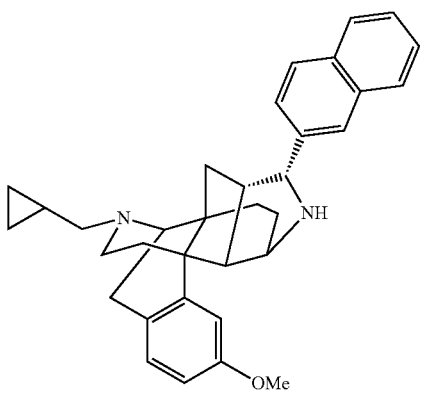

336

According to the method described in Example 248, (1), the title compound 336 was obtained as colorless oil (11 mg, 54%) by using the compound 335 (21 mg, 0.054 mmol) which was prepared in (1) mentioned above.

¹H NMR (CDCl₃, 300 MHz): δ −0.05-0.17 (m, 2H), 0.31-0.53 (m, 2H), 0.63-1.01 (m, 3H), 1.09-1.32 (m, 2H), 1.53-1.69 (m, 2H), 1.90-2.38 (m, 4H), 2.44-2.59 (m, 1H), 2.65-2.98 (m, 4H), 3.06 (br s, 1H), 3.21-3.34 (m, 1H), 3.80 (s, 3H), 3.87 (dd, J=4.5, 9.6 Hz, 1H), 4.82 (d, J=4.8 Hz, 1H), 6.68 (dd, J=2.4, 8.4 Hz, 1H), 6.71 (d, J=2.4 Hz, 1H), 7.03 (d, J=8.4 Hz, 1H), 7.36-7.52 (m, 2H), 7.53 (dd, J=1.5, 8.7 Hz, 1H), 7.70-7.90 (m, 3H), 7.95 (s, 1H)

(3) Synthesis of (1S,2S,3aR,5aS,6R,11bS,11cS)-14-(cyclopropylmethyl)-10-hydroxy-3-methyl-2-(naphthalen-2-yl)-1,2,3a,4,5,6,7,11c-octahydro-1H-6,11b-(iminoethano)-1,5a-methanonaphtho[1,2-e]indole (337)

[Formula 257]

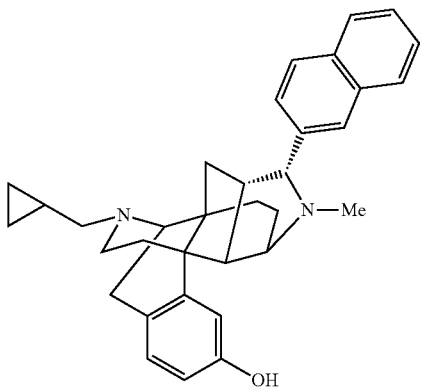

337

According to the method described in Example 58, the title compound 337 (7 mg, 36%) and the hydrochloride thereof were obtained by using the compound 336 (18 mg, 0.037 mmol) which was prepared in (2) mentioned above.

Compound 337 (free base) ¹H NMR (CDCl₃, 300 MHz): δ −0.08-0.08 (m, 2H), 0.28-0.42 (m, 2H), 0.55-0.82 (m, 2H), 1.01-1.33 (m, 4H), 1.54-1.67 (m, 1H), 1.71-1.87 (m, 1H), 1.88-2.03 (m, 2H), 2.12-2.26 (m, 2H), 2.36 (s, 3H), 2.41-2.58 (m, 2H), 2.77-3.18 (m, 6H), 4.13 (d, J=4.2 Hz, 1H), 6.58 (dd, J=2.7, 8.1 Hz, 1H), 6.63 (d, J=2.4 Hz, 1H), 6.97 (d, J=8.1 Hz, 1H), 7.38-7.52 (m, 2H), 7.52 (dd, J=1.5, 8.4 Hz, 1H), 7.76-7.92 (m, 4H)

Example 250

Synthesis of [(1S,5aS,6R,11bR)-10-hydroxy-14-[2-(pyridin-2-yl)ethyl]-4,5,6,7-tetrahydro-1H-6,11b-(iminoethano)-1,5a-methanonaphtho[1,2-e]indol-3(2H,3aH,11cH)-yl](phenyl)methanone (338)

[Formula 258]

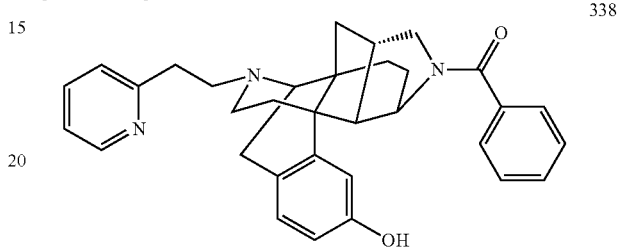

338

According to the methods described in Example 103, (1) and Example 6, the title compound 338 and the hydrochloride thereof (17 mg, 42%) were obtained by using the compound 81 (30 mg, 0.07 mmol) and toluene-4-sulfonic acid 2-(pyridin-2-yl)ethyl ester (60 mg, 0.22 mmol).

Compound 338 (hydrochloride) ¹H NMR (CD₃OD, 400 MHz): δ 0.75-1.10 (m, 1H), 1.50-2.00 (m, 5H), 2.05-2.30 (m, 1H), 2.80-2.95 (m, 1H), 3.10-3.85 (m, 12H), 4.00-4.15 (m, 1H), 4.20-4.30 (m, 0.7H), 4.70-5.00 (m, 0.3H), 6.60 (d, J=2.4 Hz, 0.3H), 6.66 (dd, J=2.4, 8.3 Hz, 0.3H), 6.75 (dd, J=2.4, 8.3 Hz, 0.7H), 6.81 (d, J=2.4 Hz, 0.7H), 7.08 (d, J=8.3 Hz, 0.3H), 7.16 (d, J=8.3 Hz, 0.7H), 7.35-7.50 (m, 5H), 7.97 (t, J=6.8 Hz, 1H), 8.04-8.11 (m, 1H), 8.50-8.59 (m, 1H), 8.82 (d, J=5.4 Hz, 1H)

Example 251

Synthesis of [(1S,5aS,6R,11bR)-10-hydroxy-14-[2-(pyridin-3-yl)ethyl]-4,5,6,7-tetrahydro-1H-6,11b-(iminoethano)-1,5a-methanonaphtho[1,2-e]indol-3(2H,3aH,11cH)-yl](phenyl)methanone (339)

[Formula 259]

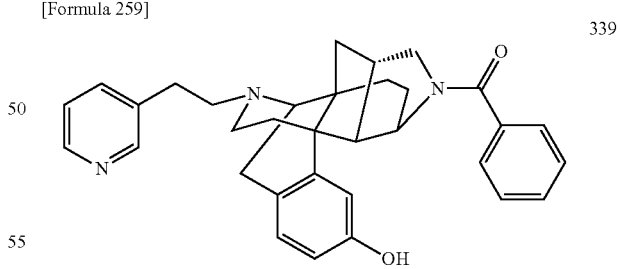

339

According to the methods described in Example 103, (1) and Example 6, the title compound 339 and the hydrochloride thereof (4.6 mg, 17%) were obtained by using the compound 81 (20 mg, 0.048 mmol) and methane-4-sulfonic acid 2-(pyridin-3-yl)ethyl ester (29 mg, 0.14 mmol).

Compound 339 (hydrochloride) ¹H NMR (CD₃OD, 400 MHz): δ 0.82-1.11 (m, 1H), 1.14-1.25 (m, 0.3H), 1.47-2.05 (m, 4.7H), 2.16-2.33 (m, 1H), 2.77-2.95 (m, 1H), 3.11-3.82 (m, 12.3H), 4.02-4.15 (m, 1H), 4.20-4.33 (m, 0.7H), 6.59 (d, J=2.4 Hz, 0.3H), 6.64 (dd, J=2.4, 8.3 Hz, 0.3H), 6.74 (dd, J=2.4, 8.3 Hz, 0.7H), 6.79 (d, J=2.4 Hz, 0.7H), 7.07 (d, J=8.3 Hz, 0.3H), 7.15 (d, J=8.3 Hz, 0.7H), 7.38-7.54 (m, 5H), 8.11 (dd, J=5.8, 7.8 Hz, 1H), 8.73 (d, J=7.8 Hz, 1H), 8.81 (d, J=5.9 Hz, 1H), 8.99 (s, 1H)

Example 252

Synthesis of 2-[(1S,5aS,6R,11bR)-3-benzoyl-10-hydroxy-2,3,3a,4,5,6,7,11c-octahydro-1H-6,11b-(iminoethano)-1,5a-methanonaphtho[1,2-e]indol-14-yl]-1-phenylethanone (340)

[Formula 260]

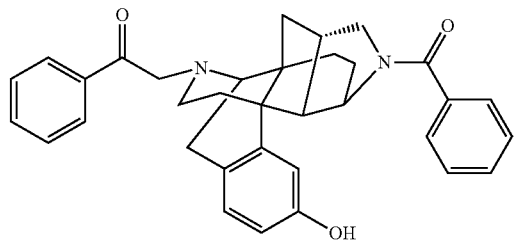

340

According to the methods described in Example 103, (1) and Example 104, (4), the title compound 340 and the hydrochloride thereof were obtained by using the compound 121 (30 mg, 0.06 mmol) and phenacyl chloride (14 mg, 0.09 mmol). Compound 340 (hydrochloride) $^1$H NMR (CD$_3$OD, 400 MHz): δ 0.75-1.10 (m, 2H), 1.50-1.95 (m, 4H), 2.20-2.35 (m, 1H), 3.00-3.25 (m, 4H), 3.25-3.80 (m, 5H), 3.94 (dd, J=6.3, 13.2 Hz, 1H), 4.28 (dd, J=8.8, 13.2 Hz, 0.7H), 4.70-5.00 (m, 1.3H), 5.27 (d, J=18.1 Hz, 0.3H), 5.29 (d, J=18.1 Hz, 0.7H), 6.60 (d, J=2.4 Hz, 0.3H), 6.67 (dd, J=2.4, 8.3 Hz, 0.3H), 6.76 (dd, J=2.4, 8.3 Hz, 0.7H), 6.81 (d, J=2.4 Hz, 0.7H), 7.07 (d, J=8.3 Hz, 0.3H), 7.15 (d, J=8.3 Hz, 0.7H), 7.35-7.50 (m, 5H), 7.61 (t, J=7.3 Hz, 2H), 7.74 (d, J=7.3 Hz, 1H), 8.09 (d, J=7.3 Hz, 2H).

Example 253

Synthesis of methyl 2-[(1S,5aS,6R,11bR)-3-benzoyl-10-hydroxy-2,3,3a,4,5,6,7,11c-octahydro-1H-6,11b-(iminoethano)-1,5a-methanonaphtho[1,2-e]indol-14-yl]acetate (341)

[Formula 261]

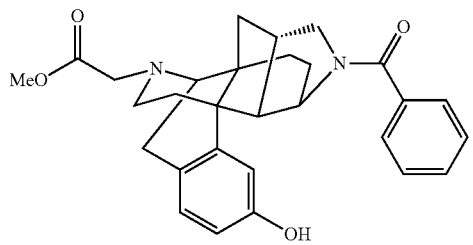

341

According to the methods described in Example 103, (1) and Example 6, the title compound 341 and the hydrochloride thereof (17.9 mg, 61%) were obtained by using the compound 121 (30 mg, 0.058 mmol) and methyl 2-bromoacetate (8 μL, 0.087 mmol).

Compound 341 (hydrochloride) $^1$H NMR (CD$_3$OD, 400 MHz): δ 0.78-1.07 (m, 1H), 1.13-1.25 (m, 0.3H), 1.50-1.93 (m, 4.7H), 2.13-2.30 (m, 1H), 2.85-3.09 (m, 2H), 3.12-3.55 (m, 5.6H), 3.62-3.81 (m, 1.7H), 3.89 (s, 3H), 3.98-4.15 (m, 2H), 4.20-4.30 (m, 0.7H), 4.40-4.51 (m, 1H), 6.57 (d, J=2.4 Hz, 0.3H), 6.66 (dd, J=2.4, 8.3 Hz, 0.3H), 6.74 (dd, J=2.4, 8.3 Hz, 0.7H), 6.79 (d, J=2.4 Hz, 0.7H), 7.05 (d, J=8.3 Hz, 0.3H), 7.13 (d, J=8.3 Hz, 0.7H), 7.37-7.52 (m, 5H)

Example 254

Synthesis of [(1S,5aS,6R,11bR)-10-hydroxy-14-[2-(methylsulfonyl)ethyl]-4,5,6,7-tetrahydro-1H-6,11b-(iminoethano)-1,5a-methanonaphtho[1,2-e]indol-3(2H,3aH,11cH)-yl](phenyl)methanone (342)

[Formula 262]

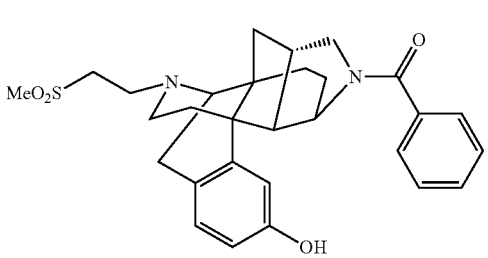

342

According to the methods described in Example 12 and Example 104, (4), the title compound 342 and the hydrochloride thereof were obtained by using the compound 121 (30 mg, 0.06 mmol) and 1-chloro-2-(methylsulfonyl)ethane (13 mg, 0.09 mmol).

Compound 342 (hydrochloride) $^1$H NMR (CD$_3$OD, 400 MHz): δ 0.75-1.10 (m, 1H), 1.50-2.00 (m, 5H), 2.10-2.25 (m, 1H), 2.75-2.95 (m, 2H), 3.16 (s, 3H), 3.10-3.60 (m, 5H), 3.60-3.95 (m, 6H), 4.06 (dd, J=6.3, 13.2 Hz, 1H), 4.20-4.30 (m, 0.7H), 4.70-4.80 (m, 0.3H), 6.58 (d, J=2.4 Hz, 0.3H), 6.66 (dd, J=2.4, 8.3 Hz, 0.3H), 6.75 (dd, J=2.4, 8.3 Hz, 0.7H), 6.79 (d, J=2.4 Hz, 0.7H), 7.07 (d, J=8.3 Hz, 0.3H), 7.14 (d, J=8.3 Hz, 0.7H), 7.35-7.50 (m, 5H)

Example 255

3-[(1S,5aS,6R,11bR)-3-Benzoyl-10-hydroxy-2,3,3a,4,5,6,7,11c-octahydro-1H-6,11b-(iminoethano)-1,5a-methanonaphtho[1,2-e]indol-14-yl]propanamide (344)

(1) Synthesis of 3-[(1S,5aS,6R,11bR)-3-benzoyl-10-methoxy-2,3,3a,4,5,6,7,11c-octahydro-1H-6,11b-(iminoethano)-1,5a-methanonaphtho[1,2-e]indol-14-yl]propanamide (343)

[Formula 263]

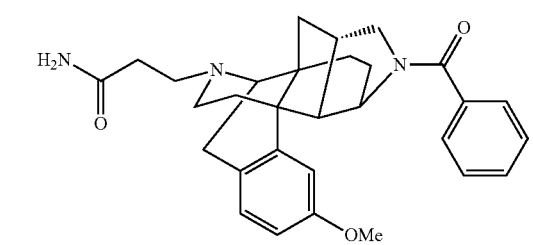

343

Under an argon atmosphere, the compound 81 (20 mg, 0.048 mmol) was dissolved in toluene (1 mL) and methanol (0.1 mL), the solution was added with acrylamide (5 mg, 0.072 mmol), and the mixture was refluxed for 22 hours. The reaction mixture was added with water, the mixture was extracted with chloroform, and then the organic layer was washed with saturated brine. The organic layer was dried over anhydrous sodium sulfate, and concentrated. The obtained crude product was purified by preparative TLC to give the title compound (15.6 mg, 67%).

$^1$H NMR (CDCl$_3$, 400 MHz): δ 0.74-1.15 (m, 2H), 1.15-1.97 (m, 4H), 2.00-2.16 (m, 1H), 2.28-2.46 (m, 2H), 2.56-2.59 (m, 1H), 2.63-2.82 (m, 2H), 2.92-3.19 (m, 6.2H), 3.51-3.76 (m, 2.4H), 3.69 (s, 1.2H), 3.79 (s, 1.8H), 4.15-4.33 (m, 0.8H), 4.76-4.86 (m, 0.6H), 5.47 (br s, 1H), 6.53 (d, J=2.4 Hz, 0.4H), 6.64 (dd, J=2.4, 8.3 Hz, 0.4H), 6.69-6.74 (m, 1.2H), 7.00 (d, J=8.3 Hz, 0.4H), 7.06 (d, J=8.3 Hz, 0.6H), 7.37-7.47 (m, 5H), 7.66 (br s, 1H)

(2) Synthesis of 3-[(1S,5aS,6R,11bR)-3-benzoyl-10-hydroxy-2,3,3a,4,5,6,7,11c-octahydro-1H-6,11b-(iminoethano)-1,5a-methanonaphtho[1,2-e]indol-14-yl]propanamide (344)

[Formula 264]

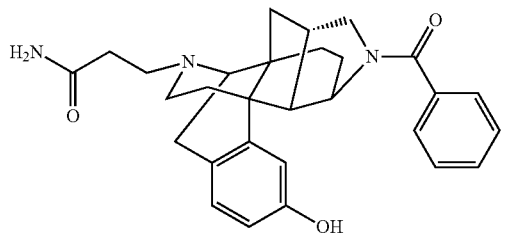

344

According to the method described in Example 6, the title compound 344 and the hydrochloride thereof (2.3 mg, 14%) were obtained by using the compound 343 (15.6 mg, 0.032 mmol) which was prepared in (1) mentioned above.

Compound 344 (hydrochloride) $^1$H NMR (CD$_3$ OD, 400 MHz): δ 0.75-1.06 (m, 1H), 1.46-1.95 (m, 5H), 2.08-2.22 (m, 1H), 2.68-2.92 (m, 4H), 3.09-3.80 (m, 9.3H), 3.88-3.99 (m, 1H), 4.19-4.31 (m, 0.7H), 6.58 (d, J=2.4 Hz, 0.3H), 6.64 (dd, J=2.4, 8.3 Hz, 0.3H), 6.74 (dd, J=2.4, 8.3 Hz, 0.7H), 6.79 (d, J=2.4 Hz, 0.7H), 7.05 (d, J=8.3 Hz, 0.3H), 7.13 (d, J=8.3 Hz, 0.7H), 7.34-7.54 (m, 5H)

Example 256

Synthesis of [(1S,5aS,6R,11bR)-10-hydroxy-14-((S)-3,3,3-trifluoro-2-hydroxypropyl)-4,5,6,7-tetrahydro-1H-6,11b-(iminoethano)-1,5a-methanonaphtho[1,2-e]indol-3(2H,3aH,11cH)-yl](phenyl)methanone (345)

[Formula 265]

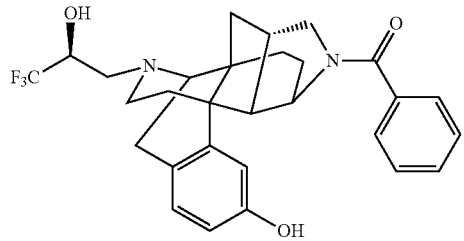

345

According to the method described in Example 107, the title compound 345 and the hydrochloride thereof (10 mg, 26%) were obtained by using the compound 81 (30 mg, 0.07 mmol) and (S)-2-(trifluoromethyl)oxirane (0.1 mL).

Compound 345 (hydrochloride) $^1$H NMR (CD$_3$ OD, 400 MHz): δ 0.80-1.10 (m, 2H), 1.50-2.00 (m, 4H), 2.10-2.25 (m, 1H), 2.80-3.10 (m, 2H), 3.10-3.35 (m, 4H), 3.40-3.95 (m, 6.3H), 4.20-4.30 (m, 0.7H), 4.60-4.90 (m, 1H), 6.58 (d, J=2.4 Hz, 0.3H), 6.66 (dd, J=2.4, 8.3 Hz, 0.3H), 6.75 (dd, J=2.4, 8.3 Hz, 0.7H), 6.79 (d, J=2.4, 8.3 Hz, 0.7H), 7.07 (d, J=8.3 Hz, 0.3H), 7.14 (d, J=8.3 Hz, 0.7H), 7.36-7.50 (m, 5H)

Example 257

Synthesis of [(1S,5aS,6R,11bR)-10-hydroxy-14-((S)-2-hydroxyhexyl)-4,5,6,7-tetrahydro-1H-6,11b-(iminoethano)-1,5a-methanonaphtho[1,2-e]indol-3(2H,3aH,11cH)-yl](phenyl)methanone (346)

[Formula 266]

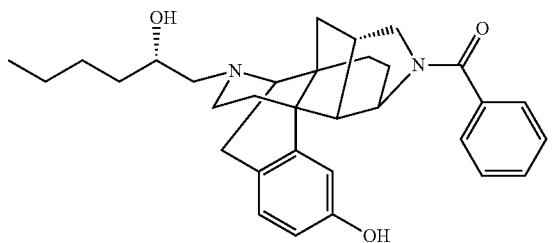

346

According to the method described in Example 107, the title compound 346 and the hydrochloride thereof (10 mg, 27%) were obtained by using the compound 81 (30 mg, 0.07 mmol) and (S)-2-butyloxirane (0.1 mL).

Compound 346 (hydrochloride) $^1$H NMR (CD$_3$ OD, 400 MHz): δ 0.75-1.05 (m, 4H), 1.10-1.95 (m, 11H), 2.10-2.25 (m, 1H), 2.75-3.00 (m, 2H), 3.10-3.30 (m, 4H), 3.35-3.80 (m, 5H), 3.90-4.10 (m, 2H), 4.20-4.30 (m, 0.7H), 4.70-4.80 (m, 0.3H), 6.57 (d, J=2.4 Hz, 0.3H), 6.64 (dd, J=2.4, 8.3 Hz, 0.3H), 6.74 (dd, J=2.4, 8.3 Hz, 0.7H), 6.78 (d, J=2.4 Hz, 0.7H), 7.05 (d, J=8.3 Hz, 0.3H), 7.13 (d, J=8.3 Hz, 0.7H), 7.30-7.50 (m, 5H)

Example 258

Synthesis of [(1S,5aS,6R,11bR)-10-hydroxy-14-[(3-methyloxetan-3-yl)methyl]-4,5,6,7-tetrahydro-1H-6,11b-(iminoethano)-1,5a-methanonaphtho[1,2-e]indol-3(2H,3aH,11cH)-yl](phenyl)methanone (347)

[Formula 267]

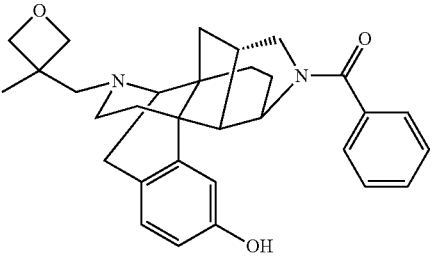

347

According to the methods described in Example 103, (1) and Example 107, the title compound 347 was obtained by using the compound 121 (24 mg, 0.047 mmol) and toluene-4-sulfonic acid (3-methyloxetan-3-yl)methyl ester (18 mg, 0.07 mmol).

Compound 347 (free base) $^1$H NMR (CDCl$_3$, 400 MHz): δ 0.75-1.78 (m, 9H), 1.78-1.95 (m, 1H), 2.12-2.32 (m, 2H), 2.46-2.56 (m, 1H), 2.60-2.72 (m, 2H), 2.85-3.16 (m, 4H), 3.30-3.44 (m, 1H), 3.52-3.72 (m, 1.7H), 4.14-4.26 (m, 0.6H), 4.26-4.35 (m, 2H), 4.43-4.53 (m, 2H), 4.82 (t, J=6.8 Hz, 0.7H), 5.74 (br s, 0.3H), 6.48 (d, J=2.4 Hz, 0.3H), 6.54 (dd, J=2.4, 8.3 Hz, 0.3H), 6.63 (dd, J=2.4, 8.3 Hz, 0.7H), 6.69 (d, J=2.4 Hz, 0.7H), 6.82 (br s, 0.7H), 6.93 (d, J=8.3 Hz, 0.3H), 6.95 (d, J=8.3 Hz, 0.7H), 7.30-7.49 (m, 5H)

Example 259

Synthesis of (1S,5aS,6R,11bR)-14-(2,2-difluoro-2-phenylethyl)-10-hydroxy-N-isopropyl-3a,4,5,6,7,11c-hexahydro-1H-6,11b-(iminoethano)-1,5a-methanonaphtho[1,2-e]indole-3(2H)-carboxamide (348)

[Formula 268]

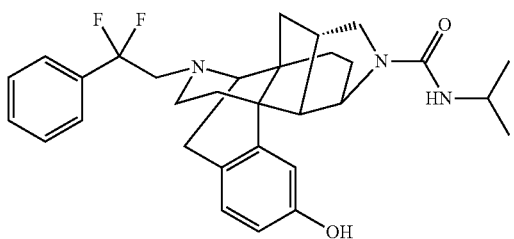

348

According to the method described in Example 122, the title compound 348 and the hydrochloride thereof (10 mg, 39%) were obtained by using the compound 130 (20 mg, 0.04 mmol) and isopropyl isocyanate (5 μL, 0.05 mmol).

Compound 348 (free base) $^1$H NMR (CDCl$_3$, 400 MHz): δ 0.70-0.85 (m, 1H), 0.85-1.05 (m, 2H), 1.08 (d, J=5.9 Hz, 3H), 1.10 (d, J=5.9 Hz, 3H), 1.15-1.30 (m, 3H), 1.65-1.80 (m, 1H), 2.26-2.38 (m, 2H), 2.70-3.15 (m, 8H), 3.30-3.45 (m, 1H), 3.65-3.80 (m, 1H), 3.90-4.05 (m, 2H), 4.11 (br s, 1H), 6.56 (d, J=2.4 Hz, 1H), 6.61 (dd, J=2.4, 8.3 Hz, 1H), 6.91 (d, J=8.3 Hz, 1H), 7.35-7.55 (m, 5H), 7.61 (br s, 1H)

Example 260

Synthesis of (1S,5aS,6R,11bR)-14-(2,2-difluoro-2-phenylethyl)-3-(pyridin-2-yl)-2,3,3a,4,5,6,7,11c-octahydro-1H-6,11b-(iminoethano)-1,5a-methanonaphtho[1,2-e]indol-10-el (349)

[Formula 269]

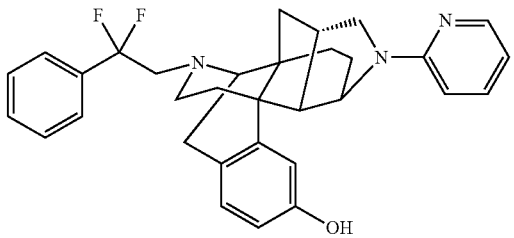

349

According to the method described in Example 164, the title compound 349 and the hydrochloride thereof (10 mg, 39%) were obtained by using the compound 130 (20 mg, 0.04 mmol).

Compound 349 (free base) $^1$H NMR (CDCl$_3$, 400 MHz): δ 0.70-0.85 (m, 1H), 1.20-1.70 (m, 5H), 1.75-1.85 (m, 1H), 2.30-2.35 (m, 2H), 2.70-3.20 (m, 8H), 3.43 (d, J=10.2 Hz, 1H), 3.60-3.70 (m, 1H), 4.50-4.66 (m, 1H), 6.32 (d, J=8.8 Hz, 1H), 6.48 (t, J=6.3 Hz, 1H), 6.59 (dd, J=2.4, 8.3 Hz, 1H), 6.67 (d, J=2.4 Hz, 1H), 6.85 (d, J=8.3 Hz, 1H), 7.35-7.46 (m, 4H), 7.46-7.50 (m, 2H), 8.00-8.10 (m, 1H)

Example 261

(1S,5aS,6R,11bR)-14-((S)-2-Hydroxypropyl)-3-(pyridin-2-yl)-2,3,3a,4,5,6,7,11c-octahydro-1H-6,11b-(iminoethano)-1,5a-methanonaphtho[1,2-e]indol-10-ol (351)

(1) Synthesis of (2S)-1-[(1S,5aS,6R,11bR)-10-methoxy-2,3,3a,4,5,6,7,11c-octahydro-1H-6,11b-(iminoethano)-1,5a-methanonaphtho[1,2-e]indol-14-yl] propan-2-ol (350)

[Formula 270]

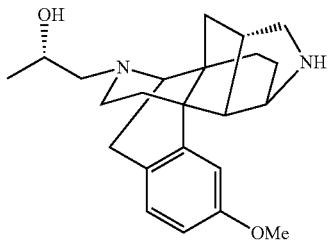

350

According to the methods described in Example 107 and Example 106, (4), a crude product of the title compound was obtained by using the compound 127 (200 mg, 0.41 mmol) and (S)-(−)-propylene oxide (1 mL).

(2) Synthesis of (1S,5aS,6R,11bR)-14-((S)-2-hydroxypropyl)-3-(pyridin-2-yl)-2,3,3a,4,5,6,7,11c-octahydro-1H-6,11b-(iminoethano)-1,5a-methanonaphtho[1,2-e]indol-10-ol (351)

[Formula 271]

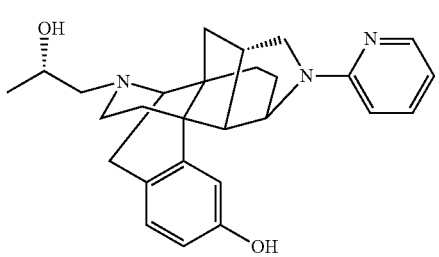

351

According to the method described in Example 164, the title compound 351 (7.2 mg, 22%) and the hydrochloride thereof were obtained by using the crude product which was prepared in (1) mentioned above (28.3 mg, 0.077 mmol) and 2-bromopyridine (11 μL, 0.12 mmol).

Compound 351 (hydrochloride) $^1$H NMR (CD$_3$ OD, 400 MHz): δ 1.00-1.14 (m, 1H), 1.24-1.41 (m, 1H), 1.28 (d, J=6.3 Hz, 3H), 1.58-1.76 (m, 3H), 1.84-1.96 (m, 1H), 2.23-2.35 (m, 1H), 2.85-2.96 (m, 1H), 3.03-3.16 (m, 1H), 3.18-3.40 (m, 4H), 3.41-3.58 (m, 3H), 3.78-3.87 (m, 1H), 3.98-4.04 (m, 1H), 4.14 (d, J=5.9 Hz, 1H), 4.20-4.32 (m, 1H), 4.54-4.62 (m, 1H), 6.76 (dd, J=2.4, 8.3 Hz, 1H), 6.81 (d, J=2.4 Hz, 1H), 6.91-6.98 (m, 1H), 7.08 (d, J=9.3 Hz, 1H), 7.16 (d, J=8.3 Hz, 1H), 7.79-7.92 (m, 1H), 7.92-8.03 (m, 1H)

Example 262

(1) Opioid Receptor Functional Test

Functional activities of the compounds of the present invention for the μ, δ, and κ opioid receptors were investigated.

Methods:

The test was performed according to a prescribed method by using Lance Ultra cAMP Kit (Perkin-Elmer). The agonist activities were evaluated as follows. The CHO cells expressing each opioid receptor (μ, δ, or κ) and a test compound were reacted in an assay buffer (1×HBSS, 1 M HEPES, pH 7.4, 250 mM IBMX (isobutylmethylxanthine), 7.5% BSA) for 30 minutes in the presence of 10 μM forskolin. Then, the cAMP detection reagent included in the kit was added, and after 1 hour, time-resolved fluorescence measurements were performed by using the EnVision plate reader (Perkin-Elmer). A dose-responce curve of the test compound was obtained from fluorescence values measured at 665 nm, and $EC_{50}$ value and $E_{max}$ value were calculated. The $E_{max}$ value was calculated as a ratio of the maximum responce of the test compound with respect to the maximum responce of each control agent (SNC80 for δ, DAMGO for μ, U-69593 for κ) taken as 100%.

(2) Results

The results are shown in Tables 24 to 26.
SNC80:
(+)-4-[(αR)-α-((2S,5R)-4-Allyl-2,5-dimethyl-1-piperazinyl)-3-methoxybenzyl]-N,N-diethylbenzamide
DAMGO:
[D-Ala$^2$,N-MePhe$^4$,Gly-ol]enkephalin
U-69593:
(+)-(5a,7a,8β)-N-Methyl-N-[7-(1-pyrrolidinyl)-1-oxaspiro[4.5]dec-8-yl]benzeneacetamide

TABLE 24

| Compound[1] | δ Receptor | | μ Receptor | | κ Receptor | |
|---|---|---|---|---|---|---|
| | $EC_{50}$ value (nM) | $E_{max}$ (%) | $EC_{50}$ value (nM) | $E_{max}$ (%) | $EC_{50}$ value (nM) | $E_{max}$ (%) |
| Compound 10 (Example 6) | <1 | 127 | N.C. | (3.9)$^a$ | N.C. | (2.9)$^a$ |
| Compound 12 (Example 8) | <1 | 94 | >1 | 103 | >10 | 96 |
| Compound 27 (Example 23) | <10 | 95 | >50 | 34 | N.C. | (33)$^a$ |
| Compound 31 (Example 27) | <10 | 46 | N.C. | (14)$^a$ | >1 | 23 |
| Compound 50 (Example 46) | <1 | 82 | N.C. | (5.4)$^a$ | N.C. | (12)$^a$ |
| Compound 57 (Example 53) | <10 | 63 | N.C. | (3.0)$^a$ | N.C. | (25)$^a$ |
| Compound 58 (Example 54) | <10 | 66 | >1 | 54 | N.C. | (19)$^a$ |
| Compound 68 (Example 61) | <10 | 90 | >100 | 56 | >100 | 99 |
| Compound 78 (Example 68) | <1 | 83 | N.C. | (4.7)$^a$ | N.C. | (5.5)$^a$ |
| Compound 79 (Example 69) | <1 | 75 | N.C. | (8.8)$^a$ | N.C. | (9.6)$^a$ |
| Compound 83 (Example 73) | <1 | 99 | N.C. | (7.9)$^a$ | N.C. | (2.1)$^a$ |
| Compound 84 (Example 74) | <10 | 99 | N.C. | (20)$^a$ | N.C. | (5.9)$^a$ |

TABLE 25

| Compound[1] | δ Receptor | | μ Receptor | | κ Receptor | |
|---|---|---|---|---|---|---|
| | $EC_{50}$ value (nM) | $E_{max}$ (%) | $EC_{50}$ value (nM) | $E_{max}$ (%) | $EC_{50}$ value (nM) | $E_{max}$ (%) |
| Compound 155 (Example 123) | <1 | 91 | N.C. | (3.0)$^a$ | >1 | 47 |
| Compound 159 (Example 126) | <1 | 76 | N.C. | (2.8)$^a$ | <1 | 37 |
| Compound 167 (Example 134) | <1 | 96 | N.C. | (4.6)$^a$ | >1 | 22 |
| Compound 195 (Example 147) | <10 | 92 | N.C. | (5.6)$^a$ | >1 | 27 |
| Compound 196 (Example 148) | <10 | 67 | N.C. | (7.6)$^a$ | >1 | 12 |
| Compound 221 (Example 164) | <1 | 90 | >1 | 30 | >1 | 42 |
| Compound 222 (Example 165) | <10 | 105 | >100 | 52 | N.C. | (43)$^a$ |
| Compound 241 (Example 183) | <10 | 81 | N.C. | (11)$^a$ | >1 | 33 |
| Compound 242 (Example 184) | <50 | 68 | N.C. | (9.2)$^a$ | >10 | 47 |
| Compound 283 (Example 217) | <50 | 91 | >500 | 101 | N.C. | (11)$^a$ |
| Compound 285 (Example 219) | <10 | 81 | >10 | 48 | >100 | 78 |
| Compound 293 (Example 225) | <10 | 91 | >50 | 17 | >50 | 51 |

TABLE 26

| Compound[1] | δ Receptor | | μ Receptor | | κ Receptor | |
|---|---|---|---|---|---|---|
| | $EC_{50}$ value (nM) | $E_{max}$ (%) | $EC_{50}$ value (nM) | $E_{max}$ (%) | $EC_{50}$ value (nM) | $E_{max}$ (%) |
| Compound 298 (Example 228) | <10 | 102 | >50 | 16 | >100 | 32 |
| Compound 300 (Example 230) | <50 | 105 | >100 | 26 | >500 | 39 |
| Compound 306 (Example 234) | <10 | 84 | N.C. | (2.8)$^a$ | N.C. | (9.5)$^a$ |
| Compound 308 (Example 235) | <10 | 94 | N.C. | (2.5)$^a$ | >100 | 38 |
| Compound 311 (Example 237) | <50 | 82 | >100 | 18 | >500 | 16 |
| Compound 334 (Example 248) | <1 | 87 | N.C. | (2.9)$^a$ | >1 | 39 |
| Compound 329 (Example 246) | <1 | 76 | N.C. | (0.9)$^a$ | >10 | 14 |

1): Hydrochloride was used.
N.C.: Since the reaction did not reach the maximum even at the maximum concentration (10 μM), the $EC_{50}$ value was not calculated.
a: Since the reaction did not reach the maximum even at the maximum concentration, the responce rate at the maximum concentration was shown as a reference value.

As shown in Tables 24 to 26, it was confirmed that the compounds of the present invention have potent agonist activities against the opioid δ receptor.

Example 263

(1) Analgesic Activity (Acetic Acid Writhing Method)

ICR male mice were used as groups each consisting of eight mice. Twenty minutes after the subcutaneous administration of a test compound (3 mg/kg), a 0.6% aqueous solution of acetic acid was intraperitoneally administered (0.1 mL/10 g body weight), and from the point 5 minutes after the administration, number of writhing observed over 20 minutes was counted. The analgesic activity was evaluated on the basis of the writhing inhibition rate (% inhibition) of the test compound administration group with respect to the writhing number of the solvent administration group.

(2) Results

The results are shown in Table 27.

TABLE 27

| Compound[1] | Inhibitory activities against writhing[2] |
|---|---|
| Compound 78 (Example 68) | + |
| Compound 79 (Example 69) | ++ |
| Compound 159 (Example 126) | ++ |
| Compound 223 (Example 166) | +++ |
| Compound 239 (Example 181) | +++ |
| Compound 243 (Example 185) | ++ |
| Compound 257 (Example 199) | ++ |
| Compound 298 (Example 228) | +++ |

1): Hydrochloride was used.
2): The evaluation results of the inhibitory activities against writhing were classified on the basis of the inhibition rate as follows.
≥90%, +++; 70≤%<90, ++; 50≤%<70, +

As shown in Table 27, it was confirmed that the compounds of the present invention have potent analgesic activity.

What is claimed is:
1. A morphinan derivative represented by the following formula (I):

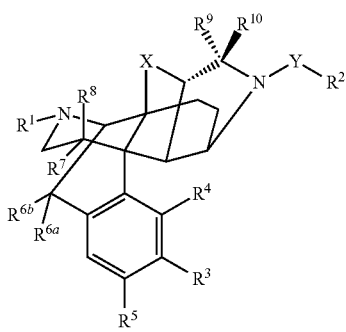

wherein $R^1$ represents hydrogen, $C_{1-10}$ alkyl, $C_{6-10}$ aryl, $C_{2-6}$ alkenyl, cycloalkylalkyl in which the cycloalkyl moiety has 3 to 6 carbon atoms and the alkylene moiety has 1 to 5 carbon atoms, aralkyl in which the aryl moiety has 6 to 10 carbon atoms and the alkylene moiety has 1 to 5 carbon atoms, $C_{3-6}$ cycloalkyl, or heteroarylalkyl in which the heteroaryl contains 1 to 4 heteroatoms selected from N, O, and S as ring-constituting atoms and the alkylene moiety has 1 to 5 carbon atoms,
$R^2$ represents hydrogen, $C_{1-10}$ alkyl, $C_{3-6}$ cycloalkyl, $C_{6-10}$ aryl, heteroaryl containing 1 to 4 heteroatoms selected from N, O, and S as ring-constituting atoms, aralkyl in which the aryl moiety has 6 to 10 carbon atoms and the alkylene moiety has 1 to 5 carbon atoms, heteroarylalkyl in which the heteroaryl contains 1 to 4 heteroatoms selected from N, O, and S as ring-constituting atoms and the alkylene moiety has 1 to 5 carbon atoms, cycloalkylalkyl in which the cycloalkyl moiety has 3 to 6 carbon atoms and the alkylene moiety has 1 to 5 carbon atoms, $C_{2-6}$ alkenyl, arylalkenyl in which the aryl moiety has 6 to 10 carbon atoms and the alkenyl moiety has 2 to 6 carbon atoms, heteroarylalkenyl in which the heteroaryl contains 1 to 4 heteroatoms selected from N, O, and S as ring-constituting atoms and the alkenyl moiety has 2 to 6 carbon atoms, cycloalkylalkenyl in which the cycloalkyl moiety has 3 to 6 carbon atoms and the alkenyl moiety has 2 to 6 carbon atoms, $C_{4-6}$ cycloalkenyl, cycloalkenylalkyl in which the cycloalkenyl moiety has 4 to 6 carbon atoms and the alkylene moiety has 1 to 5 carbon atoms, or cycloalkenylalkenyl in which the cycloalkenyl moiety has 4 to 6 carbon atoms and the alkenyl moiety has 2 to 6 carbon atoms,
$R^3$, $R^4$, and $R^5$, which are the same or different, represent hydrogen, hydroxy, halogen, cyano, carbamoyl, $C_1$-$C_6$ alkoxy, $C_{6-10}$ aryloxy, $C_1$-$C_6$ alkanoyloxy, nitro, amino, $C_{1-8}$ alkylamino, $C_{6-10}$ arylamino, or acylamino in which the acyl moiety has 2 to 6 carbon atoms,
$R^{6a}$ and $R^{6b}$, which are the same or different, represent hydrogen, fluorine or hydroxy, or $R^{6a}$ and $R^{6b}$ combine together to represent =O,
$R^7$ and $R^8$, which are the same or different, represent hydrogen, fluorine or hydroxy,
$R^9$ and $R^{10}$, which are the same or different, represent hydrogen, $C_{1-6}$ alkyl, $C_{6-10}$ aryl, heteroaryl containing 1 to 4 heteroatoms selected from N, O, and S as ring-constituting atoms, aralkyl in which the aryl moiety has 6 to 10 carbon atoms and the alkylene moiety has 1 to 5 carbon atoms, heteroarylalkyl in which the heteroaryl contains 1 to 4 heteroatoms selected from N, O, and S as ring-constituting atoms and the alkylene moiety has 1 to 5 carbon atoms, cycloalkylalkyl in which the cycloalkyl moiety has 3 to 6 carbon atoms and the alkylene moiety has 1 to 5 carbon atoms, or $C_{2-6}$ alkenyl,
X represents O or $CH_2$, and
Y represents C=O, C=S, $SO_2$, C(=O)O, C(=O)$NR^{11}$, C(=S)$NR^{11}$, or an atomic bond, where $R^{11}$ represents hydrogen, $C_{1-6}$ alkyl, aralkyl in which the aryl moiety has 6 to 10 carbon atoms and the alkylene moiety has 1 to 5 carbon atoms, heteroarylalkyl in which the heteroaryl contains 1 to 4 heteroatoms selected from N, O, and S as ring-constituting atoms and the alkylene moiety has 1 to 5 carbon atoms, or cycloalkylalkyl in which the cycloalkyl moiety has 3 to 6 carbon atoms and the alkylene moiety has 1 to 5 carbon atoms, or may form a 4- to 7-membered ring together with the N atom to which $R^{11}$ bonds and $R^2$, where the 4- to 7-membered ring may contain heteroatom(s) selected from N, O, and S atoms as a ring-constituting atom other than the N atom to which $R^{11}$ binds, and may have 1 to 3 substituents selected from halogen, hydroxy, $C_{1-6}$ alkyl, aralkyl in which the aryl moiety has 6 to 10 carbon atoms and the alkylene moiety has 1 to 5 carbon atoms, $C_{2-6}$ acyl, and oxo group,
provided that the $C_{1-10}$ alkyl as $R^1$ or $R^2$, the alkylene moiety and the cycloalkyl moiety of the cycloalkylalkyl in which the cycloalkyl moiety has 3 to 6 carbon atoms and the alkylene moiety has 1 to 5 carbon atoms as $R^1$ or $R^2$, the alkylene moiety of the aralkyl in which the aryl moiety has 6 to 10 carbon atoms and the alkylene moiety has 1 to 5 carbon atoms as $R^1$ or $R^2$, as well as the alkylene moiety of the heteroarylalkyl in which the heteroaryl contains 1 to 4 heteroatoms selected from N, O and S as ring-constituting atoms and the alkylene moiety has 1 to 5 carbon atoms as $R^1$ or $R^2$, may be substituted with at least one substituent selected from 1 to 6 halogens, hydroxy, $C_{1-6}$ alkoxy, $C_{6-10}$ aryloxy, $C_{1-6}$ alkanoyl, $C_{1-6}$ alkanoyloxy, carboxyl, alkoxycarbonyl in which the alkoxy moiety has 1 to 6 carbon atoms, carbamoyl, alkylcarbamoyl in which the alkyl moiety has 1 to 6 carbon atoms, dialkylcarbamoyl in which each alkyl moiety has 1 to 6 carbon atoms, alkylsulfonyl in which the alkyl moiety has 1 to 6 carbon atoms, alkylthio in which the alkyl moiety has 1 to 6 carbon atoms, $C_{1-6}$ alkoxy substituted with 1 to 6 halogens, arylcarbonyl, and oxetanyl, the aryl as $R^1$, aryl moiety of the aralkyl in which the aryl moiety has 6 to 10 carbon atoms and the alkylene moiety has 1 to 5 carbon atoms as $R^1$, the aryl as $R^2$, the heteroaryl containing 1 to 4 heteroatoms selected from N, O, and S as ring-constituting atoms as $R^2$, or the aryl moiety of the aralkyl in which the aryl moiety has 6 to 10 carbon atoms and the alkylene moiety has 1 to 5 carbon atoms as $R^2$, the heteroaryl moiety of the heteroarylalkyl in which the heteroaryl contains 1 to 4 heteroatoms selected from N, O, and S as ring-constituting atoms and the alkylene moiety has 1 to 5 carbon atoms as $R^2$, the aryl moiety of the arylalkenyl in which the aryl moiety has 6 to 10 carbon atoms and the alkenyl moiety has 2 to 6 carbon atoms as $R^2$, the heteroaryl moiety of the heteroarylalkenyl in which the heteroaryl contains 1 to 4 heteroatoms selected from N, O, and S as ring-constituting atoms and the alkenyl moiety has 2 to 6 carbon atoms as $R^2$, the aryl moiety of the $C_{6-10}$ aryloxy as $R^3$, $R^4$, or $R^5$, the aryl moiety of the $C_{6-10}$ arylamino as $R^3$, $R^4$, or $R^5$, the $C_{6-10}$ aryl as $R^9$ or $R^{10}$, the heteroaryl containing 1 to 4 heteroatoms selected from N, O, and S as ring-constituting atoms as $R^9$ or $R^{10}$, or the aryl moiety of the aralkyl in which the aryl moiety has 6 to 10 carbon atoms and the alkylene moiety has 1 to 5 carbon atoms as $R^9$ or $R^{10}$, and the heteroaryl moiety of the heteroarylalkyl in which the heteroaryl contains 1 to 4 heteroatoms selected from N, O, and S as ring-constituting atoms, and the alkylene moiety has 1 to 5 carbon atoms as $R^9$ or $R^{10}$, may be substituted with at least one substituent selected from $C_{1-6}$ alkyl, $C_{1-6}$ alkoxy, $C_{1-6}$ alkanoyloxy, hydroxy, alkoxycarbonyl in which the alkoxy moiety has 1 to 6 carbon atoms, carbamoyl, alkylcarbamoyl in which the alkyl moiety has 1 to 6 carbon atoms, dialkylcarbamoyl in which each alkyl moiety has 1 to 6 carbon atoms, halogen, nitro, cyano, $C_{1-6}$ alkyl substituted with 1 to 3 halogens, $C_{1-6}$ alkoxy substituted with 1 to 3 halogens, phenyl, heteroaryl containing 1 to 4 heteroatoms selected from N, O, and S as ring-constituting atoms, phenoxy, phenylalkyl in which the alkyl has 1 to 3 carbon atoms, methylenedioxy, and $NR^{12}R^{13}$ where $R^{12}$ and $R^{13}$ independently represent hydrogen, $C_{1-6}$ alkyl, $C_{2-6}$ alkenyl, $C_{3-6}$ cycloalkyl, $C_{1-6}$ alkanoyl, or alkoxycarbonyl in which the alkoxy moiety has 1 to 6 carbon atoms, or $R^{12}$ and $R^{13}$ may form a 4- to 7-membered ring together with the N atom to which they bond, where the 4- to 7-membered ring may further contain heteroatom(s) selected from N, O, and S, and furthermore, the alkylene moiety of the aralkyl in which the aryl moiety has 6 to 10 carbon atoms and the alkylene moiety has 1 to 5 carbon atoms as $R^1$ or $R^2$ may be substituted with at least one substituent selected from phenyl and $C_{1-6}$ alkyl substituted with 1 to 3 halogens, or a pharmacologically acceptable acid addition salt thereof.

2. The morphinan derivative represented by formula (I) or a pharmacologically acceptable acid addition salt thereof according to claim 1, wherein:

$R^1$ represents hydrogen, $C_{1-6}$ alkyl, $C_{6-10}$ aryl, $C_{2-6}$ alkenyl, cycloalkylalkyl in which the cycloalkyl moiety has 3 to 6 carbon atoms and the alkylene moiety has 1 to 5 carbon atoms, aralkyl in which the aryl moiety has 6 to 10 carbon atoms and the alkylene moiety has 1 to 5 carbon atoms, $C_{3-6}$ cycloalkyl, or heteroarylalkyl in which the heteroaryl contains 1 to 4 heteroatoms selected from N, O, and S as ring-constituting atoms and the alkylene moiety has 1 to 5 carbon atoms, $R^2$ represents hydrogen, $C_{1-6}$ alkyl, $C_{3-6}$ cycloalkyl, $C_{6-10}$ aryl, heteroaryl containing 1 to 4 heteroatoms selected from N, O, and S as ring-constituting atoms, aralkyl in which the aryl moiety has 6 to 10 carbon atoms and the alkylene moiety has 1 to 5 carbon atoms, heteroarylalkyl in which the heteroaryl contains 1 to 4 heteroatoms selected from N, O, and S as ring-constituting atoms and the alkylene moiety has 1 to 5 carbon atoms, cycloalkylalkyl in which the cycloalkyl moiety has 3 to 6 carbon atoms and the alkylene moiety has 1 to 5 carbon atoms, $C_{2-6}$ alkenyl, arylalkenyl in which the aryl moiety has 6 to 10 carbon atoms and the alkenyl moiety has 2 to 6 carbon atoms, heteroarylalkenyl in which the heteroaryl contains 1 to 4 heteroatoms selected from N, O, and S as ring-constituting atoms and the alkenyl moiety has 2 to 6 carbon atoms, cycloalkylalkenyl in which the cycloalkyl moiety has 3 to 6 carbon atoms and the alkenyl moiety has 2 to 6 carbon atoms, $C_{4-6}$ cycloalkenyl, cycloalkenylalkyl in which the cycloalkenyl moiety has 4 to 6 carbon atoms and the alkylene moiety has 1 to 5 carbon atoms, or cycloalkenylalkyl in which the cycloalkenyl moiety has 4 to 6 carbon atoms and the alkenyl moiety has 2 to 6 carbon atoms, $R^3$, $R^4$, and $R^5$, which are the same or different, represent hydrogen, hydroxy, halogen, cyano, carbamoyl, $C_{1-6}$ alkoxy, $C_{6-10}$ aryloxy, $C_{1-6}$ alkanoyloxy, nitro, amino, $C_{1-8}$ alkylamino, aralkylamino in which the aryl moiety has 6 to 10 carbon atoms and the alkylene moiety has 1 to 5 carbon atoms, or acylamino in which the acyl moiety has 2 to 6 carbon atoms, $R^{6a}$ and $R^{6b}$, which are the same or different, represent hydrogen, fluorine or hydroxy, or $R^{6a}$ and $R^{6b}$ combine together to represent =O, $R^7$ and $R^8$, which are the same or different, represent hydrogen, fluorine or hydroxy, $R^9$ and $R^{10}$, which are the same or different, represent hydrogen, $C_{1-6}$ alkyl, $C_{6-10}$ aryl, heteroaryl containing 1 to 4 heteroatoms selected from N, O, and S as ring-constituting atoms, aralkyl in which the aryl moiety has 6 to 10 carbon atoms and the alkylene moiety has 1 to 5 carbon atoms, heteroarylalkyl in which the heteroaryl contains 1 to 4 heteroatoms selected from N, O, and S as ring-constituting atoms and the alkylene moiety has 1 to 5 carbon atoms, cycloalkylalkyl in which the cycloalkyl moiety has 3 to 6 carbon atoms and the alkylene moiety has 1 to 5 carbon atoms, or $C_{2-6}$ alkenyl, X represents O or $CH_2$, and Y represents C=O, C=S, $SO_2$, C(=O)O, C(=O)$NR^{11}$, C(=S)$NR^{11}$, or an atomic bond, where $R^{11}$ represents hydrogen, $C_{1-6}$ alkyl, aralkyl in which the aryl moiety has 6 to 10 carbon atoms and the alkylene moiety has 1 to 5 carbon atoms, heteroarylalkyl in which the heteroaryl contains 1 to 4 heteroatoms selected from N, O, and S as ring-constituting atoms and the alkylene moiety has 1 to 5 carbon atoms, or cycloalkylalkyl in which the cycloalkyl moiety has 3 to 6 carbon atoms and the alkylene moiety has 1 to 5 carbon atoms, or may form a 4- to 7-membered ring together with the N atom to which $R^{11}$ bonds and R², where the 4- to 7-membered ring may contain heteroatom(s) selected from N, O, and S atoms as a ring-constituting atom other than the N atom to which R¹¹ bonds, and may have 1 to 3 substituents selected from halogen, hydroxy, $C_{1-6}$ alkyl, aralkyl in which the aryl moiety has 6 to 10 carbon atoms and the alkylene moiety has 1 to 5 carbon atoms, $C_{2-6}$ acyl, and oxo group, provided that the $C_{1-10}$ alkyl as R¹ or R², the alkylene moiety and the cycloalkyl moiety of the cycloalkylalkyl in which the cycloalkyl moiety has 3 to 6 carbon atoms and the alkylene moiety has 1 to 5 carbon atoms as R¹ or R², as well as the alkylene moiety of the aralkyl in which the aryl moiety has 6 to 10 carbon atoms and the alkylene moiety has 1 to 5 carbon atoms as R¹ or R² may be substituted with at least one substituent selected from 1 to 6 halogens, hydroxy, $C_{1-6}$ alkoxy, $C_{6-10}$ aryloxy, $C_{1-6}$ alkanoyl, $C_{1-6}$ alkanoyloxy, carboxyl, and alkoxycarbonyl in which the alkoxy moiety has 1 to 6 carbon atoms, the aryl as R¹, aryl moiety of the aralkyl in which the aryl moiety has 6 to 10 carbon atoms and the alkylene moiety has 1 to 5 carbon atoms as R¹, the aryl as R², the heteroaryl containing 1 to 4 heteroatoms selected from N, O, and S as ring-constituting atoms as R², or the aryl moiety of the aralkyl in which the aryl moiety has 6 to 10 carbon atoms and the alkylene moiety has 1 to 5 carbon atoms as R², the heteroaryl moiety of the heteroarylalkyl in which the heteroaryl contains 1 to 4 heteroatoms selected from N, O, and S as ring-constituting atoms and the alkylene moiety has 1 to 5 carbon atoms as R², the aryl moiety of the arylalkenyl in which the aryl moiety has 6 to 10 carbon atoms and the alkenyl moiety has 2 to 6 carbon atoms as R², the heteroaryl moiety of the heteroarylalkenyl in which the heteroaryl contains 1 to 4 heteroatoms selected from N, O, and S as ring-constituting atoms and the alkenyl moiety has 2 to 6 carbon atoms as R², the aryl moiety of the $C_{6-10}$ aryloxy as R³, R⁴, or R⁵, the aryl moiety of the aralkylamino as R³, R⁴, or R⁵, the $C_{6-10}$ aryl as R⁹ or R¹⁰, the heteroaryl containing 1 to 4 heteroatoms selected from N, O, and S as ring-constituting atoms as R⁹ or R¹⁰, or the aryl moiety of the aralkyl in which the aryl moiety has 6 to 10 carbon atoms and the alkylene moiety has 1 to 5 carbon atoms as R⁹ or R¹⁰, and the heteroaryl moiety of the heteroarylalkyl in which the heteroaryl contains 1 to 4 heteroatoms selected from N, O, and S as ring-constituting atoms and the alkylene moiety has 1 to 5 carbon atoms as R⁹ or R¹⁰, may be substituted with at least one substituent selected from $C_{1-6}$ alkyl, $C_{1-6}$ alkoxy, $C_{1-6}$ alkanoyloxy, hydroxy, alkoxycarbonyl in which the alkoxy moiety has 1 to 6 carbon atoms, carbamoyl, alkylcarbamoyl in which the alkyl moiety has 1 to 6 carbon atoms, dialkylcarbamoyl in which each alkyl moiety has 1 to 6 carbon atoms, halogen, nitro, cyano, $C_{1-6}$ alkyl substituted with 1 to 3 halogens, $C_{1-6}$ alkoxy substituted with 1 to 3 halogens, phenyl, heteroaryl containing 1 to 4 heteroatoms selected from N, O, and S as ring-constituting atoms, phenoxy, phenylalkyl in which the alkyl has 1 to 3 carbon atoms, methylenedioxy, and NR¹²R¹³, where R¹² and R¹³ independently represent hydrogen, $C_{1-6}$ alkyl, $C_{2-6}$ alkenyl, $C_{3-6}$ cycloalkyl, $C_{1-6}$ alkanoyl, or alkoxycarbonyl in which the alkoxy moiety has 1 to 6 carbon atoms, or R¹² and R¹³ may form a 4- to 7-membered ring together with the N atom to which they bond, where the 4- to 7-membered ring may further contain heteroatom(s) selected from N, O, and S, and furthermore, the alkylene moiety of the aralkyl in which the aryl moiety has 6 to 10 carbon atoms and the alkylene moiety has 1 to 5 carbon atoms as R¹ or R² may be substituted with at least one substituent selected from phenyl and $C_{1-6}$ alkyl substituted with 1 to 3 halogens.

3. The morphinan derivative or a pharmacologically acceptable acid addition salt thereof according to claim 1, wherein R¹ is $C_{1-6}$ alkyl, cycloalkylalkyl in which the cycloalkyl moiety has 3 to 6 carbon atoms and the alkylene moiety has 1 to 5 carbon atoms, or aralkyl in which the aryl moiety has 6 to 10 carbon atoms and the alkylene moiety has 1 to 5 carbon atoms.

4. The morphinan derivative or a pharmacologically acceptable acid addition salt thereof according to claim 1, wherein R¹ is $C_{2-6}$ alkyl substituted with hydroxy, $C_{1-6}$ alkyl substituted with 1 to 6 halogens, or $C_{2-6}$ alkyl substituted with $C_{1-6}$ alkoxy.

5. The morphinan derivative or a pharmacologically acceptable acid addition salt thereof according to claim 1, wherein Y is C=O, C(=O)O, C(=O)NR¹¹, or an atomic bond.

6. The morphinan derivative or a pharmacologically acceptable acid addition salt thereof according to claim 1, wherein Y is C(=O)O, or C(=O)NR¹¹.

7. The morphinan derivative or a pharmacologically acceptable acid addition salt thereof according to claim 1, wherein Y is an atomic bond, and R² is $C_{6-10}$ aryl or heteroaryl containing 1 to 4 heteroatoms selected from N, O, and S as ring-constituting atoms.

8. The morphinan derivative or a pharmacologically acceptable acid addition salt thereof according to claim 1, wherein Y is an atomic bond, and R² is heteroaryl (it contains at least one N atom as a ring-constituting atom, and may further contain 1 to 3 heteroatoms selected from N, O, and S).

9. The morphinan derivative or a pharmacologically acceptable acid addition salt thereof according to claim 1, wherein Y is C(=O), R² is $C_{1-6}$ alkyl, $C_{6-10}$ aryl, heteroaryl containing 1 to 4 heteroatoms selected from N, O, and S as ring-constituting atoms, aralkyl in which the aryl moiety has 6 to 10 carbon atoms and the alkylene moiety has 1 to 5 carbon atoms, or heteroarylalkyl in which the heteroaryl contains 1 to 4 heteroatoms selected from N, O, and S as ring-constituting atoms and the alkylene moiety has 1 to 5 carbon atoms.

10. The morphinan derivative or a pharmacologically acceptable acid addition salt thereof according to claim 1, wherein Y is C(=O), and R² is $C_{6-10}$ aryl or heteroaryl containing 1 to 4 heteroatoms selected from N, O, and S as ring-constituting atoms.

11. The morphinan derivative or a pharmacologically acceptable acid addition salt thereof according to claim 1, wherein X is $CH_2$.

12. The morphinan derivative or a pharmacologically acceptable acid addition salt thereof according to claim 1, wherein one of R³ and R⁴ is hydroxy, and the other is hydrogen.

13. The morphinan derivative or a pharmacologically acceptable acid addition salt thereof according to claim 1, wherein R³ is halogen, cyano, carbamoyl, $C_{1-6}$ alkoxy, $C_{1-6}$ alkanoyloxy, amino, or acylamino in which the acyl moiety has 2 to 6 carbon atoms, R⁴ is hydrogen or hydroxy, and R⁵ is hydrogen.

14. The morphinan derivative or a pharmacologically acceptable acid addition salt thereof according to claim 1, wherein R³ is hydroxy or carbamoyl, R⁴ is hydrogen, and R⁵ is hydrogen.

15. The morphinan derivative or a pharmacologically acceptable acid addition salt thereof according to claim 1, wherein all of $R^3$, $R^4$, and $R^5$ are hydrogens.

16. The morphinan derivative or a pharmacologically acceptable acid addition salt thereof according to claim 1, wherein all of $R^{6a}$, $R^{6b}$, $R^7$, $R^8$, $R^9$, and $R^{10}$ are hydrogens.

17. The morphinan derivative or a pharmacologically acceptable acid addition salt thereof according to claim 1, wherein:

$R^5$, $R^{6a}$, $R^{6b}$, $R^7$, $R^8$, $R^9$, and $R^{10}$ are hydrogens, $R^1$ is hydrogen, $C_{1-6}$ alkyl, $C_{2-6}$ alkenyl, cycloalkylalkyl in which the cycloalkyl moiety has 3 to 6 carbon atoms and the alkylene moiety has 1 to 5 carbon atoms, or aralkyl in which the aryl moiety has 6 to 10 carbon atoms and the alkylene moiety has 1 to 5 carbon atoms, $R^2$ is hydrogen, $C_{1-6}$ alkyl, $C_{3-6}$ cycloalkyl, $C_{6-10}$ aryl, heteroaryl containing 1 to 4 heteroatoms selected from N, O, and S as ring-constituting atoms, aralkyl in which the aryl moiety has 6 to 10 carbon atoms and the alkylene moiety has 1 to 5 carbon atoms, heteroarylalkyl in which the heteroaryl contains 1 to 4 heteroatoms selected from N, O, and S as ring-constituting atoms and the alkylene moiety has 1 to 5 carbon atoms, cycloalkylalkyl in which the cycloalkyl moiety has 3 to 6 carbon atoms and the alkylene moiety has 1 to 5 carbon atoms, $C_{2-6}$ alkenyl, arylalkenyl in which the aryl moiety has 6 to 10 carbon atoms and the alkenyl moiety has 2 to 6 carbon atoms, heteroarylalkenyl in which the heteroaryl contains 1 to 4 heteroatoms selected from N, O, and S as ring-constituting atoms and the alkenyl moiety has 2 to 6 carbon atoms, cycloalkylalkenyl in which the cycloalkyl moiety has 3 to 6 carbon atoms and the alkenyl moiety has 2 to 6 carbon atoms, $C_{4-6}$ cycloalkenyl, cycloalkenylalkyl in which the cycloalkenyl moiety has 4 to 6 carbon atoms and the alkylene moiety has 1 to 5 carbon atoms, or cycloalkenylalkenyl in which the cycloalkenyl moiety has 4 to 6 carbon atoms and the alkenyl moiety has 2 to 6 carbon atoms, $R^3$ and $R^4$, which are the same or different, are each hydrogen, hydroxy, halogen, cyano, carbamoyl, $C_{1-6}$ alkoxy, $C_{6-10}$ aryloxy, $C_{1-6}$ alkanoyloxy, amino, or acylamino in which the acyl moiety has 2 to 6 carbon atoms, X is O or $CH_2$, and Y is C=O, $SO_2$, or an atomic bond, provided that the $C_{1-6}$ alkyl as $R^1$ or $R^2$, the cycloalkyl moiety and the alkylene moiety of the cycloalkylalkyl in which the cycloalkyl moiety has 3 to 6 carbon atoms and the alkylene moiety has 1 to 5 carbon atoms as $R^1$ or $R^2$, as well as the alkylene moiety of the aralkyl in which the aryl moiety has 6 to 10 carbon atoms and the alkylene moiety has 1 to 5 carbon atoms as $R^1$ or $R^2$ may be substituted with at least one substituent selected from 1 to 3 halogens, hydroxy, $C_{1-6}$ alkoxy, $C_{6-10}$ aryloxy, $C_{1-6}$ alkanoyl, $C_{1-6}$ alkanoyloxy, and alkoxycarbonyl in which the alkoxy moiety has 1 to 6 carbon atoms, the aryl moiety of the aralkyl as $R^1$, the aryl as $R^2$, the heteroaryl as $R^2$, or the aryl moiety of the aralkyl as $R^2$, the heteroaryl moiety of the heteroarylalkyl as $R^2$, the aryl moiety of the arylalkenyl as $R^2$, the heteroaryl moiety of the heteroarylalkenyl as $R^2$, and the aryl moiety of the $C_{6-10}$ aryloxy as $R^3$ or $R^4$, may be substituted with at least one substituent selected from $C_{1-6}$ alkyl, $C_{1-6}$ alkoxy, $C_{1-6}$ alkanoyloxy, hydroxy, alkoxycarbonyl in which the alkoxy moiety has 1 to 6 carbon atoms, carbamoyl, alkylcarbamoyl in which the alkyl moiety has 1 to 6 carbon atoms, dialkylcarbamoyl in which each alkyl moiety has 1 to 6 carbon atoms, halogen, nitro, cyano, $C_{1-6}$ alkyl substituted with 1 to 3 halogens, $C_{1-6}$ alkoxy substituted with 1 to 3 halogens, phenyl, heteroaryl containing 1 to 4 heteroatoms selected from N, O, and S as ring-constituting atoms, phenoxy, phenylalkyl in which the alkyl has 1 to 3 carbon atoms, methylenedioxy, and $NR^{12}R^{13}$, where $R^{12}$ and $R^{13}$ independently represent hydrogen, $C_{1-6}$ alkyl, $C_{2-6}$ alkenyl, $C_{3-6}$ cycloalkyl, $C_{1-6}$ alkanoyl, or alkoxycarbonyl in which the alkoxy moiety has 1 to 6 carbon atoms, or $R^{12}$ and $R^{13}$ may form a 4- to 7-membered ring together with the N atom to which they bond, which 4- to 7-membered ring may further contain heteroatom(s) selected from N, O, and S, and furthermore, the alkylene moiety of the aralkyl in which the aryl moiety has 6 to 10 carbon atoms and the alkylene moiety has 1 to 5 carbon atoms as $R^1$ or $R^2$ may be substituted with at least one substituent selected from phenyl and $C_{1-6}$ alkyl substituted with 1 to 3 halogens.

18. The morphinan derivative or a pharmacologically acceptable acid addition salt thereof according to claim 17, wherein $R^1$ is $C_{1-6}$ alkyl, cycloalkylalkyl in which the cycloalkyl moiety has 3 to 6 carbon atoms and the alkylene moiety has 1 to 5 carbon atoms, or aralkyl in which the aryl moiety has 6 to 10 carbon atoms and the alkylene moiety has 1 to 5 carbon atoms.

19. The morphinan derivative or a pharmacologically acceptable acid addition salt thereof according to claim 17, wherein $R^1$ is $C_{2-6}$ alkyl substituted with hydroxy, $C_{1-6}$ alkyl substituted with 1 to 3 halogens, or $C_{2-6}$ alkyl substituted with $C_{1-6}$ alkoxy.

20. The morphinan derivative or a pharmacologically acceptable acid addition salt thereof according to claim 17, wherein $R^2$ is $C_{6-10}$ aryl.

21. The morphinan derivative or a pharmacologically acceptable acid addition salt thereof according to claim 17, wherein X is O.

22. The morphinan derivative or a pharmacologically acceptable acid addition salt thereof according to claim 17, wherein X is $CH_2$.

23. The morphinan derivative or a pharmacologically acceptable acid addition salt thereof according to claim 17, wherein Y is C=O or an atomic bond.

24. The morphinan derivative or a pharmacologically acceptable acid addition salt thereof according to claim 17, wherein Y is C=O.

25. The morphinan derivative or a pharmacologically acceptable acid addition salt thereof according to claim 17, wherein one of $R^3$ and $R^4$ is hydroxy, and the other is hydrogen.

26. The morphinan derivative or a pharmacologically acceptable acid addition salt thereof according to claim 17, wherein $R^3$ is carbamoyl, halogen, $C_{1-6}$ alkoxy, $C_{1-6}$ alkanoyloxy, cyano, amino, or acylamino in which the acyl moiety has 2 to 6 carbon atoms, and $R^4$ is hydrogen or hydroxy.

27. The morphinan derivative or a pharmacologically acceptable acid addition salt thereof according to claim 17, wherein $R^3$ is hydroxy or carbamoyl, and $R^4$ is hydrogen.

28. The morphinan derivative or a pharmacologically acceptable acid addition salt thereof according to claim 17, wherein $R^3$ is carbamoyl, and $R^4$ is hydroxy.

29. A pharmaceutical composition comprising the morphinan derivative or a pharmacologically acceptable acid addition salt thereof according to claim 1 as an active ingredient.

30. A method for treating pain, which comprises administering an effective amount of the morphinan derivative or a pharmacologically acceptable acid addition salt thereof according to claim 1 to a patient suffering from pain.

* * * * *

UNITED STATES PATENT AND TRADEMARK OFFICE
CERTIFICATE OF CORRECTION

PATENT NO.        : 8,952,030 B2                                          Page 1 of 1
APPLICATION NO.   : 14/343218
DATED             : February 10, 2015
INVENTOR(S)       : H. Nagase et al.

It is certified that error appears in the above-identified patent and that said Letters Patent is hereby corrected as shown below:

In the Claims

Column 212, line 16 (claim 1, line 36) please change "C1-C6" to -- C1-6 --

Column 212, line 17 (claim 1, line 37) please change "C1-C6" to -- C1-6 --

Signed and Sealed this
Fourteenth Day of July, 2015

Michelle K. Lee
*Director of the United States Patent and Trademark Office*